(12) United States Patent
Jarnagin et al.

(10) Patent No.: US 9,499,570 B2
(45) Date of Patent: Nov. 22, 2016

(54) BORON CONTAINING SMALL MOLECULES

(71) Applicant: ANACOR PHARMACEUTICALS, INC., Palo Alto, CA (US)

(72) Inventors: Kurt Jarnagin, San Mateo, CA (US); Tsutomu Akama, Sunnyvale, CA (US)

(73) Assignee: Anacor Pharmaceuticals, Inc., Palo Alto, CA (US)

( * ) Notice: Subject to any disclaimer, the term of this patent is extended or adjusted under 35 U.S.C. 154(b) by 0 days.

(21) Appl. No.: 14/852,122

(22) Filed: Sep. 11, 2015

(65) Prior Publication Data

US 2015/0376210 A1 Dec. 31, 2015

Related U.S. Application Data

(63) Continuation of application No. 14/133,537, filed on Dec. 18, 2013, now Pat. No. 9,145,429, which is a continuation of application No. 13/015,487, filed on Jan. 27, 2011, now Pat. No. 8,716,478.

(60) Provisional application No. 61/298,860, filed on Jan. 27, 2010, provisional application No. 61/354,187, filed on Jun. 11, 2010, provisional application No. 61/368,211, filed on Jul. 27, 2010, provisional application No. 61/368,205, filed on Jul. 27, 2010, provisional application No. 61/409,849, filed on Nov. 3, 2010, provisional application No. 61/354,188, filed on Jun. 11, 2010.

(51) Int. Cl.
*C07F 5/02* (2006.01)
*C07F 5/04* (2006.01)

(52) U.S. Cl.
CPC ........ *C07F 5/04* (2013.01); *C07F 5/025* (2013.01)

(58) Field of Classification Search
None
See application file for complete search history.

(56) References Cited

U.S. PATENT DOCUMENTS

| | | | |
|---|---|---|---|
| 2,260,336 A | 10/1941 | Prescott et al. | |
| 3,686,398 A | 8/1972 | Kohn et al. | |
| 3,873,279 A | 3/1975 | Singer | |
| 4,602,011 A | 7/1986 | West et al. | |
| 4,716,035 A | 12/1987 | Sampathkamar | |
| 4,766,113 A | 8/1988 | West et al. | |
| 4,894,220 A | 1/1990 | Nabi et al. | |
| 4,919,934 A | 4/1990 | Deckner et al. | |
| 5,274,792 A | 12/1993 | Sato et al. | |
| 5,348,947 A | 9/1994 | Patel et al. | |
| 5,348,948 A | 9/1994 | Patel et al. | |
| 5,591,731 A | 1/1997 | Kennedy et al. | |
| 5,668,258 A | 9/1997 | Stolowitz | |
| 5,688,928 A | 11/1997 | Stolowitz | |
| 5,831,045 A | 11/1998 | Stolowitz et al. | |
| 5,880,188 A | 3/1999 | Austin et al. | |
| 5,962,498 A | 10/1999 | Driedger et al. | |
| 6,083,903 A | 7/2000 | Adams et al. | |
| 6,221,640 B1 | 4/2001 | Tao et al. | |
| 6,306,628 B1 | 10/2001 | Rothschild et al. | |
| 6,369,098 B1 | 4/2002 | Pershadsingh et al. | |
| 6,521,619 B2 | 2/2003 | Link et al. | |
| 6,800,645 B1 | 10/2004 | Cox et al. | |
| 6,855,848 B2 | 2/2005 | Scherer et al. | |
| 7,169,603 B2 | 1/2007 | Hedley et al. | |
| 7,205,425 B2 | 4/2007 | Shibasaki et al. | |
| 7,217,701 B2 | 5/2007 | Mikoshiba et al. | |
| 7,390,806 B2 | 6/2008 | Lee et al. | |
| 7,446,236 B2 | 11/2008 | Naud et al. | |
| 7,465,836 B2 | 12/2008 | Lee et al. | |
| 7,582,621 B2 | 9/2009 | Baker et al. | |
| 7,652,000 B2 | 1/2010 | Perry et al. | |
| 7,767,657 B2 | 8/2010 | Baker et al. | |
| 7,816,344 B2 | 10/2010 | Baker et al. | |
| 7,888,356 B2 | 2/2011 | Lee et al. | |
| 8,039,450 B2 | 10/2011 | Akama et al. | |
| 8,039,451 B2 | 10/2011 | Baker et al. | |
| 8,106,031 B2 | 1/2012 | Lee et al. | |
| 8,115,026 B2 | 2/2012 | Baker et al. | |
| 8,168,614 B2 | 5/2012 | Baker et al. | |
| 8,343,944 B2 | 1/2013 | Xia et al. | |
| 8,440,642 B2 | 5/2013 | Baker et al. | |
| 8,461,134 B2 | 6/2013 | Hernandez et al. | |
| 8,461,135 B2 | 6/2013 | Akama et al. | |
| 8,461,336 B2 | 6/2013 | Zhou et al. | |
| 8,461,364 B2 | 6/2013 | Wheeler et al. | |
| 8,470,803 B2 | 6/2013 | Akama et al. | |
| 8,501,712 B2 | 8/2013 | Baker et al. | |
| 8,546,357 B2 | 10/2013 | Akama et al. | |
| 8,703,742 B2 | 4/2014 | Hernandez et al. | |
| 8,716,478 B2 * | 5/2014 | Jarnagin .............. | C07F 5/04 546/13 |
| 8,722,917 B2 | 5/2014 | Baker et al. | |

(Continued)

FOREIGN PATENT DOCUMENTS

| | | |
|---|---|---|
| EP | 0969531 | 1/2000 |
| EP | 1155698 A1 | 11/2001 |

(Continued)

OTHER PUBLICATIONS

Silverman, R. "The Organic Chemistry of Drug Design and Drug Action," NY 2004, Elsevier.*
U.S. Appl. No. 13/861,846, filed Apr. 12, 2013, now abandoned.
U.S. Appl. No. 13/673,860, filed Nov. 9, 2012, now abandoned.
U.S. Appl. No. 13/607, 321, filed Sep. 7, 2012, now abandoned.
U.S. Appl. No. 13/607,405, filed Sep. 7, 2012, now abandoned.
U.S. Appl. No. 13/607,250, filed Sep. 7, 2012, now abandoned.
U.S. Appl. No. 15/134,286, filed Apr. 20, 2016.
U.S. Appl. No. 15/091,394, filed Apr. 5, 2016.
U.S. Appl. No. 15/068,352, filed Mar. 11, 2016.

(Continued)

*Primary Examiner* — Heidi Reese
(74) *Attorney, Agent, or Firm* — Morgan, Lewis & Bockius LLP

(57) ABSTRACT

Compounds, pharmaceutical formulations, and methods of treating anti-inflammatory conditions and/or helminth-associated diseases are disclosed.

4 Claims, 70 Drawing Sheets

(56) References Cited

U.S. PATENT DOCUMENTS

| | | | |
|---|---|---|---|
| 8,853,186 B2 | 10/2014 | Akama et al. | |
| 8,889,656 B2 | 11/2014 | Baker et al. | |
| 8,895,534 B2 | 11/2014 | Baker et al. | |
| 9,012,431 B2 | 4/2015 | Akama | |
| 9,029,353 B2 | 5/2015 | Baker et al. | |
| 9,145,429 B2 | 9/2015 | Jarnagin et al. | |
| 9,156,860 B2 | 10/2015 | Akama et al. | |
| 9,243,003 B2 | 1/2016 | Conde et al. | |
| 9,353,133 B2 | 5/2016 | Baker et al. | |
| 2002/0028831 A1 | 3/2002 | Manley | |
| 2002/0161230 A1 | 10/2002 | Meudt et al. | |
| 2003/0032673 A1 | 2/2003 | Nagy | |
| 2004/0077601 A1 | 4/2004 | Adams et al. | |
| 2004/0224923 A1 | 11/2004 | Lee et al. | |
| 2005/0125852 A1 | 6/2005 | Caenepeel et al. | |
| 2006/0009386 A1 | 1/2006 | Stossel et al. | |
| 2006/0222671 A1 | 10/2006 | Weidner | |
| 2007/0286822 A1 | 12/2007 | Sanders et al. | |
| 2010/0048570 A1 | 2/2010 | Kim et al. | |
| 2010/0256092 A1 | 10/2010 | Xia et al. | |
| 2011/0124597 A1 | 5/2011 | Hernandez et al. | |
| 2011/0190235 A1 | 8/2011 | Chen et al. | |
| 2011/0207701 A1 | 8/2011 | Zhou et al. | |
| 2011/0207702 A1 | 8/2011 | Jacobs et al. | |
| 2012/0115813 A1 | 5/2012 | Hernandez et al. | |
| 2012/0295875 A1 | 11/2012 | Zhou et al. | |
| 2013/0231304 A1 | 9/2013 | Jacobs et al. | |
| 2013/0289000 A1 | 10/2013 | Akama et al. | |
| 2014/0200198 A1* | 7/2014 | Jarnagin | C07F 5/04 514/64 |

FOREIGN PATENT DOCUMENTS

| | | | |
|---|---|---|---|
| EP | 1 444 981 A1 | 8/2004 | |
| WO | WO 9533754 | 5/1995 | |
| WO | WO 9622023 A1 | 7/1996 | |
| WO | WO 9812206 A1 | 3/1998 | |
| WO | WO 0044387 A1 | 8/2000 | |
| WO | WO 0075142 A2 | 12/2000 | |
| WO | WO 0114578 A1 | 3/2001 | |
| WO | WO 0149303 A1 | 7/2001 | |
| WO | WO 0187846 A2 | 11/2001 | |
| WO | WO 0244184 | 6/2002 | |
| WO | WO 03033002 A1 | 4/2003 | |
| WO | WO 03059916 A2 | 7/2003 | |
| WO | WO 2004056322 A2 | 7/2004 | |
| WO | WO 2005013892 A3 | 2/2005 | |
| WO | WO 2005123094 A2 | 12/2005 | |
| WO | WO 2006007384 | 1/2006 | |
| WO | WO 2006062731 A1 | 6/2006 | |
| WO | WO 2006079843 A1 | 8/2006 | |
| WO | WO 2006089067 A2 | 8/2006 | |
| WO | WO 2006096131 A1 | 9/2006 | |
| WO | WO 2007022437 A2 | 2/2007 | |
| WO | WO 2007078340 A2 | 7/2007 | |
| WO | WO 2007095638 A2 | 8/2007 | |
| WO | WO 2007146965 A2 | 12/2007 | |
| WO | WO 2008157726 A1 | 12/2008 | |
| WO | WO 2009111676 A2 * | 9/2009 | C07F 5/025 |
| WO | WO 2009140309 A2 | 11/2009 | |
| WO | WO 2010027975 A1 | 3/2010 | |
| WO | WO 2010028005 A1 | 3/2010 | |
| WO | WO 2010045503 A | 4/2010 | |
| WO | WO 2010045505 A1 | 4/2010 | |
| WO | WO 2011/019612 A1 | 2/2011 | |
| WO | WO 2011/019618 A1 | 2/2011 | |
| WO | WO 2011017125 A1 | 2/2011 | |
| WO | WO 2011022337 A1 | 2/2011 | |
| WO | WO 2011037731 A | 3/2011 | |
| WO | WO 2011049971 A1 | 4/2011 | |
| WO | WO 2011/060196 A1 | 5/2011 | |
| WO | WO 2011/063293 A1 | 5/2011 | |
| WO | WO 2011/116348 A1 | 9/2011 | |

OTHER PUBLICATIONS

U.S. Appl. No. 15/046,322, filed Feb. 17, 2016.
U.S. Appl. No. 14/977,052, filed Dec. 21, 2015.
U.S. Appl. No. 14/537,771, filed Nov. 10, 2014.
U.S. Appl. No. 14/537,694, filed Nov. 10, 2014, now abandoned.
U.S. Appl. No. 14/165,428, filed Mar. 7, 2014, now abandoned.
U.S. Appl. No. 14/688,581, filed Apr. 16, 2015.
U.S. Appl. No. 11/762,038, filed Jun. 12, 2007, now abandoned.
U.S. Appl. No. 11/865,725, filed Oct. 1, 2007, now abandoned.
U.S. Appl. No. 12/752,789, filed Apr. 1, 2010, now abandoned.
U.S. Appl. No. 14/536,483, filed Nov. 7, 2014.
U.S. Appl. No. 14/666,075, filed Mar. 23, 2015.
U.S. Appl. No. 13/062,450, filed Mar. 4, 2011.
U.S. Appl. No. 12/464,829, filed May 12, 2009, now abandoned.
U.S. Appl. No. 12/873,036, filed Aug. 31, 2010, now abandoned.
U.S. Appl. No. 13/503,016, filed Jun. 25, 2012, now allowed.
U.S. Appl. No. 12/857,305, filed Aug. 16, 2010, now abandoned.
U.S. Appl. No. 12/852,351, filed Aug. 6, 2010.
U.S. Appl. No. 12/944,699, filed Nov. 11, 2010, now abandoned.
U.S. Appl. No. 14/969,467, filed Dec. 15, 2015.
U.S. Appl. No. 14/221,637, filed Mar. 21, 2014.
U.S. Appl. No. 14/852,220, filed Sep. 11, 2015.
U.S. Appl. No. 14/760,208, filed Jul. 10, 2015.
U.S. Appl. No. 14/394,427, filed Oct. 14, 2014.
U.S. Appl. No. 14/765,152, filed Jul. 31, 2015.
U.S. Appl. No. 14/906,849, filed Jan. 21, 2016.
U.S. Appl. No. 14/910,996, filed Feb. 8, 2016.
Adamczyk-Wozniac, et al., "Benzoxaboroles—Old Compounds with new applications", Journal of Organometalic Chemistry 694;3533-3541 (2009).
Akama T, et al., "Discovery and structure-activity study of a novel benzoxaborole anti-inflammatory agent (AN2728) for the potential topical treatment of psoriasis and atopic dermatitis," *Bioorganic & Medicinal Chemistry Letter* 19 (2009) 2129-2132.
Alley, et al., "Recent Progress on Topical Therapy of Onychomycosis", Expert Opinion Investigate Drugs(Feb. 2007) 16(2): 157-67.
Austin, et al., "Oxaboroles and Salts and their Use of Biocides for Plastics", CAS, vol. 124, pp. 234-024, (1996).
Bailey, et al., "Boron-Containing Antibacterial Agents: Effects on Growth and Morphology of Bacteria Under Various Culture Conditions," Antimicrobial Agents and Chemotherapy, 17(04):549-553, (Apr. 1980).
Baker, et al., "Identification of a Novel Boron-Containing Antibacterial Agent (AN0128) with Anti-inflammatory activity, for the Potential Treatment of Cutaneous Diseases", Bioorganic & Medicinal Chemistry Letters (2006) 16: 5963-5937.
Baker, et al., "Discovery of New Boron-Containing Antifungal Agent, 5-Fluoro-1,3-dihydro-1-hydroxy-2, 1-benzoxaborole (AN2690) for Potential Treatment of Onychomoycosis", Journal of Medicinal Chemistry, vol. 49, No. 15; pp. 4447-4450, (Jul. 27, 2006).
Baker, et al., "Progress on New Therapeutics for Fungal Nail Infections", Annual Reports in Medicinal Chemistry, vol. 40: pp. 323-335, (2005).
Baker SJ, et al., "Therapeutic potential of boron-containing compounds," *Future Med. Chern.* (2009) 1(7), 1275-1288.
Bessis, N., "Gene Therapy for Rheumatoid Arthritis," J. Gene Med, vol. 4; pp. 581-591 (2002).
Brown, et al., "Chiral Synthesis Via Organoboranes. 35. Simple Procedures for the Efficient Recycling of the Terpenyl Chiral Auxiliaries and Convenient Isolation of the Homoallylic Alcohols in Asymmetric Allyl- and Crotylboration of Aldehydes," J. Org. Chem., vol. 57, No. 24; pp. 6608-6614, (1992).
Cairns, et al., "Derivatives of 1,4-Xylene-2,5-diboronic acid and 1,4-xylene-2-boronic acid", J. Org. Chem. vol. 29; pp. 2810-2812, (1964).
Chander, et al. "Prevalence of Fungal Corneal Ulcers in Northern India", Infections, vol. 22, No. 3; pp. 207-209, (1994).
Chemical Abstracts Registry No. 845302-09-2, Entered STN Mar. 11, 2005.

(56) References Cited

OTHER PUBLICATIONS

Cui, et al., "Organoboron Compounds with an 8-Hydroxyquinolato Chelate and Its Derivatives: Substituent Effects on Structures and Luminescence," Inorganic Chemistry, vol. 44, No. 03; pp. 601-609, (Feb. 7, 2005).

Cummings, et al., "Arylboronic Acids. A Medium-Size Ring Containing Boronic Ester Groups", Arylboronic Acids, vol. 34, No. 6; pp. 1669-1674 (Jun. 1969).

Cusack, S., et al., "The 2 A Crystal Structure of leucyl-tRNA Synthetase and its Complex with a Leucyl-Adenylate Analogue." EMBO Journal, vol. 19; pp. 2351-2361, (2000).

Dale, et al., "Substituted Styrenes VIII Syntheses and some Reactions of the Vinylbenzeneboronic Acids" J. Org. Chem. vol. 27; pp. 2598-2603, (1962).

Denis, "Pharmacology 1104 Lecture: Drug Classifications & Characteristics of Antimicrobials" (2003).

Dian, "International Nomenclature of Organics", China Petrochemical Press, 1st Edition; 50-51 (Jan. 21, 2004).

Ding, et al. "Discovery of Novel Benzoxaborole-Based Potent Antitrypanosomal Agents," ACS *Med. Chem. Lett.* 2010, 1, 165-169.

Falck, et al., "Bromo-Boronolactonization of Olefins", J. Org. Chem., vol. 66; pp. 7148-7150 (2001).

Farfan, et al., "Through-Bond Modulation on N—B Ring Formation Shown by NMR and X-Ray Diffraction Studies of Borate Derivatives of Pyridyl Alcohols," J. Chem. Soc. Perkin Trans., vol. 2; pp. 527-532 (1992).

Ferrer, Targeting Aminocytl-tRNA Synthetases for the Treatment of Fungal Infections, Drug News Perspective, vol. 19, No. 6; pp. 347-348, (Jul./Aug. 2006).

Fungicide: Definition from Answer.com, (1998).

Grassberger, et al., "Degradation of 1,2-dihydro-1-hydroxy-2-(organosulfonyl)2,3,1-benzodiasaborines and -thieno[3,2-d][1,,3]diazaborines in Alkaline Aqueous Solutions", Liebigs Annalen Der Chemie, vol. 4; pp. 683-688, (1985).

Guo-Zheng, et al., "Single Site Transarylation of 2,2'-Dimetalized-1,1'-Binaphthyl to Aminocloroborates and Synthesis of 2-Binaphthyl Boron Compounds," Youji Huaxue/Organic Chemistry, Science Press, vol. 16, No. 02; pp. 139-144, (1996) (English Abstract).

Goodman, et al., "Goodman & Gilman's Manual of Pharmacology and Therapeutics" Chapter 40;681-694 (2008).

Haynes, et al., "Arylboronic Acids VIII. Reactions of boronphthalide" J. Org. Chem. vol. 29, No. 11; pp. 3229-3233, (1964).

Hauck, et al., "Preparation and Anticonvulsant Activity of Some Arydialkkylsuccinimides" Research Lab of Parke Davis Co. (1967).

He, et al., "Small-Molecule Inhibition of TNF-alpha", Science, vol. 310, No. 5750; pp. 1022-1025, (Nov. 11, 2005).

Hui, et al., "In Vitro Penetration of a Novel Oxaborole Antifungal (AN2690) into the Human Nail Plate", Journal of Pharmaceutical Sciences (2007) 96(10): 2622-2631.

Koster, et al., "Cyclisierugen von Bor-Stickstoff-Verbindugen in der Hietz" Liebigs Ann. Chem., vol. 720; pp. 23-31, (1968).

Koster, et al., "Boron Compounds, XXXIX. Alkenoxy(diorgany)boranes Substituted at the Alkeonxy Group from 2-methylacrolein and triorganylboranes," Justus Liebigs Annalen Der Chemie, No. 06; pp. 1116-1134, (1976).

Lampe, et al., "Synthesis and Protien Kinase Inhibitory Activity of Balanol Analogues with Modified Benzophenone Subunits", J. Med. Chem., vol. 45; pp. 2624-2643, (2002).

Lee, K., et al., "Molecular Study of the Editing Active Site of *Escherichia coli* Leucyl-tRNA Synthetase: Two Amino Acid Binding Site in the Editing Domain", vol. 54; pp. 693-704, (2004).

Lennarz, et al., "Arylboronic Acids. IV. Reactions of Boronophthalide" J. Am. Chem. Soc. vol. 82; pp. 2172-2175, (1960).

Li, et al., "An Improved Protocol for Preparation of 3-Pyridyl- and Some Arylboronic Acids", J. Org. Chem., vol. 67; pp. 5394-5397, (2002).

Luan, et al., "Inhibition of Experimental Periodontitis by a Topical Boron-based Antimicrobial," *J Dent Res* 87(2): 148-152 (2008).

McMillin, et al., "Systemic Aspects of Psoriasis: An Intergrative Model Based on Intestinal Etiology", Int. Med. vol. 2, Issue 2/3, (1999).

Moeder, et al., "Kinetic Analysis of the Asymmetric Amplification exhibited by B-chlorodiisopinocampheylborane," Journal of Physical Organic Chemistry, vol. 17, No. 4; pp. 317-324, (Apr. 2004).

Morissette, et al., "High-throughput Crystallization: Polymorphs, Salts, Co-Crystals and Solvates of Pharmaceutical Solids", Advanced Drug Delivery Reviews, vol. 56; pp. 273-300, (2004).

Mudran, "Drug Delivery to the Nail Following Topical Application", International Journal of Pharmaceutics, vol. 236: pp. 1-26, (2002).

Murugesan, et al., "Biphenylsulfonamide Endothelin Antagonists: Structure-Activity Relationships of a Series of Mono- and Disubstituted Analogues and Pharmacology of the Orally Active Endothelin Antagonist 2'-Amino-$N$-(3,4-dimethyl-5-isoxazoly1)-4'-(2-methylpropyl)[1,1'-biphenyl]-2-sulfonamide",J. Med. Chem vol. 41; pp. 5198-5218 (1998).

Nare et al., "Discovery of Novel Orally Bioavailable Oxaborole 6-Carboxamides That Demonstrate Cure in a Murine Model of Late-Stage Central Nervous System African Trypanosomiasis," Antimicrobial Agents and Chemotherapy, 2010, 4379-4388 vol. 54, No. 10.

Patani, et al., "Bioisosterism: A Rational Approach to Drug Design", Chem. Rev., vol. 96; pp. 3147-3176 (1996).

Perola, E., et al., "Successful Virtual Screening of a Chemical Database for Farnesltransferase Inhibitor Leads." vol. 43; pp. 401-4008, (2000).

Qin, et al., "Luminescent Organoboron Quinolate Polymers," Journal of the American Chemical Society, vol. 126, No. 22; pp. 7015-7018, (Jun. 9, 2004).

Rock, et al., "An Antifungal Agents Inhibits Aminoacyl-tRNA Synthetase by Trapping tRNA in the Editing Site", Science, vol. 316, No. 5832; pp. 1759-1761, (Jun. 22, 2007).

Seiradake E, et al., "Crystal Structures of the Human and Fungal Cytosolic Leucyl-tRNA Synthetase Editing Domains: A Structural Basis for the Rational Design of Antifungal Benzoxaboroles," *Journal of Molecular Biology* 390 (2009) 196-207.

Silverman, "The Organic Chemistry of Drug Design and Drug Action", 2nd Edition, Northwestern University, Department of Chemistry, Evanston, Illinois, Section 2: 29-32 (2004).

Snyder, et al. "Common Bacteria Whose Susceptibility to Antimicrobials in no longer Predictable" J. Med. Liban, vol. 48, No. 4, pp. 208-214, (2000).

Sporzynski, et al., "1,3-Dihydro-1-hydroxy-3-morpholin-4-yl-2,1-benzoxaborole: product of the reaction of o-formylphenylboronic acid with morpholine", Appl. Organometal. Chem., vol. 19; pp. 1202-1203, (2005).

Sugar, et al., "Comparison of Three Methods of Antifungal Susceptibility Testing with the Proposed NCCLS Stardard Broth Macrodilution Assay: Lack of Effect of Phenol Red" Diagn. Microbiol. Infect. Dis. vol. 21; pp. 129-133, (1995).

Tabuchi, et al., "Anticoccidial Activity of some Azacyclo Organoborinates," Heterocycles, vol. 60, No. 01; pp. 177-182, (2003).

Tatsumi, et al., "Therapeutic Efficacy of Topically applied KP-103 against Experimental Tinea Uguium in Guinea Pigs in Comparison with Amorolfine and Terbinafine", Antimicrobial Agents and Chemotherapy, vol. 46, No. 12; pp. 3797-3801 (2002).

Toporcer, et al., "Preparation and Properties of some Tetracoordinate Boron Compounds. The Pseudo-metal Ion Concept," Inorganic Chemistry, vol. 4, No. 11; pp. 649-1655, (Nov. 1965).

Trujillo, et al., "X-Ray Crystallographic Study of Boroxazolidones, Obtained from L-ornithine, L-methionine, Kainic acid and 2,6-pyridinedicarboxylic acid", Journal of Organometallic Chemistry, vol. 571; pp. 21-29, (1998).

Tschampel, et al., "Arylboronic Acids. VII. Some Reactions to o-Formybenzeneboronic Acids", J. Org. Chem. vol. 29, No. 8; pp. 2168-2172, (1964).

(56) References Cited

OTHER PUBLICATIONS

Turner, et al., Current Pharmaceutical Design, vol. 2; pp. 209-224 (1996).

Vippagunta, "Crystalline Solids", Advanced Drug Delivery Reviews, vol. 48; pp. 3-26, (2001).

Wang, et al., "Expression, Purification and Characterization of Human cAMP-Specific Phosphodiesterase (PDE4) Subtypes A, B, C, and D", Biochemical and Biophysical Research Communications, vol. 234; pp. 320-324, (1997).

Williams, et al., "Foye's Principles of Medicinal Chemistry", 5th Edition, 2002, Lippincoot Williams & Wilkins, p. 59.

Ye, et al., "Convenient and Versatile Syntheis of formyl-substituted Benzoxaboroles", Tetrahedron, vol. 65; pp. 8738-8744, (2009).

Zhang, et al., "Synthesis and structure-activity relationships of novel benzoxaboroles as a new class of antimalarial agents," Bioorg Med Chem Lett 2010, 21, pp. 644-651.

Zhang, et al., "Synthesis and biological evalutations of P4-benzoxaborole-substituted macrocyclic inhibitors of HCV NS3 protease," Bioorg Med Chem Lett 2010, 20, pp. 7317-7322.

Zhang, et al. "Synthesis of new acylsulfamoyl benzoxaboroles as potent inhibitors of HCV NS3 protease," *Bioorg Med Chern Lett* 2010, 20, pp. 7493-7497.

Zhang YK et al, "Design and Synthesis of Boron-Containing PDE4 Inhibitors Using Soft-Drug Strategy for Potential Dermatologic Anti-Inflammatory Application," *Bioorganic & Medicinal Chemistry Letters* 20 (2010) 2270-2274.

Zhdankin, et al., "Synthesis and Structure of Benzoboroxoles: Novel Organboron Heterocycles," Tetrahedron Letters, vol. 40; pp. 6705-6708, (1999).

Zhou, et al., "Hemodextrin: a Self-assembled Cyclodextrin-Porphyrin Construct That Binds Dioxygen," Biophysical Chemistry, 105:639-648 (2003).

Zhou, et al., "Structure-activity Studies on a Library of Potent Calix[4]arene-based PDGF Antagonists that Inhibit PDGF-stimulated PDGFR Tyrosine Phosphorylation," Org. Biomol. Chem., 4:2376-2386 (2006).

Zhou, et al., "Pattern Recognition of Proteins Based on an Array of Functionalized Porphyrins," J. Am. Chem. Soc., 128:2421-2425 (2006).

Zixing, et al., "Synthesis of Aromatic Nitrogen-containing Heterocyclic Derivatives of Asymmetric Diarylborinic Acids," Wuhan Daxue Xuebo-Wuhan University Journal, vol. 3; pp. 67-71, (1990), (English Abstract).

"A New Class of Benzoxaborole-based Potent Antitrypanosomal Agents: Probing Effect of Different Linkage Groups in *Trypanosoma brucei* Growth Inhibition", Scientific Presentation at the American Society of Tropical Medicine and Hygiene Conference, New Orleans, LA Dec. 7-11, 2008.

"A Novel Oxaborole, AN3520, Show Efficacy against Human African Trypanomiasis In Vitro and In Vivo, Including Promise in a Murine CNS Model of T. brucei Infection", Scientific Presentation at the American Society of Tropical Medicine and Hygiene Conference, New Orleans, LA Dec. 7-11, 2008.

"A Series of Potent Orally-Available Benzoxaborole PDE4 Inhibitors which Gain Potency by use of Novel Contacts Within the PDE4 Active Site," Gordon Conference on Cyclic Nucleotide Phosphodiesterases, Jun. 13-18, 2010, Waterville Valley, NH.

"An Open-Label, Multi-dose Study of Absorption and Systemic Pharmacokinetics of AN2690 Applied as a 7.5% Solution to All Toenails of Adult Patients with Moderate to Severe Onychomycosis", American Academy of Dermatology, 65th Annual Meeting, Washington, DC, Feb. 2-6, 2007.

"AN2718 has Broad Spectrum Antifungal Activity Necessary for the Topical Treatment of Skin and Nail Fungal Infections", Scientific Presentation at the American Academy of Dermatology Annual Meeting, San Francisco, CA Mar. 6-10, 2009.

"AN2728 Demonstrates Significant Efficacy in Three Phase Ib Psoriasis Microplaque Trials" Scientific Presentation at the American Academy of Dermatology Annual Meeting, San Francisco, CA Mar. 6-10, 2009.

"AN2728 Demonstrates Significant Safety and Efficacy in a Phase IIa Double Blind Trial in Plaque Type Psoriasis," American Academy of Dermatology Annual Meeting, Mar. 6-10, 2009, San Francisco, CA.

"AN2728, A Novel Oxaborole with Broad-Spectrum In Vitro Anti-Inflammatory Activity", American Academy of Dermatology, 65th Annual Meeting, Washington, DC, Feb. 2-6, 2007.

"AN2728 Ointment, a Novel Oxaborole with Anti-Inflammatory Activity, Demonstrates Safety and Significant Efficacy in a Phase Ib Psoriasis Plaque Test", Scientific Presentation at Montagna Symposium on Biology of Skin, Gleneden Beach, OR, Oct. 2-6, 2008.

"AN2728 Preclinical Studies Demonstrate an Acceptable Safety Profile for the Topical Treatment of Psoriasis and Atopic Dermatitis", Scientific Presentation at the American Academy of Dermatology Annual Meeting, San Francisco, CA May 6-10, 2009.

"AN2898 Inhibits Cytokines Relevant to Topical Treatment of Psoriasis and Atopic Dermatitis", Scientific Presentation at the American Academy of Dermatology Annual Meeting, San Francisco, CA Mar. 6-10, 2009.

"AN2920, A Novel Oxaborole, Shows In Vitro and In Vivo Activity Against *Trypanosomal brucei*", Scientific Presentation at the American Society of Tropical Medicine and Hygiene Conference, New Orleans, LA Dec. 7-11, 2008.

"AN6415: A Novel, Highly Potent, PDE4 Inhibitor with Oral Activity and Broad Spectrum Cytokine Suppression," 8th Annual Cytokines and Inflammation Conference, Jan. 28-29, 2010, La Jolla, CA.

"Antifungal Activity and Mechanism of Action of a Benzoxaborole, AN2718, which is in Development for the Treatment of Tinea Pedis", Scientific Presentation at the 48th Interscience Conference on Antimicrobial Agents and Chemotherapy, Washington, D.C. Oct. 25-28, 2008.

"Boron and non-boron HCV NS3/4 protease inhibitors: new motifs with high potency against PI-resistant mutants," HCV Drug Discovery 5th CHI Conference, Apr. 28-29, 2010, San Diego, CA.

"Discovery of Novel Boron Containing Compounds as Dual Inhibitors of TNF-a and IL-23 Release," World Congress of Inflammation, Jul. 6-10, 2009, Tokyo, Japan.

"Discovery of Novel Benzoxaboroles as a New Class of b-Lactamase Inhibitors," 8th Annual Congress of International Drug Discovery Science and Technology, Oct. 23-26, 2010, Beijing, China.

"Discovery and Mechanism of Action of AN3365: A Novel Boron-containing Antibacterial Agent in Clinical Development for Gram-negative Infections," 2010 Interscience Conference on Antimicrobial Agents and Chemotherapy, Sep. 12-15, 2010, Boston, MA.

"In Vitro Nail Penetration of AN2690, Effect of Vehicle and Co-Efficient of Efficacy", American Academy of Dermatology, 65th Annual Meeting, Washington, DC, Feb. 2-6, 2007.

"Interim Results of a Multi-Center Study to Evaluate the Safety and Efficacy of Topically Applied AN2690 5.0% and 7.5% Solutions for the Treatment of Onychomycosis of the Great Toenail", American Academy of Dermatology, 65th Annual Meeting, Washington, DC, Feb. 2-6, 2007.

"In vivo Nail Residence Time of AN2690, a Novel Broad-Spectrum Antifungal Agent in Development for the Topical Treatment of Onychomycosis", American Academy of Dermatology, 65th Annual Meeting, Washington, DC, Feb. 2-6, 2007.

"Lead Optimization Investigation of Oxaboroles for the Treatment of Human African Trypanosomiasis," American Chemical Society, Aug. 16-20, 2009, Washington, DC.

"Medicinal Chemistry Development of AN2728, A Novel Oxaborole in Development for the Topical Treatment of Psoriasis", American Academy of Dermatology, 65th Annual Meeting, Washington, DC, Feb. 2-6, 2007.

"Nail Penetration and Nail Concentration of AN2690, a Novel Broad-Spectrum Antifungal Agent in Development for the Topical Treatment of Onychomycosis", Scientific Presentation at the American Associate of Pharmaceutical Scientist, Annual Meeting, San Antonio, TX, Oct. 29-Nov. 2, 2006.

(56) References Cited

OTHER PUBLICATIONS

"Novel Boron-Containing Small Molecules Demonstrate Potent Activity Against Malaria Parasites with Excellent Drug-like Properties," The American Society of Tropical Medicine and Hygiene, Nov. 20, 2009, Washington, DC.

"Novel Boron-Containing Small Molecules as Potential Therapeutics Against Human Lymphatic Filariasis," The American Society of Tropical Medicine and Hygiene, Nov. 20, 2009, Washington, DC.

"Novel Boron-Containing Small Molecules Demonstrate Potent Activity Against *Trypanosoma cruzi*," The XIIth International Congress of Parasitology, Aug. 15-20, 2010, Melbourne, Australia.

"Novel Cyclic Boronates as HCV NS3/4A Protease Inhibitors," 7th Annual Congress of International Drug Discovery Science and Technology, Oct. 22-25, 2009, Shanghai, China.

"Novel Oxaborole 6-Carboxamides Demonstrate Potential for Treatment of CNS-Stage Human African Trypanosomiasis," Key Stone Symposium, Mar. 22-26, 2009, Breckenridge, CO.

"Preclinical Toxicology of AN2728, a Novel Borinic Acid Ester with Anti-Inflammatory Activity", American Academy of Dermatology, 65th Annual Meeting, Washington, DC, Feb. 2-6, 2007.

"Skin Penetration and Anti-Inflammatory Activity of AN2728, a Novel Oxaborole", American Academy of Dermatology, 65th Annual Meeting, Washington, DC, Feb. 2-6, 2007.

"Structure-Activity Studies of AN2728 and AN2898, Novel Oxaborole Compounds with Anti-Inflammatory Activity", Scientific Presentation at the International Investigative Dermatology Conference, Kyoto, Japan, May 14-18, 2008.

"Structure-Activity Studies led to the Discovery of AN2898 in Development for Topical Treatment of Psoriasis and Atopic Dermatitis", Scientific Presentation at the American Academy of Dermatology Annual Meeting, San Francisco, CA Mar. 6-10, 2009.

"Structure-Activity Studies Led to the Discovery of AN2898 in Development for Topical Treatment of Psoriasis and Atopic Dermatitis," Society for Investigative Dermatology Annual Meeting, May 6-9, 2009, Montreal, Canada.

"Structure-Guided Discovery of (S)-3-(aminomethyl)benzo[c][1,2]oxaborol-1 (3H)-ol hydrochloride (ABX): A First in Class Gram-negative Antibacterial," Anti-Infectives Summit, Jan. 25-27, 2010, Philadelphia, PA.

\* cited by examiner

| R⁴ | Rᶜ | Rᵈ |
|---|---|---|
| Methyl | F | CH₃ |
| | | F |
| | | Cl |
| | | H |
| | Cl | CH₃ |
| | | F |
| | | Cl |
| | | H |
| | CN | CH₃ |
| | | F |
| | | Cl |
| | | H |
| | CF₃ | CH₃ |
| | | F |
| | | Cl |
| | | H |
| | Methyl | CH₃ |
| | | F |
| | | Cl |
| | | H |
| | Ethyl | CH₃ |
| | | F |
| | | Cl |
| | | H |
| | iso-Propyl | CH₃ |
| | | F |
| | | Cl |
| | | H |
| | cyclo-Propyl | CH₃ |
| | | F |
| | | Cl |
| | | H |
| | Methoxy | CH₃ |
| | | F |
| | | Cl |
| | | H |
| | Ethoxy | CH₃ |
| | | F |
| | | Cl |
| | | H |

| R⁴ | Rᶜ | Rᵈ |
|---|---|---|
| Methyl | OCF₃ | CH₃ |
| | | F |
| | | Cl |
| | | H |
| Ethyl | F | CH₃ |
| | | F |
| | | Cl |
| | | H |
| | Cl | CH₃ |
| | | F |
| | | Cl |
| | | H |
| | CN | CH₃ |
| | | F |
| | | Cl |
| | | H |
| | CF₃ | CH₃ |
| | | F |
| | | Cl |
| | | H |
| | Methyl | CH₃ |
| | | F |
| | | Cl |
| | | H |
| | Ethyl | CH₃ |
| | | F |
| | | Cl |
| | | H |
| | iso-Propyl | CH₃ |
| | | F |
| | | Cl |
| | | H |
| | cyclo-Propyl | CH₃ |
| | | F |
| | | Cl |
| | | H |
| | Methoxy | CH₃ |
| | | F |
| | | Cl |
| | | H |

FIGURE 1B

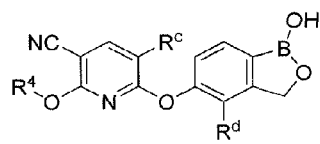

| $R^4$ | $R^c$ | $R^d$ | $R^4$ | $R^c$ | $R^d$ |
|---|---|---|---|---|---|
| Ethyl | Ethoxy | $CH_3$ | n-Propyl | Methoxy | $CH_3$ |
| | | F | | | F |
| | | Cl | | | Cl |
| | | H | | | H |
| | $OCF_3$ | $CH_3$ | | Ethoxy | $CH_3$ |
| | | F | | | F |
| | | Cl | | | Cl |
| | | H | | | H |
| n-Propyl | F | $CH_3$ | | $OCF_3$ | $CH_3$ |
| | | F | | | F |
| | | Cl | | | Cl |
| | | H | | | H |
| | Cl | $CH_3$ | iso-Propyl | F | $CH_3$ |
| | | F | | | F |
| | | Cl | | | Cl |
| | | H | | | H |
| | CN | $CH_3$ | | Cl | $CH_3$ |
| | | F | | | F |
| | | Cl | | | Cl |
| | | H | | | H |
| | $CF_3$ | $CH_3$ | | CN | $CH_3$ |
| | | F | | | F |
| | | Cl | | | Cl |
| | | H | | | H |
| | Methyl | $CH_3$ | | $CF_3$ | $CH_3$ |
| | | F | | | F |
| | | Cl | | | Cl |
| | | H | | | H |
| | Ethyl | $CH_3$ | | Methyl | $CH_3$ |
| | | F | | | F |
| | | Cl | | | Cl |
| | | H | | | H |
| | iso-Propyl | $CH_3$ | | Ethyl | $CH_3$ |
| | | F | | | F |
| | | Cl | | | Cl |
| | | H | | | H |
| | cyclo-Propyl | $CH_3$ | | iso-Propyl | $CH_3$ |
| | | F | | | F |
| | | Cl | | | Cl |
| | | H | | | H |

| R⁴ | Rᶜ | Rᵈ | R⁴ | Rᶜ | Rᵈ |
|---|---|---|---|---|---|
| iso-Propyl | cyclo-Propyl | CH₃ | n-Butyl | iso-Propyl | CH₃ |
| | | F | | | F |
| | | Cl | | | Cl |
| | | H | | | H |
| | Methoxy | CH₃ | | cyclo-Propyl | CH₃ |
| | | F | | | F |
| | | Cl | | | Cl |
| | | H | | | H |
| | Ethoxy | CH₃ | | Methoxy | CH₃ |
| | | F | | | F |
| | | Cl | | | Cl |
| | | H | | | H |
| | OCF₃ | CH₃ | | Ethoxy | CH₃ |
| | | F | | | F |
| | | Cl | | | Cl |
| | | H | | | H |
| n-Butyl | F | CH₃ | | OCF₃ | CH₃ |
| | | F | | | F |
| | | Cl | | | Cl |
| | | H | | | H |
| | Cl | CH₃ | iso-Butyl | F | CH₃ |
| | | F | | | F |
| | | Cl | | | Cl |
| | | H | | | H |
| | CN | CH₃ | | Cl | CH₃ |
| | | F | | | F |
| | | Cl | | | Cl |
| | | H | | | H |
| | CF₃ | CH₃ | | CN | CH₃ |
| | | F | | | F |
| | | Cl | | | Cl |
| | | H | | | H |
| | Methyl | CH₃ | | CF₃ | CH₃ |
| | | F | | | F |
| | | Cl | | | Cl |
| | | H | | | H |
| | Ethyl | CH₃ | | Methyl | CH₃ |
| | | F | | | F |
| | | Cl | | | Cl |
| | | H | | | H |

| R⁴ | Rᶜ | Rᵈ | R⁴ | Rᶜ | Rᵈ |
|---|---|---|---|---|---|
| iso-Butyl | Ethyl | CH₃ | sec-Butyl | Methyl | CH₃ |
| | | F | | | F |
| | | Cl | | | Cl |
| | | H | | | H |
| | iso-Propyl | CH₃ | | Ethyl | CH₃ |
| | | F | | | F |
| | | Cl | | | Cl |
| | | H | | | H |
| | cyclo-Propyl | CH₃ | | iso-Propyl | CH₃ |
| | | F | | | F |
| | | Cl | | | Cl |
| | | H | | | H |
| | Methoxy | CH₃ | | cyclo-Propyl | CH₃ |
| | | F | | | F |
| | | Cl | | | Cl |
| | | H | | | H |
| | Ethoxy | CH₃ | | Methoxy | CH₃ |
| | | F | | | F |
| | | Cl | | | Cl |
| | | H | | | H |
| | OCF₃ | CH₃ | | Ethoxy | CH₃ |
| | | F | | | F |
| | | Cl | | | Cl |
| | | H | | | H |
| sec-Butyl | F | CH₃ | | OCF₃ | CH₃ |
| | | F | | | F |
| | | Cl | | | Cl |
| | | H | | | H |
| | Cl | CH₃ | tert-Butyl | F | CH₃ |
| | | F | | | F |
| | | Cl | | | Cl |
| | | H | | | H |
| | CN | CH₃ | | Cl | CH₃ |
| | | F | | | F |
| | | Cl | | | Cl |
| | | H | | | H |
| | CF₃ | CH₃ | | CN | CH₃ |
| | | F | | | F |
| | | Cl | | | Cl |
| | | H | | | H |

| R⁴ | Rᶜ | Rᵈ |
|---|---|---|
| tert-Butyl | CF₃ | CH₃ |
| | | F |
| | | Cl |
| | | H |
| | Methyl | CH₃ |
| | | F |
| | | Cl |
| | | H |
| | Ethyl | CH₃ |
| | | F |
| | | Cl |
| | | H |
| | iso-Propyl | CH₃ |
| | | F |
| | | Cl |
| | | H |
| | cyclo-Propyl | CH₃ |
| | | F |
| | | Cl |
| | | H |
| | Methoxy | CH₃ |
| | | F |
| | | Cl |
| | | H |
| | Ethoxy | CH₃ |
| | | F |
| | | Cl |
| | | H |
| | OCF₃ | CH₃ |
| | | F |
| | | Cl |
| | | H |
| n-Pentyl | F | CH₃ |
| | | F |
| | | Cl |
| | | H |
| | Cl | CH₃ |
| | | F |
| | | Cl |
| | | H |

| R⁴ | Rᶜ | Rᵈ |
|---|---|---|
| n-Pentyl | CN | CH₃ |
| | | F |
| | | Cl |
| | | H |
| | CF₃ | CH₃ |
| | | F |
| | | Cl |
| | | H |
| | Methyl | CH₃ |
| | | F |
| | | Cl |
| | | H |
| | Ethyl | CH₃ |
| | | F |
| | | Cl |
| | | H |
| | iso-Propyl | CH₃ |
| | | F |
| | | Cl |
| | | H |
| | cyclo-Propyl | CH₃ |
| | | F |
| | | Cl |
| | | H |
| | Methoxy | CH₃ |
| | | F |
| | | Cl |
| | | H |
| | Ethoxy | CH₃ |
| | | F |
| | | Cl |
| | | H |
| | OCF₃ | CH₃ |
| | | F |
| | | Cl |
| | | H |
| iso-Pentyl | F | CH₃ |
| | | F |
| | | Cl |
| | | H |

| R⁴ | Rᶜ | Rᵈ | R⁴ | Rᶜ | Rᵈ |
|---|---|---|---|---|---|
| iso-Pentyl | Cl | CH₃ | neo-Pentyl | F | CH₃ |
| | | F | | | F |
| | | Cl | | | Cl |
| | | H | | | H |
| | CN | CH₃ | | Cl | CH₃ |
| | | F | | | F |
| | | Cl | | | Cl |
| | | H | | | H |
| | CF₃ | CH₃ | | CN | CH₃ |
| | | F | | | F |
| | | Cl | | | Cl |
| | | H | | | H |
| | Methyl | CH₃ | | CF₃ | CH₃ |
| | | F | | | F |
| | | Cl | | | Cl |
| | | H | | | H |
| | Ethyl | CH₃ | | Methyl | CH₃ |
| | | F | | | F |
| | | Cl | | | Cl |
| | | H | | | H |
| | iso-Propyl | CH₃ | | Ethyl | CH₃ |
| | | F | | | F |
| | | Cl | | | Cl |
| | | H | | | H |
| | cyclo-Propyl | CH₃ | | iso-Propyl | CH₃ |
| | | F | | | F |
| | | Cl | | | Cl |
| | | H | | | H |
| | Methoxy | CH₃ | | cyclo-Propyl | CH₃ |
| | | F | | | F |
| | | Cl | | | Cl |
| | | H | | | H |
| | Ethoxy | CH₃ | | Methoxy | CH₃ |
| | | F | | | F |
| | | Cl | | | Cl |
| | | H | | | H |
| | OCF₃ | CH₃ | | Ethoxy | CH₃ |
| | | F | | | F |
| | | Cl | | | Cl |
| | | H | | | H |

| R⁴ | Rᶜ | Rᵈ |
|---|---|---|
| neo-Pentyl | OCF₃ | CH₃ |
| | | F |
| | | Cl |
| | | H |
| sec-Pentyl | F | CH₃ |
| | | F |
| | | Cl |
| | | H |
| | Cl | CH₃ |
| | | F |
| | | Cl |
| | | H |
| | CN | CH₃ |
| | | F |
| | | Cl |
| | | H |
| | CF₃ | CH₃ |
| | | F |
| | | Cl |
| | | H |
| | Methyl | CH₃ |
| | | F |
| | | Cl |
| | | H |
| | Ethyl | CH₃ |
| | | F |
| | | Cl |
| | | H |
| | iso-Propyl | CH₃ |
| | | F |
| | | Cl |
| | | H |
| | cyclo-Propyl | CH₃ |
| | | F |
| | | Cl |
| | | H |
| | Methoxy | CH₃ |
| | | F |
| | | Cl |
| | | H |

| R⁴ | Rᶜ | Rᵈ |
|---|---|---|
| sec-Pentyl | Ethoxy | CH₃ |
| | | F |
| | | Cl |
| | | H |
| | OCF₃ | CH₃ |
| | | F |
| | | Cl |
| | | H |
| n-Hexyl | F | CH₃ |
| | | F |
| | | Cl |
| | | H |
| | Cl | CH₃ |
| | | F |
| | | Cl |
| | | H |
| | CN | CH₃ |
| | | F |
| | | Cl |
| | | H |
| | CF₃ | CH₃ |
| | | F |
| | | Cl |
| | | H |
| | Methyl | CH₃ |
| | | F |
| | | Cl |
| | | H |
| | Ethyl | CH₃ |
| | | F |
| | | Cl |
| | | H |
| | iso-Propyl | CH₃ |
| | | F |
| | | Cl |
| | | H |
| | cyclo-Propyl | CH₃ |
| | | F |
| | | Cl |
| | | H |

| R⁴ | Rᶜ | Rᵈ | R⁴ | Rᶜ | Rᵈ |
|---|---|---|---|---|---|
| n-Hexyl | Methoxy | CH₃ | iso-Hexyl | cyclo-Propyl | CH₃ |
| | | F | | | F |
| | | Cl | | | Cl |
| | | H | | | H |
| | Ethoxy | CH₃ | | Methoxy | CH₃ |
| | | F | | | F |
| | | Cl | | | Cl |
| | | H | | | H |
| | OCF₃ | CH₃ | | Ethoxy | CH₃ |
| | | F | | | F |
| | | Cl | | | Cl |
| | | H | | | H |
| iso-Hexyl | F | CH₃ | | OCF₃ | CH₃ |
| | | F | | | F |
| | | Cl | | | Cl |
| | | H | | | H |
| | Cl | CH₃ | sec-Hexyl | F | CH₃ |
| | | F | | | F |
| | | Cl | | | Cl |
| | | H | | | H |
| | CN | CH₃ | | Cl | CH₃ |
| | | F | | | F |
| | | Cl | | | Cl |
| | | H | | | H |
| | CF₃ | CH₃ | | CN | CH₃ |
| | | F | | | F |
| | | Cl | | | Cl |
| | | H | | | H |
| | Methyl | CH₃ | | CF₃ | CH₃ |
| | | F | | | F |
| | | Cl | | | Cl |
| | | H | | | H |
| | Ethyl | CH₃ | | Methyl | CH₃ |
| | | F | | | F |
| | | Cl | | | Cl |
| | | H | | | H |
| | iso-Propyl | CH₃ | | Ethyl | CH₃ |
| | | F | | | F |
| | | Cl | | | Cl |
| | | H | | | H |

| R⁴ | Rᶜ | Rᵈ | R⁴ | Rᶜ | Rᵈ |
|---|---|---|---|---|---|
| sec-Hexyl | iso-Propyl | CH₃ | tetrahydro-2H-pyran-4-yl | CF₃ | CH₃ |
| | | F | | | F |
| | | Cl | | | Cl |
| | | H | | | H |
| | cyclo-Propyl | CH₃ | | Methyl | CH₃ |
| | | F | | | F |
| | | Cl | | | Cl |
| | | H | | | H |
| | Methoxy | CH₃ | | Ethyl | CH₃ |
| | | F | | | F |
| | | Cl | | | Cl |
| | | H | | | H |
| | Ethoxy | CH₃ | | iso-Propyl | CH₃ |
| | | F | | | F |
| | | Cl | | | Cl |
| | | H | | | H |
| | OCF₃ | CH₃ | | cyclo-Propyl | CH₃ |
| | | F | | | F |
| | | Cl | | | Cl |
| | | H | | | H |
| tetrahydro-2H-pyran-4-yl | F | CH₃ | | Methoxy | CH₃ |
| | | F | | | F |
| | | Cl | | | Cl |
| | | H | | | H |
| | Cl | CH₃ | | Ethoxy | CH₃ |
| | | F | | | F |
| | | Cl | | | Cl |
| | | H | | | H |
| | CN | CH₃ | | OCF₃ | CH₃ |
| | | F | | | F |
| | | Cl | | | Cl |
| | | H | | | H |

| m5 | R³⁰ | Rᶜ | Rᵈ | m5 | R³⁰ | Rᶜ | Rᵈ |
|---|---|---|---|---|---|---|---|
| 2 | H | F | CH₃ | 2 | H | OCF₃ | CH₃ |
| | | | F | | | | F |
| | | | Cl | | | | Cl |
| | | | H | | | | H |
| | | Cl | CH₃ | | Methyl | F | CH₃ |
| | | | F | | | | F |
| | | | Cl | | | | Cl |
| | | | H | | | | H |
| | | CN | CH₃ | | | Cl | CH₃ |
| | | | F | | | | F |
| | | | Cl | | | | Cl |
| | | | H | | | | H |
| | | CF₃ | CH₃ | | | CN | CH₃ |
| | | | F | | | | F |
| | | | Cl | | | | Cl |
| | | | H | | | | H |
| | | Methyl | CH₃ | | | CF₃ | CH₃ |
| | | | F | | | | F |
| | | | Cl | | | | Cl |
| | | | H | | | | H |
| | | Ethyl | CH₃ | | | Methyl | CH₃ |
| | | | F | | | | F |
| | | | Cl | | | | Cl |
| | | | H | | | | H |
| | | iso-Propyl | CH₃ | | | Ethyl | CH₃ |
| | | | F | | | | F |
| | | | Cl | | | | Cl |
| | | | H | | | | H |
| | | cyclo-Propyl | CH₃ | | | iso-Propyl | CH₃ |
| | | | F | | | | F |
| | | | Cl | | | | Cl |
| | | | H | | | | H |
| | | Methoxy | CH₃ | | | cyclo-Propyl | CH₃ |
| | | | F | | | | F |
| | | | Cl | | | | Cl |
| | | | H | | | | H |
| | | Ethoxy | CH₃ | | | Methoxy | CH₃ |
| | | | F | | | | F |
| | | | Cl | | | | Cl |
| | | | H | | | | H |

| m5 | R³⁰ | Rᶜ | Rᵈ | m5 | R³⁰ | Rᶜ | Rᵈ |
|---|---|---|---|---|---|---|---|
| 2 | Methyl | Ethoxy | CH₃ | 2 | Ethyl | Methoxy | CH₃ |
| | | | F | | | | F |
| | | | Cl | | | | Cl |
| | | | H | | | | H |
| | | OCF₃ | CH₃ | | | Ethoxy | CH₃ |
| | | | F | | | | F |
| | | | Cl | | | | Cl |
| | | | H | | | | H |
| | Ethyl | F | CH₃ | | | OCF₃ | CH₃ |
| | | | F | | | | F |
| | | | Cl | | | | Cl |
| | | | H | | | | H |
| | | Cl | CH₃ | | n-Propyl | F | CH₃ |
| | | | F | | | | F |
| | | | Cl | | | | Cl |
| | | | H | | | | H |
| | | CN | CH₃ | | | Cl | CH₃ |
| | | | F | | | | F |
| | | | Cl | | | | Cl |
| | | | H | | | | H |
| | | CF₃ | CH₃ | | | CN | CH₃ |
| | | | F | | | | F |
| | | | Cl | | | | Cl |
| | | | H | | | | H |
| | | Methyl | CH₃ | | | CF₃ | CH₃ |
| | | | F | | | | F |
| | | | Cl | | | | Cl |
| | | | H | | | | H |
| | | Ethyl | CH₃ | | | Methyl | CH₃ |
| | | | F | | | | F |
| | | | Cl | | | | Cl |
| | | | H | | | | H |
| | | iso-Propyl | CH₃ | | | Ethyl | CH₃ |
| | | | F | | | | F |
| | | | Cl | | | | Cl |
| | | | H | | | | H |
| | | cyclo-Propyl | CH₃ | | | iso-Propyl | CH₃ |
| | | | F | | | | F |
| | | | Cl | | | | Cl |
| | | | H | | | | H |

| m5 | R³⁰ | Rᶜ | Rᵈ |
|---|---|---|---|
| 2 | | cyclo-Propyl | CH₃ |
| | | | F |
| | | | Cl |
| | | | H |
| | | Methoxy | CH₃ |
| | | | F |
| | | | Cl |
| | | | H |
| | | Ethoxy | CH₃ |
| | | | F |
| | | | Cl |
| | | | H |
| | | OCF₃ | CH₃ |
| | | | F |
| | | | Cl |
| | | | H |
| | iso-Propyl | F | CH₃ |
| | | | F |
| | | | Cl |
| | | | H |
| | | Cl | CH₃ |
| | | | F |
| | | | Cl |
| | | | H |
| | | CN | CH₃ |
| | | | F |
| | | | Cl |
| | | | H |
| | | CF₃ | CH₃ |
| | | | F |
| | | | Cl |
| | | | H |
| | | Methyl | CH₃ |
| | | | F |
| | | | Cl |
| | | | H |
| | | Ethyl | CH₃ |
| | | | F |
| | | | Cl |
| | | | H |

| m5 | R³⁰ | Rᶜ | Rᵈ |
|---|---|---|---|
| 2 | | iso-Propyl | CH₃ |
| | | | F |
| | | | Cl |
| | | | H |
| | | cyclo-Propyl | CH₃ |
| | | | F |
| | | | Cl |
| | | | H |
| | | Methoxy | CH₃ |
| | | | F |
| | | | Cl |
| | | | H |
| | | Ethoxy | CH₃ |
| | | | F |
| | | | Cl |
| | | | H |
| | | OCF₃ | CH₃ |
| | | | F |
| | | | Cl |
| | | | H |
| | cyclo-Propyl | F | CH₃ |
| | | | F |
| | | | Cl |
| | | | H |
| | | Cl | CH₃ |
| | | | F |
| | | | Cl |
| | | | H |
| | | CN | CH₃ |
| | | | F |
| | | | Cl |
| | | | H |
| | | CF₃ | CH₃ |
| | | | F |
| | | | Cl |
| | | | H |
| | | Methyl | CH₃ |
| | | | F |
| | | | Cl |
| | | | H |

FIGURE 2D

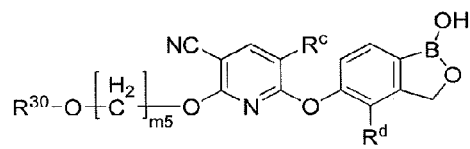

| m5 | $R^{30}$ | $R^c$ | $R^d$ |
|---|---|---|---|
| 2 | cyclo-Propyl | Ethyl | $CH_3$ |
| | | | F |
| | | | Cl |
| | | | H |
| | | iso-Propyl | $CH_3$ |
| | | | F |
| | | | Cl |
| | | | H |
| | | cyclo-Propyl | $CH_3$ |
| | | | F |
| | | | Cl |
| | | | H |
| | | Methoxy | $CH_3$ |
| | | | F |
| | | | Cl |
| | | | H |
| | | Ethoxy | $CH_3$ |
| | | | F |
| | | | Cl |
| | | | H |
| | | $OCF_3$ | $CH_3$ |
| | | | F |
| | | | Cl |
| | | | H |
| | $CF_3$ | F | $CH_3$ |
| | | | F |
| | | | Cl |
| | | | H |
| | | Cl | $CH_3$ |
| | | | F |
| | | | Cl |
| | | | H |
| | | CN | $CH_3$ |
| | | | F |
| | | | Cl |
| | | | H |
| | | $CF_3$ | $CH_3$ |
| | | | F |
| | | | Cl |
| | | | H |

| m5 | $R^{30}$ | $R^c$ | $R^d$ |
|---|---|---|---|
| 2 | $CF_3$ | Methyl | $CH_3$ |
| | | | F |
| | | | Cl |
| | | | H |
| | | Ethyl | $CH_3$ |
| | | | F |
| | | | Cl |
| | | | H |
| | | iso-Propyl | $CH_3$ |
| | | | F |
| | | | Cl |
| | | | H |
| | | cyclo-Propyl | $CH_3$ |
| | | | F |
| | | | Cl |
| | | | H |
| | | Methoxy | $CH_3$ |
| | | | F |
| | | | Cl |
| | | | H |
| | | Ethoxy | $CH_3$ |
| | | | F |
| | | | Cl |
| | | | H |
| | | $OCF_3$ | $CH_3$ |
| | | | F |
| | | | Cl |
| | | | H |
| 3 | H | F | $CH_3$ |
| | | | F |
| | | | Cl |
| | | | H |
| | | Cl | $CH_3$ |
| | | | F |
| | | | Cl |
| | | | H |
| | | CN | $CH_3$ |
| | | | F |
| | | | Cl |
| | | | H |

| m5 | R³⁰ | Rᶜ | Rᵈ | m5 | R³⁰ | Rᶜ | Rᵈ |
|---|---|---|---|---|---|---|---|
| 3 | H | CF₃ | CH₃ | 3 | Methyl | CN | CH₃ |
| | | | F | | | | F |
| | | | Cl | | | | Cl |
| | | | H | | | | H |
| | | Methyl | CH₃ | | | CF₃ | CH₃ |
| | | | F | | | | F |
| | | | Cl | | | | Cl |
| | | | H | | | | H |
| | | Ethyl | CH₃ | | | Methyl | CH₃ |
| | | | F | | | | F |
| | | | Cl | | | | Cl |
| | | | H | | | | H |
| | | iso-Propyl | CH₃ | | | Ethyl | CH₃ |
| | | | F | | | | F |
| | | | Cl | | | | Cl |
| | | | H | | | | H |
| | | cyclo-Propyl | CH₃ | | | iso-Propyl | CH₃ |
| | | | F | | | | F |
| | | | Cl | | | | Cl |
| | | | H | | | | H |
| | | Methoxy | CH₃ | | | cyclo-Propyl | CH₃ |
| | | | F | | | | F |
| | | | Cl | | | | Cl |
| | | | H | | | | H |
| | | Ethoxy | CH₃ | | | Methoxy | CH₃ |
| | | | F | | | | F |
| | | | Cl | | | | Cl |
| | | | H | | | | H |
| | | OCF₃ | CH₃ | | | Ethoxy | CH₃ |
| | | | F | | | | F |
| | | | Cl | | | | Cl |
| | | | H | | | | H |
| | Methyl | F | CH₃ | | | OCF₃ | CH₃ |
| | | | F | | | | F |
| | | | Cl | | | | Cl |
| | | | H | | | | H |
| | | Cl | CH₃ | | Ethyl | F | CH₃ |
| | | | F | | | | F |
| | | | Cl | | | | Cl |
| | | | H | | | | H |

| m5 | R³⁰ | Rᶜ | Rᵈ | m5 | R³⁰ | Rᶜ | Rᵈ |
|---|---|---|---|---|---|---|---|
| 3 | Ethyl | Cl | CH₃ | 3 | n-Propyl | F | CH₃ |
| | | | F | | | | F |
| | | | Cl | | | | Cl |
| | | | H | | | | H |
| | | CN | CH₃ | | | Cl | CH₃ |
| | | | F | | | | F |
| | | | Cl | | | | Cl |
| | | | H | | | | H |
| | | CF₃ | CH₃ | | | CN | CH₃ |
| | | | F | | | | F |
| | | | Cl | | | | Cl |
| | | | H | | | | H |
| | | Methyl | CH₃ | | | CF₃ | CH₃ |
| | | | F | | | | F |
| | | | Cl | | | | Cl |
| | | | H | | | | H |
| | | Ethyl | CH₃ | | | Methyl | CH₃ |
| | | | F | | | | F |
| | | | Cl | | | | Cl |
| | | | H | | | | H |
| | | iso-Propyl | CH₃ | | | Ethyl | CH₃ |
| | | | F | | | | F |
| | | | Cl | | | | Cl |
| | | | H | | | | H |
| | | cyclo-Propyl | CH₃ | | | iso-Propyl | CH₃ |
| | | | F | | | | F |
| | | | Cl | | | | Cl |
| | | | H | | | | H |
| | | Methoxy | CH₃ | | | cyclo-Propyl | CH₃ |
| | | | F | | | | F |
| | | | Cl | | | | Cl |
| | | | H | | | | H |
| | | Ethoxy | CH₃ | | | Methoxy | CH₃ |
| | | | F | | | | F |
| | | | Cl | | | | Cl |
| | | | H | | | | H |
| | | OCF₃ | CH₃ | | | Ethoxy | CH₃ |
| | | | F | | | | F |
| | | | Cl | | | | Cl |
| | | | H | | | | H |

| m5 | R³⁰ | Rᶜ | Rᵈ | m5 | R³⁰ | Rᶜ | Rᵈ |
|---|---|---|---|---|---|---|---|
| 3 | n-Propyl | OCF₃ | CH₃ | 3 | iso-Propyl | Ethoxy | CH₃ |
|   |   |   | F |   |   |   | F |
|   |   |   | Cl |   |   |   | Cl |
|   |   |   | H |   |   |   | H |
|   | iso-Propyl | F | CH₃ |   |   | OCF₃ | CH₃ |
|   |   |   | F |   |   |   | F |
|   |   |   | Cl |   |   |   | Cl |
|   |   |   | H |   |   |   | H |
|   |   | Cl | CH₃ |   | cyclo-Propyl | F | CH₃ |
|   |   |   | F |   |   |   | F |
|   |   |   | Cl |   |   |   | Cl |
|   |   |   | H |   |   |   | H |
|   |   | CN | CH₃ |   |   | Cl | CH₃ |
|   |   |   | F |   |   |   | F |
|   |   |   | Cl |   |   |   | Cl |
|   |   |   | H |   |   |   | H |
|   |   | CF₃ | CH₃ |   |   | CN | CH₃ |
|   |   |   | F |   |   |   | F |
|   |   |   | Cl |   |   |   | Cl |
|   |   |   | H |   |   |   | H |
|   |   | Methyl | CH₃ |   |   | CF₃ | CH₃ |
|   |   |   | F |   |   |   | F |
|   |   |   | Cl |   |   |   | Cl |
|   |   |   | H |   |   |   | H |
|   |   | Ethyl | CH₃ |   |   | Methyl | CH₃ |
|   |   |   | F |   |   |   | F |
|   |   |   | Cl |   |   |   | Cl |
|   |   |   | H |   |   |   | H |
|   |   | iso-Propyl | CH₃ |   |   | Ethyl | CH₃ |
|   |   |   | F |   |   |   | F |
|   |   |   | Cl |   |   |   | Cl |
|   |   |   | H |   |   |   | H |
|   |   | cyclo-Propyl | CH₃ |   |   | iso-Propyl | CH₃ |
|   |   |   | F |   |   |   | F |
|   |   |   | Cl |   |   |   | Cl |
|   |   |   | H |   |   |   | H |
|   |   | Methoxy | CH₃ |   |   | cyclo-Propyl | CH₃ |
|   |   |   | F |   |   |   | F |
|   |   |   | Cl |   |   |   | Cl |
|   |   |   | H |   |   |   | H |

| 3 | cyclo-Propyl | Methoxy | CH₃ |
|---|---|---|---|
|   |   |   | F |
|   |   |   | Cl |
|   |   |   | H |
|   |   | Ethoxy | CH₃ |
|   |   |   | F |
|   |   |   | Cl |
|   |   |   | H |
|   |   | OCF₃ | CH₃ |
|   |   |   | F |
|   |   |   | Cl |
|   |   |   | H |

| m1 | R⁴ᵈ | Rᶜ | Rᵈ |
|---|---|---|---|
| 1 | Methyl | F | CH₃ |
| | | | F |
| | | | Cl |
| | | | H |
| | | Cl | CH₃ |
| | | | F |
| | | | Cl |
| | | | H |
| | | CN | CH₃ |
| | | | F |
| | | | Cl |
| | | | H |
| | | CF₃ | CH₃ |
| | | | F |
| | | | Cl |
| | | | H |
| | | Methyl | CH₃ |
| | | | F |
| | | | Cl |
| | | | H |
| | | Ethyl | CH₃ |
| | | | F |
| | | | Cl |
| | | | H |
| | | iso-Propyl | CH₃ |
| | | | F |
| | | | Cl |
| | | | H |
| | | cyclo-Propyl | CH₃ |
| | | | F |
| | | | Cl |
| | | | H |
| | | Methoxy | CH₃ |
| | | | F |
| | | | Cl |
| | | | H |
| | | Ethoxy | CH₃ |
| | | | F |
| | | | Cl |
| | | | H |

| m1 | R⁴ᵈ | Rᶜ | Rᵈ |
|---|---|---|---|
| 1 | Methyl | OCF₃ | CH₃ |
| | | | F |
| | | | Cl |
| | | | H |
| | Ethyl | F | CH₃ |
| | | | F |
| | | | Cl |
| | | | H |
| | | Cl | CH₃ |
| | | | F |
| | | | Cl |
| | | | H |
| | | CN | CH₃ |
| | | | F |
| | | | Cl |
| | | | H |
| | | CF₃ | CH₃ |
| | | | F |
| | | | Cl |
| | | | H |
| | | Methyl | CH₃ |
| | | | F |
| | | | Cl |
| | | | H |
| | | Ethyl | CH₃ |
| | | | F |
| | | | Cl |
| | | | H |
| | | iso-Propyl | CH₃ |
| | | | F |
| | | | Cl |
| | | | H |
| | | cyclo-Propyl | CH₃ |
| | | | F |
| | | | Cl |
| | | | H |
| | | Methoxy | CH₃ |
| | | | F |
| | | | Cl |
| | | | H |

| m1 | R⁴ᵈ | Rᶜ | Rᵈ |
|---|---|---|---|
| 1 | Ethyl | Ethoxy | CH₃ |
| | | | F |
| | | | Cl |
| | | | H |
| | | OCF₃ | CH₃ |
| | | | F |
| | | | Cl |
| | | | H |
| | n-Propyl | F | CH₃ |
| | | | F |
| | | | Cl |
| | | | H |
| | | Cl | CH₃ |
| | | | F |
| | | | Cl |
| | | | H |
| | | CN | CH₃ |
| | | | F |
| | | | Cl |
| | | | H |
| | | CF₃ | CH₃ |
| | | | F |
| | | | Cl |
| | | | H |
| | | Methyl | CH₃ |
| | | | F |
| | | | Cl |
| | | | H |
| | | Ethyl | CH₃ |
| | | | F |
| | | | Cl |
| | | | H |
| | | iso-Propyl | CH₃ |
| | | | F |
| | | | Cl |
| | | | H |
| | | cyclo-Propyl | CH₃ |
| | | | F |
| | | | Cl |
| | | | H |

| m1 | R⁴ᵈ | Rᶜ | Rᵈ |
|---|---|---|---|
| 1 | n-Propyl | Methoxy | CH₃ |
| | | | F |
| | | | Cl |
| | | | H |
| | | Ethoxy | CH₃ |
| | | | F |
| | | | Cl |
| | | | H |
| | | OCF₃ | CH₃ |
| | | | F |
| | | | Cl |
| | | | H |
| | iso-Propyl | F | CH₃ |
| | | | F |
| | | | Cl |
| | | | H |
| | | Cl | CH₃ |
| | | | F |
| | | | Cl |
| | | | H |
| | | CN | CH₃ |
| | | | F |
| | | | Cl |
| | | | H |
| | | CF₃ | CH₃ |
| | | | F |
| | | | Cl |
| | | | H |
| | | Methyl | CH₃ |
| | | | F |
| | | | Cl |
| | | | H |
| | | Ethyl | CH₃ |
| | | | F |
| | | | Cl |
| | | | H |
| | | iso-Propyl | CH₃ |
| | | | F |
| | | | Cl |
| | | | H |

| m1 | R^{4d} | R^c | R^d |
|---|---|---|---|
| 1 | iso-Propyl | cyclo-Propyl | CH₃ |
| | | | F |
| | | | Cl |
| | | | H |
| | | Methoxy | CH₃ |
| | | | F |
| | | | Cl |
| | | | H |
| | | Ethoxy | CH₃ |
| | | | F |
| | | | Cl |
| | | | H |
| | | OCF₃ | CH₃ |
| | | | F |
| | | | Cl |
| | | | H |
| | cyclo-Propyl | F | CH₃ |
| | | | F |
| | | | Cl |
| | | | H |
| | | Cl | CH₃ |
| | | | F |
| | | | Cl |
| | | | H |
| | | CN | CH₃ |
| | | | F |
| | | | Cl |
| | | | H |
| | | CF₃ | CH₃ |
| | | | F |
| | | | Cl |
| | | | H |
| | | Methyl | CH₃ |
| | | | F |
| | | | Cl |
| | | | H |
| | | Ethyl | CH₃ |
| | | | F |
| | | | Cl |
| | | | H |

| m1 | R^{4d} | R^c | R^d |
|---|---|---|---|
| 1 | cyclo-Propyl | iso-Propyl | CH₃ |
| | | | F |
| | | | Cl |
| | | | H |
| | | cyclo-Propyl | CH₃ |
| | | | F |
| | | | Cl |
| | | | H |
| | | Methoxy | CH₃ |
| | | | F |
| | | | Cl |
| | | | H |
| | | Ethoxy | CH₃ |
| | | | F |
| | | | Cl |
| | | | H |
| | | OCF₃ | CH₃ |
| | | | F |
| | | | Cl |
| | | | H |
| 2 | Methyl | F | CH₃ |
| | | | F |
| | | | Cl |
| | | | H |
| | | Cl | CH₃ |
| | | | F |
| | | | Cl |
| | | | H |
| | | CN | CH₃ |
| | | | F |
| | | | Cl |
| | | | H |
| | | CF₃ | CH₃ |
| | | | F |
| | | | Cl |
| | | | H |
| | | Methyl | CH₃ |
| | | | F |
| | | | Cl |
| | | | H |

| m1 | R⁴ᵈ | Rᶜ | Rᵈ |
|---|---|---|---|
| 2 | Methyl | Ethyl | CH₃ |
| | | | F |
| | | | Cl |
| | | | H |
| | | iso-Propyl | CH₃ |
| | | | F |
| | | | Cl |
| | | | H |
| | | cyclo-Propyl | CH₃ |
| | | | F |
| | | | Cl |
| | | | H |
| | | Methoxy | CH₃ |
| | | | F |
| | | | Cl |
| | | | H |
| | | Ethoxy | CH₃ |
| | | | F |
| | | | Cl |
| | | | H |
| | | OCF₃ | CH₃ |
| | | | F |
| | | | Cl |
| | | | H |
| | Ethyl | F | CH₃ |
| | | | F |
| | | | Cl |
| | | | H |
| | | Cl | CH₃ |
| | | | F |
| | | | Cl |
| | | | H |
| | | CN | CH₃ |
| | | | F |
| | | | Cl |
| | | | H |
| | | CF₃ | CH₃ |
| | | | F |
| | | | Cl |
| | | | H |

| m1 | R⁴ᵈ | Rᶜ | Rᵈ |
|---|---|---|---|
| 2 | Ethyl | Methyl | CH₃ |
| | | | F |
| | | | Cl |
| | | | H |
| | | Ethyl | CH₃ |
| | | | F |
| | | | Cl |
| | | | H |
| | | iso-Propyl | CH₃ |
| | | | F |
| | | | Cl |
| | | | H |
| | | cyclo-Propyl | CH₃ |
| | | | F |
| | | | Cl |
| | | | H |
| | | Methoxy | CH₃ |
| | | | F |
| | | | Cl |
| | | | H |
| | | Ethoxy | CH₃ |
| | | | F |
| | | | Cl |
| | | | H |
| | | OCF₃ | CH₃ |
| | | | F |
| | | | Cl |
| | | | H |
| | n-Propyl | F | CH₃ |
| | | | F |
| | | | Cl |
| | | | H |
| | | Cl | CH₃ |
| | | | F |
| | | | Cl |
| | | | H |
| | | CN | CH₃ |
| | | | F |
| | | | Cl |
| | | | H |

| m1 | R4d | Rc | Rd |
|---|---|---|---|
| 2 | n-Propyl | CF3 | CH3 |
| | | | F |
| | | | Cl |
| | | | H |
| | | Methyl | CH3 |
| | | | F |
| | | | Cl |
| | | | H |
| | | Ethyl | CH3 |
| | | | F |
| | | | Cl |
| | | | H |
| | | iso-Propyl | CH3 |
| | | | F |
| | | | Cl |
| | | | H |
| | | cyclo-Propyl | CH3 |
| | | | F |
| | | | Cl |
| | | | H |
| | | Methoxy | CH3 |
| | | | F |
| | | | Cl |
| | | | H |
| | | Ethoxy | CH3 |
| | | | F |
| | | | Cl |
| | | | H |
| | | OCF3 | CH3 |
| | | | F |
| | | | Cl |
| | | | H |
| | iso-Propyl | F | CH3 |
| | | | F |
| | | | Cl |
| | | | H |
| | | Cl | CH3 |
| | | | F |
| | | | Cl |
| | | | H |

| m1 | R4d | Rc | Rd |
|---|---|---|---|
| 2 | iso-Propy | CN | CH3 |
| | | | F |
| | | | Cl |
| | | | H |
| | | CF3 | CH3 |
| | | | F |
| | | | Cl |
| | | | H |
| | | Methyl | CH3 |
| | | | F |
| | | | Cl |
| | | | H |
| | | Ethyl | CH3 |
| | | | F |
| | | | Cl |
| | | | H |
| | | iso-Propyl | CH3 |
| | | | F |
| | | | Cl |
| | | | H |
| | | cyclo-Propyl | CH3 |
| | | | F |
| | | | Cl |
| | | | H |
| | | Methoxy | CH3 |
| | | | F |
| | | | Cl |
| | | | H |
| | | Ethoxy | CH3 |
| | | | F |
| | | | Cl |
| | | | H |
| | | OCF3 | CH3 |
| | | | F |
| | | | Cl |
| | | | H |
| | cyclo-Propyl | F | CH3 |
| | | | F |
| | | | Cl |
| | | | H |

FIGURE 3F

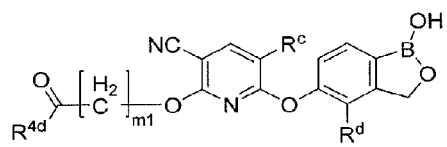

| m1 | R^{4d} | R^c | R^d |
|---|---|---|---|
| 2 | cyclo-Propyl | Cl | CH$_3$ |
| | | | F |
| | | | Cl |
| | | | H |
| | | CN | CH$_3$ |
| | | | F |
| | | | Cl |
| | | | H |
| | | CF$_3$ | CH$_3$ |
| | | | F |
| | | | Cl |
| | | | H |
| | | Methyl | CH$_3$ |
| | | | F |
| | | | Cl |
| | | | H |
| | | Ethyl | CH$_3$ |
| | | | F |
| | | | Cl |
| | | | H |
| | | iso-Propyl | CH$_3$ |
| | | | F |
| | | | Cl |
| | | | H |
| | | cyclo-Propyl | CH$_3$ |
| | | | F |
| | | | Cl |
| | | | H |
| | | Methoxy | CH$_3$ |
| | | | F |
| | | | Cl |
| | | | H |
| | | Ethoxy | CH$_3$ |
| | | | F |
| | | | Cl |
| | | | H |
| | | OCF$_3$ | CH$_3$ |
| | | | F |
| | | | Cl |
| | | | H |

| m1 | R^{4d} | R^c | R^d |
|---|---|---|---|
| 3 | Methyl | F | CH$_3$ |
| | | | F |
| | | | Cl |
| | | | H |
| | | Cl | CH$_3$ |
| | | | F |
| | | | Cl |
| | | | H |
| | | CN | CH$_3$ |
| | | | F |
| | | | Cl |
| | | | H |
| | | CF$_3$ | CH$_3$ |
| | | | F |
| | | | Cl |
| | | | H |
| | | Methyl | CH$_3$ |
| | | | F |
| | | | Cl |
| | | | H |
| | | Ethyl | CH$_3$ |
| | | | F |
| | | | Cl |
| | | | H |
| | | iso-Propyl | CH$_3$ |
| | | | F |
| | | | Cl |
| | | | H |
| | | cyclo-Propyl | CH$_3$ |
| | | | F |
| | | | Cl |
| | | | H |
| | | Methoxy | CH$_3$ |
| | | | F |
| | | | Cl |
| | | | H |
| | | Ethoxy | CH$_3$ |
| | | | F |
| | | | Cl |
| | | | H |

FIGURE 3G

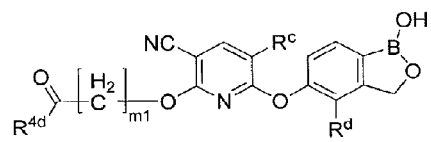

| m1 | $R^{4d}$ | $R^c$ | $R^d$ |
|---|---|---|---|
| 3 | Methyl | OCF$_3$ | CH$_3$ |
| | | | F |
| | | | Cl |
| | | | H |
| | Ethyl | F | CH$_3$ |
| | | | F |
| | | | Cl |
| | | | H |
| | | Cl | CH$_3$ |
| | | | F |
| | | | Cl |
| | | | H |
| | | CN | CH$_3$ |
| | | | F |
| | | | Cl |
| | | | H |
| | | CF$_3$ | CH$_3$ |
| | | | F |
| | | | Cl |
| | | | H |
| | | Methyl | CH$_3$ |
| | | | F |
| | | | Cl |
| | | | H |
| | | Ethyl | CH$_3$ |
| | | | F |
| | | | Cl |
| | | | H |
| | | iso-Propyl | CH$_3$ |
| | | | F |
| | | | Cl |
| | | | H |
| | | cyclo-Propyl | CH$_3$ |
| | | | F |
| | | | Cl |
| | | | H |
| | | Methoxy | CH$_3$ |
| | | | F |
| | | | Cl |
| | | | H |

| m1 | $R^{4d}$ | $R^c$ | $R^d$ |
|---|---|---|---|
| 3 | Ethyl | Ethoxy | CH$_3$ |
| | | | F |
| | | | Cl |
| | | | H |
| | | OCF$_3$ | CH$_3$ |
| | | | F |
| | | | Cl |
| | | | H |
| | n-Propyl | F | CH$_3$ |
| | | | F |
| | | | Cl |
| | | | H |
| | | Cl | CH$_3$ |
| | | | F |
| | | | Cl |
| | | | H |
| | | CN | CH$_3$ |
| | | | F |
| | | | Cl |
| | | | H |
| | | CF$_3$ | CH$_3$ |
| | | | F |
| | | | Cl |
| | | | H |
| | | Methyl | CH$_3$ |
| | | | F |
| | | | Cl |
| | | | H |
| | | Ethyl | CH$_3$ |
| | | | F |
| | | | Cl |
| | | | H |
| | | iso-Propyl | CH$_3$ |
| | | | F |
| | | | Cl |
| | | | H |
| | | cyclo-Propyl | CH$_3$ |
| | | | F |
| | | | Cl |
| | | | H |

| m1 | R^{4d} | R^c | R^d |
|---|---|---|---|
| 3 | n-Propyl | Methoxy | CH₃ |
|   |   |   | F |
|   |   |   | Cl |
|   |   |   | H |
|   |   | Ethoxy | CH₃ |
|   |   |   | F |
|   |   |   | Cl |
|   |   |   | H |
|   |   | OCF₃ | CH₃ |
|   |   |   | F |
|   |   |   | Cl |
|   |   |   | H |
|   | iso-Propyl | F | CH₃ |
|   |   |   | F |
|   |   |   | Cl |
|   |   |   | H |
|   |   | Cl | CH₃ |
|   |   |   | F |
|   |   |   | Cl |
|   |   |   | H |
|   |   | CN | CH₃ |
|   |   |   | F |
|   |   |   | Cl |
|   |   |   | H |
|   |   | CF₃ | CH₃ |
|   |   |   | F |
|   |   |   | Cl |
|   |   |   | H |
|   |   | Methyl | CH₃ |
|   |   |   | F |
|   |   |   | Cl |
|   |   |   | H |
|   |   | Ethyl | CH₃ |
|   |   |   | F |
|   |   |   | Cl |
|   |   |   | H |
|   |   | iso-Propyl | CH₃ |
|   |   |   | F |
|   |   |   | Cl |
|   |   |   | H |

| m1 | R^{4d} | R^c | R^d |
|---|---|---|---|
| 3 | iso-Propyl | cyclo-Propyl | CH₃ |
|   |   |   | F |
|   |   |   | Cl |
|   |   |   | H |
|   |   | Methoxy | CH₃ |
|   |   |   | F |
|   |   |   | Cl |
|   |   |   | H |
|   |   | Ethoxy | CH₃ |
|   |   |   | F |
|   |   |   | Cl |
|   |   |   | H |
|   |   | OCF₃ | CH₃ |
|   |   |   | F |
|   |   |   | Cl |
|   |   |   | H |
|   | cyclo-Propyl | F | CH₃ |
|   |   |   | F |
|   |   |   | Cl |
|   |   |   | H |
|   |   | Cl | CH₃ |
|   |   |   | F |
|   |   |   | Cl |
|   |   |   | H |
|   |   | CN | CH₃ |
|   |   |   | F |
|   |   |   | Cl |
|   |   |   | H |
|   |   | CF₃ | CH₃ |
|   |   |   | F |
|   |   |   | Cl |
|   |   |   | H |
|   |   | Methyl | CH₃ |
|   |   |   | F |
|   |   |   | Cl |
|   |   |   | H |
|   |   | Ethyl | CH₃ |
|   |   |   | F |
|   |   |   | Cl |
|   |   |   | H |

| m1 | R^{4d} | R^c | R^d |
|---|---|---|---|
| 3 | cyclo-Propyl | iso-Propyl | CH_3 |
| | | | F |
| | | | Cl |
| | | | H |
| | | cyclo-Propyl | CH_3 |
| | | | F |
| | | | Cl |
| | | | H |
| | | Methoxy | CH_3 |
| | | | F |
| | | | Cl |
| | | | H |
| | | Ethoxy | CH_3 |
| | | | F |
| | | | Cl |
| | | | H |
| | | OCF_3 | CH_3 |
| | | | F |
| | | | Cl |
| | | | H |
| 4 | Methyl | F | CH_3 |
| | | | F |
| | | | Cl |
| | | | H |
| | | Cl | CH_3 |
| | | | F |
| | | | Cl |
| | | | H |
| | | CN | CH_3 |
| | | | F |
| | | | Cl |
| | | | H |
| | | CF_3 | CH_3 |
| | | | F |
| | | | Cl |
| | | | H |
| | | Methyl | CH_3 |
| | | | F |
| | | | Cl |
| | | | H |

| m1 | R^{4d} | R^c | R^d |
|---|---|---|---|
| 4 | Methyl | Ethyl | CH_3 |
| | | | F |
| | | | Cl |
| | | | H |
| | | iso-Propyl | CH_3 |
| | | | F |
| | | | Cl |
| | | | H |
| | | cyclo-Propyl | CH_3 |
| | | | F |
| | | | Cl |
| | | | H |
| | | Methoxy | CH_3 |
| | | | F |
| | | | Cl |
| | | | H |
| | | Ethoxy | CH_3 |
| | | | F |
| | | | Cl |
| | | | H |
| | | OCF_3 | CH_3 |
| | | | F |
| | | | Cl |
| | | | H |
| | Ethyl | F | CH_3 |
| | | | F |
| | | | Cl |
| | | | H |
| | | Cl | CH_3 |
| | | | F |
| | | | Cl |
| | | | H |
| | | CN | CH_3 |
| | | | F |
| | | | Cl |
| | | | H |
| | | CF_3 | CH_3 |
| | | | F |
| | | | Cl |
| | | | H |

| m1 | R⁴ᵈ | Rᶜ | Rᵈ |
|---|---|---|---|
| 4 | Ethyl | Methyl | CH₃ |
| | | | F |
| | | | Cl |
| | | | H |
| | | Ethyl | CH₃ |
| | | | F |
| | | | Cl |
| | | | H |
| | | iso-Propyl | CH₃ |
| | | | F |
| | | | Cl |
| | | | H |
| | | cyclo-Propyl | CH₃ |
| | | | F |
| | | | Cl |
| | | | H |
| | | Methoxy | CH₃ |
| | | | F |
| | | | Cl |
| | | | H |
| | | Ethoxy | CH₃ |
| | | | F |
| | | | Cl |
| | | | H |
| | | OCF₃ | CH₃ |
| | | | F |
| | | | Cl |
| | | | H |
| | n-Propyl | F | CH₃ |
| | | | F |
| | | | Cl |
| | | | H |
| | | Cl | CH₃ |
| | | | F |
| | | | Cl |
| | | | H |
| | | CN | CH₃ |
| | | | F |
| | | | Cl |
| | | | H |

| m1 | R⁴ᵈ | Rᶜ | Rᵈ |
|---|---|---|---|
| 4 | n-Propyl | CF₃ | CH₃ |
| | | | F |
| | | | Cl |
| | | | H |
| | | Methyl | CH₃ |
| | | | F |
| | | | Cl |
| | | | H |
| | | Ethyl | CH₃ |
| | | | F |
| | | | Cl |
| | | | H |
| | | iso-Propyl | CH₃ |
| | | | F |
| | | | Cl |
| | | | H |
| | | cyclo-Propyl | CH₃ |
| | | | F |
| | | | Cl |
| | | | H |
| | | Methoxy | CH₃ |
| | | | F |
| | | | Cl |
| | | | H |
| | | Ethoxy | CH₃ |
| | | | F |
| | | | Cl |
| | | | H |
| | | OCF₃ | CH₃ |
| | | | F |
| | | | Cl |
| | | | H |
| | iso-Propyl | F | CH₃ |
| | | | F |
| | | | Cl |
| | | | H |
| | | Cl | CH₃ |
| | | | F |
| | | | Cl |
| | | | H |

| m1 | R^{4d} | R^c | R^d |
|----|--------|-----|-----|
| 4 | iso-Propyl | CN | CH3 |
| | | | F |
| | | | Cl |
| | | | H |
| | | CF3 | CH3 |
| | | | F |
| | | | Cl |
| | | | H |
| | | Methyl | CH3 |
| | | | F |
| | | | Cl |
| | | | H |
| | | Ethyl | CH3 |
| | | | F |
| | | | Cl |
| | | | H |
| | | iso-Propyl | CH3 |
| | | | F |
| | | | Cl |
| | | | H |
| | | cyclo-Propyl | CH3 |
| | | | F |
| | | | Cl |
| | | | H |
| | | Methoxy | CH3 |
| | | | F |
| | | | Cl |
| | | | H |
| | | Ethoxy | CH3 |
| | | | F |
| | | | Cl |
| | | | H |
| | | OCF3 | CH3 |
| | | | F |
| | | | Cl |
| | | | H |
| | cyclo-Propyl | F | CH3 |
| | | | F |
| | | | Cl |
| | | | H |

| m1 | R^{4d} | R^c | R^d |
|----|--------|-----|-----|
| 4 | cyclo-Propyl | Cl | CH3 |
| | | | F |
| | | | Cl |
| | | | H |
| | | CN | CH3 |
| | | | F |
| | | | Cl |
| | | | H |
| | | CF3 | CH3 |
| | | | F |
| | | | Cl |
| | | | H |
| | | Methyl | CH3 |
| | | | F |
| | | | Cl |
| | | | H |
| | | Ethyl | CH3 |
| | | | F |
| | | | Cl |
| | | | H |
| | | iso-Propyl | CH3 |
| | | | F |
| | | | Cl |
| | | | H |
| | | cyclo-Propyl | CH3 |
| | | | F |
| | | | Cl |
| | | | H |
| | | Methoxy | CH3 |
| | | | F |
| | | | Cl |
| | | | H |
| | | Ethoxy | CH3 |
| | | | F |
| | | | Cl |
| | | | H |
| | | OCF3 | CH3 |
| | | | F |
| | | | Cl |
| | | | H |

FIGURE 4A

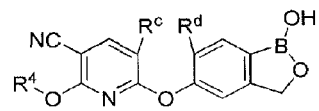

| R⁴ | Rᶜ | Rᵈ | R⁴ | Rᶜ | Rᵈ |
|---|---|---|---|---|---|
| Methyl | F | CH₃ | Ethyl | CN | CH₃ |
| | | F | | | F |
| | | Cl | | | Cl |
| | Cl | CH₃ | | CF₃ | CH₃ |
| | | F | | | F |
| | | Cl | | | Cl |
| | CN | CH₃ | | Methyl | CH₃ |
| | | F | | | F |
| | | Cl | | | Cl |
| | CF₃ | CH₃ | | Ethyl | CH₃ |
| | | F | | | F |
| | | Cl | | | Cl |
| | Methyl | CH₃ | | iso-Propyl | CH₃ |
| | | F | | | F |
| | | Cl | | | Cl |
| | Ethyl | CH₃ | | cyclo-Propyl | CH₃ |
| | | F | | | F |
| | | Cl | | | Cl |
| | iso-Propyl | CH₃ | | Methoxy | CH₃ |
| | | F | | | F |
| | | Cl | | | Cl |
| | cyclo-Propyl | CH₃ | | Ethoxy | CH₃ |
| | | F | | | F |
| | | Cl | | | Cl |
| | Methoxy | CH₃ | | OCF₃ | CH₃ |
| | | F | | | F |
| | | Cl | | | Cl |
| | Ethoxy | CH₃ | n-Propyl | F | CH₃ |
| | | F | | | F |
| | | Cl | | | Cl |
| | OCF₃ | CH₃ | | Cl | CH₃ |
| | | F | | | F |
| | | Cl | | | Cl |
| Ethyl | F | CH₃ | | CN | CH₃ |
| | | F | | | F |
| | | Cl | | | Cl |
| | Cl | CH₃ | | CF₃ | CH₃ |
| | | F | | | F |
| | | Cl | | | Cl |

FIGURE 4B

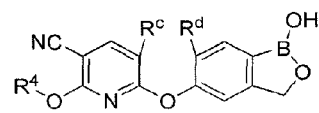

| R⁴ | Rᶜ | Rᵈ | R⁴ | Rᶜ | Rᵈ |
|---|---|---|---|---|---|
| n-Propyl | Methyl | CH₃ | iso-Propyl | iso-Propyl | CH₃ |
| | | F | | | F |
| | | Cl | | | Cl |
| | Ethyl | CH₃ | | cyclo-Propyl | CH₃ |
| | | F | | | F |
| | | Cl | | | Cl |
| | iso-Propyl | CH₃ | | Methoxy | CH₃ |
| | | F | | | F |
| | | Cl | | | Cl |
| | cyclo-Propyl | CH₃ | | Ethoxy | CH₃ |
| | | F | | | F |
| | | Cl | | | Cl |
| | Methoxy | CH₃ | | OCF₃ | CH₃ |
| | | F | | | F |
| | | Cl | | | Cl |
| | Ethoxy | CH₃ | n-Butyl | F | CH₃ |
| | | F | | | F |
| | | Cl | | | Cl |
| | OCF₃ | CH₃ | | Cl | CH₃ |
| | | F | | | F |
| | | Cl | | | Cl |
| iso-Propyl | F | CH₃ | | CN | CH₃ |
| | | F | | | F |
| | | Cl | | | Cl |
| | Cl | CH₃ | | CF₃ | CH₃ |
| | | F | | | F |
| | | Cl | | | Cl |
| | CN | CH₃ | | Methyl | CH₃ |
| | | F | | | F |
| | | Cl | | | Cl |
| | CF₃ | CH₃ | | Ethyl | CH₃ |
| | | F | | | F |
| | | Cl | | | Cl |
| | Methyl | CH₃ | | iso-Propyl | CH₃ |
| | | F | | | F |
| | | Cl | | | Cl |
| | Ethyl | CH₃ | | cyclo-Propyl | CH₃ |
| | | F | | | F |
| | | Cl | | | Cl |

FIGURE 4C

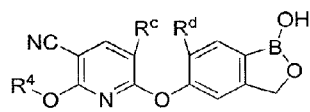

| R⁴ | Rᶜ | Rᵈ | R⁴ | Rᶜ | Rᵈ |
|---|---|---|---|---|---|
| n-Butyl | Methoxy | CH₃ | iso-Butyl | OCF₃ | CH₃ |
| | | F | | | F |
| | | Cl | | | Cl |
| | Ethoxy | CH₃ | sec-Butyl | F | CH₃ |
| | | F | | | F |
| | | Cl | | | Cl |
| | OCF₃ | CH₃ | | Cl | CH₃ |
| | | F | | | F |
| | | Cl | | | Cl |
| iso-Butyl | F | CH₃ | | CN | CH₃ |
| | | F | | | F |
| | | Cl | | | Cl |
| | Cl | CH₃ | | CF₃ | CH₃ |
| | | F | | | F |
| | | Cl | | | Cl |
| | CN | CH₃ | | Methyl | CH₃ |
| | | F | | | F |
| | | Cl | | | Cl |
| | CF₃ | CH₃ | | Ethyl | CH₃ |
| | | F | | | F |
| | | Cl | | | Cl |
| | Methyl | CH₃ | | iso-Propyl | CH₃ |
| | | F | | | F |
| | | Cl | | | Cl |
| | Ethyl | CH₃ | | cyclo-Propyl | CH₃ |
| | | F | | | F |
| | | Cl | | | Cl |
| | iso-Propyl | CH₃ | | Methoxy | CH₃ |
| | | F | | | F |
| | | Cl | | | Cl |
| | cyclo-Propyl | CH₃ | | Ethoxy | CH₃ |
| | | F | | | F |
| | | Cl | | | Cl |
| | Methoxy | CH₃ | | OCF₃ | CH₃ |
| | | F | | | F |
| | | Cl | | | Cl |
| | Ethoxy | CH₃ | tert-Butyl | F | CH₃ |
| | | F | | | F |
| | | Cl | | | Cl |

FIGURE 4D

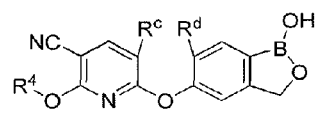

| $R^4$ | $R^c$ | $R^d$ | $R^4$ | $R^c$ | $R^d$ |
|---|---|---|---|---|---|
| tert-Butyl | Cl | $CH_3$ | n-Pentyl | $CF_3$ | $CH_3$ |
| | | F | | | F |
| | | Cl | | | Cl |
| | CN | $CH_3$ | | Methyl | $CH_3$ |
| | | F | | | F |
| | | Cl | | | Cl |
| | $CF_3$ | $CH_3$ | | Ethyl | $CH_3$ |
| | | F | | | F |
| | | Cl | | | Cl |
| | Methyl | $CH_3$ | | iso-Propyl | $CH_3$ |
| | | F | | | F |
| | | Cl | | | Cl |
| | Ethyl | $CH_3$ | | cyclo-Propyl | $CH_3$ |
| | | F | | | F |
| | | Cl | | | Cl |
| | iso-Propyl | $CH_3$ | | Methoxy | $CH_3$ |
| | | F | | | F |
| | | Cl | | | Cl |
| | cyclo-Propyl | $CH_3$ | | Ethoxy | $CH_3$ |
| | | F | | | F |
| | | Cl | | | Cl |
| | Methoxy | $CH_3$ | | $OCF_3$ | $CH_3$ |
| | | F | | | F |
| | | Cl | | | Cl |
| | Ethoxy | $CH_3$ | iso-Pentyl | F | $CH_3$ |
| | | F | | | F |
| | | Cl | | | Cl |
| | $OCF_3$ | $CH_3$ | | Cl | $CH_3$ |
| | | F | | | F |
| | | Cl | | | Cl |
| n-Pentyl | F | $CH_3$ | | CN | $CH_3$ |
| | | F | | | F |
| | | Cl | | | Cl |
| | Cl | $CH_3$ | | $CF_3$ | $CH_3$ |
| | | F | | | F |
| | | Cl | | | Cl |
| | CN | $CH_3$ | | Methyl | $CH_3$ |
| | | F | | | F |
| | | Cl | | | Cl |

FIGURE 4E

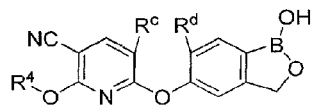

| R⁴ | Rᶜ | Rᵈ | R⁴ | Rᶜ | Rᵈ |
|---|---|---|---|---|---|
| iso-Pentyl | Ethyl | CH₃ | neo-Pentyl | cyclo-Propyl | CH₃ |
| | | F | | | F |
| | | Cl | | | Cl |
| | iso-Propyl | CH₃ | | Methoxy | CH₃ |
| | | F | | | F |
| | | Cl | | | Cl |
| | cyclo-Propyl | CH₃ | | Ethoxy | CH₃ |
| | | F | | | F |
| | | Cl | | | Cl |
| | Methoxy | CH₃ | | OCF₃ | CH₃ |
| | | F | | | F |
| | | Cl | | | Cl |
| | Ethoxy | CH₃ | sec-Pentyl | F | CH₃ |
| | | F | | | F |
| | | Cl | | | Cl |
| | OCF₃ | CH₃ | | Cl | CH₃ |
| | | F | | | F |
| | | Cl | | | Cl |
| neo-Pentyl | F | CH₃ | | CN | CH₃ |
| | | F | | | F |
| | | Cl | | | Cl |
| | Cl | CH₃ | | CF₃ | CH₃ |
| | | F | | | F |
| | | Cl | | | Cl |
| | CN | CH₃ | | Methyl | CH₃ |
| | | F | | | F |
| | | Cl | | | Cl |
| | CF₃ | CH₃ | | Ethyl | CH₃ |
| | | F | | | F |
| | | Cl | | | Cl |
| | Methyl | CH₃ | | iso-Propyl | CH₃ |
| | | F | | | F |
| | | Cl | | | Cl |
| | Ethyl | CH₃ | | cyclo-Propyl | CH₃ |
| | | F | | | F |
| | | Cl | | | Cl |
| | iso-Propyl | CH₃ | | Methoxy | CH₃ |
| | | F | | | F |
| | | Cl | | | Cl |

FIGURE 4F

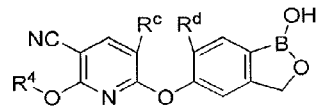

| $R^4$ | $R^c$ | $R^d$ | $R^4$ | $R^c$ | $R^d$ |
|---|---|---|---|---|---|
| sec-Pentyl | Ethoxy | CH₃ | iso-Hexyl | F | CH₃ |
| | | F | | | F |
| | | Cl | | | Cl |
| | OCF₃ | CH₃ | | Cl | CH₃ |
| | | F | | | F |
| | | Cl | | | Cl |
| n-Hexyl | F | CH₃ | | CN | CH₃ |
| | | F | | | F |
| | | Cl | | | Cl |
| | Cl | CH₃ | | CF₃ | CH₃ |
| | | F | | | F |
| | | Cl | | | Cl |
| | CN | CH₃ | | Methyl | CH₃ |
| | | F | | | F |
| | | Cl | | | Cl |
| | CF₃ | CH₃ | | Ethyl | CH₃ |
| | | F | | | F |
| | | Cl | | | Cl |
| | Methyl | CH₃ | | iso-Propyl | CH₃ |
| | | F | | | F |
| | | Cl | | | Cl |
| | Ethyl | CH₃ | | cyclo-Propyl | CH₃ |
| | | F | | | F |
| | | Cl | | | Cl |
| | iso-Propyl | CH₃ | | Methoxy | CH₃ |
| | | F | | | F |
| | | Cl | | | Cl |
| | cyclo-Propyl | CH₃ | | Ethoxy | CH₃ |
| | | F | | | F |
| | | Cl | | | Cl |
| | Methoxy | CH₃ | | OCF₃ | CH₃ |
| | | F | | | F |
| | | Cl | | | Cl |
| | Ethoxy | CH₃ | sec-Hexyl | F | CH₃ |
| | | F | | | F |
| | | Cl | | | Cl |
| | OCF₃ | CH₃ | | Cl | CH₃ |
| | | F | | | F |
| | | Cl | | | Cl |

FIGURE 4G
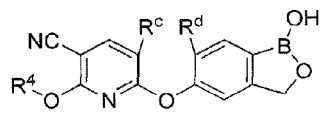
| R⁴ | Rᶜ | Rᵈ | R⁴ | Rᶜ | Rᵈ |
|---|---|---|---|---|---|
| sec-Hexyl | CN | CH₃ | tetrahydro-2*H*-pyran-4-yl | Cl | CH₃ |
|  |  | F |  |  | F |
|  |  | Cl |  |  | Cl |
|  | CF₃ | CH₃ |  | CN | CH₃ |
|  |  | F |  |  | F |
|  |  | Cl |  |  | Cl |
|  | Methyl | CH₃ |  | CF₃ | CH₃ |
|  |  | F |  |  | F |
|  |  | Cl |  |  | Cl |
|  | Ethyl | CH₃ |  | Methyl | CH₃ |
|  |  | F |  |  | F |
|  |  | Cl |  |  | Cl |
|  | iso-Propyl | CH₃ |  | Ethyl | CH₃ |
|  |  | F |  |  | F |
|  |  | Cl |  |  | Cl |
|  | cyclo-Propyl | CH₃ |  | iso-Propyl | CH₃ |
|  |  | F |  |  | F |
|  |  | Cl |  |  | Cl |
|  | Methoxy | CH₃ |  | cyclo-Propyl | CH₃ |
|  |  | F |  |  | F |
|  |  | Cl |  |  | Cl |
|  | Ethoxy | CH₃ |  | Methoxy | CH₃ |
|  |  | F |  |  | F |
|  |  | Cl |  |  | Cl |
|  | OCF₃ | CH₃ |  | Ethoxy | CH₃ |
|  |  | F |  |  | F |
|  |  | Cl |  |  | Cl |
|  tetrahydro-2*H*-pyran-4-yl | F | CH₃ |  | OCF₃ | CH₃ |
|  |  | F |  |  | F |
|  |  | Cl |  |  | Cl |

FIGURE 5A

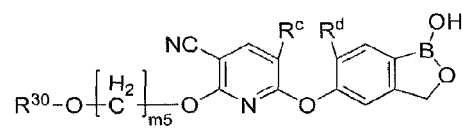

| m5 | R³⁰ | Rᶜ | Rᵈ |
|---|---|---|---|
| 2 | H | F | CH₃ |
| | | | F |
| | | | Cl |
| | | Cl | CH₃ |
| | | | F |
| | | | Cl |
| | | CN | CH₃ |
| | | | F |
| | | | Cl |
| | | CF₃ | CH₃ |
| | | | F |
| | | | Cl |
| | | Methyl | CH₃ |
| | | | F |
| | | | Cl |
| | | Ethyl | CH₃ |
| | | | F |
| | | | Cl |
| | | iso-Propyl | CH₃ |
| | | | F |
| | | | Cl |
| | | cyclo-Propyl | CH₃ |
| | | | F |
| | | | Cl |
| | | Methoxy | CH₃ |
| | | | F |
| | | | Cl |
| | | Ethoxy | CH₃ |
| | | | F |
| | | | Cl |
| | | OCF₃ | CH₃ |
| | | | F |
| | | | Cl |
| | Methyl | F | CH₃ |
| | | | F |
| | | | Cl |
| | | Cl | CH₃ |
| | | | F |
| | | | Cl |

| m5 | R³⁰ | Rᶜ | Rᵈ |
|---|---|---|---|
| 2 | Methyl | CN | CH₃ |
| | | | F |
| | | | Cl |
| | | CF₃ | CH₃ |
| | | | F |
| | | | Cl |
| | | Methyl | CH₃ |
| | | | F |
| | | | Cl |
| | | Ethyl | CH₃ |
| | | | F |
| | | | Cl |
| | | iso-Propyl | CH₃ |
| | | | F |
| | | | Cl |
| | | cyclo-Propyl | CH₃ |
| | | | F |
| | | | Cl |
| | | Methoxy | CH₃ |
| | | | F |
| | | | Cl |
| | | Ethoxy | CH₃ |
| | | | F |
| | | | Cl |
| | | OCF₃ | CH₃ |
| | | | F |
| | | | Cl |
| | Ethyl | F | CH₃ |
| | | | F |
| | | | Cl |
| | | Cl | CH₃ |
| | | | F |
| | | | Cl |
| | | CN | CH₃ |
| | | | F |
| | | | Cl |
| | | CF₃ | CH₃ |
| | | | F |
| | | | Cl |

FIGURE 5B

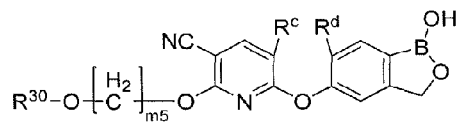

| m5 | R³⁰ | Rᶜ | Rᵈ | m5 | R³⁰ | Rᶜ | Rᵈ |
|---|---|---|---|---|---|---|---|
| 2 | Ethyl | Methyl | CH₃ | 2 | n-Propyl | iso-Propyl | CH₃ |
| | | | F | | | | F |
| | | | Cl | | | | Cl |
| | | Ethyl | CH₃ | | | cyclo-Propyl | CH₃ |
| | | | F | | | | F |
| | | | Cl | | | | Cl |
| | | iso-Propyl | CH₃ | | | Methoxy | CH₃ |
| | | | F | | | | F |
| | | | Cl | | | | Cl |
| | | cyclo-Propyl | CH₃ | | | Ethoxy | CH₃ |
| | | | F | | | | F |
| | | | Cl | | | | Cl |
| | | Methoxy | CH₃ | | | OCF₃ | CH₃ |
| | | | F | | | | F |
| | | | Cl | | | | Cl |
| | | Ethoxy | CH₃ | | iso-Propyl | F | CH₃ |
| | | | F | | | | F |
| | | | Cl | | | | Cl |
| | | OCF₃ | CH₃ | | | Cl | CH₃ |
| | | | F | | | | F |
| | | | Cl | | | | Cl |
| | n-Propyl | F | CH₃ | | | CN | CH₃ |
| | | | F | | | | F |
| | | | Cl | | | | Cl |
| | | Cl | CH₃ | | | CF₃ | CH₃ |
| | | | F | | | | F |
| | | | Cl | | | | Cl |
| | | CN | CH₃ | | | Methyl | CH₃ |
| | | | F | | | | F |
| | | | Cl | | | | Cl |
| | | CF₃ | CH₃ | | | Ethyl | CH₃ |
| | | | F | | | | F |
| | | | Cl | | | | Cl |
| | | Methyl | CH₃ | | | iso-Propyl | CH₃ |
| | | | F | | | | F |
| | | | Cl | | | | Cl |
| | | Ethyl | CH₃ | | | cyclo-Propyl | CH₃ |
| | | | F | | | | F |
| | | | Cl | | | | Cl |

FIGURE 5C

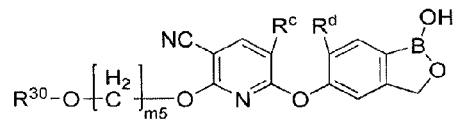

| m5 | R30 | Rc | Rd |
|---|---|---|---|
| 2 | iso-Propyl | Methoxy | CH3 |
| | | | F |
| | | | Cl |
| | | Ethoxy | CH3 |
| | | | F |
| | | | Cl |
| | | OCF3 | CH3 |
| | | | F |
| | | | Cl |
| | cyclo-Propyl | F | CH3 |
| | | | F |
| | | | Cl |
| | | Cl | CH3 |
| | | | F |
| | | | Cl |
| | | CN | CH3 |
| | | | F |
| | | | Cl |
| | | CF3 | CH3 |
| | | | F |
| | | | Cl |
| | | Methyl | CH3 |
| | | | F |
| | | | Cl |
| | | Ethyl | CH3 |
| | | | F |
| | | | Cl |
| | | iso-Propyl | CH3 |
| | | | F |
| | | | Cl |
| | | cyclo-Propyl | CH3 |
| | | | F |
| | | | Cl |
| | | Methoxy | CH3 |
| | | | F |
| | | | Cl |
| | | Ethoxy | CH3 |
| | | | F |
| | | | Cl |

| m5 | R30 | Rc | Rd |
|---|---|---|---|
| 2 | cyclo-Propyl | OCF3 | CH3 |
| | | | F |
| | | | Cl |
| | CF3 | F | CH3 |
| | | | F |
| | | | Cl |
| | | Cl | CH3 |
| | | | F |
| | | | Cl |
| | | CN | CH3 |
| | | | F |
| | | | Cl |
| | | CF3 | CH3 |
| | | | F |
| | | | Cl |
| | | Methyl | CH3 |
| | | | F |
| | | | Cl |
| | | Ethyl | CH3 |
| | | | F |
| | | | Cl |
| | | iso-Propyl | CH3 |
| | | | F |
| | | | Cl |
| | | cyclo-Propyl | CH3 |
| | | | F |
| | | | Cl |
| | | Methoxy | CH3 |
| | | | F |
| | | | Cl |
| | | Ethoxy | CH3 |
| | | | F |
| | | | Cl |
| | | OCF3 | CH3 |
| | | | F |
| | | | Cl |
| 3 | H | F | CH3 |
| | | | F |
| | | | Cl |

FIGURE 5D

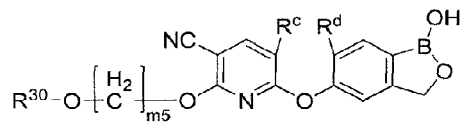

| m5 | R³⁰ | Rᶜ | Rᵈ |
|---|---|---|---|
| 3 | H | Cl | CH₃ |
| | | | F |
| | | | Cl |
| | | CN | CH₃ |
| | | | F |
| | | | Cl |
| | | CF₃ | CH₃ |
| | | | F |
| | | | Cl |
| | | Methyl | CH₃ |
| | | | F |
| | | | Cl |
| | | Ethyl | CH₃ |
| | | | F |
| | | | Cl |
| | | iso-Propyl | CH₃ |
| | | | F |
| | | | Cl |
| | | cyclo-Propyl | CH₃ |
| | | | F |
| | | | Cl |
| | | Methoxy | CH₃ |
| | | | F |
| | | | Cl |
| | | Ethoxy | CH₃ |
| | | | F |
| | | | Cl |
| | | OCF₃ | CH₃ |
| | | | F |
| | | | Cl |
| | Methyl | F | CH₃ |
| | | | F |
| | | | Cl |
| | | Cl | CH₃ |
| | | | F |
| | | | Cl |
| | | CN | CH₃ |
| | | | F |
| | | | Cl |

| m5 | R³⁰ | Rᶜ | Rᵈ |
|---|---|---|---|
| 3 | Methyl | CF₃ | CH₃ |
| | | | F |
| | | | Cl |
| | | Methyl | CH₃ |
| | | | F |
| | | | Cl |
| | | Ethyl | CH₃ |
| | | | F |
| | | | Cl |
| | | iso-Propyl | CH₃ |
| | | | F |
| | | | Cl |
| | | cyclo-Propyl | CH₃ |
| | | | F |
| | | | Cl |
| | | Methoxy | CH₃ |
| | | | F |
| | | | Cl |
| | | Ethoxy | CH₃ |
| | | | F |
| | | | Cl |
| | | OCF₃ | CH₃ |
| | | | F |
| | | | Cl |
| | Ethyl | F | CH₃ |
| | | | F |
| | | | Cl |
| | | Cl | CH₃ |
| | | | F |
| | | | Cl |
| | | CN | CH₃ |
| | | | F |
| | | | Cl |
| | | CF₃ | CH₃ |
| | | | F |
| | | | Cl |
| | | Methyl | CH₃ |
| | | | F |
| | | | Cl |

FIGURE 5E

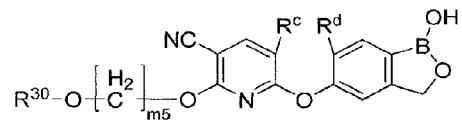

| m5 | $R^{30}$ | $R^c$ | $R^d$ | m5 | $R^{30}$ | $R^c$ | $R^d$ |
|---|---|---|---|---|---|---|---|
| 3 | Ethyl | Ethyl | CH₃ | 3 | n-Propyl | cyclo-Propyl | CH₃ |
| | | | F | | | | F |
| | | | Cl | | | | Cl |
| | | iso-Propyl | CH₃ | | | Methoxy | CH₃ |
| | | | F | | | | F |
| | | | Cl | | | | Cl |
| | | cyclo-Propyl | CH₃ | | | Ethoxy | CH₃ |
| | | | F | | | | F |
| | | | Cl | | | | Cl |
| | | Methoxy | CH₃ | | | OCF₃ | CH₃ |
| | | | F | | | | F |
| | | | Cl | | | | Cl |
| | | Ethoxy | CH₃ | | iso-Propyl | F | CH₃ |
| | | | F | | | | F |
| | | | Cl | | | | Cl |
| | | OCF₃ | CH₃ | | | Cl | CH₃ |
| | | | F | | | | F |
| | | | Cl | | | | Cl |
| | n-Propyl | F | CH₃ | | | CN | CH₃ |
| | | | F | | | | F |
| | | | Cl | | | | Cl |
| | | Cl | CH₃ | | | CF₃ | CH₃ |
| | | | F | | | | F |
| | | | Cl | | | | Cl |
| | | CN | CH₃ | | | Methyl | CH₃ |
| | | | F | | | | F |
| | | | Cl | | | | Cl |
| | | CF₃ | CH₃ | | | Ethyl | CH₃ |
| | | | F | | | | F |
| | | | Cl | | | | Cl |
| | | Methyl | CH₃ | | | iso-Propyl | CH₃ |
| | | | F | | | | F |
| | | | Cl | | | | Cl |
| | | Ethyl | CH₃ | | | cyclo-Propyl | CH₃ |
| | | | F | | | | F |
| | | | Cl | | | | Cl |
| | | iso-Propyl | CH₃ | | | Methoxy | CH₃ |
| | | | F | | | | F |
| | | | Cl | | | | Cl |

| m5 | R³⁰ | R^c | R^d |
|----|-----|-----|-----|
| 3 | iso-Propyl | Ethoxy | CH₃ |
| | | | F |
| | | | Cl |
| | | OCF₃ | CH₃ |
| | | | F |
| | | | Cl |
| | cyclo-Propyl | F | CH₃ |
| | | | F |
| | | | Cl |
| | | Cl | CH₃ |
| | | | F |
| | | | Cl |
| | | CN | CH₃ |
| | | | F |
| | | | Cl |
| | | CF₃ | CH₃ |
| | | | F |
| | | | Cl |
| | | Methyl | CH₃ |
| | | | F |
| | | | Cl |

| m5 | R³⁰ | R^c | R^d |
|----|-----|-----|-----|
| 3 | cyclo-Propyl | Ethyl | CH₃ |
| | | | F |
| | | | Cl |
| | | iso-Propyl | CH₃ |
| | | | F |
| | | | Cl |
| | | cyclo-Propyl | CH₃ |
| | | | F |
| | | | Cl |
| | | Methoxy | CH₃ |
| | | | F |
| | | | Cl |
| | | Ethoxy | CH₃ |
| | | | F |
| | | | Cl |
| | | OCF₃ | CH₃ |
| | | | F |
| | | | Cl |

| m1 | R4d | Rc | Rd |
|---|---|---|---|
| 1 | Methyl | F | CH3 |
|   |   |   | F |
|   |   |   | Cl |
|   |   | Cl | CH3 |
|   |   |   | F |
|   |   |   | Cl |
|   |   | CN | CH3 |
|   |   |   | F |
|   |   |   | Cl |
|   |   | CF3 | CH3 |
|   |   |   | F |
|   |   |   | Cl |
|   |   | Methyl | CH3 |
|   |   |   | F |
|   |   |   | Cl |
|   |   | Ethyl | CH3 |
|   |   |   | F |
|   |   |   | Cl |
|   |   | iso-Propyl | CH3 |
|   |   |   | F |
|   |   |   | Cl |
|   |   | cyclo-Propyl | CH3 |
|   |   |   | F |
|   |   |   | Cl |
|   |   | Methoxy | CH3 |
|   |   |   | F |
|   |   |   | Cl |
|   |   | Ethoxy | CH3 |
|   |   |   | F |
|   |   |   | Cl |
|   |   | OCF3 | CH3 |
|   |   |   | F |
|   |   |   | Cl |
|   | Ethyl | F | CH3 |
|   |   |   | F |
|   |   |   | Cl |
|   |   | Cl | CH3 |
|   |   |   | F |
|   |   |   | Cl |

| m1 | R4d | Rc | Rd |
|---|---|---|---|
| 1 | Ethyl | CN | CH3 |
|   |   |   | F |
|   |   |   | Cl |
|   |   | CF3 | CH3 |
|   |   |   | F |
|   |   |   | Cl |
|   |   | Methyl | CH3 |
|   |   |   | F |
|   |   |   | Cl |
|   |   | Ethyl | CH3 |
|   |   |   | F |
|   |   |   | Cl |
|   |   | iso-Propyl | CH3 |
|   |   |   | F |
|   |   |   | Cl |
|   |   | cyclo-Propyl | CH3 |
|   |   |   | F |
|   |   |   | Cl |
|   |   | Methoxy | CH3 |
|   |   |   | F |
|   |   |   | Cl |
|   |   | Ethoxy | CH3 |
|   |   |   | F |
|   |   |   | Cl |
|   |   | OCF3 | CH3 |
|   |   |   | F |
|   |   |   | Cl |
|   | n-Propyl | F | CH3 |
|   |   |   | F |
|   |   |   | Cl |
|   |   | Cl | CH3 |
|   |   |   | F |
|   |   |   | Cl |
|   |   | CN | CH3 |
|   |   |   | F |
|   |   |   | Cl |
|   |   | CF3 | CH3 |
|   |   |   | F |
|   |   |   | Cl |

FIGURE 6B

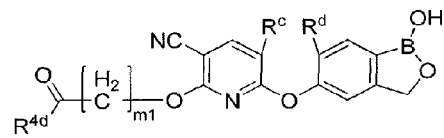

| m1 | R^{4d} | R^c | R^d | m1 | R^{4d} | R^c | R^d |
|---|---|---|---|---|---|---|---|
| 1 | n-Propyl | Methyl | CH$_3$ | 1 | iso-Propyl | cyclo-Propyl | CH$_3$ |
|   |   |   | F |   |   |   | F |
|   |   |   | Cl |   |   |   | Cl |
|   |   | Ethyl | CH$_3$ |   |   | Methoxy | CH$_3$ |
|   |   |   | F |   |   |   | F |
|   |   |   | Cl |   |   |   | Cl |
|   |   | iso-Propyl | CH$_3$ |   |   | Ethoxy | CH$_3$ |
|   |   |   | F |   |   |   | F |
|   |   |   | Cl |   |   |   | Cl |
|   |   | cyclo-Propyl | CH$_3$ |   |   | OCF$_3$ | CH$_3$ |
|   |   |   | F |   |   |   | F |
|   |   |   | Cl |   |   |   | Cl |
|   |   | Methoxy | CH$_3$ |   | cyclo-Propyl | F | CH$_3$ |
|   |   |   | F |   |   |   | F |
|   |   |   | Cl |   |   |   | Cl |
|   |   | Ethoxy | CH$_3$ |   |   | Cl | CH$_3$ |
|   |   |   | F |   |   |   | F |
|   |   |   | Cl |   |   |   | Cl |
|   |   | OCF$_3$ | CH$_3$ |   |   | CN | CH$_3$ |
|   |   |   | F |   |   |   | F |
|   |   |   | Cl |   |   |   | Cl |
|   | iso-Propyl | F | CH$_3$ |   |   | CF$_3$ | CH$_3$ |
|   |   |   | F |   |   |   | F |
|   |   |   | Cl |   |   |   | Cl |
|   |   | Cl | CH$_3$ |   |   | Methyl | CH$_3$ |
|   |   |   | F |   |   |   | F |
|   |   |   | Cl |   |   |   | Cl |
|   |   | CN | CH$_3$ |   |   | Ethyl | CH$_3$ |
|   |   |   | F |   |   |   | F |
|   |   |   | Cl |   |   |   | Cl |
|   |   | CF$_3$ | CH$_3$ |   |   | iso-Propyl | CH$_3$ |
|   |   |   | F |   |   |   | F |
|   |   |   | Cl |   |   |   | Cl |
|   |   | Methyl | CH$_3$ |   |   | cyclo-Propyl | CH$_3$ |
|   |   |   | F |   |   |   | F |
|   |   |   | Cl |   |   |   | Cl |
|   |   | Ethyl | CH$_3$ |   |   | Methoxy | CH$_3$ |
|   |   |   | F |   |   |   | F |
|   |   |   | Cl |   |   |   | Cl |
|   |   | iso-Propyl | CH$_3$ |   |   | Ethoxy | CH$_3$ |
|   |   |   | F |   |   |   | F |
|   |   |   | Cl |   |   |   | Cl |

FIGURE 6C

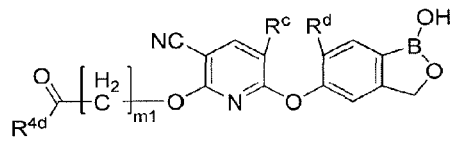

| m1 | R⁴ᵈ | Rᶜ | Rᵈ |
|---|---|---|---|
| 1 | cyclo-Propyl | OCF₃ | CH₃ |
|   |   |   | F |
|   |   |   | Cl |
| 2 | Methyl | F | CH₃ |
|   |   |   | F |
|   |   |   | Cl |
|   |   | Cl | CH₃ |
|   |   |   | F |
|   |   |   | Cl |
|   |   | CN | CH₃ |
|   |   |   | F |
|   |   |   | Cl |
|   |   | CF₃ | CH₃ |
|   |   |   | F |
|   |   |   | Cl |
|   |   | Methyl | CH₃ |
|   |   |   | F |
|   |   |   | Cl |
|   |   | Ethyl | CH₃ |
|   |   |   | F |
|   |   |   | Cl |
|   |   | iso-Propyl | CH₃ |
|   |   |   | F |
|   |   |   | Cl |
|   |   | cyclo-Propyl | CH₃ |
|   |   |   | F |
|   |   |   | Cl |
|   |   | Methoxy | CH₃ |
|   |   |   | F |
|   |   |   | Cl |
|   |   | Ethoxy | CH₃ |
|   |   |   | F |
|   |   |   | Cl |
|   |   | OCF₃ | CH₃ |
|   |   |   | F |
|   |   |   | Cl |
|   | Ethyl | F | CH₃ |
|   |   |   | F |
|   |   |   | Cl |
|   |   | Cl | CH₃ |
|   |   |   | F |
|   |   |   | Cl |

| m1 | R⁴ᵈ | Rᶜ | Rᵈ |
|---|---|---|---|
| 2 | Ethyl | CN | CH₃ |
|   |   |   | F |
|   |   |   | Cl |
|   |   | CF₃ | CH₃ |
|   |   |   | F |
|   |   |   | Cl |
|   |   | Methyl | CH₃ |
|   |   |   | F |
|   |   |   | Cl |
|   |   | Ethyl | CH₃ |
|   |   |   | F |
|   |   |   | Cl |
|   |   | iso-Propyl | CH₃ |
|   |   |   | F |
|   |   |   | Cl |
|   |   | cyclo-Propyl | CH₃ |
|   |   |   | F |
|   |   |   | Cl |
|   |   | Methoxy | CH₃ |
|   |   |   | F |
|   |   |   | Cl |
|   |   | Ethoxy | CH₃ |
|   |   |   | F |
|   |   |   | Cl |
|   |   | OCF₃ | CH₃ |
|   |   |   | F |
|   |   |   | Cl |
|   | n-Propyl | F | CH₃ |
|   |   |   | F |
|   |   |   | Cl |
|   |   | Cl | CH₃ |
|   |   |   | F |
|   |   |   | Cl |
|   |   | CN | CH₃ |
|   |   |   | F |
|   |   |   | Cl |
|   |   | CF₃ | CH₃ |
|   |   |   | F |
|   |   |   | Cl |
|   |   | Methyl | CH₃ |
|   |   |   | F |
|   |   |   | Cl |

FIGURE 6D

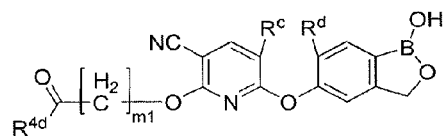

| m1 | R^4d | R^c | R^d |
|---|---|---|---|
| 2 | n-Propyl | Ethyl | CH₃ |
| | | | F |
| | | | Cl |
| | | iso-Propyl | CH₃ |
| | | | F |
| | | | Cl |
| | | cyclo-Propyl | CH₃ |
| | | | F |
| | | | Cl |
| | | Methoxy | CH₃ |
| | | | F |
| | | | Cl |
| | | Ethoxy | CH₃ |
| | | | F |
| | | | Cl |
| | | OCF₃ | CH₃ |
| | | | F |
| | | | Cl |
| | iso-Propyl | F | CH₃ |
| | | | F |
| | | | Cl |
| | | Cl | CH₃ |
| | | | F |
| | | | Cl |
| | | CN | CH₃ |
| | | | F |
| | | | Cl |
| | | CF₃ | CH₃ |
| | | | F |
| | | | Cl |
| | | Methyl | CH₃ |
| | | | F |
| | | | Cl |
| | | Ethyl | CH₃ |
| | | | F |
| | | | Cl |
| | | iso-Propyl | CH₃ |
| | | | F |
| | | | Cl |
| | | cyclo-Propyl | CH₃ |
| | | | F |
| | | | Cl |

| m1 | R^4d | R^c | R^d |
|---|---|---|---|
| 2 | iso-Propyl | Methoxy | CH₃ |
| | | | F |
| | | | Cl |
| | | Ethoxy | CH₃ |
| | | | F |
| | | | Cl |
| | | OCF₃ | CH₃ |
| | | | F |
| | | | Cl |
| | cyclo-Propyl | F | CH₃ |
| | | | F |
| | | | Cl |
| | | Cl | CH₃ |
| | | | F |
| | | | Cl |
| | | CN | CH₃ |
| | | | F |
| | | | Cl |
| | | CF₃ | CH₃ |
| | | | F |
| | | | Cl |
| | | Methyl | CH₃ |
| | | | F |
| | | | Cl |
| | | Ethyl | CH₃ |
| | | | F |
| | | | Cl |
| | | iso-Propyl | CH₃ |
| | | | F |
| | | | Cl |
| | | cyclo-Propyl | CH₃ |
| | | | F |
| | | | Cl |
| | | Methoxy | CH₃ |
| | | | F |
| | | | Cl |
| | | Ethoxy | CH₃ |
| | | | F |
| | | | Cl |
| | | OCF₃ | CH₃ |
| | | | F |
| | | | Cl |

FIGURE 6E

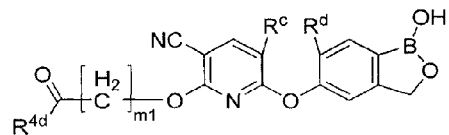

| m1 | R^{4d} | R^c | R^d | m1 | R^{4d} | R^c | R^d |
|---|---|---|---|---|---|---|---|
| 3 | Methyl | F | CH$_3$ | 3 | Ethyl | CF$_3$ | CH$_3$ |
|  |  |  | F |  |  |  | F |
|  |  |  | Cl |  |  |  | Cl |
|  |  | Cl | CH$_3$ |  |  | Methyl | CH$_3$ |
|  |  |  | F |  |  |  | F |
|  |  |  | Cl |  |  |  | Cl |
|  |  | CN | CH$_3$ |  |  | Ethyl | CH$_3$ |
|  |  |  | F |  |  |  | F |
|  |  |  | Cl |  |  |  | Cl |
|  |  | CF$_3$ | CH$_3$ |  |  | iso-Propyl | CH$_3$ |
|  |  |  | F |  |  |  | F |
|  |  |  | Cl |  |  |  | Cl |
|  |  | Methyl | CH$_3$ |  |  | cyclo-Propyl | CH$_3$ |
|  |  |  | F |  |  |  | F |
|  |  |  | Cl |  |  |  | Cl |
|  |  | Ethyl | CH$_3$ |  |  | Methoxy | CH$_3$ |
|  |  |  | F |  |  |  | F |
|  |  |  | Cl |  |  |  | Cl |
|  |  | iso-Propyl | CH$_3$ |  |  | Ethoxy | CH$_3$ |
|  |  |  | F |  |  |  | F |
|  |  |  | Cl |  |  |  | Cl |
|  |  | cyclo-Propyl | CH$_3$ |  |  | OCF$_3$ | CH$_3$ |
|  |  |  | F |  |  |  | F |
|  |  |  | Cl |  |  |  | Cl |
|  |  | Methoxy | CH$_3$ |  | n-Propyl | F | CH$_3$ |
|  |  |  | F |  |  |  | F |
|  |  |  | Cl |  |  |  | Cl |
|  |  | Ethoxy | CH$_3$ |  |  | Cl | CH$_3$ |
|  |  |  | F |  |  |  | F |
|  |  |  | Cl |  |  |  | Cl |
|  |  | OCF$_3$ | CH$_3$ |  |  | CN | CH$_3$ |
|  |  |  | F |  |  |  | F |
|  |  |  | Cl |  |  |  | Cl |
|  | Ethyl | F | CH$_3$ |  |  | CF$_3$ | CH$_3$ |
|  |  |  | F |  |  |  | F |
|  |  |  | Cl |  |  |  | Cl |
|  |  | Cl | CH$_3$ |  |  | Methyl | CH$_3$ |
|  |  |  | F |  |  |  | F |
|  |  |  | Cl |  |  |  | Cl |
|  |  | CN | CH$_3$ |  |  | Ethyl | CH$_3$ |
|  |  |  | F |  |  |  | F |
|  |  |  | Cl |  |  |  | Cl |

FIGURE 6F

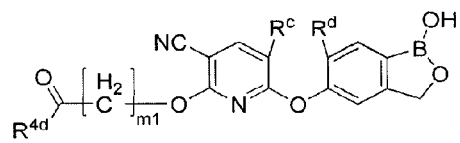

| m1 | R⁴ᵈ | Rᶜ | Rᵈ |
|---|---|---|---|
| 3 | n-Propyl | iso-Propyl | CH₃ |
| | | | F |
| | | | Cl |
| | | cyclo-Propyl | CH₃ |
| | | | F |
| | | | Cl |
| | | Methoxy | CH₃ |
| | | | F |
| | | | Cl |
| | | Ethoxy | CH₃ |
| | | | F |
| | | | Cl |
| | | OCF₃ | CH₃ |
| | | | F |
| | | | Cl |
| | iso-Propyl | F | CH₃ |
| | | | F |
| | | | Cl |
| | | Cl | CH₃ |
| | | | F |
| | | | Cl |
| | | CN | CH₃ |
| | | | F |
| | | | Cl |
| | | CF₃ | CH₃ |
| | | | F |
| | | | Cl |
| | | Methyl | CH₃ |
| | | | F |
| | | | Cl |
| | | Ethyl | CH₃ |
| | | | F |
| | | | Cl |
| | | iso-Propyl | CH₃ |
| | | | F |
| | | | Cl |
| | | cyclo-Propyl | CH₃ |
| | | | F |
| | | | Cl |
| | | Methoxy | CH₃ |
| | | | F |
| | | | Cl |

| m1 | R⁴ᵈ | Rᶜ | Rᵈ |
|---|---|---|---|
| 3 | iso-Propyl | Ethoxy | CH₃ |
| | | | F |
| | | | Cl |
| | | OCF₃ | CH₃ |
| | | | F |
| | | | Cl |
| | cyclo-Propyl | F | CH₃ |
| | | | F |
| | | | Cl |
| | | Cl | CH₃ |
| | | | F |
| | | | Cl |
| | | CN | CH₃ |
| | | | F |
| | | | Cl |
| | | CF₃ | CH₃ |
| | | | F |
| | | | Cl |
| | | Methyl | CH₃ |
| | | | F |
| | | | Cl |
| | | Ethyl | CH₃ |
| | | | F |
| | | | Cl |
| | | iso-Propyl | CH₃ |
| | | | F |
| | | | Cl |
| | | cyclo-Propyl | CH₃ |
| | | | F |
| | | | Cl |
| | | Methoxy | CH₃ |
| | | | F |
| | | | Cl |
| | | Ethoxy | CH₃ |
| | | | F |
| | | | Cl |
| | | OCF₃ | CH₃ |
| | | | F |
| | | | Cl |
| 4 | Methyl | F | CH₃ |
| | | | F |
| | | | Cl |

FIGURE 6G

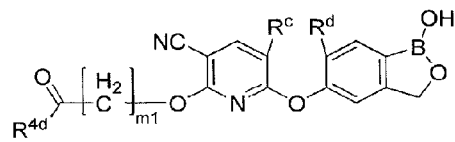

| m1 | R^{4d} | R^c | R^d |
|---|---|---|---|
| 4 | Methyl | Cl | CH_3 |
| | | | F |
| | | | Cl |
| | | CN | CH_3 |
| | | | F |
| | | | Cl |
| | | CF_3 | CH_3 |
| | | | F |
| | | | Cl |
| | | Methyl | CH_3 |
| | | | F |
| | | | Cl |
| | | Ethyl | CH_3 |
| | | | F |
| | | | Cl |
| | | iso-Propyl | CH_3 |
| | | | F |
| | | | Cl |
| | | cyclo-Propyl | CH_3 |
| | | | F |
| | | | Cl |
| | | Methoxy | CH_3 |
| | | | F |
| | | | Cl |
| | | Ethoxy | CH_3 |
| | | | F |
| | | | Cl |
| | | OCF_3 | CH_3 |
| | | | F |
| | | | Cl |
| | Ethyl | F | CH_3 |
| | | | F |
| | | | Cl |
| | | Cl | CH_3 |
| | | | F |
| | | | Cl |
| | | CN | CH_3 |
| | | | F |
| | | | Cl |
| | | CF_3 | CH_3 |
| | | | F |
| | | | Cl |

| m1 | R^{4d} | R^c | R^d |
|---|---|---|---|
| 4 | Ethyl | Methyl | CH_3 |
| | | | F |
| | | | Cl |
| | | Ethyl | CH_3 |
| | | | F |
| | | | Cl |
| | | iso-Propyl | CH_3 |
| | | | F |
| | | | Cl |
| | | cyclo-Propyl | CH_3 |
| | | | F |
| | | | Cl |
| | | Methoxy | CH_3 |
| | | | F |
| | | | Cl |
| | | Ethoxy | CH_3 |
| | | | F |
| | | | Cl |
| | | OCF_3 | CH_3 |
| | | | F |
| | | | Cl |
| | n-Propyl | F | CH_3 |
| | | | F |
| | | | Cl |
| | | Cl | CH_3 |
| | | | F |
| | | | Cl |
| | | CN | CH_3 |
| | | | F |
| | | | Cl |
| | | CF_3 | CH_3 |
| | | | F |
| | | | Cl |
| | | Methyl | CH_3 |
| | | | F |
| | | | Cl |
| | | Ethyl | CH_3 |
| | | | F |
| | | | Cl |
| | | iso-Propyl | CH_3 |
| | | | F |
| | | | Cl |

FIGURE 6H

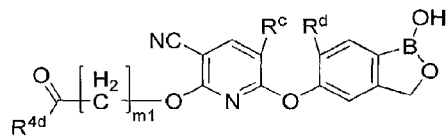

| m1 | R^{4d} | R^c | R^d |
|----|--------|-----|-----|
| 4 | n-Propyl | cyclo-Propyl | CH$_3$ |
| | | | F |
| | | | Cl |
| | | Methoxy | CH$_3$ |
| | | | F |
| | | | Cl |
| | | Ethoxy | CH$_3$ |
| | | | F |
| | | | Cl |
| | | OCF$_3$ | CH$_3$ |
| | | | F |
| | | | Cl |
| | iso-Propyl | F | CH$_3$ |
| | | | F |
| | | | Cl |
| | | Cl | CH$_3$ |
| | | | F |
| | | | Cl |
| | | CN | CH$_3$ |
| | | | F |
| | | | Cl |
| | | CF$_3$ | CH$_3$ |
| | | | F |
| | | | Cl |
| | | Methyl | CH$_3$ |
| | | | F |
| | | | Cl |
| | | Ethyl | CH$_3$ |
| | | | F |
| | | | Cl |
| | | iso-Propyl | CH$_3$ |
| | | | F |
| | | | Cl |
| | | cyclo-Propyl | CH$_3$ |
| | | | F |
| | | | Cl |
| | | Methoxy | CH$_3$ |
| | | | F |
| | | | Cl |

| m1 | R^{4d} | R^c | R^d |
|----|--------|-----|-----|
| 4 | iso-Propyl | Ethoxy | CH$_3$ |
| | | | F |
| | | | Cl |
| | | OCF$_3$ | CH$_3$ |
| | | | F |
| | | | Cl |
| | cyclo-Propyl | F | CH$_3$ |
| | | | F |
| | | | Cl |
| | | Cl | CH$_3$ |
| | | | F |
| | | | Cl |
| | | CN | CH$_3$ |
| | | | F |
| | | | Cl |
| | | CF$_3$ | CH$_3$ |
| | | | F |
| | | | Cl |
| | | Methyl | CH$_3$ |
| | | | F |
| | | | Cl |
| | | Ethyl | CH$_3$ |
| | | | F |
| | | | Cl |
| | | iso-Propyl | CH$_3$ |
| | | | F |
| | | | Cl |
| | | cyclo-Propyl | CH$_3$ |
| | | | F |
| | | | Cl |
| | | Methoxy | CH$_3$ |
| | | | F |
| | | | Cl |
| | | Ethoxy | CH$_3$ |
| | | | F |
| | | | Cl |
| | | OCF$_3$ | CH$_3$ |
| | | | F |
| | | | Cl |

FIGURE 7A

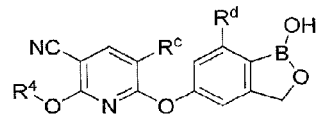

| $R^4$ | $R^c$ | $R^d$ | $R^4$ | $R^c$ | $R^d$ |
|---|---|---|---|---|---|
| Methyl | F | CH₃ | Ethyl | CN | CH₃ |
| | | F | | | F |
| | | Cl | | | Cl |
| | Cl | CH₃ | | CF₃ | CH₃ |
| | | F | | | F |
| | | Cl | | | Cl |
| | CN | CH₃ | | Methyl | CH₃ |
| | | F | | | F |
| | | Cl | | | Cl |
| | CF₃ | CH₃ | | Ethyl | CH₃ |
| | | F | | | F |
| | | Cl | | | Cl |
| | Methyl | CH₃ | | iso-Propyl | CH₃ |
| | | F | | | F |
| | | Cl | | | Cl |
| | Ethyl | CH₃ | | cyclo-Propyl | CH₃ |
| | | F | | | F |
| | | Cl | | | Cl |
| | iso-Propyl | CH₃ | | Methoxy | CH₃ |
| | | F | | | F |
| | | Cl | | | Cl |
| | cyclo-Propyl | CH₃ | | Ethoxy | CH₃ |
| | | F | | | F |
| | | Cl | | | Cl |
| | Methoxy | CH₃ | | OCF₃ | CH₃ |
| | | F | | | F |
| | | Cl | | | Cl |
| | Ethoxy | CH₃ | n-Propyl | F | CH₃ |
| | | F | | | F |
| | | Cl | | | Cl |
| | OCF₃ | CH₃ | | Cl | CH₃ |
| | | F | | | F |
| | | Cl | | | Cl |
| Ethyl | F | CH₃ | | CN | CH₃ |
| | | F | | | F |
| | | Cl | | | Cl |
| | Cl | CH₃ | | CF₃ | CH₃ |
| | | F | | | F |
| | | Cl | | | Cl |

FIGURE 7B

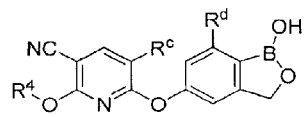

| R⁴ | Rᶜ | Rᵈ | R⁴ | Rᶜ | Rᵈ |
|---|---|---|---|---|---|
| n-Propyl | Methyl | CH₃ | iso-Propyl | cyclo-Propyl | CH₃ |
| | | F | | | F |
| | | Cl | | | Cl |
| | Ethyl | CH₃ | | Methoxy | CH₃ |
| | | F | | | F |
| | | Cl | | | Cl |
| | iso-Propyl | CH₃ | | Ethoxy | CH₃ |
| | | F | | | F |
| | | Cl | | | Cl |
| | cyclo-Propyl | CH₃ | | OCF₃ | CH₃ |
| | | F | | | F |
| | | Cl | | | Cl |
| | Methoxy | CH₃ | n-Butyl | F | CH₃ |
| | | F | | | F |
| | | Cl | | | Cl |
| | Ethoxy | CH₃ | | Cl | CH₃ |
| | | F | | | F |
| | | Cl | | | Cl |
| | OCF₃ | CH₃ | | CN | CH₃ |
| | | F | | | F |
| | | Cl | | | Cl |
| iso-Propyl | F | CH₃ | | CF₃ | CH₃ |
| | | F | | | F |
| | | Cl | | | Cl |
| | Cl | CH₃ | | Methyl | CH₃ |
| | | F | | | F |
| | | Cl | | | Cl |
| | CN | CH₃ | | Ethyl | CH₃ |
| | | F | | | F |
| | | Cl | | | Cl |
| | CF₃ | CH₃ | | iso-Propyl | CH₃ |
| | | F | | | F |
| | | Cl | | | Cl |
| | Methyl | CH₃ | | cyclo-Propyl | CH₃ |
| | | F | | | F |
| | | Cl | | | Cl |
| | Ethyl | CH₃ | | Methoxy | CH₃ |
| | | F | | | F |
| | | Cl | | | Cl |
| | iso-Propyl | CH₃ | | Ethoxy | CH₃ |
| | | F | | | F |
| | | Cl | | | Cl |

FIGURE 7C

| R⁴ | Rᶜ | Rᵈ | R⁴ | Rᶜ | Rᵈ |
|---|---|---|---|---|---|
| n-Butyl | OCF₃ | CH₃ | sec-Butyl | CN | CH₃ |
| | | F | | | F |
| | | Cl | | | Cl |
| iso-Butyl | F | CH₃ | | CF₃ | CH₃ |
| | | F | | | F |
| | | Cl | | | Cl |
| | Cl | CH₃ | | Methyl | CH₃ |
| | | F | | | F |
| | | Cl | | | Cl |
| | CN | CH₃ | | Ethyl | CH₃ |
| | | F | | | F |
| | | Cl | | | Cl |
| | CF₃ | CH₃ | | iso-Propyl | CH₃ |
| | | F | | | F |
| | | Cl | | | Cl |
| | Methyl | CH₃ | | cyclo-Propyl | CH₃ |
| | | F | | | F |
| | | Cl | | | Cl |
| | Ethyl | CH₃ | | Methoxy | CH₃ |
| | | F | | | F |
| | | Cl | | | Cl |
| | iso-Propyl | CH₃ | | Ethoxy | CH₃ |
| | | F | | | F |
| | | Cl | | | Cl |
| | cyclo-Propyl | CH₃ | | OCF₃ | CH₃ |
| | | F | | | F |
| | | Cl | | | Cl |
| | Methoxy | CH₃ | tert-Butyl | F | CH₃ |
| | | F | | | F |
| | | Cl | | | Cl |
| | Ethoxy | CH₃ | | Cl | CH₃ |
| | | F | | | F |
| | | Cl | | | Cl |
| | OCF₃ | CH₃ | | CN | CH₃ |
| | | F | | | F |
| | | Cl | | | Cl |
| sec-Butyl | F | CH₃ | | CF₃ | CH₃ |
| | | F | | | F |
| | | Cl | | | Cl |
| | Cl | CH₃ | | Methyl | CH₃ |
| | | F | | | F |
| | | Cl | | | Cl |

FIGURE 7D

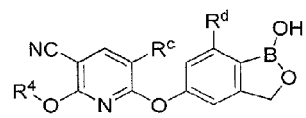

| $R^4$ | $R^c$ | $R^d$ | $R^4$ | $R^c$ | $R^d$ |
|---|---|---|---|---|---|
| tert-Butyl | Ethyl | CH₃ | n-Pentyl | Methoxy | CH₃ |
| | | F | | | F |
| | | Cl | | | Cl |
| | iso-Propyl | CH₃ | | Ethoxy | CH₃ |
| | | F | | | F |
| | | Cl | | | Cl |
| | cyclo-Propyl | CH₃ | | OCF₃ | CH₃ |
| | | F | | | F |
| | | Cl | | | Cl |
| | Methoxy | CH₃ | iso-Pentyl | F | CH₃ |
| | | F | | | F |
| | | Cl | | | Cl |
| | Ethoxy | CH₃ | | Cl | CH₃ |
| | | F | | | F |
| | | Cl | | | Cl |
| | OCF₃ | CH₃ | | CN | CH₃ |
| | | F | | | F |
| | | Cl | | | Cl |
| n-Pentyl | F | CH₃ | | CF₃ | CH₃ |
| | | F | | | F |
| | | Cl | | | Cl |
| | Cl | CH₃ | | Methyl | CH₃ |
| | | F | | | F |
| | | Cl | | | Cl |
| | CN | CH₃ | | Ethyl | CH₃ |
| | | F | | | F |
| | | Cl | | | Cl |
| | CF₃ | CH₃ | | iso-Propyl | CH₃ |
| | | F | | | F |
| | | Cl | | | Cl |
| | Methyl | CH₃ | | cyclo-Propyl | CH₃ |
| | | F | | | F |
| | | Cl | | | Cl |
| | Ethyl | CH₃ | | Methoxy | CH₃ |
| | | F | | | F |
| | | Cl | | | Cl |
| | iso-Propyl | CH₃ | | Ethoxy | CH₃ |
| | | F | | | F |
| | | Cl | | | Cl |
| | cyclo-Propyl | CH₃ | | OCF₃ | CH₃ |
| | | F | | | F |
| | | Cl | | | Cl |

FIGURE 7E

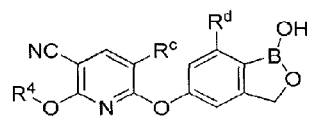

| $R^4$ | $R^c$ | $R^d$ | $R^4$ | $R^c$ | $R^d$ |
|---|---|---|---|---|---|
| neo-Pentyl | F | CH₃ | sec-Pentyl | CF₃ | CH₃ |
| | | F | | | F |
| | | Cl | | | Cl |
| | Cl | CH₃ | | Methyl | CH₃ |
| | | F | | | F |
| | | Cl | | | Cl |
| | CN | CH₃ | | Ethyl | CH₃ |
| | | F | | | F |
| | | Cl | | | Cl |
| | CF₃ | CH₃ | | iso-Propyl | CH₃ |
| | | F | | | F |
| | | Cl | | | Cl |
| | Methyl | CH₃ | | cyclo-Propyl | CH₃ |
| | | F | | | F |
| | | Cl | | | Cl |
| | Ethyl | CH₃ | | Methoxy | CH₃ |
| | | F | | | F |
| | | Cl | | | Cl |
| | iso-Propyl | CH₃ | | Ethoxy | CH₃ |
| | | F | | | F |
| | | Cl | | | Cl |
| | cyclo-Propyl | CH₃ | | OCF₃ | CH₃ |
| | | F | | | F |
| | | Cl | | | Cl |
| | Methoxy | CH₃ | n-Hexyl | F | CH₃ |
| | | F | | | F |
| | | Cl | | | Cl |
| | Ethoxy | CH₃ | | Cl | CH₃ |
| | | F | | | F |
| | | Cl | | | Cl |
| | OCF₃ | CH₃ | | CN | CH₃ |
| | | F | | | F |
| | | Cl | | | Cl |
| sec-Pentyl | F | CH₃ | | CF₃ | CH₃ |
| | | F | | | F |
| | | Cl | | | Cl |
| | Cl | CH₃ | | Methyl | CH₃ |
| | | F | | | F |
| | | Cl | | | Cl |
| | CN | CH₃ | | Ethyl | CH₃ |
| | | F | | | F |
| | | Cl | | | Cl |

FIGURE 7F

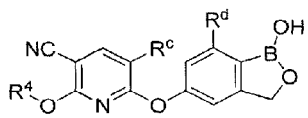

| $R^4$ | $R^c$ | $R^d$ |
|---|---|---|
| n-Hexyl | iso-Propyl | CH3 |
| | | F |
| | | Cl |
| | cyclo-Propyl | CH3 |
| | | F |
| | | Cl |
| | Methoxy | CH3 |
| | | F |
| | | Cl |
| | Ethoxy | CH3 |
| | | F |
| | | Cl |
| | OCF3 | CH3 |
| | | F |
| | | Cl |
| iso-Hexyl | F | CH3 |
| | | F |
| | | Cl |
| | Cl | CH3 |
| | | F |
| | | Cl |
| | CN | CH3 |
| | | F |
| | | Cl |
| | CF3 | CH3 |
| | | F |
| | | Cl |
| | Methyl | CH3 |
| | | F |
| | | Cl |
| | Ethyl | CH3 |
| | | F |
| | | Cl |
| | iso-Propyl | CH3 |
| | | F |
| | | Cl |
| | cyclo-Propyl | CH3 |
| | | F |
| | | Cl |
| | Methoxy | CH3 |
| | | F |
| | | Cl |
| iso-Hexyl | Ethoxy | CH3 |
| | | F |
| | | Cl |
| | OCF3 | CH3 |
| | | F |
| | | Cl |
| sec-Hexyl | F | CH3 |
| | | F |
| | | Cl |
| | Cl | CH3 |
| | | F |
| | | Cl |
| | CN | CH3 |
| | | F |
| | | Cl |
| | CF3 | CH3 |
| | | F |
| | | Cl |
| | Methyl | CH3 |
| | | F |
| | | Cl |
| | Ethyl | CH3 |
| | | F |
| | | Cl |
| | iso-Propyl | CH3 |
| | | F |
| | | Cl |
| | cyclo-Propyl | CH3 |
| | | F |
| | | Cl |
| | Methoxy | CH3 |
| | | F |
| | | Cl |
| | Ethoxy | CH3 |
| | | F |
| | | Cl |
| | OCF3 | CH3 |
| | | F |
| | | Cl |

| R⁴ | Rᶜ | Rᵈ | R⁴ | Rᶜ | Rᵈ |
|---|---|---|---|---|---|
| tetrahydro-2H-pyran-4-yl | F | CH₃ | tetrahydro-2H-pyran-4-yl | iso-Propyl | CH₃ |
| | | F | | | F |
| | | Cl | | | Cl |
| | Cl | CH₃ | | cyclo-Propyl | CH₃ |
| | | F | | | F |
| | | Cl | | | Cl |
| | CN | CH₃ | | Methoxy | CH₃ |
| | | F | | | F |
| | | Cl | | | Cl |
| | CF₃ | CH₃ | | Ethoxy | CH₃ |
| | | F | | | F |
| | | Cl | | | Cl |
| | Methyl | CH₃ | | OCF₃ | CH₃ |
| | | F | | | F |
| | | Cl | | | Cl |
| | Ethyl | CH₃ | | | |
| | | F | | | |
| | | Cl | | | |

FIGURE 8A

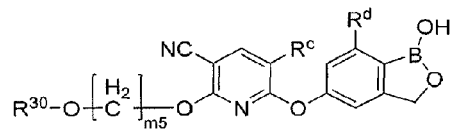

| | $R^{30}$ | $R^c$ | $R^d$ |
|---|---|---|---|
| 2 | H | F | CH₃ |
| | | | F |
| | | | Cl |
| | | Cl | CH₃ |
| | | | F |
| | | | Cl |
| | | CN | CH₃ |
| | | | F |
| | | | Cl |
| | | CF₃ | CH₃ |
| | | | F |
| | | | Cl |
| | | Methyl | CH₃ |
| | | | F |
| | | | Cl |
| | | Ethyl | CH₃ |
| | | | F |
| | | | Cl |
| | | iso-Propyl | CH₃ |
| | | | F |
| | | | Cl |
| | | cyclo-Propyl | CH₃ |
| | | | F |
| | | | Cl |
| | | Methoxy | CH₃ |
| | | | F |
| | | | Cl |
| | | Ethoxy | CH₃ |
| | | | F |
| | | | Cl |
| | | OCF₃ | CH₃ |
| | | | F |
| | | | Cl |
| | Methyl | F | CH₃ |
| | | | F |
| | | | Cl |
| | | Cl | CH₃ |
| | | | F |
| | | | Cl |
| 2 | Methyl | CN | CH₃ |
| | | | F |

| | $R^{30}$ | $R^c$ | $R^d$ |
|---|---|---|---|
| | | | Cl |
| | | CF₃ | CH₃ |
| | | | F |
| | | | Cl |
| | | Methyl | CH₃ |
| | | | F |
| | | | Cl |
| | | Ethyl | CH₃ |
| | | | F |
| | | | Cl |
| | | iso-Propyl | CH₃ |
| | | | F |
| | | | Cl |
| | | cyclo-Propyl | CH₃ |
| | | | F |
| | | | Cl |
| | | Methoxy | CH₃ |
| | | | F |
| | | | Cl |
| | | Ethoxy | CH₃ |
| | | | F |
| | | | Cl |
| | | OCF₃ | CH₃ |
| | | | F |
| | | | Cl |
| | Ethyl | F | CH₃ |
| | | | F |
| | | | Cl |
| | | Cl | CH₃ |
| | | | F |
| | | | Cl |
| | | CN | CH₃ |
| | | | F |
| | | | Cl |
| | | CF₃ | CH₃ |
| | | | F |
| | | | Cl |
| 2 | Ethyl | Methyl | CH₃ |
| | | | F |
| | | | Cl |
| | | Ethyl | CH₃ |

FIGURE 8B

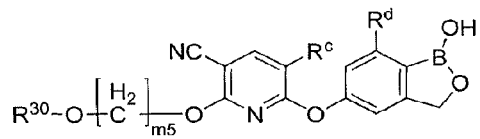

| R30 | Rc | Rd |  | R30 | Rc | Rd |
|---|---|---|---|---|---|---|
|  |  | F |  |  |  | F |
|  |  | Cl |  |  |  | Cl |
|  | iso-Propyl | CH3 |  |  | Ethoxy | CH3 |
|  |  | F |  |  |  | F |
|  |  | Cl |  |  |  | Cl |
|  | cyclo-Propyl | CH3 |  |  | OCF3 | CH3 |
|  |  | F |  |  |  | F |
|  |  | Cl |  |  |  | Cl |
|  | Methoxy | CH3 |  | iso-Propyl | F | CH3 |
|  |  | F |  |  |  | F |
|  |  | Cl |  |  |  | Cl |
|  | Ethoxy | CH3 |  |  | Cl | CH3 |
|  |  | F |  |  |  | F |
|  |  | Cl |  |  |  | Cl |
|  | OCF3 | CH3 |  |  | CN | CH3 |
|  |  | F |  |  |  | F |
|  |  | Cl |  |  |  | Cl |
| n-Propyl | F | CH3 |  |  | CF3 | CH3 |
|  |  | F |  |  |  | F |
|  |  | Cl |  |  |  | Cl |
|  | Cl | CH3 |  |  | Methyl | CH3 |
|  |  | F |  |  |  | F |
|  |  | Cl |  |  |  | Cl |
|  | CN | CH3 |  |  | Ethyl | CH3 |
|  |  | F |  |  |  | F |
|  |  | Cl |  |  |  | Cl |
|  | CF3 | CH3 |  |  | iso-Propyl | CH3 |
|  |  | F |  |  |  | F |
|  |  | Cl |  |  |  | Cl |
|  | Methyl | CH3 |  |  | cyclo-Propyl | CH3 |
|  |  | F |  |  |  | F |
|  |  | Cl |  |  |  | Cl |
|  | Ethyl | CH3 | 2 | iso-Propyl | Methoxy | CH3 |
|  |  | F |  |  |  | F |
|  |  | Cl |  |  |  | Cl |
| 2 | n-Propyl | iso-Propyl | CH3 |  | Ethoxy | CH3 |
|  |  | F |  |  |  | F |
|  |  | Cl |  |  |  | Cl |
|  | cyclo-Propyl | CH3 |  |  | OCF3 | CH3 |
|  |  | F |  |  |  | F |
|  |  | Cl |  |  |  | Cl |
|  | Methoxy | CH3 |  | cyclo-Propyl | F | CH3 |

FIGURE 8C

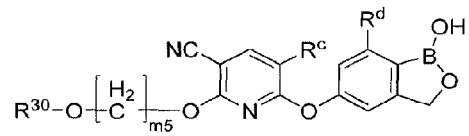

| | R³⁰ | Rᶜ | Rᵈ |
|---|---|---|---|
| | | | F |
| | | | Cl |
| | | Cl | CH₃ |
| | | | F |
| | | | Cl |
| | | CN | CH₃ |
| | | | F |
| | | | Cl |
| | | CF₃ | CH₃ |
| | | | F |
| | | | Cl |
| | | Methyl | CH₃ |
| | | | F |
| | | | Cl |
| | | Ethyl | CH₃ |
| | | | F |
| | | | Cl |
| | | iso-Propyl | CH₃ |
| | | | F |
| | | | Cl |
| | | cyclo-Propyl | CH₃ |
| | | | F |
| | | | Cl |
| | | Methoxy | CH₃ |
| | | | F |
| | | | Cl |
| | | Ethoxy | CH₃ |
| | | | F |
| | | | Cl |
| 2 | cyclo-Propyl | OCF₃ | CH₃ |
| | | | F |
| | | | Cl |
| | CF₃ | F | CH₃ |
| | | | F |
| | | | Cl |
| | | Cl | CH₃ |
| | | | F |
| | | | Cl |
| | | CN | CH₃ |
| | | | F |
| | | | Cl |
| | | CF₃ | CH₃ |

| | R³⁰ | Rᶜ | Rᵈ |
|---|---|---|---|
| | | | F |
| | | | Cl |
| | | Methyl | CH₃ |
| | | | F |
| | | | Cl |
| | | Ethyl | CH₃ |
| | | | F |
| | | | Cl |
| | | iso-Propyl | CH₃ |
| | | | F |
| | | | Cl |
| | | cyclo-Propyl | CH₃ |
| | | | F |
| | | | Cl |
| | | Methoxy | CH₃ |
| | | | F |
| | | | Cl |
| | | Ethoxy | CH₃ |
| | | | F |
| | | | Cl |
| | | OCF₃ | CH₃ |
| | | | F |
| | | | Cl |
| | H | F | CH₃ |
| | | | F |
| | | | Cl |
| 3 | H | Cl | CH₃ |
| | | | F |
| | | | Cl |
| | | CN | CH₃ |
| | | | F |
| | | | Cl |
| | | CF₃ | CH₃ |
| | | | F |
| | | | Cl |
| | | Methyl | CH₃ |
| | | | F |
| | | | Cl |
| | | Ethyl | CH₃ |
| | | | F |
| | | | Cl |
| | | iso-Propyl | CH₃ |

FIGURE 8D

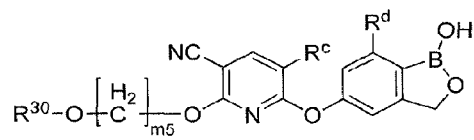

| m5 | R³⁰ | Rᶜ | Rᵈ |
|---|---|---|---|
| | | | F |
| | | | Cl |
| | | cyclo-Propyl | CH₃ |
| | | | F |
| | | | Cl |
| | | Methoxy | CH₃ |
| | | | F |
| | | | Cl |
| | | Ethoxy | CH₃ |
| | | | F |
| | | | Cl |
| | | OCF₃ | CH₃ |
| | | | F |
| | | | Cl |
| | Methyl | F | CH₃ |
| | | | F |
| | | | Cl |
| | | Cl | CH₃ |
| | | | F |
| | | | Cl |
| | | CN | CH₃ |
| | | | F |
| | | | Cl |
| 3 | Methyl | CF₃ | CH₃ |
| | | | F |
| | | | Cl |
| | | Methyl | CH₃ |
| | | | F |
| | | | Cl |
| | | Ethyl | CH₃ |
| | | | F |
| | | | Cl |
| | | iso-Propyl | CH₃ |
| | | | F |
| | | | Cl |
| | | cyclo-Propyl | CH₃ |
| | | | F |
| | | | Cl |
| | | Methoxy | CH₃ |
| | | | F |
| | | | Cl |
| | | Ethoxy | CH₃ |

| m5 | R³⁰ | Rᶜ | Rᵈ |
|---|---|---|---|
| | | | F |
| | | | Cl |
| | | OCF₃ | CH₃ |
| | | | F |
| | | | Cl |
| | Ethyl | F | CH₃ |
| | | | F |
| | | | Cl |
| | | Cl | CH₃ |
| | | | F |
| | | | Cl |
| | | CN | CH₃ |
| | | | F |
| | | | Cl |
| | | CF₃ | CH₃ |
| | | | F |
| | | | Cl |
| | | Methyl | CH₃ |
| | | | F |
| | | | Cl |
| 3 | Ethyl | Ethyl | CH₃ |
| | | | F |
| | | | Cl |
| | | iso-Propyl | CH₃ |
| | | | F |
| | | | Cl |
| | | cyclo-Propyl | CH₃ |
| | | | F |
| | | | Cl |
| | | Methoxy | CH₃ |
| | | | F |
| | | | Cl |
| | | Ethoxy | CH₃ |
| | | | F |
| | | | Cl |
| | | OCF₃ | CH₃ |
| | | | F |
| | | | Cl |
| | n-Propyl | F | CH₃ |
| | | | F |
| | | | Cl |
| | | Cl | CH₃ |

FIGURE 8E

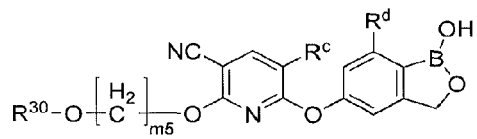

| $R^{30}$ | $R^c$ | $R^d$ |
|---|---|---|
| | | F |
| | | Cl |
| | CN | CH₃ |
| | | F |
| | | Cl |
| | CF₃ | CH₃ |
| | | F |
| | | Cl |
| | Methyl | CH₃ |
| | | F |
| | | Cl |
| | Ethyl | CH₃ |
| | | F |
| | | Cl |
| | iso-Propyl | CH₃ |
| | | F |
| | | Cl |
| 3 n-Propyl | cyclo-Propyl | CH₃ |
| | | F |
| | | Cl |
| | Methoxy | CH₃ |
| | | F |
| | | Cl |
| | Ethoxy | CH₃ |
| | | F |
| | | Cl |
| | OCF₃ | CH₃ |
| | | F |
| | | Cl |
| iso-Propyl | F | CH₃ |
| | | F |
| | | Cl |
| | Cl | CH₃ |
| | | F |
| | | Cl |
| | CN | CH₃ |
| | | F |
| | | Cl |
| | CF₃ | CH₃ |
| | | F |
| | | Cl |
| | Methyl | CH₃ |

| $R^{30}$ | $R^c$ | $R^d$ |
|---|---|---|
| | | F |
| | | Cl |
| | Ethyl | CH₃ |
| | | F |
| | | Cl |
| | iso-Propyl | CH₃ |
| | | F |
| | | Cl |
| | cyclo-Propyl | CH₃ |
| | | F |
| | | Cl |
| | Methoxy | CH₃ |
| | | F |
| | | Cl |
| 3 iso-Propyl | Ethoxy | CH₃ |
| | | F |
| | | Cl |
| | OCF₃ | CH₃ |
| | | F |
| | | Cl |
| | cyclo-Propyl | F |
| | | F |
| | | Cl |
| | Cl | CH₃ |
| | | F |
| | | Cl |
| | CN | CH₃ |
| | | F |
| | | Cl |
| | CF₃ | CH₃ |
| | | F |
| | | Cl |
| | Methyl | CH₃ |
| | | F |
| | | Cl |
| 3 cyclo-Propyl | Ethyl | CH₃ |
| | | F |
| | | Cl |
| | iso-Propyl | CH₃ |
| | | F |
| | | Cl |
| | cyclo-Propyl | CH₃ |

| $R^{30}$ | $R^c$ | $R^d$ |
|---|---|---|
| | | F |
| | | Cl |
| | Methoxy | CH$_3$ |
| | | F |
| | | Cl |
| | Ethoxy | CH$_3$ |
| | | F |

| $R^{30}$ | $R^c$ | $R^d$ |
|---|---|---|
| | | Cl |
| | OCF$_3$ | CH$_3$ |
| | | F |
| | | Cl |

FIGURE 9A

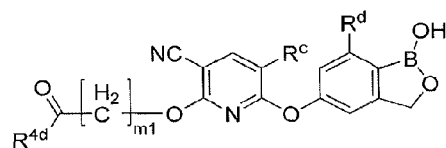

| m1 | R^4d | R^c | R^d |
|----|------|-----|-----|
| 1 | Methyl | F | CH_3 |
|  |  |  | F |
|  |  |  | Cl |
|  |  | Cl | CH_3 |
|  |  |  | F |
|  |  |  | Cl |
|  |  | CN | CH_3 |
|  |  |  | F |
|  |  |  | Cl |
|  |  | CF_3 | CH_3 |
|  |  |  | F |
|  |  |  | Cl |
|  |  | Methyl | CH_3 |
|  |  |  | F |
|  |  |  | Cl |
|  |  | Ethyl | CH_3 |
|  |  |  | F |
|  |  |  | Cl |
|  |  | iso-Propyl | CH_3 |
|  |  |  | F |
|  |  |  | Cl |
|  |  | cyclo-Propyl | CH_3 |
|  |  |  | F |
|  |  |  | Cl |
|  |  | Methoxy | CH_3 |
|  |  |  | F |
|  |  |  | Cl |
|  |  | Ethoxy | CH_3 |
|  |  |  | F |
|  |  |  | Cl |
|  |  | OCF_3 | CH_3 |
|  |  |  | F |
|  |  |  | Cl |
|  | Ethyl | F | CH_3 |
|  |  |  | F |
|  |  |  | Cl |
|  |  | Cl | CH_3 |
|  |  |  | F |
|  |  |  | Cl |
| 1 | Ethyl | CN | CH_3 |
|  |  |  | F |

| m1 | R^4d | R^c | R^d |
|----|------|-----|-----|
|  |  |  | Cl |
|  |  | CF_3 | CH_3 |
|  |  |  | F |
|  |  |  | Cl |
|  |  | Methyl | CH_3 |
|  |  |  | F |
|  |  |  | Cl |
|  |  | Ethyl | CH_3 |
|  |  |  | F |
|  |  |  | Cl |
|  |  | iso-Propyl | CH_3 |
|  |  |  | F |
|  |  |  | Cl |
|  |  | cyclo-Propyl | CH_3 |
|  |  |  | F |
|  |  |  | Cl |
|  |  | Methoxy | CH_3 |
|  |  |  | F |
|  |  |  | Cl |
|  |  | Ethoxy | CH_3 |
|  |  |  | F |
|  |  |  | Cl |
|  |  | OCF_3 | CH_3 |
|  |  |  | F |
|  |  |  | Cl |
|  | n-Propyl | F | CH_3 |
|  |  |  | F |
|  |  |  | Cl |
|  |  | Cl | CH_3 |
|  |  |  | F |
|  |  |  | Cl |
|  |  | CN | CH_3 |
|  |  |  | F |
|  |  |  | Cl |
|  |  | CF_3 | CH_3 |
|  |  |  | F |
|  |  |  | Cl |
| 1 | n-Propyl | Methyl | CH_3 |
|  |  |  | F |
|  |  |  | Cl |
|  |  | Ethyl | CH_3 |

FIGURE 9B

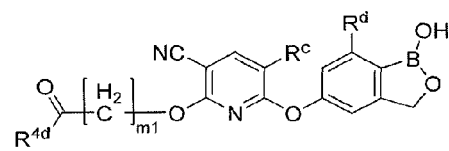

| m1 | R⁴ᵈ | Rᶜ | Rᵈ |
|---|---|---|---|
|  |  |  | F |
|  |  |  | Cl |
|  |  | iso-Propyl | CH₃ |
|  |  |  | F |
|  |  |  | Cl |
|  |  | cyclo-Propyl | CH₃ |
|  |  |  | F |
|  |  |  | Cl |
|  |  | Methoxy | CH₃ |
|  |  |  | F |
|  |  |  | Cl |
|  |  | Ethoxy | CH₃ |
|  |  |  | F |
|  |  |  | Cl |
|  |  | OCF₃ | CH₃ |
|  |  |  | F |
|  |  |  | Cl |
|  | iso-Propyl | F | CH₃ |
|  |  |  | F |
|  |  |  | Cl |
|  |  | Cl | CH₃ |
|  |  |  | F |
|  |  |  | Cl |
|  |  | CN | CH₃ |
|  |  |  | F |
|  |  |  | Cl |
|  |  | CF₃ | CH₃ |
|  |  |  | F |
|  |  |  | Cl |
|  |  | Methyl | CH₃ |
|  |  |  | F |
|  |  |  | Cl |
|  |  | Ethyl | CH₃ |
|  |  |  | F |
|  |  |  | Cl |
| 1 | iso-Propyl | iso-Propyl | CH₃ |
|  |  |  | F |
|  |  |  | Cl |
|  |  | cyclo-Propyl | CH₃ |
|  |  |  | F |
|  |  |  | Cl |
|  |  | Methoxy | CH₃ |

| m1 | R⁴ᵈ | Rᶜ | Rᵈ |
|---|---|---|---|
|  |  |  | F |
|  |  |  | Cl |
|  |  | Ethoxy | CH₃ |
|  |  |  | F |
|  |  |  | Cl |
|  |  | OCF₃ | CH₃ |
|  |  |  | F |
|  |  |  | Cl |
|  | cyclo-Propyl | F | CH₃ |
|  |  |  | F |
|  |  |  | Cl |
|  |  | Cl | CH₃ |
|  |  |  | F |
|  |  |  | Cl |
|  |  | CN | CH₃ |
|  |  |  | F |
|  |  |  | Cl |
|  |  | CF₃ | CH₃ |
|  |  |  | F |
|  |  |  | Cl |
|  |  | Methyl | CH₃ |
|  |  |  | F |
|  |  |  | Cl |
|  |  | Ethyl | CH₃ |
|  |  |  | F |
|  |  |  | Cl |
|  |  | iso-Propyl | CH₃ |
|  |  |  | F |
|  |  |  | Cl |
|  |  | cyclo-Propyl | CH₃ |
|  |  |  | F |
|  |  |  | Cl |
| 1 | cyclo-Propyl | Methoxy | CH₃ |
|  |  |  | F |
|  |  |  | Cl |
|  |  | Ethoxy | CH₃ |
|  |  |  | F |
|  |  |  | Cl |
|  |  | OCF₃ | CH₃ |
|  |  |  | F |
|  |  |  | Cl |
| 2 | Methyl | F | CH₃ |

FIGURE 9C

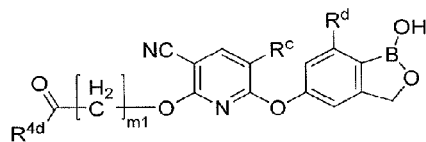

| m1 | R<sup>4d</sup> | R<sup>c</sup> | R<sup>d</sup> |
|---|---|---|---|
| | | | F |
| | | | Cl |
| | | Cl | CH₃ |
| | | | F |
| | | | Cl |
| | | CN | CH₃ |
| | | | F |
| | | | Cl |
| | | CF₃ | CH₃ |
| | | | F |
| | | | Cl |
| | | Methyl | CH₃ |
| | | | F |
| | | | Cl |
| | | Ethyl | CH₃ |
| | | | F |
| | | | Cl |
| | | iso-Propyl | CH₃ |
| | | | F |
| | | | Cl |
| | | cyclo-Propyl | CH₃ |
| | | | F |
| | | | Cl |
| | | Methoxy | CH₃ |
| | | | F |
| | | | Cl |
| | | Ethoxy | CH₃ |
| | | | F |
| | | | Cl |
| 2 | Methyl | OCF₃ | CH₃ |
| | | | F |
| | | | Cl |
| | Ethyl | F | CH₃ |
| | | | F |
| | | | Cl |
| | | Cl | CH₃ |
| | | | F |
| | | | Cl |
| | | CN | CH₃ |
| | | | F |
| | | | Cl |
| | | CF₃ | CH₃ |

| m1 | R<sup>4d</sup> | R<sup>c</sup> | R<sup>d</sup> |
|---|---|---|---|
| | | | F |
| | | | Cl |
| | | Methyl | CH₃ |
| | | | F |
| | | | Cl |
| | | Ethyl | CH₃ |
| | | | F |
| | | | Cl |
| | | iso-Propyl | CH₃ |
| | | | F |
| | | | Cl |
| | | cyclo-Propyl | CH₃ |
| | | | F |
| | | | Cl |
| | | Methoxy | CH₃ |
| | | | F |
| | | | Cl |
| | | Ethoxy | CH₃ |
| | | | F |
| | | | Cl |
| | | OCF₃ | CH₃ |
| | | | F |
| | | | Cl |
| | n-Propyl | F | CH₃ |
| | | | F |
| | | | Cl |
| 2 | n-Propyl | Cl | CH₃ |
| | | | F |
| | | | Cl |
| | | CN | CH₃ |
| | | | F |
| | | | Cl |
| | | CF₃ | CH₃ |
| | | | F |
| | | | Cl |
| | | Methyl | CH₃ |
| | | | F |
| | | | Cl |
| | | Ethyl | CH₃ |
| | | | F |
| | | | Cl |
| | | iso-Propyl | CH₃ |

FIGURE 9D

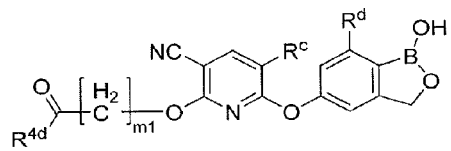

| m1 | R<sup>4d</sup> | R<sup>c</sup> | R<sup>d</sup> |
|---|---|---|---|
| | | | F |
| | | | Cl |
| | | cyclo-Propyl | CH₃ |
| | | | F |
| | | | Cl |
| | | Methoxy | CH₃ |
| | | | F |
| | | | Cl |
| | | Ethoxy | CH₃ |
| | | | F |
| | | | Cl |
| | | OCF₃ | CH₃ |
| | | | F |
| | | | Cl |
| | iso-Propyl | F | CH₃ |
| | | | F |
| | | | Cl |
| | | Cl | CH₃ |
| | | | F |
| | | | Cl |
| | | CN | CH₃ |
| | | | F |
| | | | Cl |
| 2 | iso-Propyl | CF₃ | CH₃ |
| | | | F |
| | | | Cl |
| | | Methyl | CH₃ |
| | | | F |
| | | | Cl |
| | | Ethyl | CH₃ |
| | | | F |
| | | | Cl |
| | | iso-Propyl | CH₃ |
| | | | F |
| | | | Cl |
| | | cyclo-Propyl | CH₃ |
| | | | F |
| | | | Cl |
| | | Methoxy | CH₃ |
| | | | F |
| | | | Cl |
| | | Ethoxy | CH₃ |

| m1 | R<sup>4d</sup> | R<sup>c</sup> | R<sup>d</sup> |
|---|---|---|---|
| | | | F |
| | | | Cl |
| | | OCF₃ | CH₃ |
| | | | F |
| | | | Cl |
| | | cyclo-Propyl | F |
| | | | CH₃ |
| | | | F |
| | | | Cl |
| | | Cl | CH₃ |
| | | | F |
| | | | Cl |
| | | CN | CH₃ |
| | | | F |
| | | | Cl |
| | | CF₃ | CH₃ |
| | | | F |
| | | | Cl |
| | | Methyl | CH₃ |
| | | | F |
| | | | Cl |
| 2 | cyclo-Propyl | Ethyl | CH₃ |
| | | | F |
| | | | Cl |
| | | iso-Propyl | CH₃ |
| | | | F |
| | | | Cl |
| | | cyclo-Propyl | CH₃ |
| | | | F |
| | | | Cl |
| | | Methoxy | CH₃ |
| | | | F |
| | | | Cl |
| | | Ethoxy | CH₃ |
| | | | F |
| | | | Cl |
| | | OCF₃ | CH₃ |
| | | | F |
| | | | Cl |
| 3 | Methyl | F | CH₃ |
| | | | F |
| | | | Cl |
| | | Cl | CH₃ |

FIGURE 9E

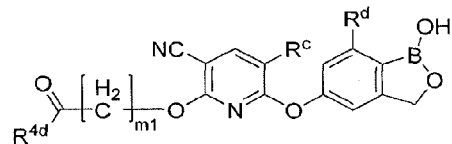

| m1 | R⁴ᵈ | Rᶜ | Rᵈ |
|---|---|---|---|
|  |  |  | F |
|  |  |  | Cl |
|  |  | CN | CH₃ |
|  |  |  | F |
|  |  |  | Cl |
|  |  | CF₃ | CH₃ |
|  |  |  | F |
|  |  |  | Cl |
|  |  | Methyl | CH₃ |
|  |  |  | F |
|  |  |  | Cl |
|  |  | Ethyl | CH₃ |
|  |  |  | F |
|  |  |  | Cl |
|  |  | iso-Propyl | CH₃ |
|  |  |  | F |
|  |  |  | Cl |
| 3 | Methyl | cyclo-Propyl | CH₃ |
|  |  |  | F |
|  |  |  | Cl |
|  |  | Methoxy | CH₃ |
|  |  |  | F |
|  |  |  | Cl |
|  |  | Ethoxy | CH₃ |
|  |  |  | F |
|  |  |  | Cl |
|  |  | OCF₃ | CH₃ |
|  |  |  | F |
|  |  |  | Cl |
|  | Ethyl | F | CH₃ |
|  |  |  | F |
|  |  |  | Cl |
|  |  | Cl | CH₃ |
|  |  |  | F |
|  |  |  | Cl |
|  |  | CN | CH₃ |
|  |  |  | F |
|  |  |  | Cl |
|  |  | CF₃ | CH₃ |
|  |  |  | F |
|  |  |  | Cl |
|  |  | Methyl | CH₃ |

| m1 | R⁴ᵈ | Rᶜ | Rᵈ |
|---|---|---|---|
|  |  |  | F |
|  |  |  | Cl |
|  |  | Ethyl | CH₃ |
|  |  |  | F |
|  |  |  | Cl |
|  |  | iso-Propyl | CH₃ |
|  |  |  | F |
|  |  |  | Cl |
|  |  | cyclo-Propyl | CH₃ |
|  |  |  | F |
|  |  |  | Cl |
|  |  | Methoxy | CH₃ |
|  |  |  | F |
|  |  |  | Cl |
| 3 | Ethyl | Ethoxy | CH₃ |
|  |  |  | F |
|  |  |  | Cl |
|  |  | OCF₃ | CH₃ |
|  |  |  | F |
|  |  |  | Cl |
|  | n-Propyl | F | CH₃ |
|  |  |  | F |
|  |  |  | Cl |
|  |  | Cl | CH₃ |
|  |  |  | F |
|  |  |  | Cl |
|  |  | CN | CH₃ |
|  |  |  | F |
|  |  |  | Cl |
|  |  | CF₃ | CH₃ |
|  |  |  | F |
|  |  |  | Cl |
|  |  | Methyl | CH₃ |
|  |  |  | F |
|  |  |  | Cl |
|  |  | Ethyl | CH₃ |
|  |  |  | F |
|  |  |  | Cl |
|  |  | iso-Propyl | CH₃ |
|  |  |  | F |
|  |  |  | Cl |
|  |  | cyclo-Propyl | CH₃ |

FIGURE 9F

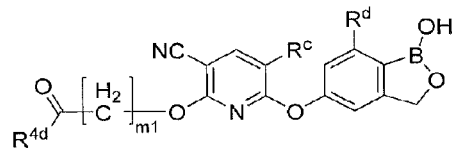

| m1 | R4d | Rc | Rd |
|----|-----|-----|-----|
| 3 | iso-Propyl | | F |
| | | | Cl |
| | | Methoxy | CH3 |
| | | | F |
| | | | Cl |
| | | Ethoxy | CH3 |
| | | | F |
| | | | Cl |
| | | OCF3 | CH3 |
| | | | F |
| | | | Cl |
| | | F | CH3 |
| | | | F |
| | | | Cl |
| | | Cl | CH3 |
| | | | F |
| | | | Cl |
| | | CN | CH3 |
| | | | F |
| | | | Cl |
| | | CF3 | CH3 |
| | | | F |
| | | | Cl |
| | | Methyl | CH3 |
| | | | F |
| | | | Cl |
| | | Ethyl | CH3 |
| | | | F |
| | | | Cl |
| | | iso-Propyl | CH3 |
| | | | F |
| | | | Cl |
| | | cyclo-Propyl | CH3 |
| | | | F |
| | | | Cl |
| | | Methoxy | CH3 |
| | | | F |
| | | | Cl |
| | | Ethoxy | CH3 |
| | | | F |
| | | | Cl |
| | | OCF3 | CH3 |

| m1 | R4d | Rc | Rd |
|----|-----|-----|-----|
| | | | F |
| | | | Cl |
| | cyclo-Propyl | F | CH3 |
| | | | F |
| | | | Cl |
| | | Cl | CH3 |
| | | | F |
| | | | Cl |
| 3 | cyclo-Propyl | CN | CH3 |
| | | | F |
| | | | Cl |
| | | CF3 | CH3 |
| | | | F |
| | | | Cl |
| | | Methyl | CH3 |
| | | | F |
| | | | Cl |
| | | Ethyl | CH3 |
| | | | F |
| | | | Cl |
| | | iso-Propyl | CH3 |
| | | | F |
| | | | Cl |
| | | cyclo-Propyl | CH3 |
| | | | F |
| | | | Cl |
| | | Methoxy | CH3 |
| | | | F |
| | | | Cl |
| | | Ethoxy | CH3 |
| | | | F |
| | | | Cl |
| | | OCF3 | CH3 |
| | | | F |
| | | | Cl |
| 4 | Methyl | F | CH3 |
| | | | F |
| | | | Cl |
| | | Cl | CH3 |
| | | | F |
| | | | Cl |
| | | CN | CH3 |

FIGURE 9G

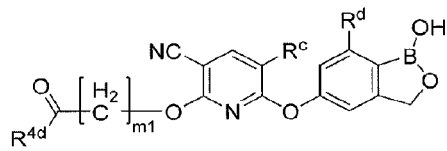

| m1 | R^{4d} | R^c | R^d |
|---|---|---|---|
| | | | F |
| | | | Cl |
| | | CF_3 | CH_3 |
| | | | F |
| | | | Cl |
| 4 | Methyl | Methyl | CH_3 |
| | | | F |
| | | | Cl |
| | | Ethyl | CH_3 |
| | | | F |
| | | | Cl |
| | | iso-Propyl | CH_3 |
| | | | F |
| | | | Cl |
| | | cyclo-Propyl | CH_3 |
| | | | F |
| | | | Cl |
| | | Methoxy | CH_3 |
| | | | F |
| | | | Cl |
| | | Ethoxy | CH_3 |
| | | | F |
| | | | Cl |
| | | OCF_3 | CH_3 |
| | | | F |
| | | | Cl |
| | Ethyl | F | CH_3 |
| | | | F |
| | | | Cl |
| | | Cl | CH_3 |
| | | | F |
| | | | Cl |
| | | CN | CH_3 |
| | | | F |
| | | | Cl |
| | | CF_3 | CH_3 |
| | | | F |
| | | | Cl |
| | | Methyl | CH_3 |
| | | | F |
| | | | Cl |
| | | Ethyl | CH_3 |

| m1 | R^{4d} | R^c | R^d |
|---|---|---|---|
| | | | F |
| | | | Cl |
| 4 | Ethyl | iso-Propyl | CH_3 |
| | | | F |
| | | | Cl |
| | | cyclo-Propyl | CH_3 |
| | | | F |
| | | | Cl |
| | | Methoxy | CH_3 |
| | | | F |
| | | | Cl |
| | | Ethoxy | CH_3 |
| | | | F |
| | | | Cl |
| | | OCF_3 | CH_3 |
| | | | F |
| | | | Cl |
| | n-Propyl | F | CH_3 |
| | | | F |
| | | | Cl |
| | | Cl | CH_3 |
| | | | F |
| | | | Cl |
| | | CN | CH_3 |
| | | | F |
| | | | Cl |
| | | CF_3 | CH_3 |
| | | | F |
| | | | Cl |
| | | Methyl | CH_3 |
| | | | F |
| | | | Cl |
| | | Ethyl | CH_3 |
| | | | F |
| | | | Cl |
| | | iso-Propyl | CH_3 |
| | | | F |
| | | | Cl |
| | | cyclo-Propyl | CH_3 |
| | | | F |
| | | | Cl |

FIGURE 9H

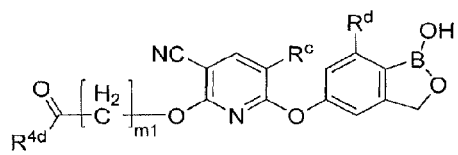

| m1 | R^{4d} | R^c | R^d |
|---|---|---|---|
| 4 | n-Propyl | Methoxy | CH_3 |
| | | | F |
| | | | Cl |
| | | Ethoxy | CH_3 |
| | | | F |
| | | | Cl |
| | | OCF_3 | CH_3 |
| | | | F |
| | | | Cl |
| | iso-Propyl | F | CH_3 |
| | | | F |
| | | | Cl |
| | | Cl | CH_3 |
| | | | F |
| | | | Cl |
| | | CN | CH_3 |
| | | | F |
| | | | Cl |
| | | CF_3 | CH_3 |
| | | | F |
| | | | Cl |
| | | Methyl | CH_3 |
| | | | F |
| | | | Cl |
| | | Ethyl | CH_3 |
| | | | F |
| | | | Cl |
| | | iso-Propyl | CH_3 |
| | | | F |
| | | | Cl |
| | | cyclo-Propyl | CH_3 |
| | | | F |
| | | | Cl |
| | | Methoxy | CH_3 |
| | | | F |
| | | | Cl |
| | | Ethoxy | CH_3 |
| | | | F |

| m1 | R^{4d} | R^c | R^d |
|---|---|---|---|
| | | | Cl |
| 4 | iso-Propyl | OCF_3 | CH_3 |
| | | | F |
| | | | Cl |
| | cyclo-Propyl | F | CH_3 |
| | | | F |
| | | | Cl |
| | | Cl | CH_3 |
| | | | F |
| | | | Cl |
| | | CN | CH_3 |
| | | | F |
| | | | Cl |
| | | CF_3 | CH_3 |
| | | | F |
| | | | Cl |
| | | Methyl | CH_3 |
| | | | F |
| | | | Cl |
| 4 | cyclo-Propyl | Ethyl | CH_3 |
| | | | F |
| | | | Cl |
| | | iso-Propyl | CH_3 |
| | | | F |
| | | | Cl |
| | | cyclo-Propyl | CH_3 |
| | | | F |
| | | | Cl |
| | | Methoxy | CH_3 |
| | | | F |
| | | | Cl |
| | | Ethoxy | CH_3 |
| | | | F |
| | | | Cl |
| | | OCF_3 | CH_3 |
| | | | F |
| | | | Cl |

BORON CONTAINING SMALL MOLECULES

CROSS-REFERENCE TO RELATED APPLICATIONS

This application is a continuation of U.S. patent application Ser. No. 14/133,537, filed Dec. 18, 2013, now U.S. Pat. No. 9,145,429, which is a continuation of U.S. patent application Ser. No. 13/015,487, filed Jan. 27, 2011, now U.S. Pat. No. 8,716,478, which claims the benefit of U.S. Provisional Patent Application No. 61/298,860, filed Jan. 27, 2010; U.S. Provisional Patent Application No. 61/354,187, filed Jun. 11, 2010; U.S. Provisional Patent Application No. 61/368,211, filed Jul. 27, 2010; U.S. Provisional Patent Application No. 61/368,205, filed Jul. 27, 2010; U.S. Provisional Patent Application No. 61/409,849, filed Nov. 3, 2010; and U.S. Provisional Patent Application No. 61/354,188, filed Jun. 11, 2010, each of which is incorporated by reference in its entirety for all purposes.

BACKGROUND FOR THE INVENTION

Boron-containing molecules, such as benzoxaboroles, useful as antiinflammatories, have been described previously, such as in U.S. patent application Ser. No. 12/399,015. Generally speaking, a benzoxaborole has the following structure and substituent numbering system:

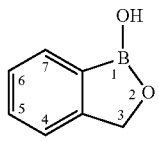

It has now been discovered that particular benzoxaborole classes are surprisingly effective antiinflammatory agents. This, and other uses of these benzoxaboroles are described herein.

Compounds which can inhibit the biological moieties described above, or treat diseases involving those biological moieties, would be a significant advance in the art.

SUMMARY OF THE INVENTION

In a first aspect, the invention provides a compound of the invention. In an exemplary embodiment, the compound is described herein or a pharmaceutically acceptable salt thereof. In an exemplary embodiment, the compound is according to a formula described herein.

The invention also provides pharmaceutical formulations, and methods of making and using the compounds described herein.

BRIEF DESCRIPTION OF THE DRAWINGS

FIG. 1B provides exemplary compounds of the invention.
FIG. 1I provides exemplary compounds of the invention.
FIG. 2D provides exemplary compounds of the invention.
FIG. 3F provides exemplary compounds of the invention.
FIG. 3G provides exemplary compounds of the invention.
FIG. 4A provides exemplary compounds of the invention.
FIG. 4B provides exemplary compounds of the invention.
FIG. 4C provides exemplary compounds of the invention.
FIG. 4D provides exemplary compounds of the invention.
FIG. 4E provides exemplary compounds of the invention.
FIG. 4F provides exemplary compounds of the invention.
FIG. 4G provides exemplary compounds of the invention.
FIG. 5A provides exemplary compounds of the invention.
FIG. 5B provides exemplary compounds of the invention.
FIG. 5C provides exemplary compounds of the invention.
FIG. 5D provides exemplary compounds of the invention.
FIG. 5E provides exemplary compounds of the invention.
FIG. 6B provides exemplary compounds of the invention.
FIG. 6C provides exemplary compounds of the invention.
FIG. 6D provides exemplary compounds of the invention.
FIG. 6E provides exemplary compounds of the invention.
FIG. 6F provides exemplary compounds of the invention.
FIG. 6G provides exemplary compounds of the invention.
FIG. 6H provides exemplary compounds of the invention.
FIG. 7A provides exemplary compounds of the invention.
FIG. 7B provides exemplary compounds of the invention.
FIG. 7C provides exemplary compounds of the invention.
FIG. 7D provides exemplary compounds of the invention.
FIG. 7E provides exemplary compounds of the invention.
FIG. 7F provides exemplary compounds of the invention.
FIG. 8A provides exemplary compounds of the invention.
FIG. 8B provides exemplary compounds of the invention.
FIG. 8C provides exemplary compounds of the invention.
FIG. 8D provides exemplary compounds of the invention.
FIG. 8E provides exemplary compounds of the invention.
FIG. 9A provides exemplary compounds of the invention.
FIG. 9B provides exemplary compounds of the invention.
FIG. 9C provides exemplary compounds of the invention.
FIG. 9D provides exemplary compounds of the invention.
FIG. 9E provides exemplary compounds of the invention.
FIG. 9F provides exemplary compounds of the invention.
FIG. 9G provides exemplary compounds of the invention.
FIG. 9H provides exemplary compounds of the invention.

DETAILED DESCRIPTION OF THE INVENTION

I. Definitions and Abbreviations

Figure 1A:
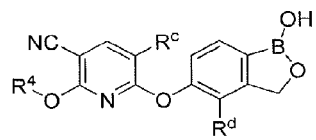
FIG. 1A provides exemplary compounds of the invention.
Figure 1C:
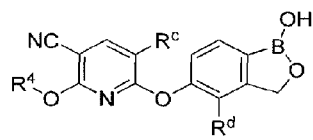
FIG. 1C provides exemplary compounds of the invention.
Figure 1D:
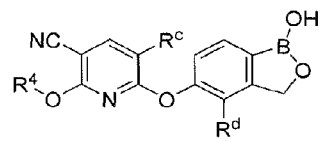
FIG. 1D provides exemplary compounds of the invention.
Figure 1E:
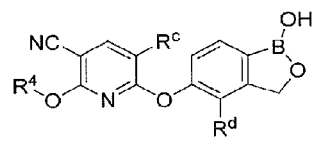
FIG. 1E provides exemplary compounds of the invention.
Figure 1F:
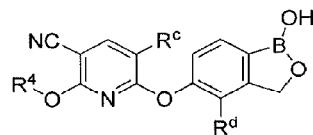
FIG. 1F provides exemplary compounds of the invention.
Figure 1G:
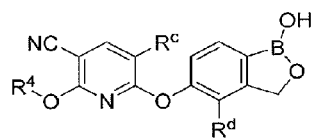
FIG. 1G provides exemplary compounds of the invention.
Figure 1H:
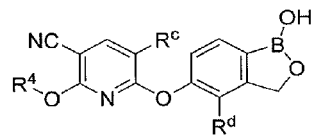
FIG. 1H provides exemplary compounds of the invention.
Figure 11:
Figure 2A:
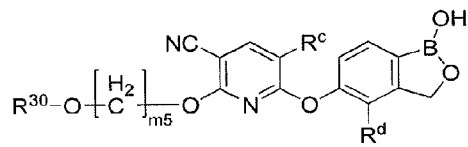
FIG. 2A provides exemplary compounds of the invention.
Figure 2B:
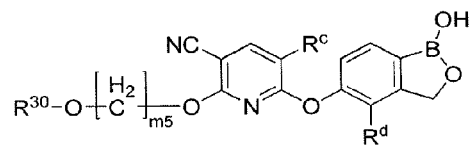
FIG. 2B provides exemplary compounds of the invention.
Figure 2C:
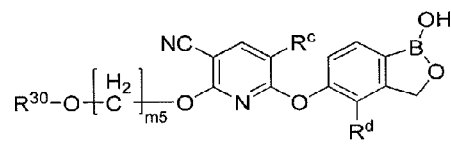
FIG. 2C provides exemplary compounds of the invention.
Figure 2E:
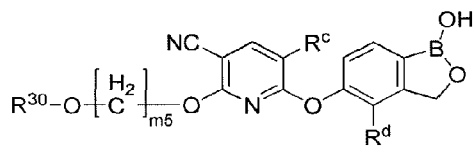
FIG. 2E provides exemplary compounds of the invention.
Figure 2F:
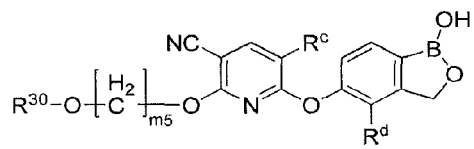
FIG. 2F provides exemplary compounds of the invention.
Figure 2G:
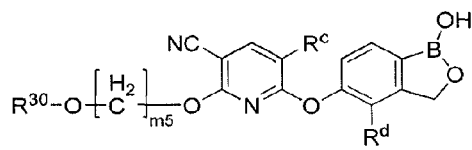
FIG. 2G provides exemplary compounds of the invention.
Figure 2H:
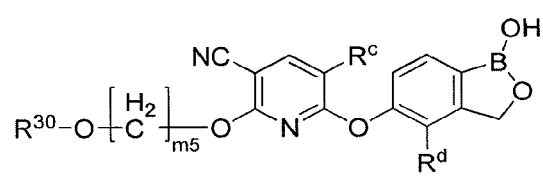
FIG. 2H provides exemplary compounds of the invention.
Figure 3A:
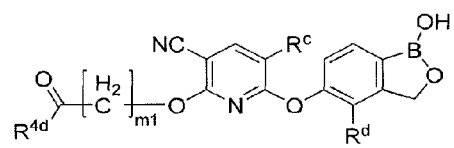
FIG. 3A provides exemplary compounds of the invention.
Figure 3B:
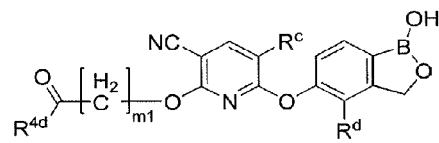
FIG. 3B provides exemplary compounds of the invention.
Figure 3C:
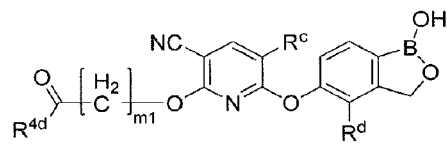
FIG. 3C provides exemplary compounds of the invention.
Figure 3D:
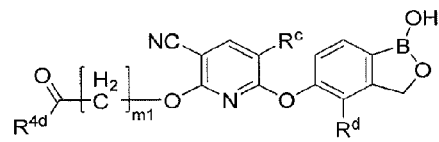
FIG. 3D provides exemplary compounds of the invention.
Figure 3E:
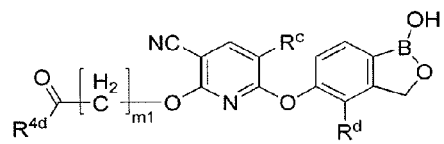
FIG. 3E provides exemplary compounds of the invention.
Figure 3H:
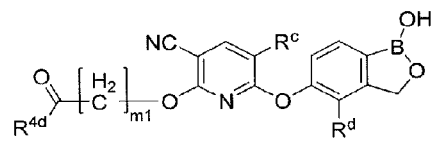
FIG. 3H provides exemplary compounds of the invention.
Figure 3I:
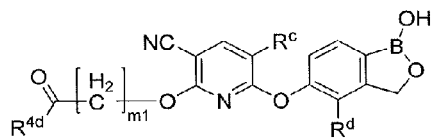
FIG. 3I provides exemplary compounds of the invention.
Figure 3J:
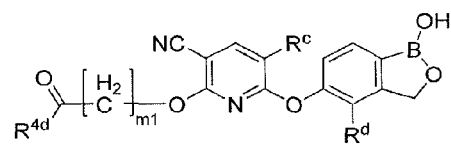
FIG. 3J provides exemplary compounds of the invention.
Figure 3K:
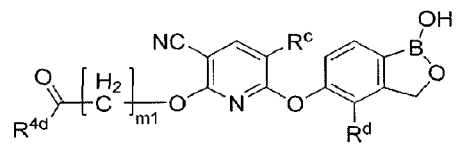
FIG. 3K provides exemplary compounds of the invention.
Figure 5F:
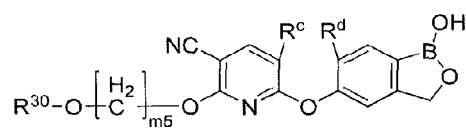
FIG. 5F provides exemplary compounds of the invention.
Figure 6A:
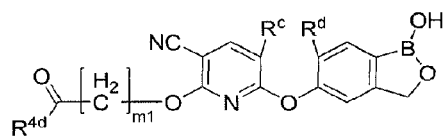
FIG. 6A provides exemplary compounds of the invention.
Figure 7G:
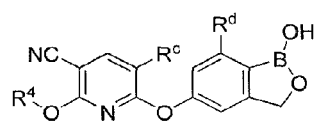
FIG. 7G provides exemplary compounds of the invention.
Figure 8F:
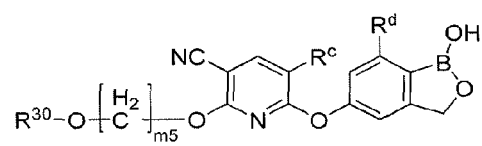
FIG. 8F provides exemplary compounds of the invention.

As used herein, the singular forms "a," "an", and "the" include plural references unless the context clearly dictates otherwise. For example, reference to "an active agent" includes a single active agent as well as two or more different active agents in combination. It is to be understood that present teaching is not limited to the specific dosage forms, carriers, or the like, disclosed herein and as such may vary.

The abbreviations used herein generally have their conventional meaning within the chemical and biological arts.

The following abbreviations have been used: Ac is acetyl; AcOH is acetic acid; ACTBr is cetyltrimethylammonium bromide; AIBN is azobisisobutyronitrile or 2,2 azobisisobutyronitrile; aq. is aqueous; Ar is aryl; $B_2pin_2$ is bis(pinacolato)diboron; Bn is, in general, benzyl [see Cbz for one example of an exception]; $(BnS)_2$ is benzyl disulfide; BnSH is benzyl thiol or benzyl mercaptan; BnBr is benzyl bromide; Boc is tert-butoxy carbonyl; $Boc_2O$ is di-tert-butyl dicarbonate; Bz is, is general, benzoyl; BzOOH is benzoyl peroxide; Cbz or Z is benzyloxycarbonyl or carboxybenzyl; $Cs_2CO_3$ is cesium carbonate; CSA is camphor sulfonic acid; CTAB is cetyltrimethylammonium bromide; Cy is cyclohexyl; DABCO is 1,4-diazabicyclo[2.2.2]octane; DCM is dichloromethane or methylene chloride; DHP is dihydropyran; DIAD is diisopropyl azodicarboxylate; DIEA or DIPEA is N,N-diisopropylethylamine; DMAP is 4-(dimethylamino)pyridine; DME is 1,2-dimethoxyethane; DMF is N,N-dimethylformamide; DMSO is dimethylsulfoxide; equiv or eq. is equivalent; EtOAc is ethyl acetate; EtOH is ethanol; $Et_2O$ is diethyl ether; EDCI is N-(3-dimethylaminopropyl)-N'-ethylcarbodiimide hydrochloride; ELS is evaporative light scattering; equiv or eq is equivalent; h is hours; HATU is O-(7-azabenzotriazol-1-yl)-N,N,N',N'-tetramethyluronium hexafluorophosphate; HOBt is N-hydroxybenzotriazole; HCl is hydrochloric acid; HPLC is high pressure liquid chromatography; ISCO Companion is automated flash chromatography equipment with fraction analysis by UV absorption available from Presearch; KOAc or AcOK is potassium acetate; $K_2CO_3$ is potassium carbonate; $LiAlH_4$ or LAH is lithium aluminum hydride; LDA is lithium diisopropylamide; LHMDS is lithium bis(trimethylsilyl) amide; KHMDS is potassium bis(trimethylsilyl) amide; LiOH is lithium hydroxide; m-CPBA is 3-chloroperoxybenzoic acid; MeCN or ACN is methyl cyanide or cyanomethane or ethanenitrile or acetonitrile which are all names for the same compound; MeOH is methanol; $MgSO_4$ is magnesium sulfate; mins or min is minutes; Mp or MP is melting point; $NaCNBH_3$ is sodium cyanoborohydride; NaOH is sodium hydroxide; $Na_2SO_4$ is sodium sulfate; NBS is N-bromosuccinimide; $NH_4Cl$ is ammonium chloride; NIS is N-iodosuccinimide; $N_2$ is nitrogen; NMM is N-methylmorpholine; n-BuLi is n-butyllithium; overnight is O/N; $PdCl_2(pddf)$ is 1,1'-Bis(diphenylphosphino) ferrocene]dichloropalladium(II); Pd/C is the catalyst known as palladium on carbon; $Pd_2(dba)_3$ is an organometallic catalyst known as tris(dibenzylideneacetone) dipalladium(0); Ra Ni or Raney Ni is Raney nickel; Ph is phenyl; PMB is p-methoxybenzyl; PrOH is 1-propanol; iPrOH is 2-propanol; $POCl_3$ is phosphorus chloride oxide; PTSA is para-toluene sulfonic acid; Pyr, or Pyr or Py as used herein means pyridine; RT or rt or r.t. is room temperature; sat. is saturated; Si-amine or Si—$NH_2$ is amino-functionalized silica, available from SiliCycle; Si-pyr is pyridyl-functionalized silica, available from SiliCycle; TEA or $Et_3N$ is triethylamine; TFA is trifluoroacetic acid; $Tf_2O$ is trifluoromethanesulfonic anhydride; THF is tetrahydrofuran; TFAA is trifluoroacetic anhydride; THP is tetrahydropyranyl; TMSI is trimethylsilyl iodide; $H_2O$ is water; $diNO_2PhSO_2Cl$ is dinitrophenyl sulfonyl chloride; $3$-F-$4$-$NO_2$-$PhSO_2Cl$ is 3-fluoro-4-nitrophenylsulfonyl chloride; $2$-MeO-$4$-$NO_2$-$PhSO_2Cl$ is 2-methoxy-4-nitrophenylsulfonyl chloride; and $(EtO)_2POCH_2COOEt$ is a triethylester of phosphonoacetic acid known as triethyl phosphonoacetate.

"Compound of the invention," as used herein refers to the compounds discussed herein, salts (such as pharmaceutically acceptable salts), prodrugs, solvates and hydrates of these compounds.

"Inhibiting" and "blocking," are used interchangeably herein to refer to the partial or full blockade of the expression of a pro-inflammatory cytokine by a method of the invention, which leads to a decrease in the amount of the cytokine in the animal.

Where substituent groups are specified by their conventional chemical formulae, written from left to right, they equally encompass the chemically identical substituents, which would result from writing the structure from right to left, e.g., —$CH_2O$— is intended to also recite —$OCH_2$—.

The term "poly" as used herein means at least 2. For example, a polyvalent metal ion is a metal ion having a valency of at least 2.

"Moiety" refers to the radical of a molecule that is attached to another moiety.

The symbol , whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "unsubstituted alkyl" encompasses straight or branched chain saturated hydrocarbon radicals. Examples of saturated hydrocarbon radicals include, but are not limited to, groups such as methyl, ethyl, n-propyl, isopropyl, n-butyl, t-butyl, isobutyl, sec-butyl, n-pentyl.

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, 6-quinolyl, dioxaborolane, dioxaborinane and dioxaborepane. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes those radicals in which an aryl group is attached through the next moiety to the rest of the molecule. Thus, the term "arylalkyl" is meant to include those radicals in which an aryl group is attached to an alkyl group (e.g., benzyl, 1-(3-nitrophenyl)ethyl and the like). A substituent such as benzyl or 1-(3-nitrophenyl)ethyl can also be represented by 'substituted alkyl' wherein the ethyl radical is substituted with a 3-nitrophenyl moiety. The term "aryloxy" is meant to include those radicals in which an aryl group is attached to an oxygen atom. The term "aryloxyalkyl" is meant to include those radicals in which an aryl group is attached to an oxygen atom which is then attached to an alkyl group (e.g., phenoxymethyl, 3-(1-naphthyloxy)propyl, and the like).

For brevity, the term "heteroaryl" when used in combination with other terms (e.g., heteroaryloxy, heteroarylthioxy, heteroarylalkyl) includes those radicals in which a heteroaryl group is attached through the next moiety to the rest of the molecule. Thus, the term "heteroarylalkyl" is meant to include those radicals in which a heteroaryl group is attached to an alkyl group (e.g., pyridylmethyl and the like). The term "heteroaryloxy" is meant to include those radicals in which a heteroaryl group is attached to an oxygen atom. The term "heteroaryloxyalkyl" is meant to include those radicals in which an aryl group is attached to an oxygen atom which is then attached to an alkyl group. (e.g., 2-pyridyloxymethyl and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR'R''', —NR"C(O)$_2$R', —NR'''—C(NR'R"R''')=NR"", —NR""—C(NR'R")=NR''', —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to (2m'+1), where m' is the total number of carbon atoms in such radical. R', R", R''', R"" and R""' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''', R'''' and R''''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: —R', —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR'R'', —NR"C(O)$_2$R', —NR''''—C(NR'R"R''')=NR'''', —NR''''—C(NR'R")=NR''', —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''', R'''' and R''''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''', R'''' and R''''' groups when more than one of these groups is present.

Two of the substituents on adjacent atoms of the aryl or heteroaryl ring may optionally be replaced with a substituent of the formula -T-C(O)—(CRR')$_q$-U-, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$-B-, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR'R'''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 to 7 atoms in the encircling arrangement. Unless otherwise specified, the ring optionally includes a heteroatom. Thus, the term "5- to 7-membered ring" includes, for example phenyl, pyridinyl and piperidinyl. The term "5- to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), germanium (Ge), aluminum (Al) and boron (B).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of a active agent to provide the desired local or systemic effect. A "Topically effective," "Cosmetically effective," "pharmaceutically effective," or "therapeutically effective" amount refers to the amount of drug needed to effect the desired therapeutic result.

"Topically effective" refers to a material that, when applied to the skin, nail, hair, claw or hoof produces a desired pharmacological result either locally at the place of application or systemically as a result of transdermal passage of an active ingredient in the material.

"Cosmetically effective" refers to a material that, when applied to the skin, nail, hair, claw or hoof, produces a desired cosmetic result locally at the place of application of an active ingredient in the material.

The terms "pharmaceutically acceptable salts" or "a salt thereof" are meant to include salts of the compounds of the invention which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the present invention provides compounds which are in a prodrug form. Prodrugs of the compounds or complexes described herein readily undergo chemical changes under physiological conditions to provide the compounds of the present invention. Additionally, prodrugs can be converted to the compounds of the present invention by chemical or biochemical methods in an ex vivo environment.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention. The graphic representations of racemic, ambiscalemic and scalemic or enantiomerically pure compounds used herein are taken from Maehr, *J. Chem. Ed.* 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The term "pharmaceutically acceptable carrier" or "pharmaceutically acceptable vehicle" refers to any formulation or carrier medium that provides the appropriate delivery of an effective amount of a active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in *Remington: The Science and Practice of Pharmacy*, 21st Ed., Lippincott, Williams & Wilkins (2005) which is incorporated herein by reference.

"Pharmaceutically acceptable topical carrier" and equivalent terms refer to pharmaceutically acceptable carriers, as described herein above, suitable for topical application. An inactive liquid or cream vehicle capable of suspending or dissolving the active agent(s), and having the properties of being nontoxic and non-inflammatory when applied to the skin, nail, hair, claw or hoof is an example of a pharmaceutically-acceptable topical carrier. This term is specifically intended to encompass carrier materials approved for use in topical cosmetics as well.

The term "pharmaceutically acceptable additive" refers to preservatives, antioxidants, fragrances, emulsifiers, dyes and excipients known or used in the field of drug formulation and that do not unduly interfere with the effectiveness of the biological activity of the active agent, and that is sufficiently non-toxic to the host or patient. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, other permeation enhancers, and other conventional components of topical or transdermal delivery formulations as are known in the art.

The terms "enhancement," "penetration enhancement" or "permeation enhancement" relate to an increase in the permeability of the skin, nail, hair, claw or hoof to a drug, so as to increase the rate at which the drug permeates through the skin, nail, hair, claw or hoof. The enhanced permeation effected through the use of such enhancers can be observed, for example, by measuring the rate of diffusion of the drug through animal skin, nail, hair, claw or hoof using a diffusion cell apparatus. A diffusion cell is described by Merritt et al. Diffusion Apparatus for Skin Penetration, *J of Controlled Release*, 1 (1984) pp. 161-162. The term "permeation enhancer" or "penetration enhancer" intends an agent or a mixture of agents, which, alone or in combination, act to increase the permeability of the skin, nail, hair or hoof to a drug.

The term "excipients" is conventionally known to mean carriers, diluents and/or vehicles used in formulating drug compositions effective for the desired use.

The terms "effective amount" or a "therapeutically effective amount" of a drug or pharmacologically active agent refers to a nontoxic but sufficient amount of the drug or agent to provide the desired effect. In the oral dosage forms of the present disclosure, an "effective amount" of one active of the combination is the amount of that active that is effective to provide the desired effect when used in combination with the other active of the combination. The amount that is "effective" will vary from subject to subject, depending on the age and general condition of the individual, the particular active agent or agents, and the appropriate "effective" amount in any individual case may be determined by one of ordinary skill in the art using routine experimentation.

The phrases "active ingredient", "therapeutic agent", "active", or "active agent" mean a chemical entity which can be effective in treating a targeted disorder, disease or condition.

The phrase "pharmaceutically acceptable" means moieties or compounds that are, within the scope of medical judgment, suitable for use in humans without causing undesirable biological effects such as undue toxicity, irritation, allergic response, and the like, for example.

The phrase "oral dosage form" means any pharmaceutical composition administered to a subject via the oral cavity, in which one or more antiplatelet agents and one or more acid inhibitors are administered concurrently in combination, optionally with one or more additional drugs. Exemplary oral dosage forms include tablets, capsules, films, powders, sachets, granules, solutions, solids, suspensions or as more than one distinct unit (e.g., granules, tablets, and/or capsules containing different actives) packaged together for co-administration, and other formulations known in the art. An oral dosage form can be one, two, three, four, five or six units. When the oral dosage form has multiple units, all of the units are contained within a single package, (e.g. a bottle or other form of packaging such as a blister pack). When the oral dosage form is a single unit, it may or may not be in a single package. In a preferred embodiment, the oral dosage form is one, two or three units. In a particularly preferred embodiment, the oral dosage form is one unit.

The phrase "unit", as used herein, refers to the number of discrete objects to be administered which comprise the dosage form. In some embodiments, the dosage form includes a compound of the invention in one capsule. This is a single unit. In some embodiments, the dosage form includes a compound of the invention as part of a therapeutically effective dosage of a cream or ointment. This is also a single unit. In some embodiments, the dosage form includes a compound of the invention and another active ingredient contained within one capsule, or as part of a therapeutically effective dosage of a cream or ointment or lotion. This is a single unit, whether or not the interior of the capsule includes multiple discrete granules of the active ingredient. In some embodiments, the dosage form includes a compound of the invention in one capsule, and the active ingredient in a second capsule. This is a two unit dosage form, such as two capsules or tablets, and so such units are contained in a single package. Thus the term 'unit' refers to the object which is administered to the animal, not to the interior components of the object.

The term, "prodrug", as defined herein, is a biologically inactive derivative of a parent drug molecule that exerts its pharmacological effect only after chemical and/or enzymatic conversion to its active form in vivo. Prodrugs include those designed to circumvent problems associated with delivery of the parent drug. This may be due to poor physicochemical properties, such as poor chemical stability or low aqueous solubility, and may also be due to poor pharmacokinetic properties, such as poor bioavailability or poor half-life. Thus, certain advantages of prodrugs may include improved chemical stability, absorption, and/or PK properties of the parent carboxylic acids. Prodrugs may also be used to make drugs more "patient friendly," by minimizing the frequency (e.g., once daily) or route of dosing (e.g., oral), or to improve the taste or odor if given orally, or to minimize pain if given parenterally.

In some embodiments, the prodrugs effect a "slow-release" of the active drug, thereby changing the time-course of D-serine increase in a manner that improves the efficacy of the parent compound. For example, compounds of the invention that extend D-serine level increases demonstrate improved efficacy in animal models of cognition (e.g., Contextual Fear Conditioning or Novel Object Recognition).

In some embodiments, the prodrugs are chemically more stable than the active drug, thereby improving formulation and delivery of the parent drug, compared to the drug alone.

Prodrugs for carboxylic acid analogs of the invention may include a variety of esters. In an exemplary embodiment, the pharmaceutical compositions of the invention include a carboxylic acid ester. In an exemplary embodiment, the prodrug is suitable for treatment/prevention of those diseases and conditions that require the drug molecule to cross the blood brain barrier. In an exemplary embodiment, the prodrug enters the brain, where it is converted into the active form of the drug molecule. In one embodiment, a prodrug is used to enable an active drug molecule to reach the inside of the eye after topical application of the prodrug to the eye. Additionally, a prodrug can be converted to its parent compound by chemical or biochemical methods in an ex vivo environment. For example, a prodrug can be slowly converted to its parent compound when placed in a transdermal patch reservoir with a suitable enzyme or chemical reagent.

The term "substrates" means pharmaceutically acceptable particulate materials such as beads, particles, granules, pellets, and the like, in an oral dosage form.

The term, "substantially free", as used herein, refers to a composition which contains none of the substance or less than a therapeutically effective amount of the substance for any known purpose for which the composition is intended.

The term "topical administration" refers to the application of a pharmaceutical agent to the external surface of the skin, nail, hair, claw or hoof, such that the agent crosses the external surface of the skin, nail, hair, claw or hoof and enters the underlying tissues. Topical administration includes application of the composition to intact skin, nail, hair, claw or hoof, or to an broken, raw or open wound of skin, nail, hair, claw or hoof. Topical administration of a pharmaceutical agent can result in a limited distribution of the agent to the skin and surrounding tissues or, when the agent is removed from the treatment area by the bloodstream, can result in systemic distribution of the agent.

The term "transdermal delivery" refers to the diffusion of an agent across the barrier of the skin, nail, hair, claw or hoof resulting from topical administration or other application of a composition. The stratum corneum acts as a barrier and few pharmaceutical agents are able to penetrate intact skin. In contrast, the epidermis and dermis are permeable to many solutes and absorption of drugs therefore occurs more readily through skin, nail, hair, claw or hoof that is abraded or otherwise stripped of the stratum corneum to expose the epidermis. Transdermal delivery includes injection or other delivery through any portion of the skin, nail, hair, claw or hoof or mucous membrane and absorption or permeation through the remaining portion. Absorption through intact skin, nail, hair, claw or hoof can be enhanced by placing the active agent in an appropriate pharmaceutically acceptable vehicle before application to the skin, nail, hair, claw or hoof. Passive topical administration may consist of applying the active agent directly to the treatment site in combination with emollients or penetration enhancers. As used herein, transdermal delivery is intended to include delivery by permeation through or past the integument, i.e. skin, nail, hair, claw or hoof.

The term "substrates" means pharmaceutically acceptable particulate materials such as beads, particles, granules, pellets, and the like, in an oral dosage form.

The term, "substantially free", as used herein, refers to a composition which contains none of the substance or less than a therapeutically effective amount of the substance for any known purpose for which the composition is intended.

The term "microbial infection" refers to any infection of a host tissue by an infectious agent including, but not limited to, viruses, bacteria, mycobacteria, fungus and parasites (see, e.g., Harrison's Principles of Internal Medicine, pp. 93-98 (Wilson et al., eds., 12th ed. 1991); Williams et al., *J. of Medicinal Chem.* 42:1481-1485 (1999), herein each incorporated by reference in their entirety).

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

A "human nail unit", as defined herein, can be the nail plate, the nail bed, proximal nail fold, lateral nail fold and combinations thereof.

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The term "amino-protecting group" means a protecting group suitable for preventing undesired reactions at an amino nitrogen. Representative amino-protecting groups include, but are not limited to, formyl; acyl groups, for example alkanoyl groups, such as acetyl, trichloroacetyl or trifluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like.

The term "hydroxy-protecting group" means a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

Also of use in the present invention are compounds that are poly- or multi-valent species, including, for example, species such as dimers, trimers, tetramers and higher homologs of the compounds of use in the invention or reactive analogues thereof. The poly- and multi-valent species can be assembled from a single species or more than one species of the invention. For example, a dimeric construct can be "homo-dimeric" or "heterodimeric." Moreover, poly- and multi-valent constructs in which a compound of the invention or a reactive analogue thereof, is attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of use in the invention). Moreover, the framework can be derivatized with a single species of the invention or more than one species of the invention.

Moreover, the present invention includes the use of compounds within the motif set forth in the formulae contained herein, which are functionalized to afford compounds having water-solubility that is enhanced relative to analogous compounds that are not similarly functionalized. Thus, any of the substituents set forth herein can be replaced with analogous radicals that have enhanced water solubility. For example, it is within the scope of the invention to replace a hydroxyl group with a diol, or an amine with a quaternary amine, hydroxy amine or similar more water-soluble moiety. In a preferred embodiment, additional water solubility is imparted by substitution at a site not essential for the activity towards the editing domain of the compounds set forth herein with a moiety that enhances the water solubility of the parent compounds. Methods of enhancing the water-solubility of organic compounds are known in the art. Such methods include, but are not limited to, functionalizing an organic nucleus with a permanently charged moiety, e.g., quaternary ammonium, or a group that is charged at a physiologically relevant pH, e.g. carboxylic acid, amine Other methods include, appending to the organic nucleus hydroxyl- or amine-containing groups, e.g. alcohols, polyols, polyethers, and the like. Representative examples include, but are not limited to, polylysine, polyethyleneimine, poly(ethyleneglycol) and poly(propyleneglycol). Suitable functionalization chemistries and strategies for these compounds are known in the art. See, for example, Dunn, R. L., et al., Eds. POLYMERIC DRUGS AND DRUG DELIVERY SYSTEMS, ACS Symposium Series Vol. 469, American Chemical Society, Washington, D.C. 1991.

II. Introduction

The present invention has multiple aspects. These aspects include inventions directed to compounds, pharmaceutical formulations, methods of treating a condition, enhancing an effect, increasing the production of a cytokine and/or chemokine, decreasing the production of a cytokine and/or chemokine, increasing the release of a cytokine and/or chemokine, decreasing the release of a cytokine and/or chemokine, or inhibiting a phosphodiesterase.

III. Compounds

IIIa

In a first aspect, the invention is a compound of the invention. In an exemplary embodiment, the invention is a compound described herein. In an exemplary embodiment, the compound is according to a formula described herein. In an exemplary embodiment, the compound is described in a figure described herein. In an exemplary embodiment, the compound is D230, D231, D232, D233, D234, D235, D236, D237, D238, D239, D240, D241, D242, D243, D244, D245, D246, D247, D248, D249, D250, D251, D252, D253, or D254.

In another aspect, the invention provides a compound having a structure according to the formula:

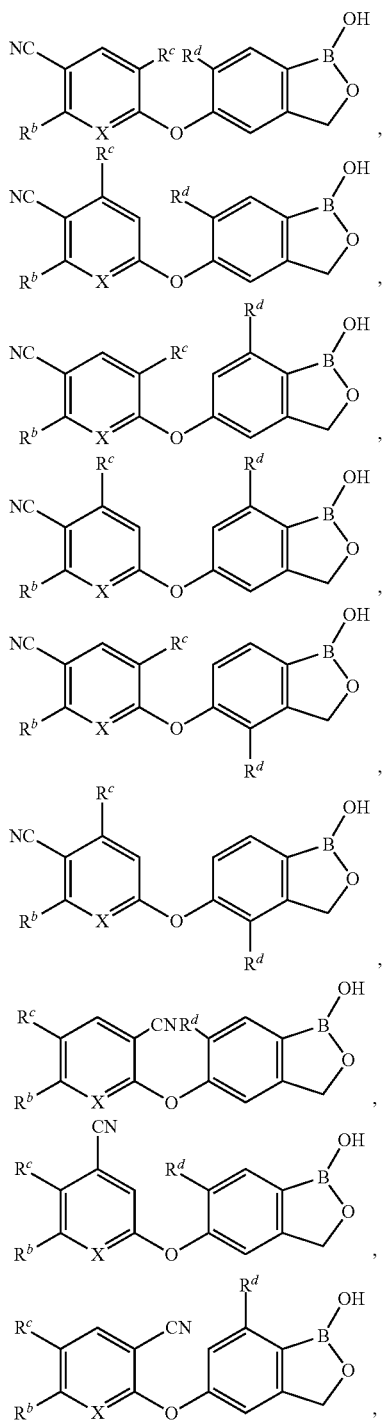

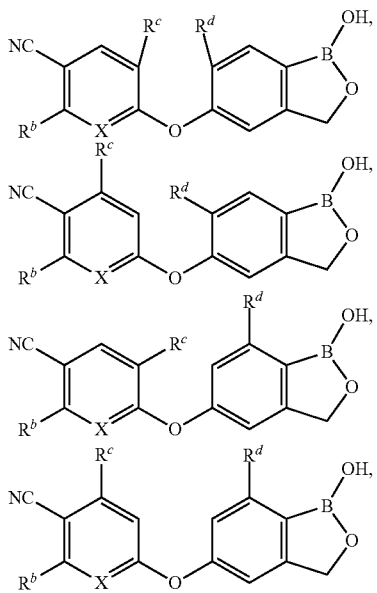

wherein $R^d$ is selected from the group consisting of H, halogen, and unsubstituted alkyl; $R^c$ is selected from the group consisting of cyano, halogen, substituted or unsubstituted alkyl, substituted or unsubstituted cycloalkyl, substituted or unsubstituted alkoxy, and substituted or unsubstituted cycloalkyloxy; X is N or CH; $R^b$ is selected from the group consisting of substituted or unsubstituted alkyl, C(O)$R^4$, C(O)O$R^4$, O$R^4$ and N$R^4R^5$; wherein $R^4$ and $R^5$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, with the proviso that $R^4$ and $R^5$, together with the atoms to which they are attached, are optionally combined to form a 4- or 5- or 6- or 7- or 8-membered substituted or unsubstituted heterocycloalkyl ring. In an exemplary embodiment, the compound has a structure according to the formula:

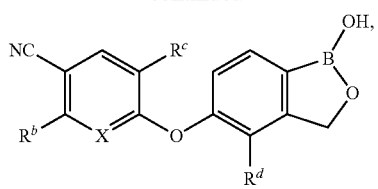

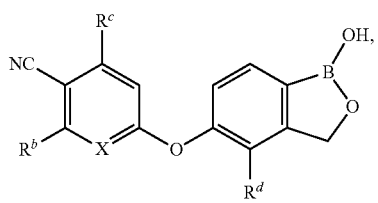

wherein $R^b$, $R^c$ and $R^d$ are as described herein. In an exemplary embodiment, the compound has a structure according to the formula:

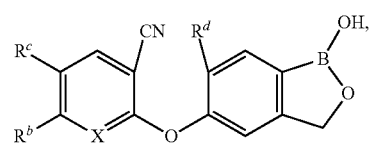

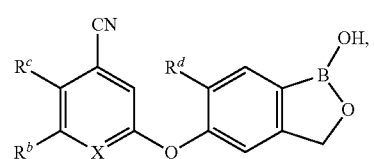

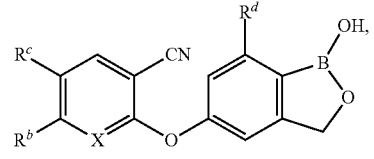

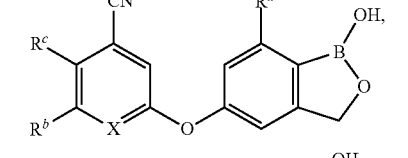

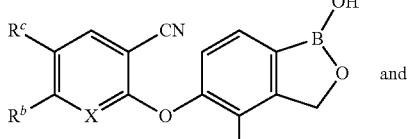

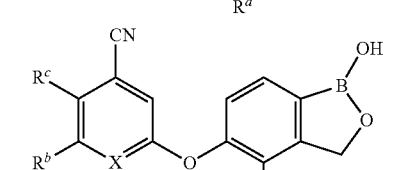

wherein $R^b$, $R^c$ and $R^d$ are as described herein.

In another aspect, the invention provides a compound having a structure according to the formula:

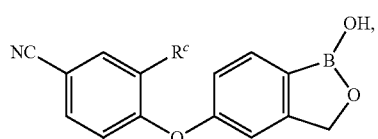

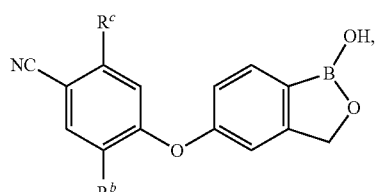

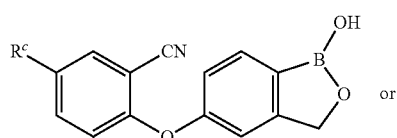

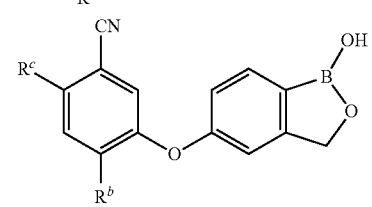

wherein $R^c$ is halogen; $R^b$ is selected from the group consisting of substituted or unsubstituted alkyl, $C(O)R^4$, $C(O)OR^4$, $OR^4$ and $NR^4R^5$; wherein $R^4$ and $R^5$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, with the proviso that $R^4$ and $R^5$, together with the atoms to which they are attached, are optionally combined to form a 4- to 8-membered substituted or unsubstituted heterocycloalkyl ring. In an exemplary embodiment, the compound has a structure according to the formula:

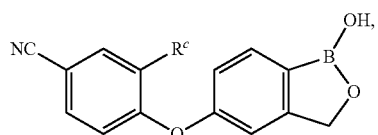

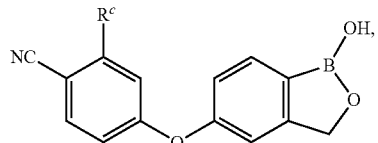

wherein $R^b$ and $R^c$ are as described herein. In an exemplary embodiment, the compound has a structure according to the formula:

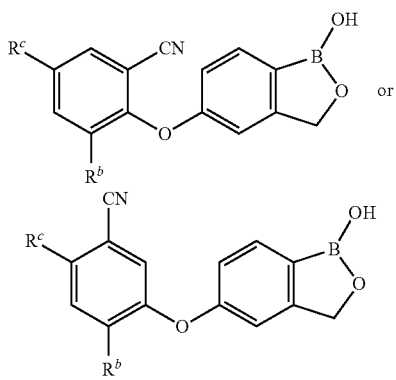

or wherein $R^b$ and $R^c$ are as described herein.

In another aspect, the invention provides a compound having a structure according to the formula:

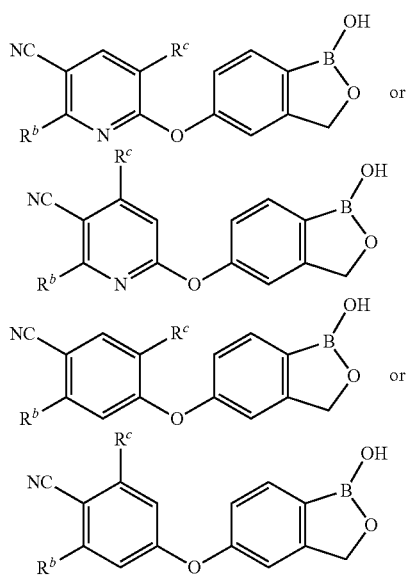

wherein $R^c$ and $R^b$ are as described herein. In another aspect, the invention provides a compound having a structure according to the formula:

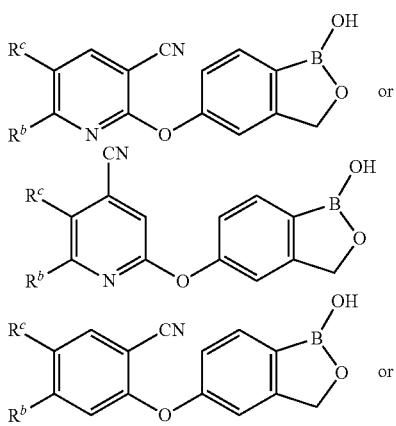

or

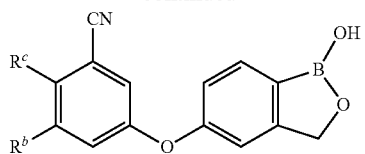

wherein $R^c$ and $R^b$ are as described herein.

In an exemplary embodiment, the compound has a formula which is:

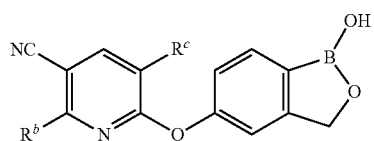

wherein $R^c$ and $R^b$ are as described herein. In an exemplary embodiment, the compound has a formula which is:

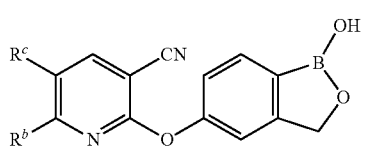

wherein $R^c$ and $R^b$ are as described herein.

In an exemplary embodiment, the compound has a formula which is:

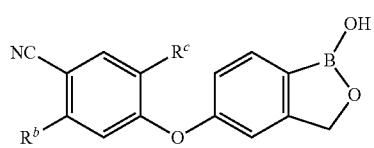

wherein $R^c$ and $R^b$ are as described herein. In an exemplary embodiment, the compound has a formula which is:

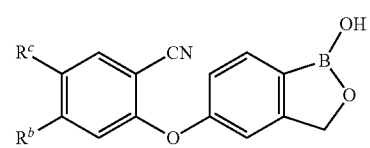

wherein $R^c$ and $R^b$ are as described herein

In another aspect, the invention provides a compound having a structure according to the formula:

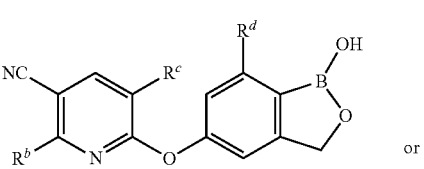

or

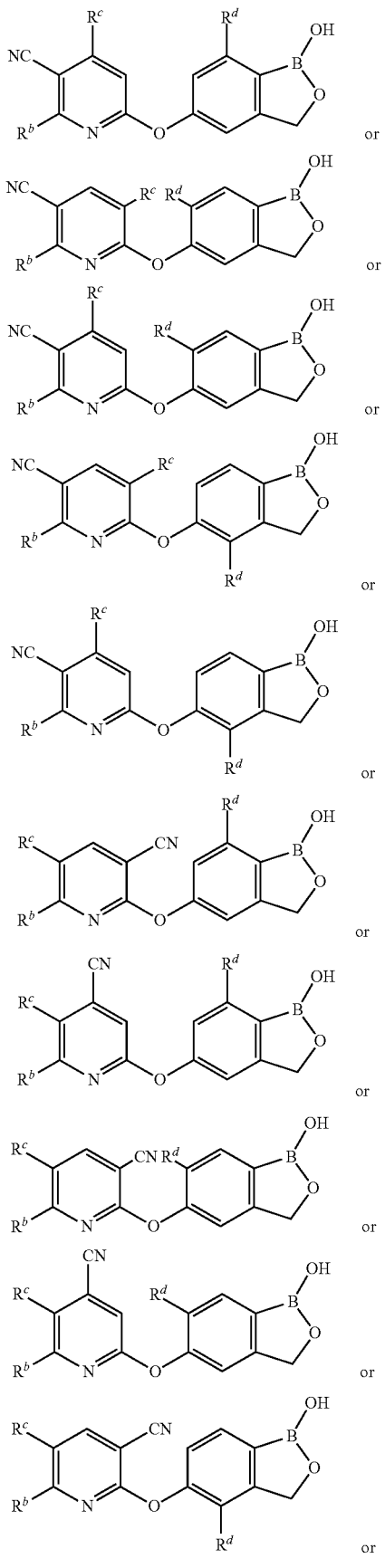

wherein $R^b$ and $R^c$ are as described herein and $R^d$ is halogen or unsubstituted alkyl. In an exemplary embodiment, $R^b$ and $R^c$ are as described herein and $R^d$ is halogen. In an exemplary embodiment, $R^b$ and $R^c$ are as described herein and $R^d$ is chlorine. In an exemplary embodiment, $R^b$ and $R^c$ are as described herein and $R^d$ is fluorine. In an exemplary embodiment, $R^b$ and $R^c$ are as described herein and $R^d$ is selected from the group consisting of methyl, ethyl, propyl, and isopropyl. In an exemplary embodiment, $R^b$ and $R^c$ are as described herein and $R^d$ is methyl. In an exemplary embodiment, the compound has a structure according to the formula:

wherein $R^b$ and $R^c$ are as described herein, and $R^d$ is halogen or unsubstituted alkyl. In an exemplary embodiment, the compound has a structure according to the formula:

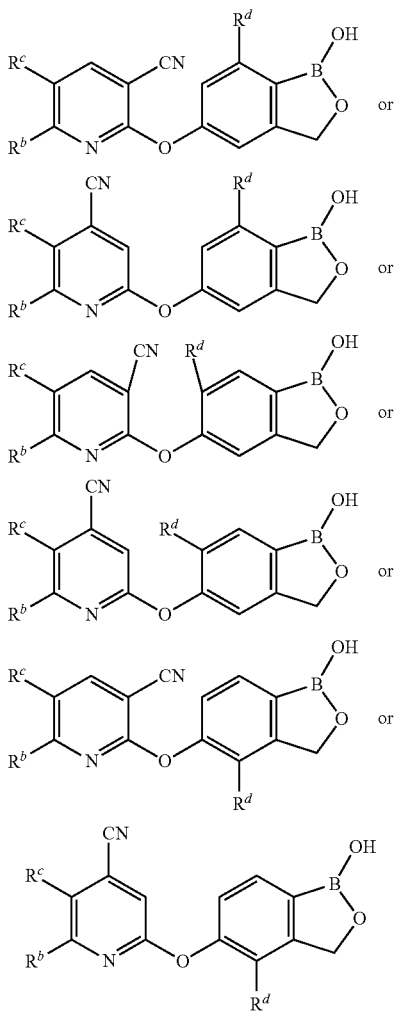

wherein $R^b$ and $R^c$ are as described herein, and $R^d$ is halogen or unsubstituted alkyl.

In another aspect, the invention provides a compound having a structure according to the formula:

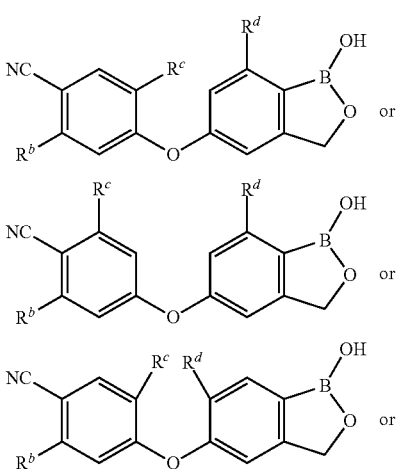

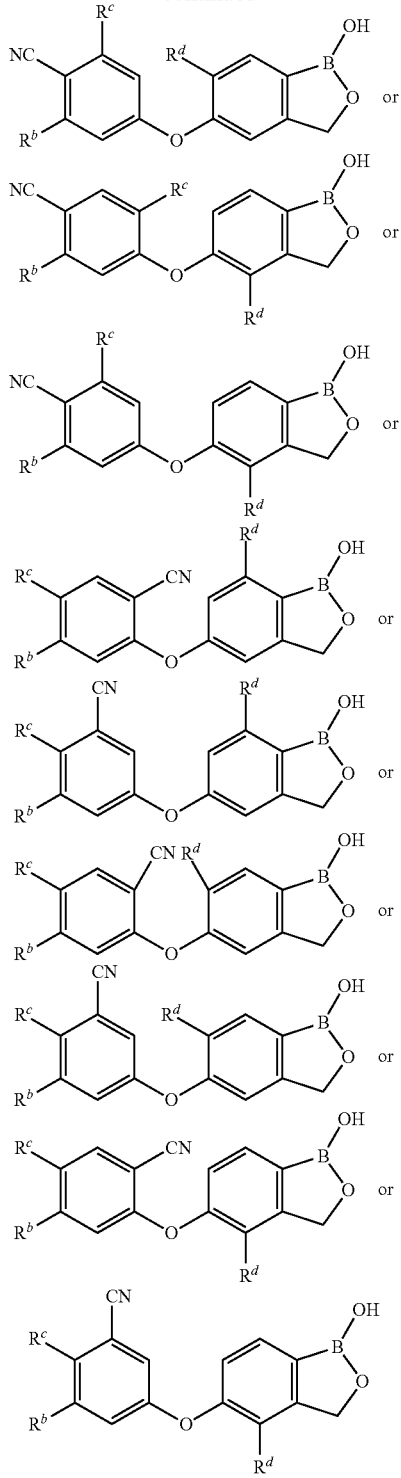

wherein $R^b$ and $R^c$ are as described herein and $R^d$ is halogen or unsubstituted alkyl. In an exemplary embodiment, $R^b$ and $R^c$ are as described herein and $R^d$ is halogen. In an exemplary embodiment, $R^b$ and $R^c$ are as described herein and $R^d$ is chlorine. In an exemplary embodiment, $R^b$ and $R^c$ are as described herein and $R^d$ is fluorine. In an exemplary embodiment, $R^b$ and $R^c$ are as described herein and $R^d$ is selected from the group consisting of methyl, ethyl, propyl, and isopropyl. In an exemplary embodiment, $R^b$ and $R^c$ are as described herein and $R^d$ is methyl. In an exemplary embodiment, the compound has a structure according to the formula:

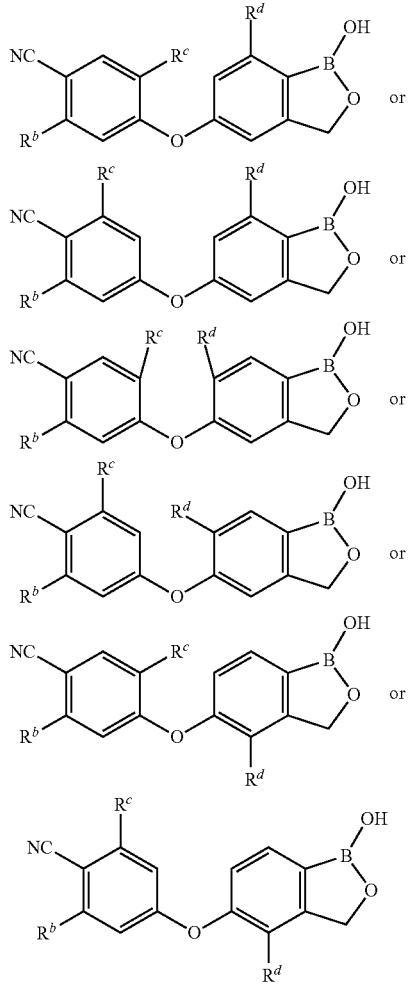

wherein $R^b$ and $R^c$ are as described herein, and $R^d$ is halogen or unsubstituted alkyl. In an exemplary embodiment, the compound has a structure according to the formula:

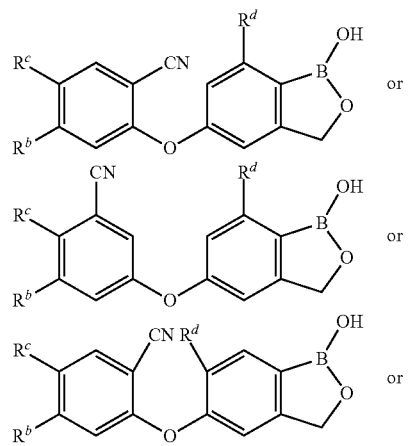

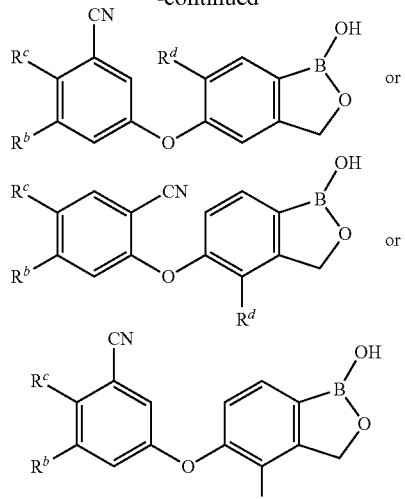

wherein $R^b$ and $R^c$ are as described herein, and $R^d$ is halogen or unsubstituted alkyl.

In an exemplary embodiment, X is CH, $R^b$ and $R^d$ are as described herein, and $R^c$ is fluorine. In an exemplary embodiment, X is N, $R^b$ and $R^d$ are as described herein, and $R^c$ is fluorine. In an exemplary embodiment, X is CH, $R^b$ and $R^d$ are as described herein, and $R^c$ is chlorine. In an exemplary embodiment, X is N, $R^b$ and $R^d$ are as described herein, and $R^c$ is chlorine. In an exemplary embodiment, X is CH, $R^b$ and $R^d$ are as described herein, and $R^c$ is bromine. In an exemplary embodiment, X is N, $R^b$ and $R^d$ are as described herein, and $R^c$ is bromine. In an exemplary embodiment, X is CH, $R^b$ and $R^d$ are as described herein, and $R^c$ is iodine. In an exemplary embodiment, X is N, $R^b$ and $R^d$ are as described herein, and $R^c$ is iodine. In an exemplary embodiment, X is CH, $R^b$ and $R^d$ are as described herein, and $R^c$ is cyano. In an exemplary embodiment, X is N, $R^b$ and $R^d$ are as described herein, and $R^c$ is cyano.

In an exemplary embodiment, X is CH, $R^d$ is H, $R^b$ is as described herein, and $R^c$ is fluorine. In an exemplary embodiment, X is CH, $R^d$ is F, $R^b$ is as described herein, and $R^c$ is fluorine. In an exemplary embodiment, X is N, $R^d$ is H, $R^b$ is as described herein, and $R^c$ is fluorine. In an exemplary embodiment, X is N, $R^d$ is F, $R^b$ is as described herein, and $R^c$ is fluorine. In an exemplary embodiment, X is CH, $R^d$ is H, $R^b$ is as described herein, and $R^c$ is chlorine. In an exemplary embodiment, X is CH, $R^d$ is F, $R^b$ is as described herein, and $R^c$ is chlorine. In an exemplary embodiment, X is N, $R^d$ is H, $R^b$ is as described herein, and $R^c$ is chlorine. In an exemplary embodiment, X is N, $R^d$ is F, $R^b$ is as described herein, and $R^c$ is chlorine. In an exemplary embodiment, X is CH, $R^d$ is H, $R^b$ is as described herein, and $R^c$ is bromine. In an exemplary embodiment, X is CH, $R^d$ is F, $R^b$ is as described herein, and $R^c$ is bromine. In an exemplary embodiment, X is N, $R^d$ is H, $R^b$ is as described herein, and $R^c$ is bromine. In an exemplary embodiment, X is N, $R^d$ is F, $R^b$ is as described herein, and $R^c$ is bromine. In an exemplary embodiment, X is CH, $R^d$ is H, $R^b$ is as described herein, and $R^c$ is iodine. In an exemplary embodiment, X is CH, $R^d$ is F, $R^b$ is as described herein, and $R^c$ is iodine. In an exemplary embodiment, X is N, $R^d$ is H, $R^b$ is as described herein, and $R^c$ is iodine. In an exemplary embodiment, X is N, $R^d$ is F, $R^b$ is as described herein, and $R^c$ is iodine. In an exemplary embodiment, X is CH, $R^d$ is H, $R^b$ is as described herein, and $R^c$ is cyano. In an exemplary embodiment, X is CH, $R^d$ is F, $R^b$ is as described herein, and $R^c$ is cyano. In an exemplary embodiment, X is N, $R^d$ is H, $R^b$ is as described herein, and $R^c$ is cyano. In an exemplary embodiment, X is N, $R^d$ is F, $R^b$ is as described herein, and $R^c$ is cyano.

In an exemplary embodiment, X is CH, $R^b$ and $R^d$ are as described herein, and $R^c$ is methyl or ethyl or propyl or isopropyl. In an exemplary embodiment, X is N, $R^b$ and $R^d$ are as described herein, and $R^c$ is methyl or ethyl or propyl or isopropyl. In an exemplary embodiment, X is CH or N, $R^b$ and $R^d$ are as described herein, and $R^c$ is butyl or isobutyl or sec-butyl or tertbutyl. In an exemplary embodiment, X is CH or N, $R^b$ and $R^d$ are as described herein, and $R^c$ is pentyl or isopentyl or neopentyl or secpentyl or hexyl or isohexyl or sec-hexyl. In an exemplary embodiment, X is CH, $R^b$ and $R^d$ are as described herein, and $R^c$ is cyclopropyl. In an exemplary embodiment, X is CH, $R^d$ is H, and $R^b$ is as described herein, and $R^c$ is cyclopropyl. In an exemplary embodiment, X is CH, $R^d$ is F, and $R^b$ is as described herein, and $R^c$ is cyclopropyl. In an exemplary embodiment, X is N, $R^b$ and $R^d$ are as described herein, and $R^c$ is cyclopropyl. In an exemplary embodiment, X is N, $R^d$ is H, and $R^b$ is as described herein, and $R^c$ is cyclopropyl. In an exemplary embodiment, X is N, $R^d$ is F, and $R^b$ is as described herein, and $R^c$ is cyclopropyl. In an exemplary embodiment, X is CH, $R^b$ and $R^d$ are as described herein, and $R^c$ is cyclobutyl. In an exemplary embodiment, X is CH, $R^d$ is H, and $R^b$ is as described herein, and $R^c$ is cyclobutyl. In an exemplary embodiment, X is CH, $R^d$ is F, and $R^b$ is as described herein, and $R^c$ is cyclobutyl. In an exemplary embodiment, X is N, $R^b$ and $R^d$ are as described herein, and $R^c$ is cyclobutyl. In an exemplary embodiment, X is N, $R^d$ is H, and $R^b$ is as described herein, and $R^c$ is cyclobutyl. In an exemplary embodiment, X is N, $R^d$ is F, and $R^b$ is as described herein, and $R^c$ is cyclobutyl. In an exemplary embodiment, X is CH or N, $R^b$ and $R^d$ are as described herein, and $R^c$ is cyclopentyl or cyclohexyl.

In an exemplary embodiment, X, $R^b$ and $R^d$ are as described herein, and $R^c$ is methoxy or ethoxy or propyloxy or isopropyloxy. In an exemplary embodiment, X, $R^b$ and $R^d$ are as described herein, and $R^c$ is butyloxy or isobutyloxy or sec-butyloxy or tertbutyloxy. In an exemplary embodiment, X, $R^b$ and $R^d$ are as described herein, and $R^c$ is pentyloxy or isopentyloxy or neopentyloxy or secpentyloxy or hexyloxy or isohexyloxy or sec-hexyloxy. In an exemplary embodiment, X, $R^b$ and $R^d$ are as described herein, and $R^c$ is cyclopropyloxy or cyclobutyloxy. In an exemplary embodiment, X, $R^b$ and $R^d$ are as described herein, and $R^c$ is cyclopentyloxy or cyclohexyloxy.

In an exemplary embodiment, $R^c$ is methoxy or ethoxy or propyloxy or isopropyloxy, wherein each is substituted with at least one halogen, and X, $R^b$ and $R^d$ are as described herein. In an exemplary embodiment, $R^c$ is methoxy or ethoxy or propyloxy or isopropyloxy, wherein each is substituted with one halogen, and X, $R^b$ and $R^d$ are as described herein. In an exemplary embodiment, $R^c$ is methoxy or ethoxy or propyloxy or isopropyloxy, wherein each is substituted with two halogens, and X, $R^b$ and $R^d$ are as described herein. In an exemplary embodiment, $R^c$ is methoxy or ethoxy or propyloxy or isopropyloxy, wherein each is substituted with three halogens, and X, $R^b$ and $R^d$ are as described herein.

In an exemplary embodiment, $R^c$ is butyloxy or isobutyloxy or sec-butyloxy or tertbutyloxy, wherein each is substituted with at least one halogen, and X, $R^b$ and $R^d$ are as described herein. In an exemplary embodiment, $R^c$ is butyloxy or isobutyloxy or sec-butyloxy or tertbutyloxy, wherein each is substituted with one halogen, and X, $R^b$ and $R^d$ are as described herein. In an exemplary embodiment, $R^c$ is butyloxy or isobutyloxy or sec-butyloxy or tertbutyloxy, wherein each is substituted with two halogens, and X, $R^b$ and $R^d$ are as described herein. In an exemplary embodiment, $R^c$ is butyloxy or isobutyloxy or sec-butyloxy or tertbutyloxy, wherein each is substituted with three halogens, and X, $R^b$ and $R^d$ are as described herein.

In an exemplary embodiment, $R^c$ is pentyloxy or isopentyloxy or neopentyloxy or secpentyloxy or hexyloxy or isohexyloxy or sec-hexyloxy, wherein each is substituted with at least one halogen, and X, $R^b$ and $R^d$ are as described herein. In an exemplary embodiment, $R^c$ is pentyloxy or isopentyloxy or neopentyloxy or secpentyloxy or hexyloxy or isohexyloxy or sec-hexyloxy, wherein each is substituted with one halogen, and X, $R^b$ and $R^d$ are as described herein. In an exemplary embodiment, $R^c$ is pentyloxy or isopentyloxy or neopentyloxy or secpentyloxy or hexyloxy or isohexyloxy or sec-hexyloxy, wherein each is substituted with at least two halogens, and X, $R^b$ and $R^d$ are as described herein. In an exemplary embodiment, $R^c$ is pentyloxy or isopentyloxy or neopentyloxy or secpentyloxy or hexyloxy or isohexyloxy or sec-hexyloxy, wherein each is substituted with three halogens, and X, $R^b$ and $R^d$ are as described herein.

In an exemplary embodiment, X is CH, $R^b$ and $R^d$ are as described herein, and $R^c$ is trifluoromethyl. In an exemplary embodiment, X is CH, $R^d$ is H, and $R^b$ is as described herein, and $R^c$ is trifluoromethyl. In an exemplary embodiment, X is CH, $R^d$ is F, and $R^b$ is as described herein, and $R^c$ is trifluoromethyl. In an exemplary embodiment, X is N, $R^b$ and $R^d$ are as described herein, and $R^c$ is trifluoromethyl. In an exemplary embodiment, X is N, $R^d$ is H, and $R^b$ is as described herein, and $R^c$ is trifluoromethyl. In an exemplary embodiment, X is N, $R^d$ is F, and $R^b$ is as described herein, and $R^c$ is trifluoromethyl. In an exemplary embodiment, X is CH, $R^b$ and $R^d$ are as described herein, and $R^c$ is difluoromethyl. In an exemplary embodiment, X is CH, $R^d$ is H, and $R^b$ is as described herein, and $R^c$ is difluoromethyl. In an exemplary embodiment, X is CH, $R^d$ is F, and $R^b$ is as described herein, and $R^c$ is difluoromethyl. In an exemplary embodiment, X is N, $R^b$ and $R^d$ are as described herein, and $R^c$ is difluoromethyl. In an exemplary embodiment, X is N, $R^d$ is H, and $R^b$ is as described herein, and $R^c$ is difluoromethyl. In an exemplary embodiment, X is N, $R^d$ is F, and $R^b$ is as described herein, and $R^c$ is difluoromethyl. In an exemplary embodiment, X is CH, $R^b$ and $R^d$ are as described herein, and $R^c$ is fluoromethyl. In an exemplary embodiment, X is CH, $R^d$ is H, and $R^b$ is as described herein, and $R^c$ is fluoromethyl. In an exemplary embodiment, X is CH, $R^d$ is F, and $R^b$ is as described herein, and $R^c$ is fluoromethyl. In an exemplary embodiment, X is N, $R^b$ and $R^d$ are as described herein, and $R^c$ is fluoromethyl. In an exemplary embodiment, X is N, $R^d$ is H, and $R^b$ is as described herein, and $R^c$ is fluoromethyl. In an exemplary embodiment, X is N, $R^d$ is F, and $R^b$ is as described herein, and $R^c$ is fluoromethyl. In an exemplary embodiment, X is CH, $R^b$ and $R^d$ are as described herein, and $R^c$ is trichloromethyl. In an exemplary embodiment, X is CH, $R^d$ is H, and $R^b$ is as described herein, and $R^c$ is trichloromethyl. In an exemplary embodiment, X is CH, $R^d$ is F, and $R^b$ is as described herein, and $R^c$ is trichloromethyl. In an exemplary embodiment, X is N, $R^b$ and $R^d$ are as described herein, and $R^c$ is trichloromethyl. In an exemplary embodiment, X is N, $R^d$ is H, and $R^b$ is as described herein, and $R^c$ is trichloromethyl. In an exemplary embodiment, X is N, $R^d$ is F, and $R^b$ is as described herein, and $R^c$ is trichloromethyl. In an exemplary embodiment, X is CH, $R^b$ and $R^d$ are as described herein, and $R^c$ is dichloromethyl. In an exemplary embodiment, X is CH, $R^d$ is H, and $R^b$ is as described herein, and $R^c$ is dichloromethyl. In an exemplary embodiment, X is CH, $R^d$ is F, and $R^b$ is as described herein, and $R^c$ is dichloromethyl. In an exemplary embodiment, X is N, $R^b$ and $R^d$ are as described herein, and $R^c$ is dichloromethyl. In an exemplary embodiment, X is N, $R^d$ is H, and $R^b$ is as described herein, and $R^c$ is dichloromethyl. In an exemplary embodiment, X is N, $R^d$ is F, and $R^b$ is as described herein, and $R^c$ is dichloromethyl. In an exemplary embodiment, X is CH, $R^b$ and $R^d$ are as described herein, and $R^c$ is chloromethyl. In an exemplary embodiment, X is CH, $R^d$ is H, and $R^b$ is as described herein, and $R^c$ is chloromethyl. In an exemplary embodiment, X is CH, $R^d$ is F, and $R^b$ is as described herein, and $R^c$ is chloromethyl. In an exemplary embodiment, X is N, $R^b$ and $R^d$ are as described herein, and $R^c$ is chloromethyl. In an exemplary embodiment, X is N, $R^d$ is H, and $R^b$ is as described herein, and $R^c$ is chloromethyl. In an exemplary embodiment, X is N, $R^d$ is F, and $R^b$ is as described herein, and $R^c$ is chloromethyl.

In an exemplary embodiment, X, $R^c$ and $R^d$ are as described herein, and $R^b$ is selected from the group consisting of —$CH_2C(O)OR^6$, —$CH_2NHC(O)R^6$, —$CH_2NR^6R^7$, wherein each $R^6$ and $R^7$ are independently selected from the group consisting of H, methyl, trifluoromethyl, ethyl, propyl, butyl, t-butyl, —C(O)H, wherein $R^6$ and $R^7$, together with the nitrogen to which they are attached, are optionally combined to form a member selected from the group consisting of 4-methylpiperazinyl, piperidinyl, morpholino and pyrrolidinyl. In an exemplary embodiment, X, $R^c$ and $R^d$ are as described herein, and $R^b$ is selected from the group consisting of methyl, trifluoromethyl, —$CH_2OH$, —$CH_2N(CH_3)_2$,

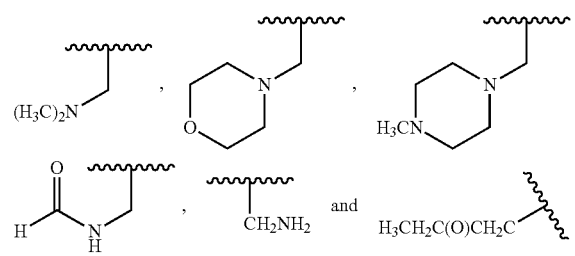

In an exemplary embodiment, $R^c$ and $R^d$ are as described herein, and $R^b$ is selected from the group consisting of —$OR^4$, —$C(O)R^4$, —$C(O)OR^4$ and —$C(O)NR^4R^5$, wherein each $R^4$ and $R^5$ are independently selected from the group consisting of H, methyl, ethyl, methoxyethyl, cyclopropyl, —$CH_2C(O)OR^8$, —$CH_2C(O)NR^8R^9$, 2-(dimethylamino)ethyl, 2-pyridinylmethyl, 2-(4-cyano)pyridinyl, with the proviso that $R^8$ and $R^9$, together with the atoms to which they are attached, are optionally combined to form a 5- to 7-membered substituted or unsubstituted heterocycloalkyl ring.

In an exemplary embodiment, X, $R^c$ and $R^d$ are as described herein, and $R^b$ is selected from the group consisting of —OH, —$OCH_3$, —$OCH_2CH_3$, —$OCH_2CH_2OCH_3$, —$OCH_2C(O)OH$, —$OCH_2C(O)OCH_2CH_3$, —$OCH_2C(O)OC(CH_3)_3$, —$C(O)OCH_3$, —C(O)OH, —C(O)H, —$OCH_2C(O)N(CH_2CH_3)_2$,

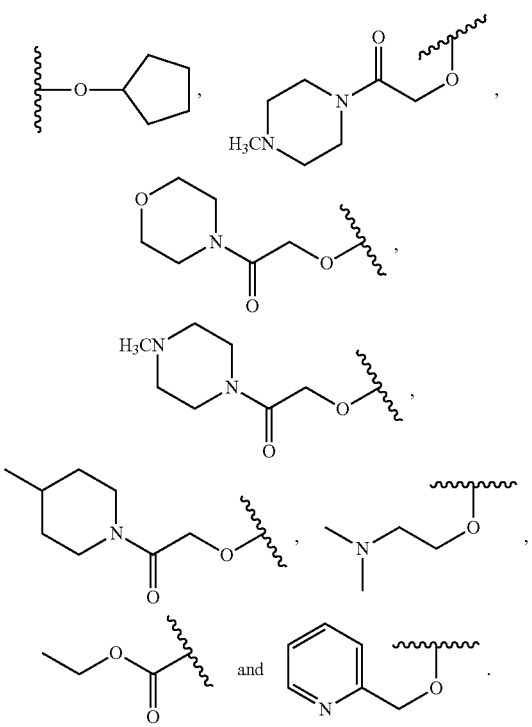

In an exemplary embodiment, X, $R^c$ and $R^d$ are as described herein, and $R^b$ is selected from the group consisting of F, Cl, methyl, trifluoromethyl, —$CH_2OH$, —$CH_2N(CH_3)_2$, —OH, —$OCH_3$, —$OCH_2CH_3$, —$OCH_2CH_2OCH_3$, —$OCH_2C(O)OH$, —$OCH_2C(O)OCH_2CH_3$, —$OCH_2C(O)OC(CH_3)_3$, —$C(O)OCH_3$, —C(O)OH, —C(O)H, —$OCH_2C(O)N(CH_2CH_3)_2$,

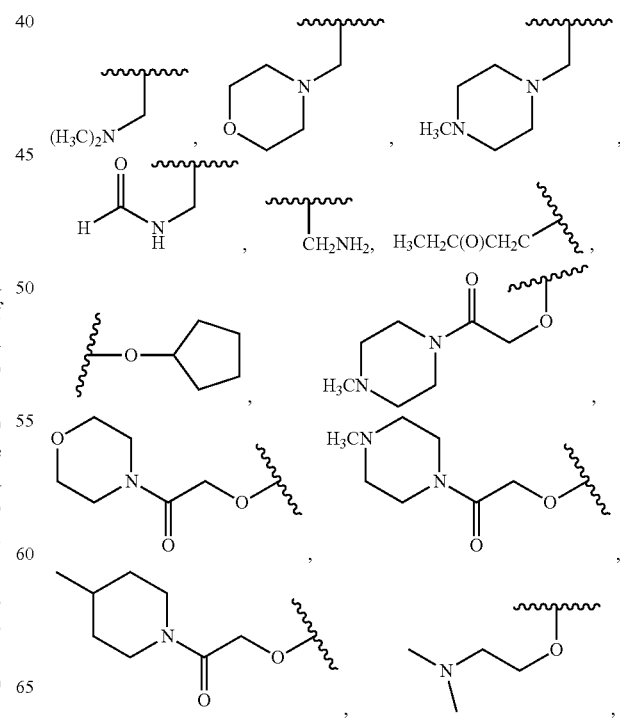

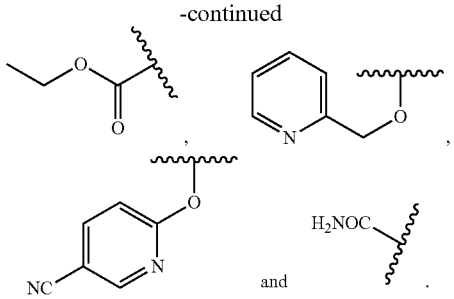

In an exemplary embodiment, X, $R^c$ and $R^d$ are as described herein, and $R^b$ is selected from the group consisting of halogen, haloalkyl, —C(O)$R^4$, —C(O)O$R^4$, —C(O)N$R^4R^5$, —CH$_2$C(O)O$R^4$, —CH$_2$NHC(O)$R^4$ and O$R^4$, wherein $R^4$ and $R^5$ are members independently selected from H and substituted or unsubstituted alkyl.

In an exemplary embodiment, X, $R^c$ and $R^d$ are as described herein, and $R^b$ is selected from the group consisting of F, Cl, methyl, trifluoromethyl, —CH$_2$OH, —CH$_2$N(CH$_3$)$_2$, —OH, —OCH$_3$, —OCH$_2$CH$_3$, —OCH$_2$CH$_2$OCH$_3$, —OCH$_2$C(O)OH, —OCH$_2$C(O)OCH$_2$CH$_3$, —OCH$_2$C(O)OC(CH$_3$)$_3$, —C(O)OCH$_3$, —C(O)OH, —C(O)H, —OCH$_2$C(O)N(CH$_2$CH$_3$)$_2$,

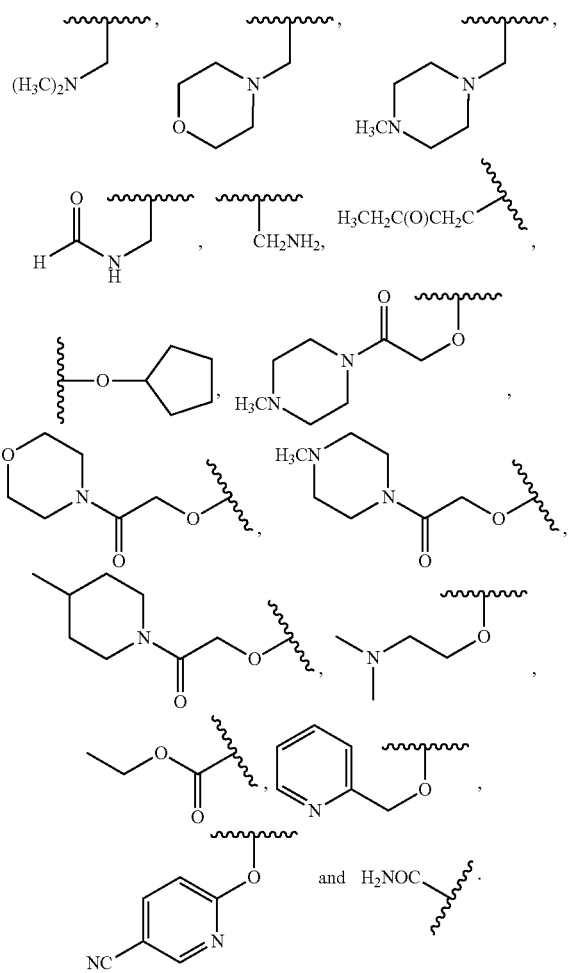

In an exemplary embodiment, X, $R^c$ and $R^d$ are as described herein, and $R^b$ is selected from the group consisting of F, Cl, methyl, trifluoromethyl, —CH$_2$OH, —CH$_2$N(CH$_3$)$_2$, —OH, —OCH$_3$, —OCH$_2$CH$_3$, —OCH$_2$C(O)OH, —OCH$_2$CH$_2$OCH$_3$, —OCH$_2$C(O)OCH$_2$CH$_3$, —OCH$_2$C(O)OC(CH$_3$)$_3$, —C(O)OCH$_3$, —C(O)OH, —C(O)H, —OCH$_2$C(O)N(CH$_2$CH$_3$)$_2$,

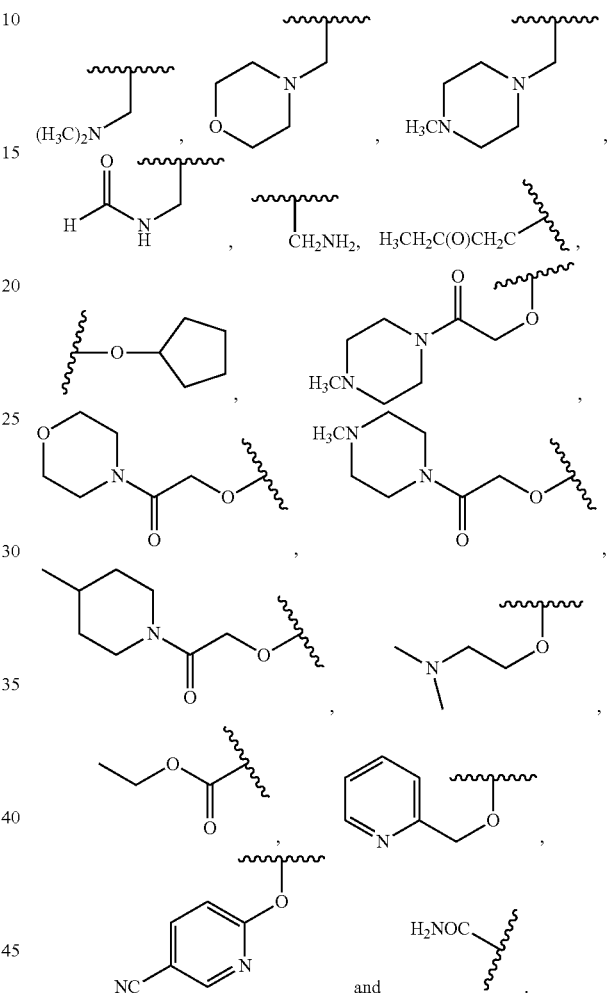

In an exemplary embodiment, X, $R^c$ and $R^d$ are as described herein, and $R^b$ is alkyl, optionally substituted with a member selected from the group consisting of halogen, O$R^{4a}$, C(O)O$R^{4a}$, N$R^{4a}R^{4b}$, substituted or unsubstituted heterocycloalkyl or unsubstituted heteroaryl, wherein $R^{4a}$ and $R^{4b}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, X, $R^c$ and $R^d$ are as described herein, and $R^b$ is alkyl, substituted with O$R^{4a}$ or C(O)O$R^{4a}$, and $R^{4a}$ is H or unsubstituted alkyl. In an exemplary embodiment, X, $R^c$ and $R^d$ are as described herein, $R^b$ is alkyl, substituted with N$R^{4a}R^{4b}$, $R^{4b}$ is H or unsubstituted alkyl or C(O)H. In an exemplary embodiment, X, $R^d$, and $R^c$ is as described herein and $R^b$ is fluoro. In an exemplary embodiment, X, $R^d$, and $R^c$ is as described herein and $R^b$ is chloro.

In an exemplary embodiment, X is CH or N, $R^c$ and $R^d$ are as described herein, and $R^b$ is OH. In an exemplary embodiment, X is CH or N, $R^c$ and $R^d$ are as described herein, and $R^b$ is $OR^4$, wherein $R^4$ is alkyl optionally substituted with at least one halogen, hydroxyl, alkoxy, ether, carboxy or ester moiety. In an exemplary embodiment, X is CH or N, $R^c$ and $R^d$ are as described herein, and $R^b$ is $OR^4$, wherein $R^4$ is unsubstituted alkyl. In an exemplary embodiment, X is CH or N, $R^c$ and $R^d$ are as described herein, and $R^b$ is $OR^4$, wherein $R^4$ is unsubstituted $C_1$ or $C_2$ or $C_3$ alkyl. In an exemplary embodiment, X is CH or N, $R^c$ is as described herein, $R^b$ is $OR^4$, wherein $R^4$ is unsubstituted $C_4$ or $C_5$ or $C_6$ alkyl. In an exemplary embodiment, X is CH or N, $R^c$ is as described herein, $R^b$ is $OR^4$, wherein $R^4$ is methyl or ethyl or propyl or isopropyl or isobutyl.

In an exemplary embodiment, X is CH or N, $R^c$ and $R^d$ are as described herein, and $R^b$ is $OR^4$, wherein $R^4$ is alkyl substituted with at least one halogen. In an exemplary embodiment, X is CH or N, $R^c$ and $R^d$ are as described herein, and $R^b$ is $OR^4$, wherein $R^4$ is alkyl substituted with one or two or three halogen(s). In an exemplary embodiment, X is CH or N, $R^c$ and $R^d$ are as described herein, and $R^b$ is $O(CH_2)_{m1}R^{31}$, wherein m1 is 0 or 1 or 2 or 3 or 4 or 5 or 6 and $R^{31}$ is a methyl moiety wherein at least one of the methyl hydrogens is substituted with a halogen. In an exemplary embodiment, X is CH or N, $R^c$ and $R^d$ are as described herein, and $R^b$ is $O(CH_2)_{m1}R^{31}$, wherein m1 is 0 or 1 or 2 or 3 or 4 or 5 or 6 and $R^{31}$ is a methyl moiety wherein at least one of the methyl hydrogens is substituted with a chloro. In an exemplary embodiment, X is CH or N, $R^c$ and $R^d$ are as described herein, and $R^b$ is $O(CH_2)_{m1}R^{31}$, wherein m1 is 0 or 1 or 2 or 3 or 4 or 5 or 6 and $R^{31}$ is a methyl moiety wherein at least one of the methyl hydrogens is substituted with a fluoro. In an exemplary embodiment, X is CH or N, $R^c$ and $R^d$ are as described herein, and $R^b$ is $O(CH_2)_{m1}R^{31}$, wherein m1 is 0 or 1 or 2 or 3 or 4 or 5 or 6 and $R^{31}$ is $-CF_3$. In an exemplary embodiment, X is CH or N, $R^c$ and $R^d$ are as described herein, and $R^b$ is $O(CH_2)_{m1}R^{31}$, wherein m1 is 0 or 1 or 2 or 3 or 4 or 5 or 6 and $R^{31}$ is $-CHF_2$. In an exemplary embodiment, X is CH or N, $R^c$ and $R^d$ are as described herein, and $R^b$ is $O(CH_2)_{m1}R^{31}$, wherein m1 is 0 or 1 or 2 and $R^{31}$ is $-CF_3$ or $-CHF_2$. In an exemplary embodiment, X is CH or N, $R^c$ and $R^d$ are as described herein, and $R^b$ is $-OCH_2CF_3$. In an exemplary embodiment, X is CH or N, $R^c$ and $R^d$ are as described herein, and $R^b$ is $-OCH_2CHF_2$.

In an exemplary embodiment, X is CH or N, $R^c$ and $R^d$ are as described herein, and $R^b$ is $-O(CH_2)_{m1}OC(O)R^{4d}$, wherein m1 is a number selected from 1 or 2 or 3 or 4 or 5 or 6 and $R^{4d}$ is unsubstituted alkyl. In an exemplary embodiment, X is CH or N, $R^c$ and $R^d$ are as described herein, and $R^b$ is $-O(CH_2)_{m1}OC(O)R^{4d}$, wherein m1 is a number selected from 1 or 2 or 3 and $R^{4d}$ is unsubstituted alkyl. In an exemplary embodiment, X is CH or N, $R^c$ and $R^d$ are as described herein, and $R^b$ is $-O(CH_2)_{m1}OC(O)R^{4d}$, wherein m1 is 2 and $R^{4d}$ is unsubstituted alkyl. In an exemplary embodiment, X is CH or N, $R^c$ and $R^d$ are as described herein, and $R^b$ is $-O(CH_2)_{m1}OC(O)R^{4d}$, wherein m1 is a number selected from 1 or 2 or 3 or 4 or 5 or 6 and $R^{4d}$ is unsubstituted $C_1$ or $C_2$ or $C_3$ alkyl. In an exemplary embodiment, X is CH or N, $R^c$ and $R^d$ are as described herein, and $R^b$ is $-O(CH_2)_{m1}OC(O)R^{4d}$, wherein m1 is a number selected from 1 or 2 or 3 or 4 or 5 or 6 and $R^{4d}$ is unsubstituted $C_4$ or $C_5$ or $C_6$ alkyl. In an exemplary embodiment, X is CH or N, $R^c$ and $R^d$ are as described herein, and $R^b$ is $-O(CH_2)_{m1}OC(O)R^{4d}$, wherein m1 is a number selected from 1 or 2 or 3 or 4 or 5 or 6 and $R^{4d}$ is methyl. In an exemplary embodiment, X is CH or N, $R^c$ and $R^d$ are as described herein, and $R^b$ is $-O(CH_2)_2OC(O)CH_3$.

In an exemplary embodiment, X is CH or N, $R^c$ and $R^d$ are as described herein, and $R^b$ is $-O(CH_2)_{m1}C(O)R^{4d}$, wherein m1 is a number selected from 1 or 2 or 3 or 4 or 5 or 6 and $R^{4d}$ is unsubstituted alkyl. In an exemplary embodiment, X is CH or N, $R^c$ and $R^d$ are as described herein, and $R^b$ is $-O(CH_2)_{m1}C(O)R^{4d}$, wherein m1 is a number selected from 2 or 3 or 4 and $R^{4d}$ is unsubstituted alkyl. In an exemplary embodiment, X is CH or N, $R^c$ and $R^d$ are as described herein, and $R^b$ is $-O(CH_2)_{m1}C(O)R^{4d}$, wherein m1 is 3 and $R^{4d}$ is unsubstituted alkyl. In an exemplary embodiment, X is CH or N, $R^c$ and $R^d$ are as described herein, and $R^b$ is $-O(CH_2)_{m1}C(O)R^{4d}$, wherein m1 is a number selected from 1 or 2 or 3 or 4 or 5 or 6 and $R^{4d}$ is unsubstituted $C_1$ or $C_2$ or $C_3$ alkyl. In an exemplary embodiment, X is CH or N, $R^c$ and $R^d$ are as described herein, and $R^b$ is $-O(CH_2)_{m1}C(O)R^{4d}$, wherein m1 is a number selected from 1 or 2 or 3 or 4 or 5 or 6 and $R^{4d}$ is unsubstituted $C_4$ or $C_5$ or $C_6$ alkyl. In an exemplary embodiment, X is CH or N, $R^c$ and $R^d$ are as described herein, and $R^b$ is $-O(CH_2)_{m1}C(O)R^{4d}$, wherein m1 is a number selected from 1 or 2 or 3 or 4 or 5 or 6 and $R^{4d}$ is methyl. In an exemplary embodiment, X is CH or N, $R^c$ and $R^d$ are as described herein, and $R^b$ is $-O(CH_2)_3C(O)CH_3$.

In an exemplary embodiment, X is CH or N, $R^c$ and $R^d$ are as described herein, and $R^b$ is $-O(CH_2)_{m1}C(O)OR^{4d}$, wherein m1 is a number selected from 1 or 2 or 3 or 4 or 5 or 6 and $R^{4d}$ is H or unsubstituted alkyl. In an exemplary embodiment, X is CH or N, $R^c$ and $R^d$ are as described herein, and $R^b$ is $-OCH_2C(O)OR^{4d}$, wherein $R^{4d}$ is as described herein. In an exemplary embodiment, $R^{4d}$ is H or methyl or ethyl or t-butyl. In an exemplary embodiment, X is CH or N, $R^c$ and $R^d$ are as described herein, and $R^b$ is $-O(CH_2)C(O)OCH_2CH_3$ or $-O(CH_2)C(O)OH$ or $-O(CH_2)C(O)OC(CH_3)_3$.

In an exemplary embodiment, X is CH or N, $R^c$ and $R^d$ are as described herein, and $R^b$ is $OR^4$, wherein $R^4$ is alkyl substituted with a substituted or unsubstituted amino. In an exemplary embodiment, X is CH or N, $R^c$ and $R^d$ are as described herein, and $R^b$ is $-O(CH_2)_{m2}NR^{4e}R^{4f}$, wherein m2 is 1 or 2 or 3 or 4 or 5 or 6 and $R^{4e}$ and $R^{4f}$ are each independently selected from H or unsubstituted alkyl or unsubstituted cycloalkyl, or $R^{4e}$ and $R^{4f}$, together with the nitrogen to which they are attached, are optionally joined to form a substituted or unsubstituted 4 to 8 membered ring. In an exemplary embodiment, X is CH or N, $R^c$ and $R^d$ are as described herein, and $R^b$ is $-O(CH_2)_{m2}NR^{4e}R^{4f}$, wherein m2 is 1 or 2 or 3 or 4 or 5 or 6 and $R^{4e}$ and $R^{4f}$ are each independently selected from H or $C_1$ or $C_2$ or $C_3$ or $C_4$ or $C_5$ or $C_6$ alkyl. In an exemplary embodiment, X is CH or N, $R^c$, $R^d$, $R^e$ and $R^f$ are as described herein, and $R^b$ is $-O(CH_2)_{m2}NR^{4e}R^{4f}$, wherein m2 is 1 or 2 or 3. In an exemplary embodiment, X is CH or N, $R^c$, $R^d$, $R^e$ and $R^f$ are as described herein, and $R^b$ is $-O(CH_2)_{m2}NR^{4e}R^{4f}$, wherein m2 is 4 or 5 or 6. In an exemplary embodiment, X is CH or N, $R^c$, $R^d$, $R^e$ and $R^f$ are as described herein, and $R^b$ is $-O(CH_2)_{m2}NR^{4e}R^{4f}$, wherein m2 is 2 or 3 or 4. In an exemplary embodiment, X is CH or N, m2, $R^c$ and $R^d$ are as described herein, and $R^b$ is $-O(CH_2)_{m2}NH_2$. In an exemplary embodiment, X is CH or N, m2, $R^c$ and $R^d$ are as described herein, and $R^b$ is $-O(CH_2)_{m2}NR^{4e}R^{4f}$, wherein $R^{4e}$ is unsubstituted $C_1$ or $C_2$ or $C_3$ or $C_4$ or $C_5$ or $C_6$ alkyl and $R^{4f}$ is unsubstituted $C_1$ or $C_2$ or $C_3$ or $C_4$ or $C_5$ or $C_6$ alkyl. In an exemplary embodiment, X is CH or N, m2, $R^c$ and $R^d$ are as described herein, and $R^b$ is —O(CH$_2$)$_{m2}$NHR$^{4f}$, wherein R$^{4f}$ is unsubstituted C$_1$ or C$_2$ or C$_3$ or C$_4$ or C$_5$ or C$_6$ alkyl. In an exemplary embodiment, X is CH or N, m2, R$^c$ and R$^d$ are as described herein, and R$^b$ is —O(CH$_2$)$_{m2}$NHR$^{4f}$, wherein R$^{4f}$ is unsubstituted C$_3$ or C$_4$ or C$_5$ or C$_6$ cycloalkyl. In an exemplary embodiment, X is CH or N, m2, R$^c$ and R$^d$ are as described herein, and R$^b$ is —O(CH$_2$)$_{m2}$NR$^{4e}$R$^{4f}$ wherein R$^{4e}$ is unsubstituted C$_3$ or C$_4$ or C$_5$ or C$_6$ cycloalkyl and R$^{4f}$ is unsubstituted C$_1$ or C$_2$ or C$_3$ or C$_4$ or C$_5$ or C$_6$ alkyl. In an exemplary embodiment, X is CH or N, m2, R$^c$ and R$^d$ are as described herein, and R$^b$ is —O(CH$_2$)$_{m2}$NR$^{4e}$R$^{4f}$, wherein R$^{4e}$ is unsubstituted C$_1$ or C$_2$ or C$_3$ or C$_4$ or C$_5$ or C$_6$ alkyl and R$^{4f}$ is unsubstituted C$_3$ or C$_4$ or C$_5$ or C$_6$ cycloalkyl. In an exemplary embodiment, X is CH or N, m2, R$^c$ and R$^d$ are as described herein, and R$^b$ is —O(CH$_2$)$_{m2}$NR$^{4e}$R$^{4f}$, wherein NR$^{4e}$R$^{4f}$ is

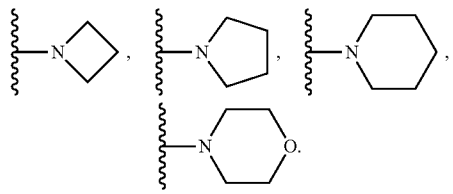

In an exemplary embodiment, X is CH or N, R$^c$ and R$^d$ are as described herein, and R$^b$ is OR$^4$, wherein R$^4$ is alkyl substituted with a substituted or unsubstituted amide. In an exemplary embodiment, X is CH or N, R$^c$ and R$^d$ are as described herein, and R$^b$ is —OCH$_2$C(O)NR$^{4e}$R$^{4f}$ wherein R$^{4e}$ and R$^{4f}$ are as described herein. In an exemplary embodiment, X is CH or N, R$^c$ and R$^d$ are as described herein, and R$^b$ is —OCH$_2$C(O)NR$^{4e}$R$^{4f}$, R$^{4e}$ and R$^{4f}$ are the same and are independently selected unsubstituted alkyl. In an exemplary embodiment, X is CH or N, R$^c$ and R$^d$ are as described herein, and R$^b$ is —OCH$_2$C(O)NR$^{4e}$R$^{4f}$, R$^{4e}$ and R$^{4f}$ are different and are independently selected unsubstituted alkyl. In an exemplary embodiment, In an exemplary embodiment, X is CH or N, R$^c$ and R$^d$ are as described herein, and R$^b$ is —OCH$_2$C(O)NR$^{4e}$R$^{4f}$, R$^{4e}$ is H and R$^{4f}$ is as described herein. In an exemplary embodiment, X is CH or N, R$^c$ and R$^d$ are as described herein, and R$^b$ is —OCH$_2$C(O)NR$^{4e}$R$^{4f}$, R$^{4f}$ is H and R$^e$ is as described herein. In an exemplary embodiment, X is CH or N, R$^c$ and R$^d$ are as described herein, and R$^b$ is —OCH$_2$C(O)NR$^{4e}$R$^{4f}$, R$^{4e}$ and R$^{4f}$ are ethyl. In an exemplary embodiment, X is CH or N, R$^c$ and R$^d$ are as described herein, and R$^b$ is —OCH$_2$C(O)NR$^{4e}$R$^{4f}$, R$^{4e}$ and R$^{4f}$, together with the nitrogen to which they are attached, are joined to form piperazinyl, either unsubstituted or substituted with unsubstituted alkyl on the nitrogen at the 4-position. In an exemplary embodiment, X is CH or N, R$^c$ and R$^d$ are as described herein, and R$^b$ is —OCH$_2$C(O)NR$^{4e}$R$^{4f}$, R$^{4e}$ and R$^{4f}$, together with the nitrogen to which they are attached, are joined to form N-methyl piperazinyl. In an exemplary embodiment, X is CH or N, R$^c$ and R$^d$ are as described herein, and R$^b$ is —OCH$_2$C(O)NR$^{4e}$R$^{4f}$, R$^{4e}$ and R$^{4f}$, together with the nitrogen to which they are attached, are joined to form piperidinyl, either unsubstituted or substituted with unsubstituted alkyl. In an exemplary embodiment, X is CH or N, R$^c$ and R$^d$ are as described herein, and R$^b$ is —OCH$_2$C(O)NR$^{4e}$R$^{4f}$, R$^{4e}$ and R$^{4f}$, together with the nitrogen to which they are attached, are joined to form 4-methyl piperidinyl. In an exemplary embodiment, X is CH or N, R$^c$ and R$^d$ are as described herein, and R$^b$ is —OCH$_2$C(O)NR$^{4e}$R$^{4f}$, R$^{4e}$ and R$^{4f}$, together with the nitrogen to which they are attached, are joined to form unsubstituted morpholinyl.

In an exemplary embodiment, X is CH or N, R$^c$ and R$^d$ are as described herein, and R$^b$ is OR$^4$, wherein R$^4$ is alkyl substituted with unsubstituted pyridinyl. In an exemplary embodiment, X is CH or N, R$^c$ and R$^d$ are as described herein, and R$^b$ is

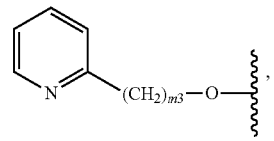

wherein m3 is 1 or 2 or 3 or 4 or 5 or 6. In an exemplary embodiment, m3 is 1.

In an exemplary embodiment, X is CH or N, R$^c$ and R$^d$ are as described herein, and R$^b$ is OR$^4$, wherein R$^4$ is substituted or unsubstituted cycloalkyl. In an exemplary embodiment, X is CH or N, R$^c$ and R$^d$ are as described herein, and R$^b$ is OR$^4$, wherein R$^4$ is unsubstituted cycloalkyl. In an exemplary embodiment, X is CH or N, R$^c$ and R$^d$ are as described herein, and R$^b$ is OR$^4$, wherein R$^4$ is cyclopropyl. In an exemplary embodiment, X is CH or N, R$^c$ and R$^d$ are as described herein, and R$^b$ is OR$^4$, wherein R$^4$ is unsubstituted cyclobutyl. In an exemplary embodiment, X is CH or N, R$^c$ and R$^d$ are as described herein, and R$^b$ is OR$^4$, wherein R$^4$ is cyclopentyl. In an exemplary embodiment, X is CH or N, R$^c$ and R$^d$ are as described herein, and R$^b$ is OR$^4$, wherein R$^4$ is unsubstituted cyclohexyl.

In an exemplary embodiment, X is CH or N, R$^c$ and R$^d$ are as described herein, and R$^b$ is OR$^4$, wherein R$^4$ is alkyl substituted with unsubstituted alkoxy. In an exemplary embodiment, X is CH or N, R$^c$ and R$^d$ are as described herein, and R$^b$ is —O(CH$_2$)$_{m5}$OR$^{30}$, wherein m5 is 1 or 2 or 3 or 4 or 5 or 6 and R$^{30}$ is H or unsubstituted alkyl or unsubstituted tetrahydropyran. In an exemplary embodiment, X is CH or N, R$^c$ and R$^d$ are as described herein, and R$^b$ is —O(CH$_2$)$_{m5}$OR$^{30}$, wherein m5 is 1 or 2 or 3 or 4 or 5 or 6 and R$^{30}$ is C$_1$ or C$_2$ or C$_3$ or C$_4$ or C$_5$ or C$_6$ alkyl. In an exemplary embodiment, X is CH or N, R$^c$ and R$^d$ are as described herein, and R$^b$ is —O(CH$_2$)$_{m5}$OR$^{30}$, wherein m5 is 1 or 2 or 3 or 4 or 5 or 6 and R$^{30}$ is unsubstituted C$_1$ or C$_2$ or C$_3$ or C$_4$ or C$_5$ or C$_6$ alkyl. In an exemplary embodiment, X is CH or N, R$^c$ and R$^d$ are as described herein, and R$^b$ is —O(CH$_2$)$_{m5}$OR$^{30}$, wherein m5 is 1 or 2 or 3 and R$^{30}$ is C$_1$ or C$_2$ or C$_3$ or C$_4$ or C$_5$ or C$_6$ alkyl. In an exemplary embodiment, X is CH or N, R$^c$ and R$^d$ are as described herein, and R$^b$ is —O(CH$_2$)$_2$OR$^{30}$, wherein R$^{30}$ is C$_1$ or C$_2$ or C$_3$ or C$_4$ or C$_5$ or C$_6$ alkyl. In an exemplary embodiment, X is CH or N, R$^c$ and R$^d$ are as described herein, and R$^b$ is —O(CH$_2$)$_{m5}$OR$^{30}$, wherein m5 is 1 or 2 or 3 or 4 or 5 or 6 and R$^{30}$ is C$_1$ or C$_2$ or C$_3$ alkyl. In an exemplary embodiment, X is CH or N, R$^c$ and R$^d$ are as described herein, and R$^b$ is —O(CH$_2$)$_{m5}$OR$^{30}$, wherein m5 is 1 or 2 or 3 or 4 or 5 or 6 and R$^{30}$ is C$_4$ or C$_5$ or C$_6$ alkyl. In an exemplary embodiment, X is CH or N, R$^c$ and R$^d$ are as described herein, and R$^b$ is —O(CH$_2$)$_{m5}$OR$^{30}$, wherein m5 is 1 or 2 or 3 or 4 or 5 or 6 and R$^{30}$ is H. In an exemplary embodiment, X is CH or N, R$^c$ and R$^d$ are as described herein, and R$^b$ is —O(CH$_2$)$_{m5}$OR$^{30}$, wherein m5 is 1 or 2 or 3 or 4 or 5 or 6 and R$^{30}$ is methyl or ethyl or isopropyl. In an exemplary embodiment, X is CH or N, R$^c$ and R$^d$ are as described herein, and R$^b$ is —O(CH$_2$)$_{m5}$OR$^{30}$, wherein m5 is 1 or 2 or 3 or 4 or 5 or 6 and R$^{30}$ is 2-tetrahydropyran. In an exemplary embodiment, X is CH or N, $R^c$ and $R^d$ are as described herein, and $R^b$ is —O(CH$_2$)$_2$OC(CH$_3$)$_2$ or —O(CH$_2$)$_2$OCH$_2$CH$_3$ or —O(CH$_2$)$_2$OH or —O(CH$_2$)$_2$O-THP (TetraHydroPyran).

In another aspect, the invention provides a compound having a structure according to the formula:

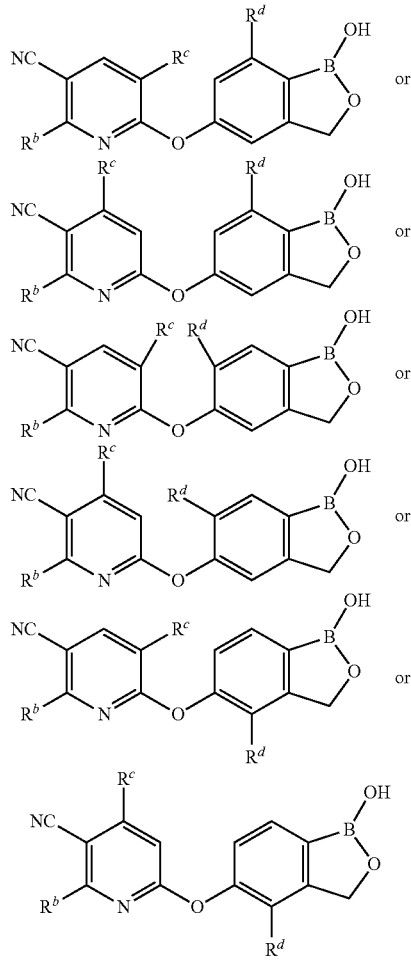

wherein $R^c$ and $R^d$ are as described herein, $R^b$ is —O(CH$_2$)OR$^{30}$, and R$^{30}$ is C$_1$ or C$_2$ or C$_3$ or C$_4$ or C$_5$ or C$_6$ alkyl. In an exemplary embodiment, $R^c$ and $R^d$ are as described herein, $R^b$ is —O(CH$_2$)OR$^{30}$, and R$^{30}$ is methyl or ethyl or isopropyl or propyl or butyl or isobutyl or secbutyl or tert-butyl. In an exemplary embodiment, $R^d$ is H, $R^c$ is as described herein, $R^b$ is —O(CH$_2$)OR$^{30}$, and R$^{30}$ is methyl or ethyl or isopropyl or propyl or butyl or isobutyl or secbutyl or tert-butyl. In an exemplary embodiment, $R^d$ is F, $R^c$ is as described herein, $R^b$ is —O(CH$_2$)OR$^{30}$, and R$^{30}$ is methyl or ethyl or isopropyl or propyl or butyl or isobutyl or secbutyl or tert-butyl. In an exemplary embodiment, $R^d$ is H, $R^c$ is Cl or CF$_3$ or cyclopropyl or cyano, $R^b$ is —O(CH$_2$)OR$^{30}$, and R$^{30}$ is methyl or ethyl or isopropyl or propyl or butyl or isobutyl or secbutyl or tert-butyl. In an exemplary embodiment, $R^d$ is F, $R^c$ is Cl or CF$_3$ or cyclopropyl or cyano, $R^b$ is —O(CH$_2$)OR$^{30}$, and R$^{30}$ is methyl or ethyl or isopropyl or propyl or butyl or isobutyl or secbutyl or tert-butyl.

In another aspect, the invention provides a compound having a structure according to the formula:

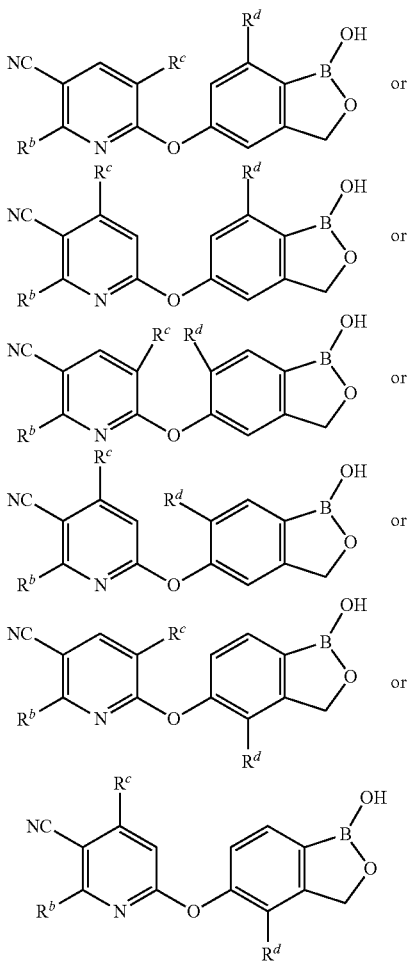

wherein $R^c$ and $R^d$ are as described herein, $R^b$ is —O(CH$_2$)$_{m5}$OR$^{30}$, wherein m5 is 1 or 2 or 3 or 4 or 5 or 6, and R$^{30}$ is C$_4$ alkyl. In an exemplary embodiment, $R^c$ and $R^d$ are as described herein, $R^b$ is —O(CH$_2$)$_{m5}$OR$^{30}$, wherein m5 is 1 or 2 or 3 or 4 or 5 or 6, and R$^{30}$ is butyl or isobutyl or secbutyl or tert-butyl. In an exemplary embodiment, $R^d$ is H, $R^c$ is as described herein, $R^b$ is —O(CH$_2$)$_{m5}$OR$^{30}$, wherein m5 is 1 or 2 or 3 or 4 or 5 or 6, and R$^{30}$ is butyl or isobutyl or secbutyl or tert-butyl. In an exemplary embodiment, $R^d$ is F, $R^c$ is as described herein, $R^b$ is —O(CH$_2$)$_{m5}$OR$^{30}$, wherein m5 is 1 or 2 or 3 or 4 or 5 or 6, and R$^{30}$ is butyl or isobutyl or secbutyl or tert-butyl. In an exemplary embodiment, $R^d$ is H, $R^c$ is Cl or CF$_3$ or cyclopropyl or cyano, $R^b$ is —O(CH$_2$)$_{m5}$OR$^{30}$, wherein m5 is 1 or 2 or 3 or 4 or 5 or 6, and R$^{30}$ is butyl or isobutyl or secbutyl or tert-butyl. In an exemplary embodiment, $R^d$ is F, $R^c$ is Cl or CF$_3$ or cyclopropyl or cyano, $R^b$ is —O(CH$_2$)$_{m5}$OR$^{30}$, wherein m5 is 1 or 2 or 3 or 4 or 5 or 6, and R$^{30}$ is butyl or isobutyl or secbutyl or tert-butyl.

In an exemplary embodiment, X is CH or N, $R^c$ and $R^d$ are as described herein, and $R^b$ is OR$^4$, wherein R$^4$ is alkyl substituted with unsubstituted cycloalkyl. In an exemplary embodiment, X is CH or N, $R^c$ and $R^d$ are as described herein, and $R^b$ is —O(CH$_2$)$_{m5}$R$^{30}$, wherein m5 is 1 or 2 or 3 or 4 or 5 or 6 and R$^{30}$ is a 3 or 4 or 5 or 6 or 7 or 8 membered cycloalkyl. In an exemplary embodiment, X is CH or N, $R^c$ and $R^d$ are as described herein, and $R^b$ is —O(CH$_2$)$_{m5}$R$^{30}$, wherein m5 is 1 or 2 or 3 or 4 or 5 or 6 and $R^{30}$ is a 3 or 4 or 5 or 6 membered cycloalkyl. In an exemplary embodiment, X is CH or N, $R^c$ and $R^d$ are as described herein, and $R^b$ is —O(CH$_2$)$_{m5}$R$^{30}$, wherein m5 is 1 or 2 or 3 or 4 or 5 or 6 and $R^{30}$ is cyclopropyl. In an exemplary embodiment, X is CH or N, $R^c$ and $R^d$ are as described herein, and $R^b$ is —O(CH$_2$)$_{m5}$R$^{30}$, wherein m5 is 1 or 2 or 3 or 4 or 5 or 6 and $R^{30}$ is cyclobutyl. In an exemplary embodiment, X is CH or N, $R^c$ and $R^d$ are as described herein, and $R^b$ is —O(CH$_2$)$_{m5}$R$^{30}$, wherein m5 is 1 or 2 or 3 or 4 or 5 or 6 and $R^{30}$ is cyclopentyl. In an exemplary embodiment, X is CH or N, $R^c$ and $R^d$ are as described herein, and $R^b$ is —O(CH$_2$)$_{m5}$R$^{30}$, wherein m5 is 1 or 2 or 3 or 4 or 5 or 6 and $R^{30}$ is cyclohexyl. In an exemplary embodiment, X is CH or N, $R^c$ and $R^d$ are as described herein, and $R^b$ is —O(CH$_2$)$_{m5}$R$^{30}$, wherein m5 is 1 or 2 or 3 and $R^{30}$ is a 3 or 4 or 5 or 6 membered cycloalkyl. In an exemplary embodiment, X is CH or N, $R^c$ and $R^d$ are as described herein, and $R^b$ is —O(CH$_2$)R$^{30}$, wherein $R^{30}$ is a 3 or 4 or 5 or 6 membered cycloalkyl.

In an exemplary embodiment, X is CH or N, $R^c$ and $R^d$ are as described herein, and $R^b$ is C(O)R$^4$, wherein $R^4$ is unsubstituted alkyl. In an exemplary embodiment, X is CH or N, $R^c$ and $R^d$ are as described herein, and $R^b$ is C(O)R$^4$, wherein $R^4$ is $C_1$ or $C_2$ or $C_3$ or $C_4$ or $C_5$ or $C_6$ alkyl. In an exemplary embodiment, X is CH or N, $R^c$ and $R^d$ are as described herein, and $R^b$ is C(O)CH$_3$. In an exemplary embodiment, X is CH or N, $R^c$ and $R^d$ are as described herein, and $R^b$ is C(O)H. In an exemplary embodiment, X is CH or N, $R^c$ and $R^d$ are as described herein, and $R^b$ is $C_1$ or $C_2$ or $C_3$ or $C_4$ or $C_5$ or $C_6$ alkyl. In an exemplary embodiment, X is CH or N, $R^c$ and $R^d$ are as described herein, and $R^b$ is $C_1$ alkyl. In an exemplary embodiment, X is CH or N, $R^c$ and $R^d$ are as described herein, and $R^b$ is alkyl substituted with halogen. In an exemplary embodiment, X is CH or N, $R^c$ and $R^d$ are as described herein, and $R^b$ is alkyl substituted with at least one halogen. In an exemplary embodiment, X is CH or N, $R^c$ and $R^d$ are as described herein, and $R^b$ is alkyl substituted with at least one fluoro. In an exemplary embodiment, X is CH or N, $R^c$ and $R^d$ are as described herein, and $R^b$ is CF$_3$.

In an exemplary embodiment, X is CH or N, $R^c$ and $R^d$ are as described herein, and $R^b$ is alkyl substituted with hydroxy. In an exemplary embodiment, X is CH or N, $R^c$ and $R^d$ are as described herein, and $R^b$ is —(CH$_2$)$_{m4}$OH, wherein m4 is a number selected from 1 or 2 or 3 or 4 or 5 or 6. In an exemplary embodiment, X is CH or N, $R^c$ and $R^d$ are as described herein, and $R^b$ is —(CH$_2$)OH.

In an exemplary embodiment, X is CH or N, $R^c$ and $R^d$ are as described herein, and $R^b$ is alkyl substituted with carboxy or ester. In an exemplary embodiment, X is CH or N, $R^c$ and $R^d$ are as described herein, and $R^b$ is —(CH$_2$)$_{m1}$C(O)OR$^{4a}$, wherein m1 is a number selected from 1 or 2 or 3 or 4 or 5 or 6 and $R^{4a}$ is H or unsubstituted alkyl.

In an exemplary embodiment, X is CH or N, $R^c$ and $R^d$ are as described herein, and $R^b$ is —CH$_2$C(O)OR$^{4a}$, wherein $R^{4a}$ is as described herein. In an exemplary embodiment, X is CH or N, $R^c$ and $R^d$ are as described herein, and $R^b$ is —CH$_2$C(O)OR$^{4a}$, wherein $R^{4a}$ is H or methyl or ethyl or t-butyl.

In an exemplary embodiment, X is CH or N, $R^c$ and $R^d$ are as described herein, and $R^b$ is alkyl substituted with amino. In an exemplary embodiment, X is CH or N, $R^c$ and $R^d$ are as described herein, and $R^b$ is —(CH$_2$)$_{m7}$NR$^{4a}$R$^{4b}$, wherein m7 is a number selected from 1 or 2 or 3 or 4 or 5 or 6 and $R^{4a}$ and $R^{4b}$ are independently selected from the group consisting of H and unsubstituted alkyl and formyl, or $R^{4a}$ and $R^{4b}$, together with the nitrogen to which they are attached, are optionally joined to form a substituted or unsubstituted 4 to 8 membered ring. In an exemplary embodiment, X is CH or N, $R^c$ and $R^d$ are as described herein, and $R^b$ is —(CH$_2$)$_{m7}$NR$^{4a}$R$^{4b}$, wherein m7 is a number selected from 1 or 2 or 3 or 4 or 5 or 6 and $R^{4b}$ is as described herein, $R^{4a}$ is H. In an exemplary embodiment, X is CH or N, $R^c$ and $R^d$ are as described herein, and $R^b$ is —(CH$_2$)$_{m7}$NR$^{4a}$R$^{4b}$, wherein m7 is a number selected from 1 or 2 or 3 or 4 or 5 or 6 and $R^{4a}$ is as described herein, $R^{4b}$ is H. In an exemplary embodiment, X is CH or N, $R^c$ and $R^d$ are as described herein, and $R^b$ is —(CH$_2$)$_{m7}$N(CH$_3$)R$^{4b}$, wherein m7 is a number selected from 1 or 2 or 3 or 4 or 5 or 6 and $R^{4b}$ is as described herein. In an exemplary embodiment, $R^{4a}$ is as described herein, $R^{4b}$ is methyl. In an exemplary embodiment, X is CH or N, $R^c$ and $R^d$ are as described herein, and $R^b$ is —(CH$_2$)NR$^{4a}$R$^{4b}$, wherein $R^{4a}$ and $R^{4b}$ are as described herein. In an exemplary embodiment, In an exemplary embodiment, X is CH or N, $R^c$ and $R^d$ are as described herein, and $R^b$ is —(CH$_2$)NR$^{4a}$R$^{4b}$, $R^{4a}$ and $R^{4b}$, together with the nitrogen to which they are attached, are joined to form piperazinyl, either unsubstituted or substituted with unsubstituted alkyl on the nitrogen at the 4-position. In an exemplary embodiment, In an exemplary embodiment, X is CH or N, $R^c$ and $R^d$ are as described herein, and $R^b$ is —(CH$_2$)NR$^{4a}$R$^{4b}$, $R^{4a}$ and $R^{4b}$, together with the nitrogen to which they are attached, are joined to form N-methyl piperazinyl. In an exemplary embodiment, In an exemplary embodiment, X is CH or N, $R^c$ and $R^d$ are as described herein, and $R^b$ is —(CH$_2$)NR$^{4a}$R$^{4b}$, $R^{4a}$ and $R^{4b}$, together with the nitrogen to which they are attached, are joined to form piperidinyl, either unsubstituted or substituted with unsubstituted alkyl. In an exemplary embodiment, In an exemplary embodiment, X is CH or N, $R^c$ and $R^d$ are as described herein, and $R^b$ is —(CH$_2$)NR$^{4a}$R$^{4b}$, $R^{4a}$ and $R^{4b}$, together with the nitrogen to which they are attached, are joined to form 4-methyl piperidinyl. In an exemplary embodiment, In an exemplary embodiment, X is CH or N, $R^c$ and $R^d$ are as described herein, and $R^b$ is —(CH$_2$)NR$^{4a}$R$^{4b}$, $R^{4a}$ and $R^{4b}$, together with the nitrogen to which they are attached, are joined to form unsubstituted morpholinyl.

In an exemplary embodiment, X is CH or N, $R^c$ and $R^d$ are as described herein, and $R^b$ is NH$_2$. In an exemplary embodiment, X is CH or N, $R^c$ and $R^d$ are as described herein, and $R^b$ is NR$^4$R$^5$ wherein $R^4$ is H or unsubstituted alkyl, and $R^5$ is selected from the group consisting of substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, X is CH or N, $R^c$ and $R^d$ are as described herein, and $R^b$ is NR$^4$R$^5$, $R^4$ is as described herein, $R^5$ is unsubstituted alkyl. In an exemplary embodiment, X is CH or N, $R^c$ and $R^d$ are as described herein, and $R^b$ is NR$^4$R$^5$, wherein $R^4$ is H, $R^5$ is as described herein. In an exemplary embodiment, X is CH or N, $R^c$ and $R^d$ are as described herein, and $R^b$ is NR$^4$R$^5$, wherein $R^4$ is unsubstituted alkyl, $R^5$ is as described herein. In an exemplary embodiment, X is CH or N, $R^c$ and $R^d$ are as described herein, and $R^b$ is NR$^4$R$^5$, wherein $R^5$ is as described herein, $R^4$ is unsubstituted $C_1$ or $C_2$ or $C_3$ or $C_4$ or $C_5$ or $C_6$ alkyl. In an exemplary embodiment, X is CH or N, $R^c$ and $R^d$ are as described herein, and $R^b$ is NR$^4$R$^5$, wherein $R^4$ is unsubstituted $C_1$ or $C_2$ or $C_3$ alkyl and $R^5$ is as described herein. In an exemplary embodiment, X is CH or N, $R^c$ and $R^d$ are as described herein, and $R^b$ is NR$^4$R$^5$, wherein $R^4$ is methyl and $R^5$ is as described herein. In an exemplary embodiment, X is CH or N, $R^c$ and $R^d$ are as described herein, and $R^b$ is $NR^4R^5$, wherein $R^4$ is as described herein $R^5$ is unsubstituted $C_1$ or $C_2$ or $C_3$ or $C_4$ or $C_5$ or $C_6$ alkyl. In an exemplary embodiment, X is CH or N, $R^c$ and $R^d$ are as described herein, and $R^b$ is $NR^4R^5$, wherein $R^5$ is methyl or tert-butyl, and $R^4$ is as described herein.

In an exemplary embodiment, X is CH or N, $R^c$ and $R^d$ are as described herein, and $R^b$ is $NR^4R^5$, wherein $R^4$ is as described herein, $R^5$ is alkyl, substituted with a member selected from the group consisting of OH, unsubstituted arylalkoxy, unsubstituted alkoxy, unsubstituted cycloalkoxy, and unsubstituted aryl. In an exemplary embodiment, X is CH or N, $R^c$ and $R^d$ are as described herein, and $R^b$ is $NR^4R^5$, wherein $R^5$ is —$(CH_2)_{m8}$Ph.

In an exemplary embodiment, X is CH or N, $R^c$ and $R^d$ are as described herein, and $R^b$ is $NR^4R^5$, wherein $R^4$ is H or unsubstituted alkyl, $R^5$ is —$(CH_2)_{m8}OR^{26}$, wherein m8 is a number selected from 1 or 2 or 3 or 4 or 5 or 6 and $R^{26}$ is H or unsubstituted alkyl or alkyl substituted with halogen or unsubstituted cycloalkyl or aryl substituted $C_1$ or $C_2$ or $C_3$ or $C_4$ or $C_5$ or $C_6$ alkyl. In an exemplary embodiment, m8 is 1 or 2 or 3. In an exemplary embodiment, m8 is 2. In an exemplary embodiment, $R^{26}$ is unsubstituted $C_1$ or $C_2$ or $C_3$ or $C_4$ or $C_5$ or $C_6$ alkyl. In an exemplary embodiment, $R^{26}$ is methyl. In an exemplary embodiment, $R^{26}$ is trifluoromethyl. In an exemplary embodiment, $R^{26}$ is ethyl. In an exemplary embodiment, $R^{26}$ is cyclopropyl. In an exemplary embodiment, $R^{26}$ is isopropyl. In an exemplary embodiment, $R^{26}$ is benzyl. In an exemplary embodiment, X is CH or N, $R^c$ and $R^d$ are as described herein, and $R^b$ is $NR^4R^5$, wherein $R^4$ is as described herein, $R^5$ is —$(CH_2)_{m8}O(CH_2)_{m9}$Ph, wherein m8 and m9 are each independently selected from 1 or 2 or 3 or 4 or 5 or 6. In an exemplary embodiment, X is CH or N, $R^c$ and $R^d$ are as described herein, and $R^b$ is $NR^4R^5$, wherein $R^4$ is as described herein $R^5$ is —$(CH_2)_{m8}O(CH_2)_{m9}$Ph, wherein m8 and m9 are each independently selected from 1 or 2 or 3. In an exemplary embodiment, X is CH or N, $R^c$ and $R^d$ are as described herein, and $R^b$ is $NR^4R^5$, wherein $R^4$ is as described herein, $R^5$ is —$(CH_2)_{m8}O(CH_2)$Ph. In an exemplary embodiment, X is CH or N, $R^c$ and $R^d$ are as described herein, and $R^b$ is $NR^4R^5$, wherein $R^4$ is as described herein $R^5$ is —$(CH_2)_2O(CH_2)_{m9}$Ph. In an exemplary embodiment, X is CH or N, $R^c$ and $R^d$ are as described herein, and $R^b$ is $NR^4R^5$, wherein $R^4$ is as described herein $R^5$ is —$(CH_2)_2O(CH_2)$Ph.

In an exemplary embodiment, X is CH or N, $R^c$ and $R^d$ are as described herein, and $R^b$ is selected from the group consisting of —$NH(CH_2)_2OH$, —$NH(CH_2)_2OCH_3$, —$NHCH_3$, —$NHC(CH_3)_3$, —$NH(CH_2)Ph$, —$NH(CH_2)_2O(CH_2)Ph$. In an exemplary embodiment, X is CH or N, $R^c$ and $R^d$ are as described herein, and $R^b$ is selected from the group consisting of —$NH(CH_2)_{m8}OH$, —$NH(CH_2)_{m8}OCH_3$, —$NH(CH_2)_{m8}OCF_3$, —$NH(CH_2)_{m8}OCH_2CH_3$, —$NH(CH_2)_{m8}OCH(CH_3)_2$, —$NH(CH_2)_{m8}O$-cyclopropyl. In an exemplary embodiment, X is CH or N, $R^c$ and $R^d$ are as described herein, and $R^b$ is selected from the group consisting of —$N(CH_3)(CH_2)_{m8}OH$, —$N(CH_3)(CH_2)_{m8}OCH_3$, —$N(CH_3)(CH_2)_{m8}OCF_3$, —$N(CH_3)(CH_2)_{m8}OCH_2CH_3$, —$N(CH_3)(CH_2)_{m8}OCH(CH_3)_2$, —$N(CH_3)(CH_2)_{m8}O$-cyclopropyl.

In an exemplary embodiment, X is CH or N, $R^c$ and $R^d$ are as described herein, and $R^b$ is selected from the group consisting of —$N(CH_3)_2$, —$N(CH_3)(CH_2)_2OH$, —$N(CH_3)(CH_2)_2OCH_3$, —$NHCH_3$, —$NHC(CH_3)_3$, —$NH(CH_2)Ph$, —$NH(CH_2)_2O(CH_2)Ph$.

In an exemplary embodiment, X is CH or N, $R^c$ and $R^d$ are as described herein, and $R^b$ is —$NR^4R^5$, wherein $R^4$ and $R^5$, together with the nitrogen to which they are attached, are joined to form a substituted or unsubstituted 4 to 8 membered ring. In an exemplary embodiment, the only non-carbon atom which forms the ring is the nitrogen to which $R^4$ and $R^5$ are attached. In an exemplary embodiment, X is CH or N, $R^c$ and $R^d$ are as described herein, and $R^b$ is —$NR^4R^5$, wherein $R^4$ and $R^5$, together with the nitrogen to which they are attached, are joined to form a member selected from the group consisting of substituted or unsubstituted pyrrolidinyl and substituted or unsubstituted piperidinyl. In an exemplary embodiment, X is CH or N, $R^c$ and $R^d$ are as described herein, and $R^b$ is —$NR^4R^5$, wherein $R^4$ and $R^5$, together with the nitrogen to which they are attached, are joined to form unsubstituted pyrrolidinyl or unsubstituted piperidinyl. In an exemplary embodiment, the only non-carbon atom which forms the ring is nitrogen. In an exemplary embodiment, the ring contains one nitrogen atom and one oxygen atom. In an exemplary embodiment, the ring contains one nitrogen atom and one oxygen atom. In an exemplary embodiment, X is CH or N, $R^c$ and $R^d$ are as described herein, and $R^b$ is —$NR^4R^5$, wherein $R^4$ and $R^5$, together with the nitrogen to which they are attached, are joined to form substituted or unsubstituted morpholinyl. In an exemplary embodiment, X is CH or N, $R^c$ and $R^d$ are as described herein, and $R^b$ is —$NR^4R^5$, wherein $R^4$ and $R^5$, together with the nitrogen to which they are attached, are joined to form unsubstituted morpholinyl.

In an exemplary embodiment, the compound has a formula which is:

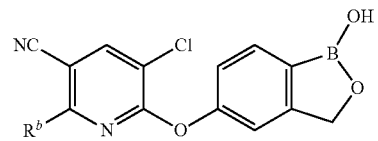

wherein $R^b$ is as described herein. In an exemplary embodiment, the compound has a formula which is:

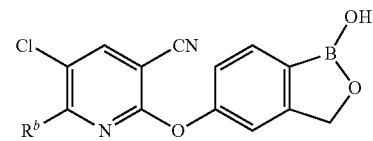

wherein $R^b$ is as described herein.

In an exemplary embodiment, the compound has a formula which is:

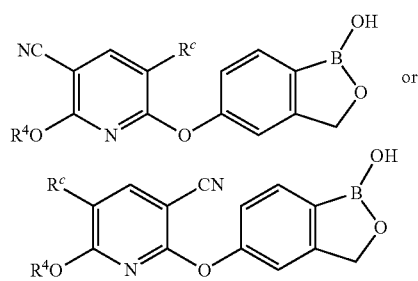

wherein $R^c$ is as described herein and $R^4$ is selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound has a formula which is:

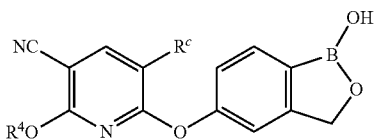

wherein $R^c$ is as described herein and $R^4$ is substituted or unsubstituted alkyl or substituted or unsubstituted heteroalkyl. In an exemplary embodiment, the compound has a formula which is:

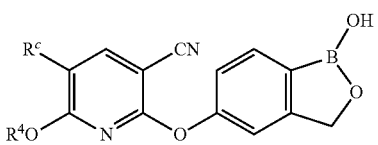

wherein $R^c$ is as described herein and $R^4$ is substituted or unsubstituted alkyl or substituted or unsubstituted heteroalkyl.

In an exemplary embodiment, the compound has a formula which is:

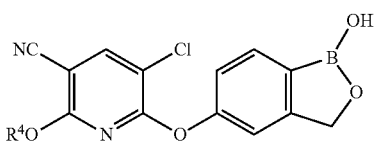

wherein $R^4$ is selected from the group consisting of H, substituted or unsubstituted alkyl, substituted or unsubstituted heteroalkyl. In an exemplary embodiment, the compound has a formula which is:

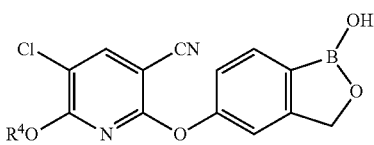

wherein $R^4$ is selected from the group consisting of H, substituted or unsubstituted alkyl, substituted or unsubstituted heteroalkyl.

In an exemplary embodiment, the compound has a formula which is:

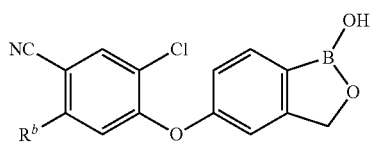

wherein $R^b$ is as described herein. In an exemplary embodiment, the compound has a formula which is:

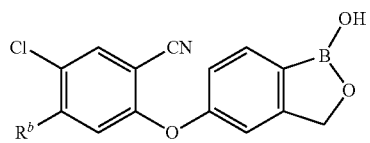

wherein $R^b$ is as described herein.

In an exemplary embodiment, the compound has a formula which is:

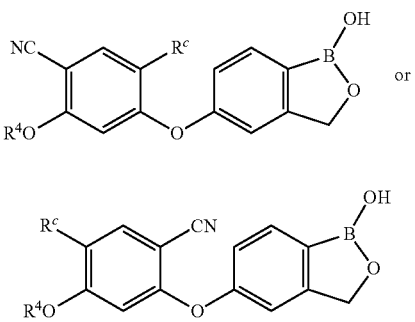

wherein $R^c$ is as described herein and $R^4$ is selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound has a formula which is:

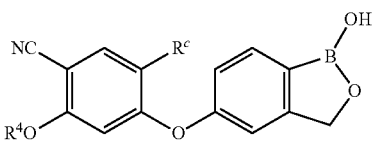

wherein $R^c$ is as described herein and $R^4$ is substituted or unsubstituted alkyl or substituted or unsubstituted heteroalkyl. In an exemplary embodiment, the compound has a formula which is:

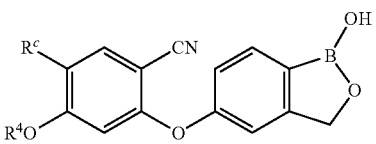

wherein $R^c$ is as described herein and $R^4$ is substituted or unsubstituted alkyl or substituted or unsubstituted heteroalkyl.

In an exemplary embodiment, the compound has a formula which is:

[Structure 5]

wherein R⁴ is selected from the group consisting of H, substituted or unsubstituted alkyl, substituted or unsubstituted heteroalkyl. In an exemplary embodiment, the compound has a formula which is:

[Structure]

wherein R⁴ is selected from the group consisting of H, substituted or unsubstituted alkyl, substituted or unsubstituted heteroalkyl.

In an exemplary embodiment, the compound has a formula which is:

[Structure]

wherein R⁴ is as described herein. In an exemplary embodiment, the compound has a formula which is:

[Structure]

wherein R⁴ is as described herein.

In another aspect, the invention provides a compound having a structure according to the formula:

[Structures] or wherein $R^b$ is as described herein and $R^d$ is halogen or unsubstituted alkyl. In an exemplary embodiment, $R^b$ is as described herein and $R^d$ is halogen. In an exemplary embodiment, $R^b$ is as described herein and $R^d$ is chlorine. In an exemplary embodiment, $R^b$ is as described herein and $R^d$ is fluorine. In an exemplary embodiment, $R^b$ is as described herein and $R^d$ is selected from the group consisting of methyl, ethyl, propyl, and isopropyl. In an exemplary embodiment, $R^b$ is as described herein and $R^d$ is methyl. In an exemplary embodiment, the compound has a formula which is:

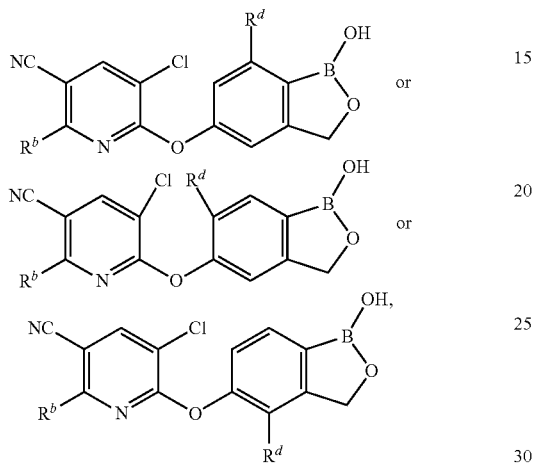

wherein $R^b$ is as described herein and $R^d$ is halogen or unsubstituted alkyl. In an exemplary embodiment, the compound has a formula which is:

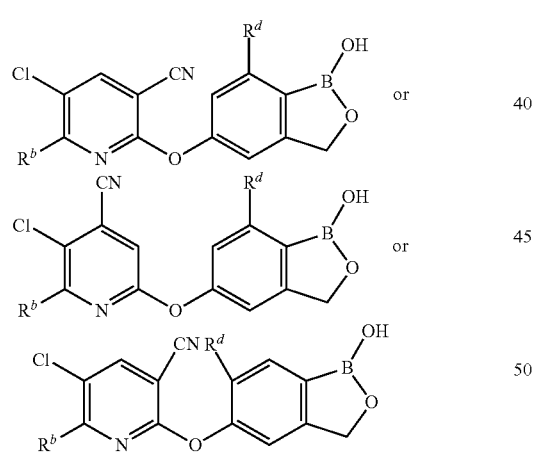

or wherein $R^b$ is as described herein and $R^d$ is halogen or unsubstituted alkyl.

In another aspect, the invention provides a compound having a structure according to the formula:

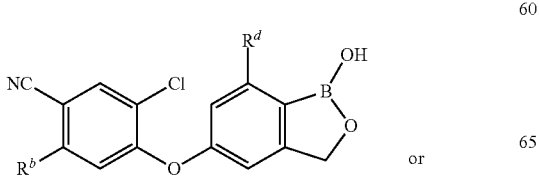

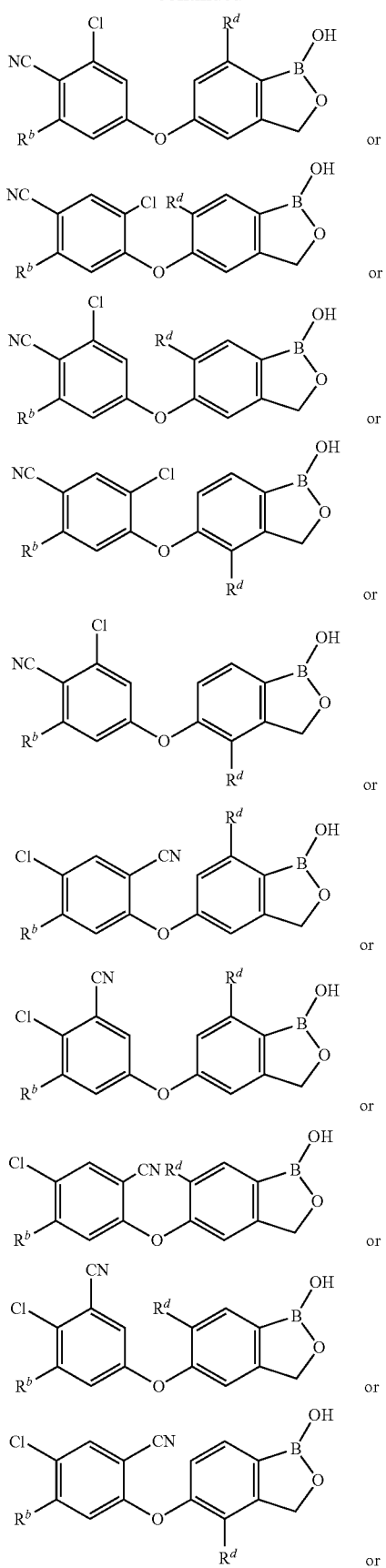

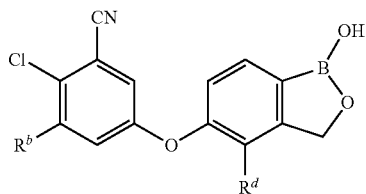

wherein $R^b$ is as described herein and $R^d$ is halogen or unsubstituted alkyl. In an exemplary embodiment, $R^b$ is as described herein and $R^d$ is halogen. In an exemplary embodiment, $R^b$ is as described herein and $R^d$ is chlorine. In an exemplary embodiment, $R^b$ is as described herein and $R^d$ is fluorine. In an exemplary embodiment, $R^b$ is as described herein and $R^d$ is selected from the group consisting of methyl, ethyl, propyl, and isopropyl. In an exemplary embodiment, $R^b$ is as described herein and $R^d$ is methyl. In an exemplary embodiment, the compound has a formula which is:

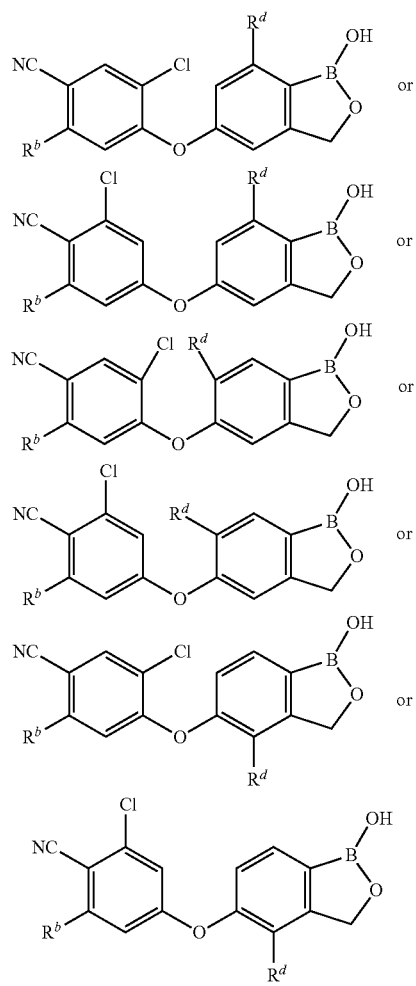

wherein $R^b$ is as described herein and $R^d$ is halogen or unsubstituted alkyl.

In an exemplary embodiment, the compound has a formula which is:

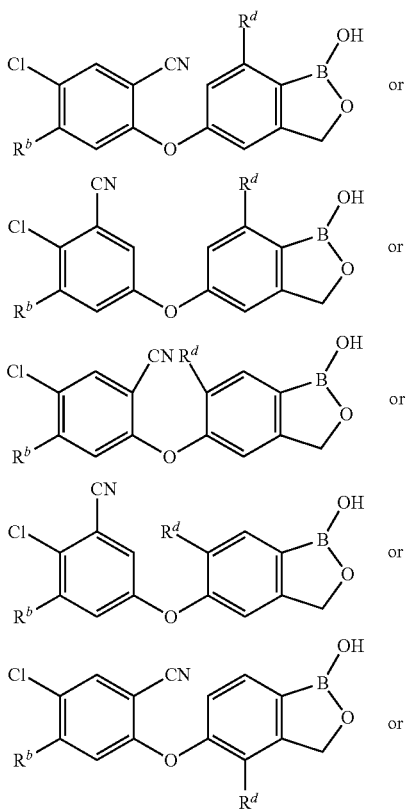

wherein $R^b$ is as described herein and $R^d$ is halogen or unsubstituted alkyl.

In another aspect, the invention provides a compound having a structure according to the formula:

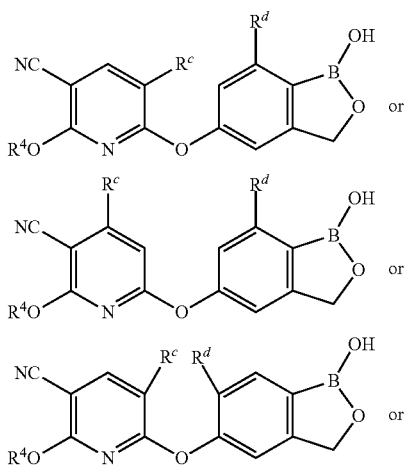

-continued

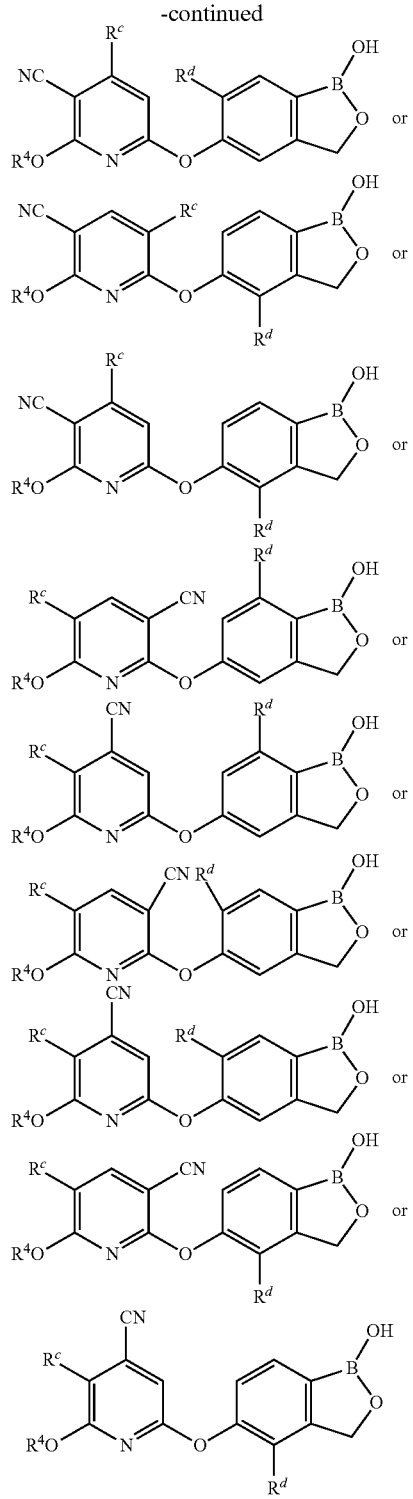

wherein $R^4$ and $R^c$ are as described herein and $R^d$ is halogen or unsubstituted alkyl. In an exemplary embodiment, $R^4$ and $R^c$ are as described herein and $R^d$ is halogen. In an exemplary embodiment, $R^4$ and $R^c$ are as described herein and $R^d$ is chlorine. In an exemplary embodiment, $R^4$ and $R^c$ are as described herein and $R^d$ is fluorine. In an exemplary embodiment, $R^4$ and $R^c$ are as described herein and $R^d$ is selected from the group consisting of methyl, ethyl, propyl, and isopropyl. In an exemplary embodiment, $R^4$ and $R^c$ are as described herein and $R^d$ is methyl. In an exemplary embodiment, the compound has a formula which is:

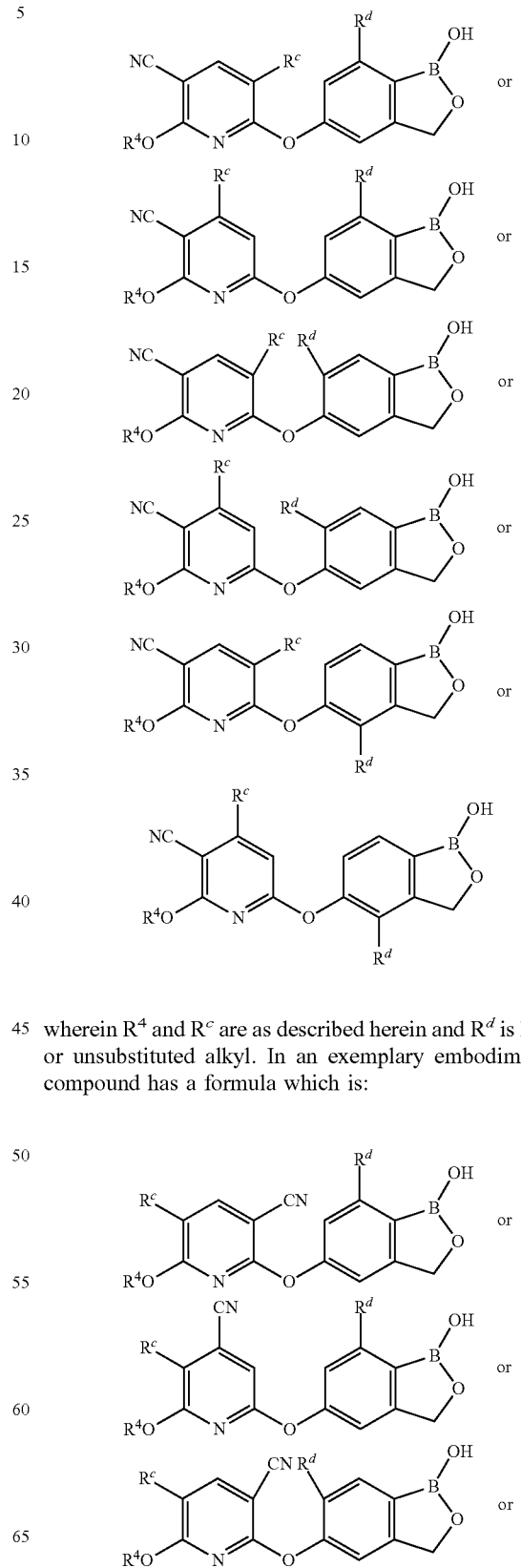

wherein $R^4$ and $R^c$ are as described herein and $R^d$ is halogen or unsubstituted alkyl. In an exemplary embodiment, the compound has a formula which is:

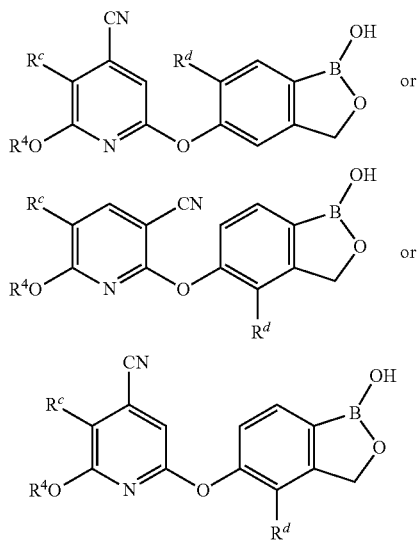

wherein $R^4$ and $R^c$ are as described herein and $R^d$ is halogen or unsubstituted alkyl In another aspect, the invention provides a compound having a structure according to the formula:

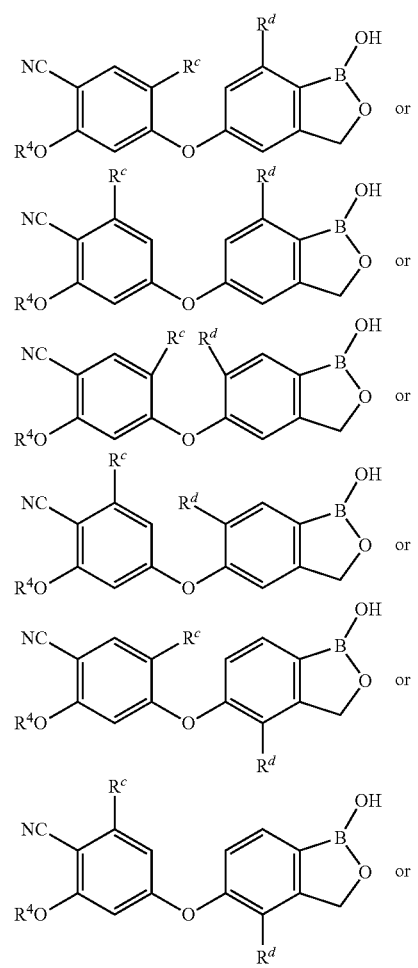

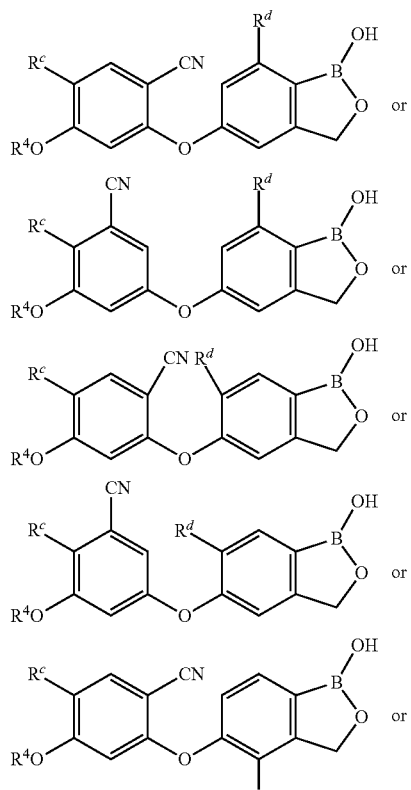

wherein $R^4$ and $R^c$ are as described herein and $R^d$ is halogen or unsubstituted alkyl. In an exemplary embodiment, $R^4$ and $R^c$ are as described herein and $R^d$ is halogen. In an exemplary embodiment, $R^4$ and $R^c$ are as described herein and $R^d$ is chlorine. In an exemplary embodiment, $R^4$ and $R^c$ are as described herein and $R^d$ is fluorine. In an exemplary embodiment, $R^4$ and $R^c$ are as described herein and $R^d$ is selected from the group consisting of methyl, ethyl, propyl, and isopropyl. In an exemplary embodiment, $R^4$ and $R^c$ are as described herein and $R^d$ is methyl. In an exemplary embodiment, the compound has a formula which is:

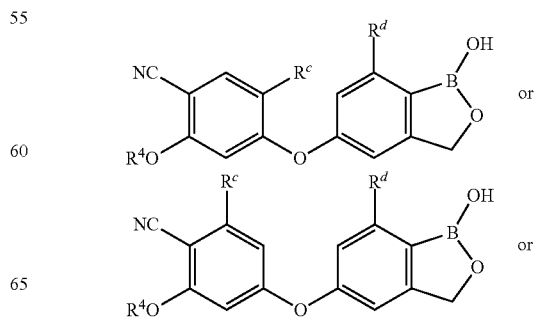

-continued

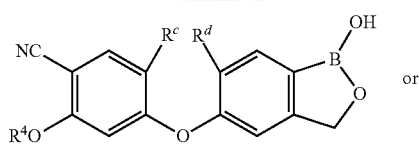

or

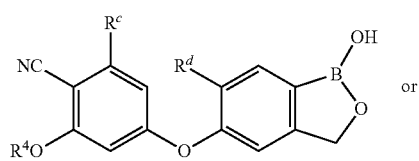

or

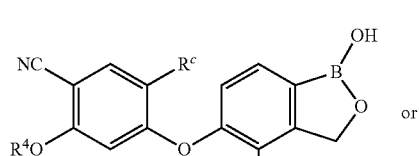

or

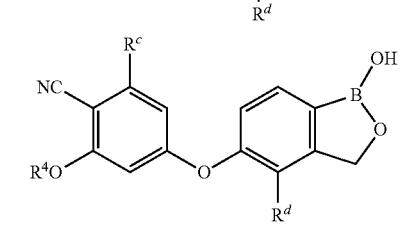

wherein R⁴ and R^c are as described herein and R^d is halogen or unsubstituted alkyl. In an exemplary embodiment, the compound has a formula which is:

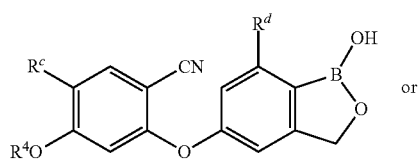

or

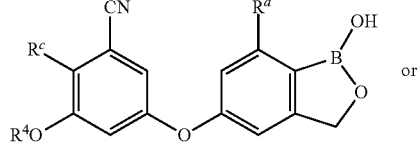

or

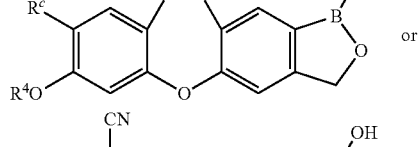

or

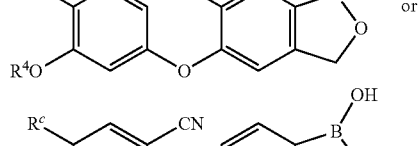

or

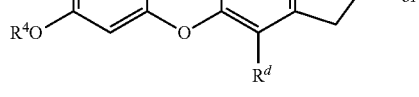

or

-continued

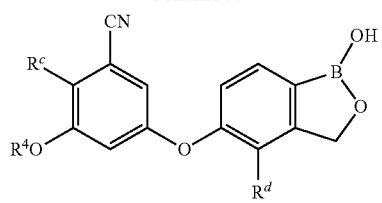

wherein R⁴ and R^c are as described herein and R^d is halogen or unsubstituted alkyl.

In another aspect, the invention provides a compound having a structure according to the formula:

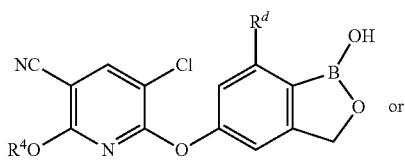

or

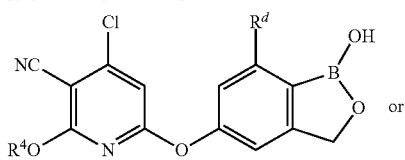

or

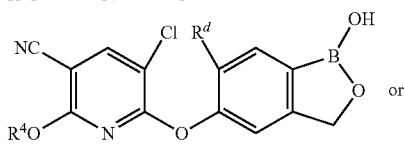

or

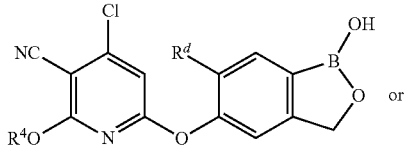

or

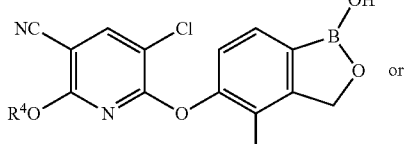

or

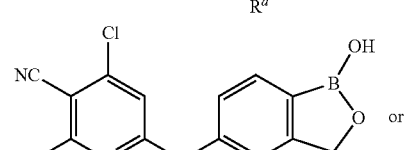

or

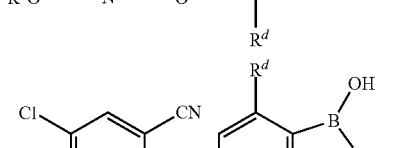

or

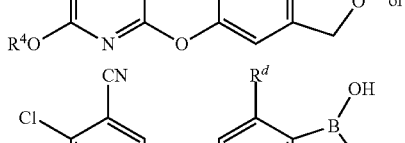

or

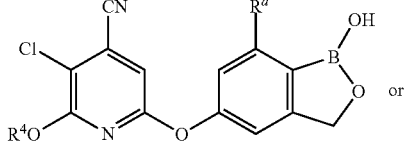

or

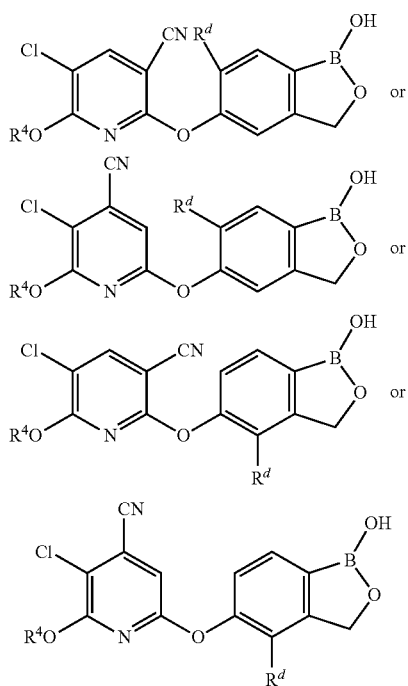

wherein $R^4$ is as described herein and $R^d$ is halogen or unsubstituted alkyl. In an exemplary embodiment, $R^4$ is as described herein and $R^d$ is halogen. In an exemplary embodiment, $R^4$ is as described herein and $R^d$ is chlorine. In an exemplary embodiment, $R^4$ is as described herein and $R^d$ is fluorine. In an exemplary embodiment, $R^4$ is as described herein and $R^d$ is selected from the group consisting of methyl, ethyl, propyl, and isopropyl. In an exemplary embodiment, $R^4$ is as described herein and $R^d$ is methyl. In an exemplary embodiment, the compound has a formula which is:

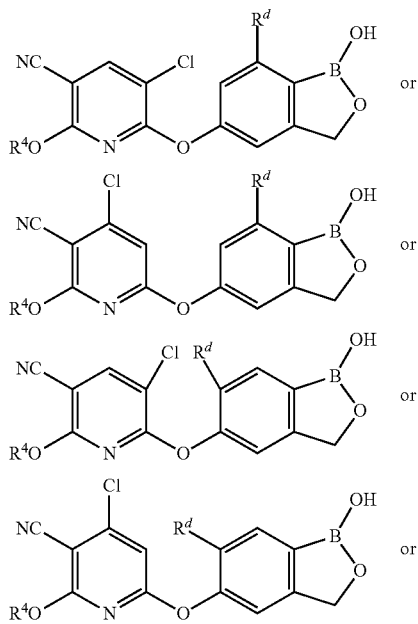

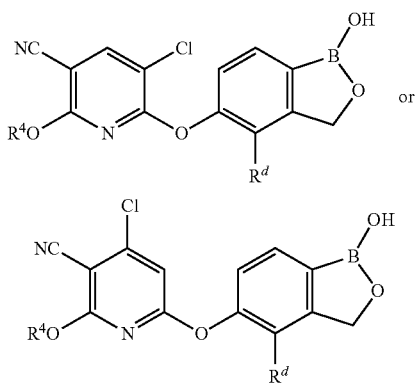

wherein $R^4$ is as described herein and $R^d$ is halogen or unsubstituted alkyl. In an exemplary embodiment, the compound has a formula which is:

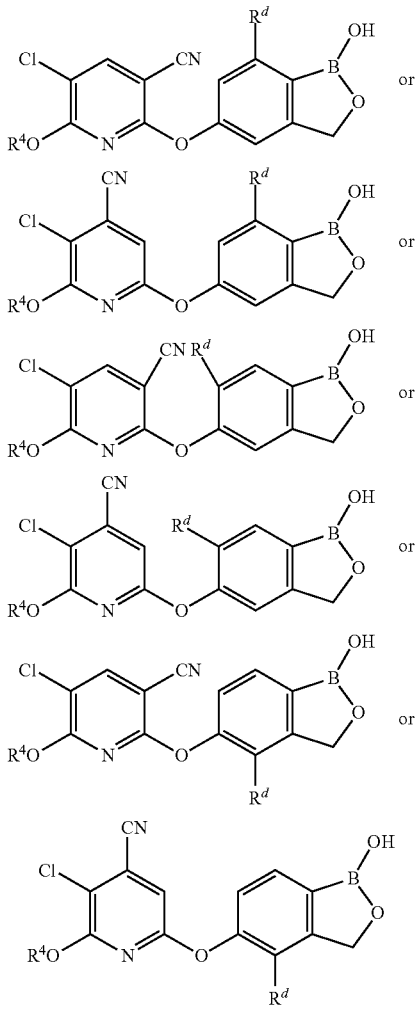

wherein $R^4$ is as described herein and $R^d$ is halogen or unsubstituted alkyl.

In another aspect, the invention provides a compound having a structure according to the formula:

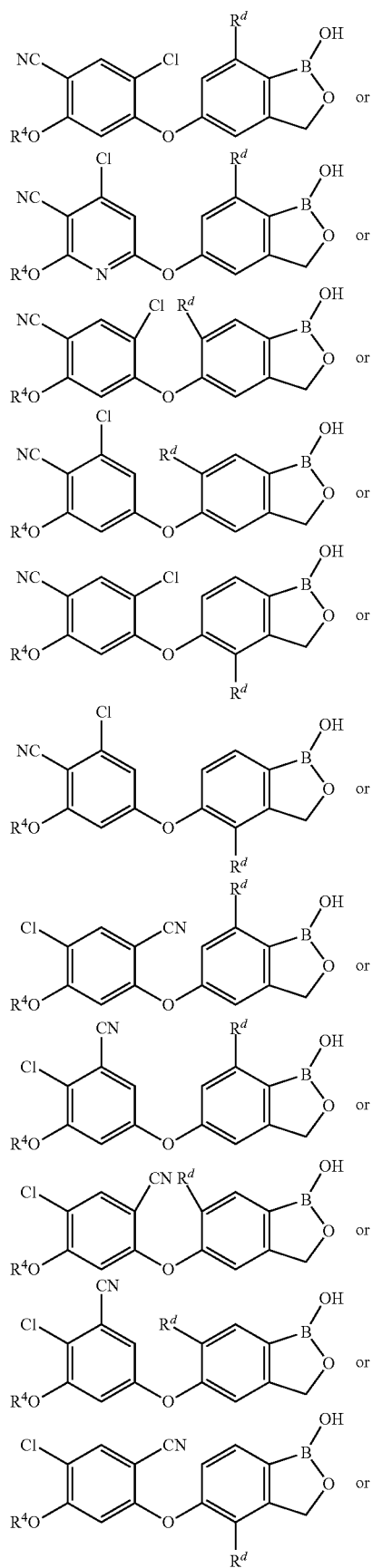

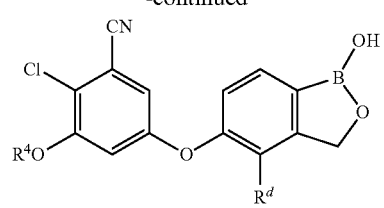

wherein $R^4$ is as described herein and $R^d$ is halogen or unsubstituted alkyl. In an exemplary embodiment, $R^4$ is as described herein and $R^d$ is halogen. In an exemplary embodiment, $R^4$ is as described herein and $R^d$ is chlorine. In an exemplary embodiment, $R^4$ is as described herein and $R^d$ is fluorine. In an exemplary embodiment, $R^4$ is as described herein and $R^d$ is selected from the group consisting of methyl, ethyl, propyl, and isopropyl. In an exemplary embodiment, $R^4$ is as described herein and $R^d$ is methyl. In an exemplary embodiment, the compound has a formula which is:

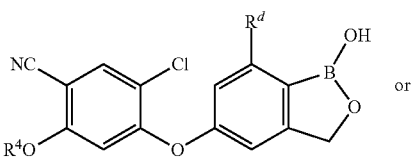

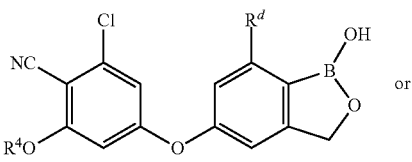

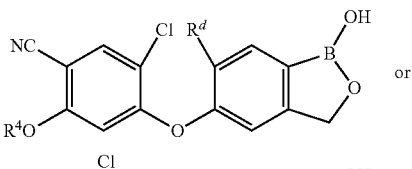

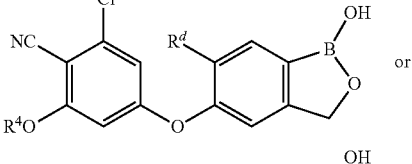

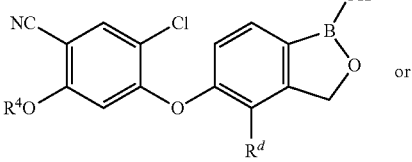

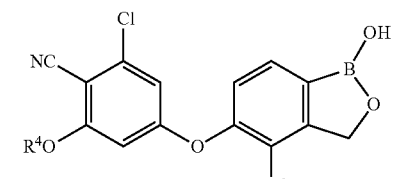

wherein $R^4$ is as described herein and $R^d$ is halogen or unsubstituted alkyl. In an exemplary embodiment, the compound has a formula which is:

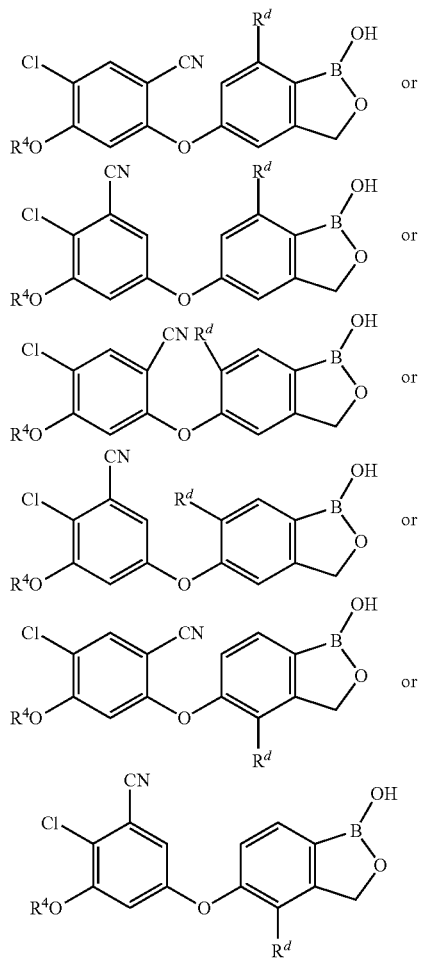

wherein $R^4$ is as described herein and $R^d$ is halogen or unsubstituted alkyl.

In an exemplary embodiment, the compound has a formula which is:

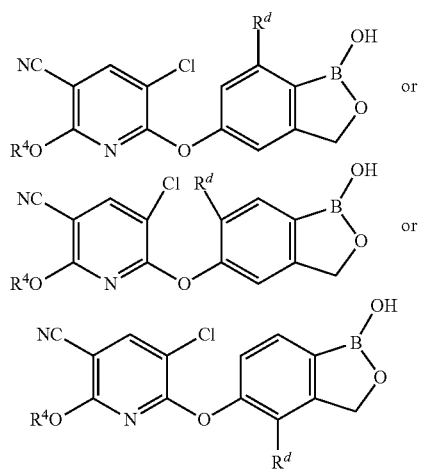

wherein $R^4$ is selected from the group consisting of H, substituted or unsubstituted alkyl, and substituted or unsubstituted heteroalkyl, $R^d$ is as described herein.

In an exemplary embodiment, the compound has a formula which is:

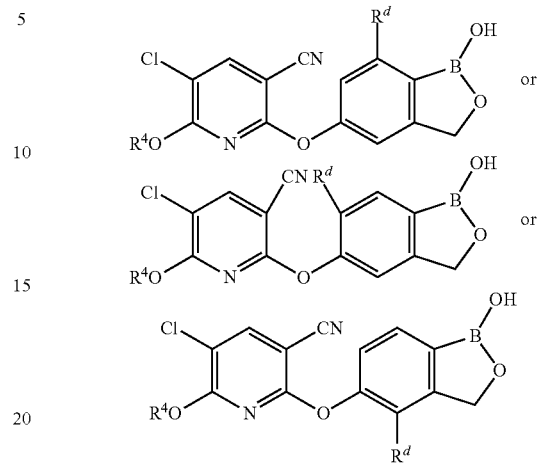

wherein $R^4$ is selected from the group consisting of H, substituted or unsubstituted alkyl, and substituted or unsubstituted heteroalkyl, $R^d$ is as described herein.

In an exemplary embodiment, the compound has a formula which is:

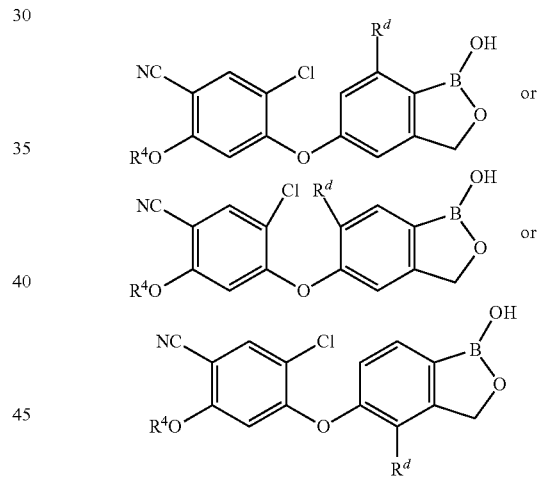

wherein $R^4$ is selected from the group consisting of H, substituted or unsubstituted alkyl, and substituted or unsubstituted heteroalkyl, $R^d$ is as described herein.

In an exemplary embodiment, the compound has a formula which is:

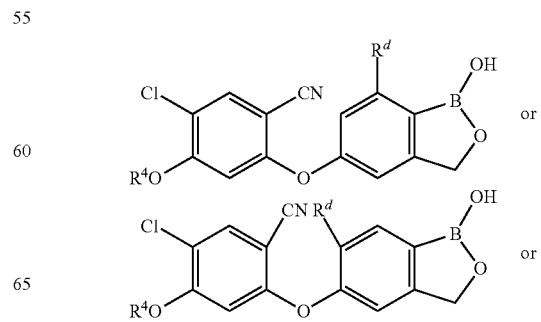

-continued

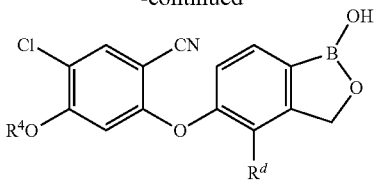

wherein $R^4$ is selected from the group consisting of H, substituted or unsubstituted alkyl, and substituted or unsubstituted heteroalkyl, $R^d$ is as described herein.

In another aspect, the invention provides a compound having a structure according to the formula:

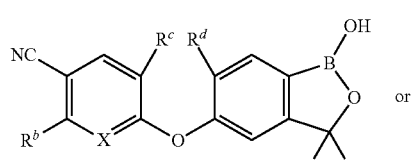

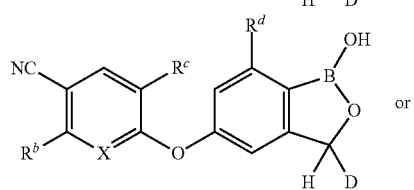

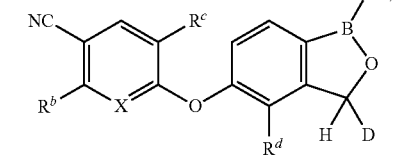

wherein $R^d$, $R^c$, X, and $R^b$ are as described herein.

In another aspect, the invention provides a compound having a structure according to the formula:

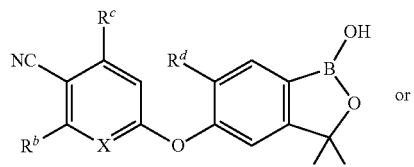

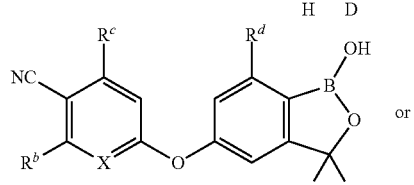

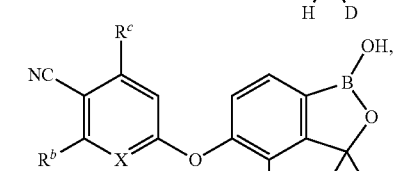

wherein $R^d$, $R^c$, X, and $R^b$ are as described herein.

In another aspect, the invention provides a compound having a structure according to the formula:

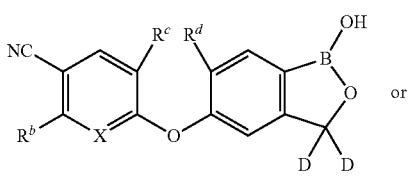

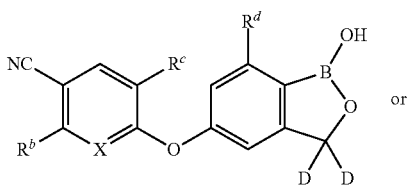

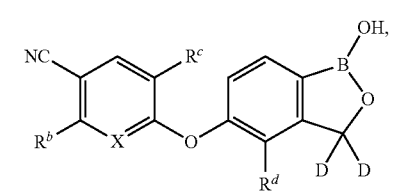

wherein $R^d$, $R^c$, X, and $R^b$ are as described herein.

In another aspect, the invention provides a compound having a structure according to the formula:

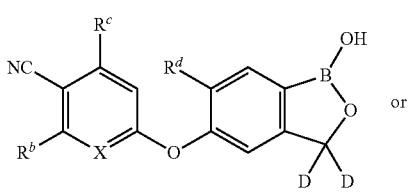

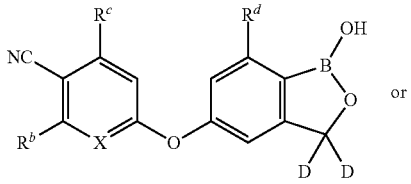

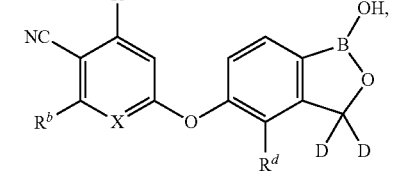

wherein $R^d$, $R^c$, X, and $R^b$ are as described herein.

In another aspect, the invention provides a compound having a structure according to the formula:

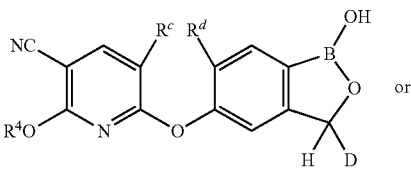

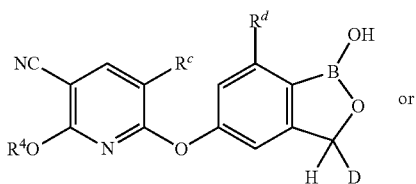

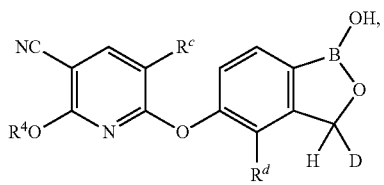

wherein $R^4$, $R^d$ and $R^c$ are as described herein.

In another aspect, the invention provides a compound having a structure according to the formula:

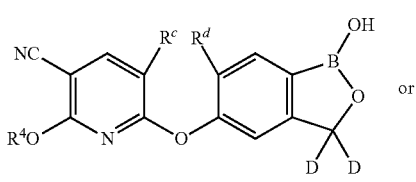

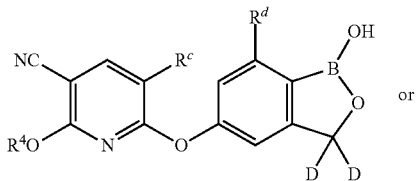

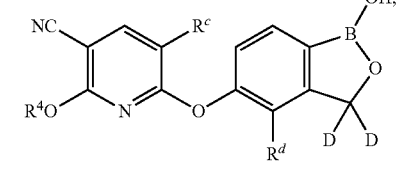

wherein $R^4$, $R^d$ and $R^c$ are as described herein.

In another aspect, the invention provides a compound having a structure according to the formula:

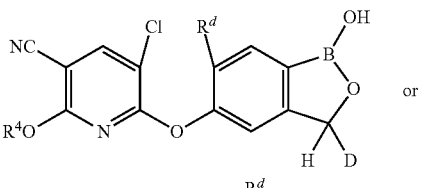

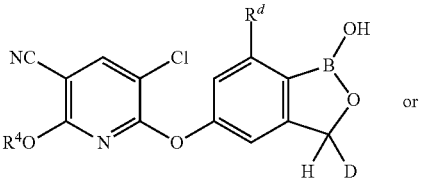

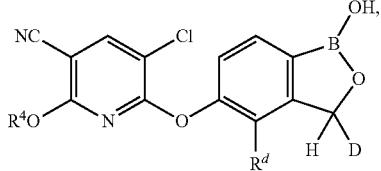

wherein $R^4$ and $R^d$ are as described herein.

In another aspect, the invention provides a compound having a structure according to the formula:

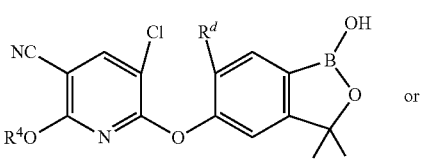

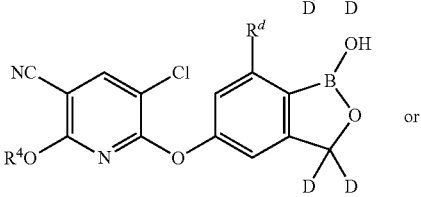

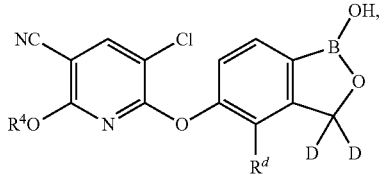

wherein $R^4$ and $R^d$ are as described herein.

In another aspect, the invention provides a compound having a structure according to the formula:

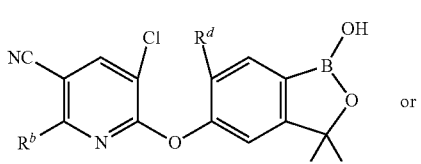

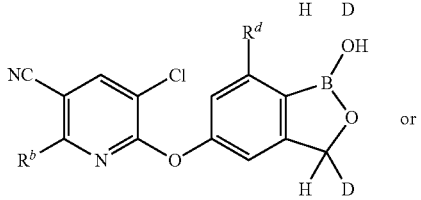

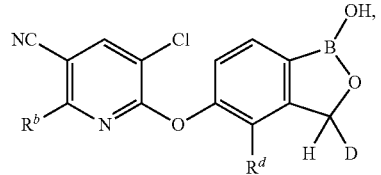

wherein $R^d$ is as described herein and $R^b$ is —O(CH$_2$)$_{m5}$OR$^{30}$, wherein m5 is 1 or 2 or 3 or 4 or 5 or 6 and $R^{30}$ is unsubstituted $C_1$ or $C_2$ or $C_3$ or $C_4$ or $C_5$ or $C_6$ alkyl.

In another aspect, the invention provides a compound having a structure according to the formula:

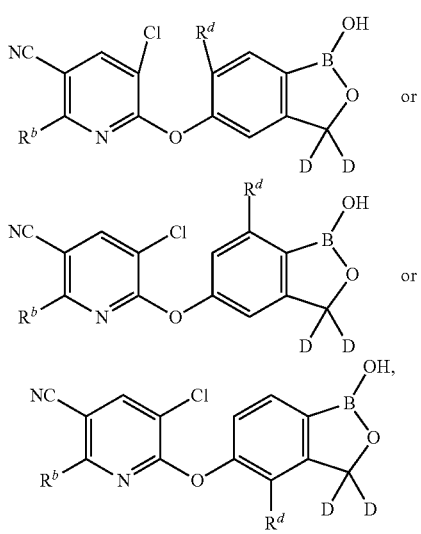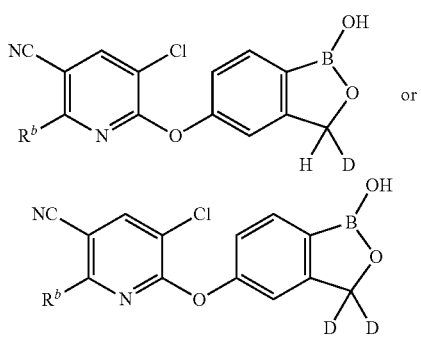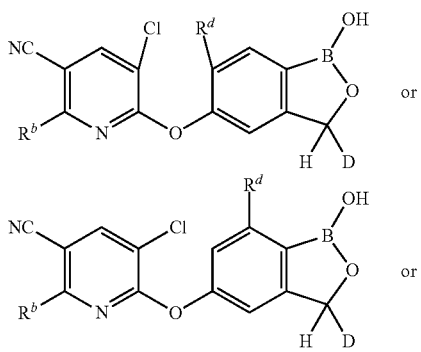

wherein $R^d$ is as described herein and $R^b$ is $-O(CH_2)_{m5}OR^{30}$, wherein m5 is 1 or 2 or 3 or 4 or 5 or 6 and $R^{30}$ is unsubstituted $C_1$ or $C_2$ or $C_3$ or $C_4$ or $C_5$ or $C_6$ alkyl.

In another aspect, the invention provides a compound having a structure according to the formula:

wherein $R^b$ is $-O(CH_2)_{m5}OR^{30}$, wherein m5 is 1 or 2 or 3 or 4 or 5 or 6 and $R^{30}$ is unsubstituted $C_1$ or $C_2$ or $C_3$ or $C_4$ or $C_5$ or $C_6$ alkyl. In an exemplary embodiment, m5 is 2 and $R^{30}$ is $C_3$ alkyl. In an exemplary embodiment, m5 is 2 and $R^{30}$ is isopropyl.

In another aspect, the invention provides a compound having a structure according to the formula:

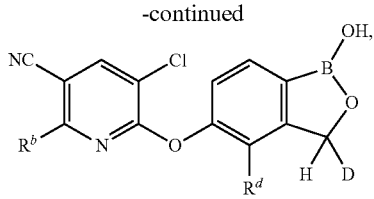

wherein $R^d$ is as described herein and $R^b$ is $-O(CH_2)_{m1}C(O)R^{4d}$, wherein m1 is a number selected from 1 or 2 or 3 or 4 or 5 or 6 and $R^{4d}$ is unsubstituted $C_1$ or $C_2$ or $C_3$ or $C_4$ or $C_5$ or $C_6$ alkyl. In an exemplary embodiment, m1 is 2 or 3 or 4 and $R^{4d}$ is methyl. In an exemplary embodiment, m1 is 3 and $R^{4d}$ is methyl.

In another aspect, the invention provides a compound having a structure according to the formula:

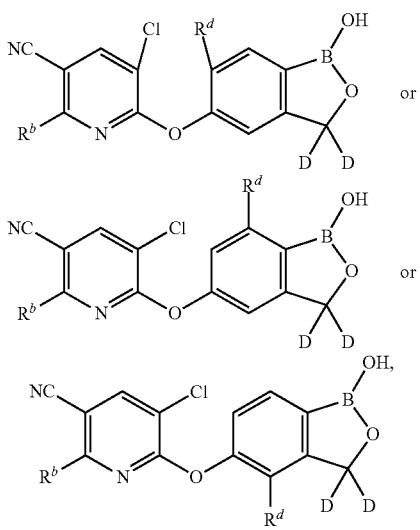

wherein $R^d$ is as described herein and $R^b$ is $-O(CH_2)_{m1}C(O)R^{4d}$, wherein m1 is a number selected from 1 or 2 or 3 or 4 or 5 or 6 and $R^{4d}$ is unsubstituted $C_1$ or $C_2$ or $C_3$ or $C_4$ or $C_5$ or $C_6$ alkyl. In an exemplary embodiment, m1 is 2 or 3 or 4 and $R^{4d}$ is methyl. In an exemplary embodiment, m1 is 3 and $R^{4d}$ is methyl.

In another aspect, the invention provides a compound having a structure according to the formula:

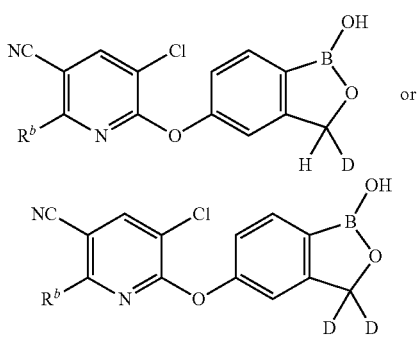

wherein $R^d$ is as described herein and $R^b$ is $-O(CH_2)_{m1}C(O)R^{4d}$, wherein m1 is a number selected from 1 or 2 or 3 or 4 or 5 or 6 and $R^{4d}$ is unsubstituted $C_1$ or $C_2$ or $C_3$ or $C_4$ or $C_5$ or $C_6$ alkyl. In an exemplary embodiment, m1 is 2 or 3 or 4 and $R^{4d}$ is methyl. In an exemplary embodiment, m1 is 3 and $R^{4d}$ is methyl.

In another aspect, the invention provides a compound having a structure according to the formula:

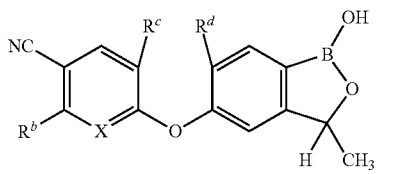

or

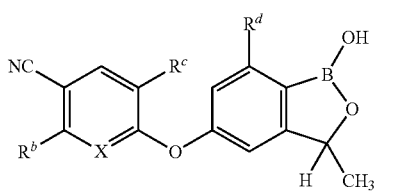

or

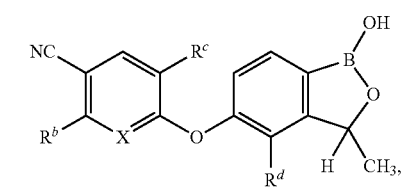

or

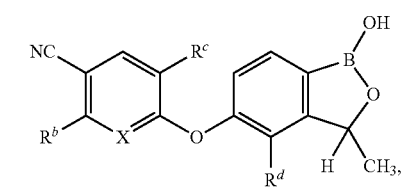

wherein $R^d$, $R^c$, X, and $R^b$ are as described herein.

In another aspect, the invention provides a compound having a structure according to the formula:

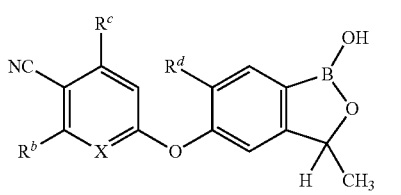

or

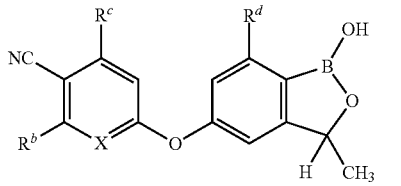

or

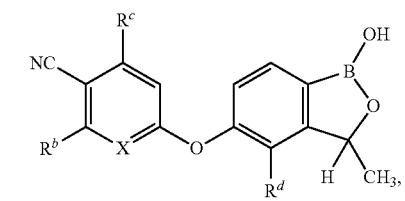

wherein $R^d$, $R^c$, X, and $R^b$ are as described herein.

In another aspect, the invention provides a compound having a structure according to the formula:

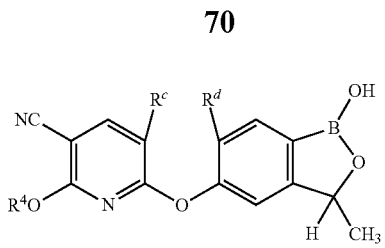

or

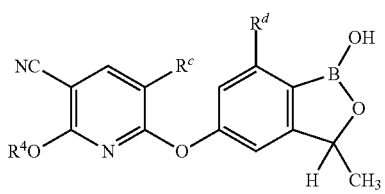

or

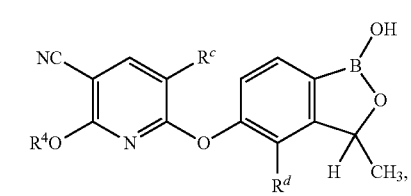

or

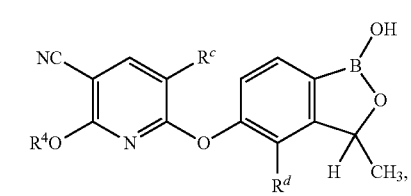

wherein $R^4$, $R^d$ and $R^c$ are as described herein.

In another aspect, the invention provides a compound having a structure according to the formula:

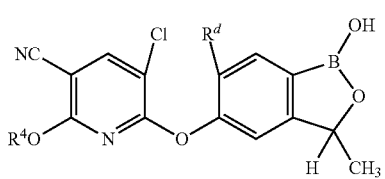

or

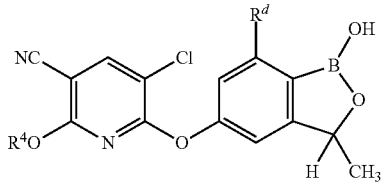

or

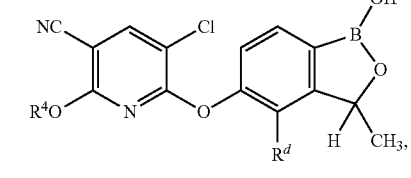

wherein $R^4$ and $R^d$ are as described herein.

In another aspect, the invention provides a compound having a structure according to the formula:

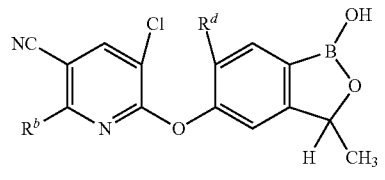

or

-continued

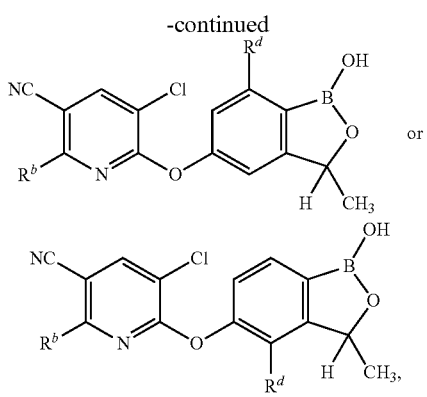

wherein $R^d$ is as described herein and $R^b$ is —O(CH$_2$)$_{m5}$OR$^{30}$, wherein m5 is 1 or 2 or 3 or 4 or 5 or 6 and R$^{30}$ is unsubstituted C$_1$ or C$_2$ or C$_3$ or C$_4$ or C$_5$ or C$_6$ alkyl.

In another aspect, the invention provides a compound having a structure according to the formula:

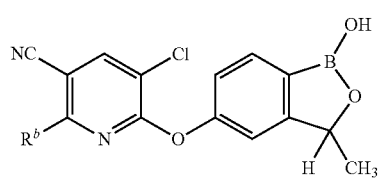

wherein $R^b$ is —O(CH$_2$)$_{m5}$OR$^{30}$, wherein m5 is 1 or 2 or 3 or 4 or 5 or 6 and R$^{30}$ is unsubstituted C$_1$ or C$_2$ or C$_3$ or C$_4$ or C$_5$ or C$_6$ alkyl. In an exemplary embodiment, m5 is 2 and R$^{30}$ is C$_3$ alkyl. In an exemplary embodiment, m5 is 2 and R$^{30}$ is isopropyl.

In another aspect, the invention provides a compound having a structure according to the formula:

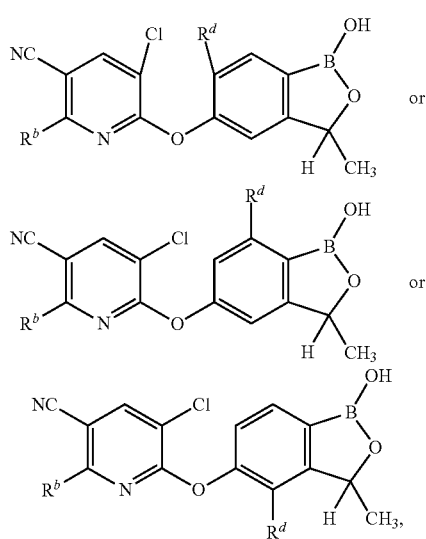

wherein $R^d$ is as described herein and $R^b$ is —O(CH$_2$)$_{m1}$C(O)R$^{4d}$, wherein m1 is a number selected from 1 or 2 or 3 or 4 or 5 or 6 and R$^{4d}$ is unsubstituted C$_1$ or C$_2$ or C$_3$ or C$_4$ or C$_5$ or C$_6$ alkyl. In an exemplary embodiment, m1 is 2 or 3 or 4 and R$^{4d}$ is methyl. In an exemplary embodiment, m1 is 3 and R$^{4d}$ is methyl.

In another aspect, the invention provides a compound having a structure according to the formula:

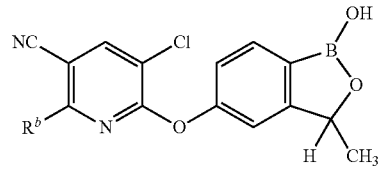

wherein $R^d$ is as described herein and $R^b$ is —O(CH$_2$)$_{m1}$C(O)R$^{4d}$, wherein m1 is a number selected from 1 or 2 or 3 or 4 or 5 or 6 and R$^{4d}$ is unsubstituted C$_1$ or C$_2$ or C$_3$ or C$_4$ or C$_5$ or C$_6$ alkyl. In an exemplary embodiment, m1 is 2 or 3 or 4 and R$^{4d}$ is methyl. In an exemplary embodiment, m1 is 3 and R$^{4d}$ is methyl.

In another aspect, the invention provides a compound having a structure according to the formula:

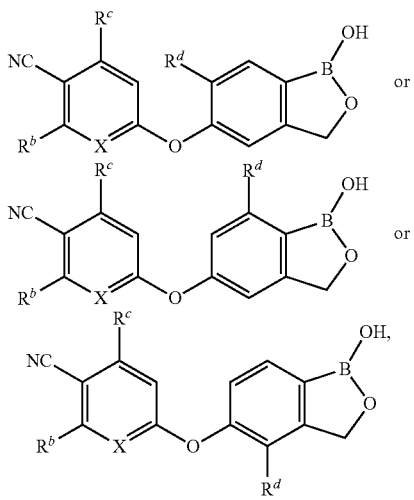

wherein $R^d$, X, and $R^b$ are as described herein, and $R^c$ is unsubstituted alkyl or halosubstituted alkyl. In an exemplary embodiment, $R^d$, X, and $R^b$ are as described herein, and $R^c$ is unsubstituted C$_1$ or C$_2$ or C$_3$ alkyl or halosubstituted C$_1$ or C$_2$ or C$_3$ alkyl. In an exemplary embodiment, X is CH, $R^d$ and $R^b$ are as described herein, and $R^c$ is trifluoromethyl. In an exemplary embodiment, X is CH, $R^d$ is H, $R^b$ is as described herein, and $R^c$ is trifluoromethyl. In an exemplary embodiment, X is CH, $R^d$ is F, $R^b$ is as described herein, and $R^c$ is trifluoromethyl. In an exemplary embodiment, X is N, $R^d$ and $R^b$ are as described herein, and $R^c$ is trifluoromethyl. In an exemplary embodiment, X is N, $R^d$ is H, $R^b$ is as described herein, and $R^c$ is trifluoromethyl. In an exemplary embodiment, X is N, $R^d$ is F, $R^b$ is as described herein, and $R^c$ is trifluoromethyl. In an exemplary embodiment, X is CH, $R^d$ and $R^b$ are as described herein, and $R^c$ is methyl. In an exemplary embodiment, X is CH, $R^d$ is H, $R^b$ is as described herein, and $R^c$ is methyl. In an exemplary embodiment, X is CH, $R^d$ is F, $R^b$ is as described herein, and $R^c$ is methyl. In an exemplary embodiment, X is N, $R^d$ and $R^b$ are as described herein, and $R^c$ is methyl. In an exemplary embodiment, X is N, $R^d$ is H, $R^b$ is as described herein, and $R^c$ is methyl. In an exemplary embodiment, X is N, $R^d$ is F, $R^b$ is as described herein, and $R^c$ is methyl. In an exemplary embodiment, X is CH, $R^d$ and $R^b$ are as described herein, and $R^c$ is ethyl. In an exemplary embodiment, X is CH, $R^d$ is H, $R^b$ is as described herein, and $R^c$ is ethyl. In an exemplary embodiment, X is CH, $R^d$ is F, $R^b$ is as described herein, and $R^c$ is ethyl. In an exemplary embodiment, X is N, $R^d$ and $R^b$ are as described herein, and $R^c$ is ethyl. In an exemplary embodiment, X is N, $R^d$ is H, $R^b$ is as described herein, and $R^c$ is ethyl. In an exemplary embodiment, X is N, $R^d$ is F, $R^b$ is as described herein, and $R^c$ is ethyl.

In an exemplary embodiment, the invention provides a compound described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the salt is a pharmaceutically acceptable salt. In an exemplary embodiment, the invention provides a compound described herein, or a hydrate thereof. In an exemplary embodiment, the invention provides a compound described herein, or a solvate thereof. In an exemplary embodiment, the invention provides a compound described herein, or a prodrug thereof. In an exemplary embodiment, the invention provides a salt of a compound described herein. In an exemplary embodiment, the invention provides a pharmaceutically acceptable salt of a compound described herein. In an exemplary embodiment, the invention provides a hydrate of a compound described herein. In an exemplary embodiment, the invention provides a solvate of a compound described herein. In an exemplary embodiment, the invention provides a prodrug of a compound described herein.

In an exemplary embodiment, alkyl is linear alkyl. In an exemplary embodiment, alkyl is branched alkyl. In another exemplary embodiment, heteroalkyl is linear heteroalkyl. In another exemplary embodiment, heteroalkyl is branched heteroalkyl.

IIIb. Additional Compounds

In an exemplary embodiment, the compound has a structure according to the formula:

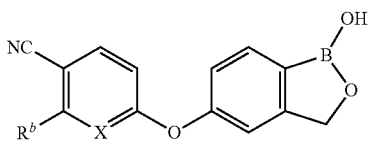

wherein X is N or CH, $R^b$ is a member selected from halogen and substituted or unsubstituted alkyl, $C(O)R^4$, $C(O)OR^4$, $OR^4$, $NR^4R^5$, wherein $R^4$ and $R^5$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, with the proviso that $R^4$ and $R^5$, together with the atoms to which they are attached, are optionally combined to form a 5- to 7-membered substituted or unsubstituted heterocycloalkyl ring, and salts thereof. In an exemplary embodiment, $R^b$ is a member selected from $OR^4$ and $NR^4R^5$, wherein $R^4$ and $R^5$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, with the proviso that $R^4$ and $R^5$, together with the atoms to which they are attached, are optionally combined to form a 5- to 7-membered substituted or unsubstituted heterocycloalkyl ring.

In an exemplary embodiment, X is N or CH, $R^b$ is alkyl, optionally substituted with a member selected from halogen, $OR^{4a}$, $C(O)OR^{4a}$, $NR^{4a}R^{4b}$, substituted or unsubstituted heterocycloalkyl or unsubstituted heteroaryl, wherein $R^{4a}$ and $R^{4b}$ are independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{4a}$ is H or unsubstituted alkyl. In an exemplary embodiment, $R^{4b}$ is H or unsubstituted alkyl or C(O)H. In an exemplary embodiment, X is N or CH, $R^b$ is fluoro. In an exemplary embodiment, X is N or CH, $R^b$ is chloro.

In an exemplary embodiment, X is N or CH, $R^b$ is OH. In an exemplary embodiment, X is N or CH, $R^b$ is $OR^4$, wherein $R^4$ is alkyl is optionally substituted with at least one halogen, hydroxyl, ether, carboxy or ester moiety.

In an exemplary embodiment, X is N or CH, $R^b$ is $OR^4$, wherein $R^4$ is unsubstituted alkyl. In an exemplary embodiment, X is N or CH, $R^b$ is $OR^4$, wherein $R^4$ is unsubstituted $C_1$ or $C_2$ or $C_3$ alkyl. In an exemplary embodiment, X is N or CH, $R^b$ is $OR^4$, wherein $R^4$ is unsubstituted $C_4$ or $C_5$ or $C_6$ alkyl. In an exemplary embodiment, X is N or CH, $R^b$ is $OR^4$, wherein $R^4$ is methyl or ethyl or propyl or isopropyl or isobutyl.

In an exemplary embodiment, X is N or CH, $R^b$ is $OR^4$, wherein $R^4$ is alkyl substituted with at least one halogen. In an exemplary embodiment, X is N or CH, $R^b$ is $OR^4$, wherein $R^4$ is alkyl substituted with one or two or three halogen(s). In an exemplary embodiment, X is N or CH, $R^b$ is $O(CH_2)_{m1}R^{31}$, wherein m1 is 1 or 2 or 3 or 4 or 5 or 6 and $R^{31}$ is a methyl moiety wherein at least one of the methyl hydrogens is substituted with a halogen. In an exemplary embodiment, the halogen is chloro. In an exemplary embodiment, the halogen is fluoro. In an exemplary embodiment, $R^{31}$ is —$CF_3$. In an exemplary embodiment, $R^{31}$ is —$CHF_2$. In an exemplary embodiment, m1 is 1 or 2 or 3. In an exemplary embodiment, X is N or CH, $R^b$ is —$OCH_2CF_3$. In an exemplary embodiment, X is N or CH, $R^b$ is —$OCH_2CHF_2$.

In an exemplary embodiment, X is N or CH, $R^b$ is —$O(CH_2)_{m1}OC(O)R^{4d}$, wherein m1 is a number selected from 1 or 2 or 3 or 4 or 5 or 6 and $R^{4d}$ is unsubstituted alkyl. In an exemplary embodiment, m1 is 1 or 2 or 3. In an exemplary embodiment, m1 is 2. In an exemplary embodiment, $R^{4d}$ is unsubstituted $C_1$ or $C_2$ or $C_3$ alkyl. In an exemplary embodiment, $R^{4d}$ is unsubstituted $C_4$ or $C_5$ or $C_6$ alkyl. In an exemplary embodiment, $R^{4d}$ is methyl. In an exemplary embodiment, X is N or CH, $R^b$ is —$O(CH_2)_2OC(O)CH_3$.

In an exemplary embodiment, X is N or CH, $R^b$ is —$O(CH_2)_{m1}C(O)R^{4d}$, wherein m1 is a number selected from 1 or 2 or 3 or 4 or 5 or 6 and $R^{4d}$ is unsubstituted alkyl. In an exemplary embodiment, m1 is 2 or 3 or 4. In an exemplary embodiment, m1 is 3. In an exemplary embodiment, $R^{4d}$ is unsubstituted $C_1$ or $C_2$ or $C_3$ alkyl. In an exemplary embodiment, $R^{4d}$ is unsubstituted $C_4$ or $C_5$ or $C_6$ alkyl. In an exemplary embodiment, $R^{4d}$ is methyl. In an exemplary embodiment, X is N or CH, $R^b$ is —$O(CH_2)_3C(O)CH_3$.

In an exemplary embodiment, X is N or CH, $R^b$ is —$O(CH_2)_{m1}C(O)OR^{4d}$, wherein m1 is a number selected from 1 or 2 or 3 or 4 or 5 or 6 and $R^{4d}$ is H or unsubstituted alkyl. In an exemplary embodiment, X is N or CH, $R^b$ is —OCH$_2$C(O)OR$^{4d}$, wherein R$^{4d}$ is as described herein. In an exemplary embodiment, R$^{4d}$ is H or methyl or ethyl or t-butyl. In an exemplary embodiment, X is N or CH, R$^b$ is —O(CH$_2$)C(O)OCH$_2$CH$_3$ or —O(CH$_2$)C(O)OH or —O(CH$_2$)C(O)OC(CH$_3$)$_3$.

In an exemplary embodiment, X is N or CH, R$^b$ is OR$^4$, wherein R$^4$ is alkyl substituted with a substituted or unsubstituted amino. In an exemplary embodiment, X is N or CH, R$^b$ is —O(CH$_2$)$_{m2}$C(O)NR$^{4e}$R$^{4f}$, wherein m2 is a number selected from 1 or 2 or 3 or 4 or 5 or 6, and R$^{4e}$ and R$^{4f}$ are independently selected from H or unsubstituted alkyl, or R$^{4e}$ and R$^{4f}$, together with the nitrogen to which they are attached, are optionally joined to form a substituted or unsubstituted 4 to 8 membered ring.

In an exemplary embodiment, X is N or CH, R$^b$ is —OCH$_2$C(O)NR$^{4e}$R$^{4f}$, wherein R$^{4e}$ and R$^{4f}$ are as described herein. In an exemplary embodiment, R$^{4e}$ and R$^{4f}$ are the same and are independently selected unsubstituted alkyl. In an exemplary embodiment, R$^{4e}$ and R$^{4f}$ are different and are independently selected unsubstituted alkyl. In an exemplary embodiment, R$^{4e}$ is H. In an exemplary embodiment, R$^{4f}$ is H. In an exemplary embodiment, R$^{4e}$ and R$^{4f}$ are ethyl. In an exemplary embodiment, R$^{4e}$ and R$^{4f}$, together with the nitrogen to which they are attached, are joined to form piperazinyl, either unsubstituted or substituted with unsubstituted alkyl on the nitrogen at the 4-position. In an exemplary embodiment, R$^{4e}$ and R$^{4f}$, together with the nitrogen to which they are attached, are joined to form N-methyl piperazinyl. In an exemplary embodiment, R$^{4e}$ and R$^{4f}$, together with the nitrogen to which they are attached, are joined to form piperidinyl, either unsubstituted or substituted with unsubstituted alkyl. In an exemplary embodiment, R$^{4e}$ and R$^{4f}$, together with the nitrogen to which they are attached, are joined to form 4-methyl piperidinyl. In an exemplary embodiment, R$^{4e}$ and R$^{4f}$, together with the nitrogen to which they are attached, are joined to form unsubstituted morpholinyl.

In an exemplary embodiment, X is N or CH, R$^b$ is OR$^4$, wherein R$^4$ is unsubstituted alkyl. In an exemplary embodiment, R$^4$ is C$_1$ or C$_2$ or C$_3$ or C$_4$ or C$_5$ or C$_6$ alkyl. In an exemplary embodiment, R$^4$ is C$_1$ alkyl. In an exemplary embodiment, R$^b$ is OR$^4$, wherein R$^4$ is alkyl substituted with unsubstituted pyridinyl. In an exemplary embodiment, X is N or CH, R$^b$ is

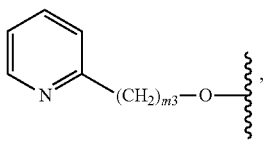

wherein m3 is 1 or 2 or 3 or 4 or 5 or 6. In an exemplary embodiment, m3 is 1.

In an exemplary embodiment, X is N or CH, R$^b$ is OR$^4$, wherein R$^4$ is substituted or unsubstituted cycloalkyl. In an exemplary embodiment, X is N or CH, R$^b$ is OR$^4$, wherein R$^4$ is unsubstituted cycloalkyl. In an exemplary embodiment, X is N or CH, R$^b$ is OR$^4$, wherein R$^4$ is cyclopentyl. In an exemplary embodiment, R$^4$ is unsubstituted cyclohexyl.

In an exemplary embodiment, X is N or CH, R$^b$ is OR$^4$, wherein R$^4$ is alkyl substituted with unsubstituted alkoxy. In an exemplary embodiment, X is N or CH, R$^b$ is —O(CH$_2$)$_{m5}$OR$^{30}$, wherein m5 is 1 or 2 or 3 or 4 or 5 or 6 and R$^{30}$ is H or unsubstituted alkyl or unsubstituted tetrahydropyran. In an exemplary embodiment, R$^{30}$ is C$_1$ or C$_2$ or C$_3$ or C$_4$ or C$_5$ or C$_6$ alkyl. In an exemplary embodiment, m5 is 1 or 2 or 3. In an exemplary embodiment, m5 is 2. In an exemplary embodiment, R$^{30}$ is C$_1$ or C$_2$ or C$_3$ alkyl. In an exemplary embodiment, R$^{30}$ is C$_4$ or C$_5$ or C$_6$ alkyl. In an exemplary embodiment, R$^{30}$ is H. In an exemplary embodiment, R$^{30}$ is methyl or isopropyl. In an exemplary embodiment, R$^{30}$ is 2-tetrahydropyran. In an exemplary embodiment, X is N or CH, R$^b$ is —O(CH$_2$)$_2$OC(CH$_3$)$_2$ or —O(CH$_2$)$_2$OH or —O(CH$_2$)$_2$O-THP (TetraHydroPyran).

In an exemplary embodiment, X is N or CH, R$^b$ is OR$^4$, wherein R$^4$ is alkyl substituted with unsubstituted cycloalkyl. In an exemplary embodiment, X is N or CH, R$^b$ is —O(CH$_2$)$_{m5}$OR$^{30}$, wherein m5 is 1 or 2 or 3 or 4 or 5 or 6 and R$^{30}$ is a 3-8 membered cycloalkyl. In an exemplary embodiment, R$^{30}$ is a 3-6 membered cycloalkyl. In an exemplary embodiment, R$^{30}$ is a member selected from cyclopropyl and cyclopentyl. In an exemplary embodiment, m5 is 1 or 2 or 3. In an exemplary embodiment, m5 is 1.

In an exemplary embodiment, X is N or CH, R$^b$ is C(O)R$^4$, wherein R$^4$ is unsubstituted alkyl. In an exemplary embodiment, R$^4$ is C$_1$ or C$_2$ or C$_3$ or C$_4$ or C$_5$ or C$_6$ alkyl. In an exemplary embodiment, R$^4$ is C$_1$ alkyl. In an exemplary embodiment, R$^b$ is C(O)H. In an exemplary embodiment, X is N or CH, R$^b$ is C$_1$ or C$_2$ or C$_3$ or C$_4$ or C$_5$ or C$_6$ alkyl. In an exemplary embodiment, X is N or CH, R$^b$ is C$_1$ alkyl. In an exemplary embodiment, X is N or CH, R$^b$ is alkyl substituted with halogen. In an exemplary embodiment, X is N or CH, R$^b$ is alkyl substituted with at least one halogen. In an exemplary embodiment, X is N or CH, R$^b$ is alkyl substituted with at least one fluoro. In an exemplary embodiment, X is N or CH, R$^b$ is CF$_3$.

In an exemplary embodiment, X is N or CH, R$^b$ is alkyl substituted with hydroxy. In an exemplary embodiment, X is N or CH, R$^b$ is —(CH$_2$)$_{m4}$OH, wherein m4 is a number selected from 1 or 2 or 3 or 4 or 5 or 6. In an exemplary embodiment, m4 is 1.

In an exemplary embodiment, X is N or CH, R$^b$ is alkyl substituted with carboxy or ester. In an exemplary embodiment, X is N or CH, R$^b$ is —(CH$_2$)$_{m1}$C(O)OR$^{4a}$, wherein m1 is a number selected from 1 or 2 or 3 or 4 or 5 or 6 and R$^{4a}$ is H or unsubstituted alkyl.

In an exemplary embodiment, X is N or CH, R$^b$ is —CH$_2$C(O)OR$^{4a}$, wherein R$^{4a}$ is as described herein. In an exemplary embodiment, R$^{4a}$ is H or methyl or ethyl or t-butyl.

In an exemplary embodiment, X is N or CH, R$^b$ is alkyl substituted with amino. In an exemplary embodiment, R$^b$ is —(CH$_2$)$_{m7}$NR$^{4a}$R$^{4b}$, wherein m7 is a number selected from 1 or 2 or 3 or 4 or 5 or 6 and R$^{4a}$ and R$^{4b}$ are members independently selected from H and unsubstituted alkyl and formyl, or R$^{4a}$ and R$^{4b}$, together with the nitrogen to which they are attached, are optionally joined to form a substituted or unsubstituted 4 to 8 membered ring. In an exemplary embodiment, R$^{4b}$ is as described herein, R$^{4a}$ is H. In an exemplary embodiment, R$^{4a}$ is as described herein, R$^{4b}$ is H. In an exemplary embodiment, X is N or CH, R$^{4b}$ is as described herein, R$^{4a}$ is methyl. In an exemplary embodiment, R$^{4a}$ is as described herein, R$^{4b}$ is methyl. In an exemplary embodiment, m7 is 1. In an exemplary embodiment, R$^{4a}$ and R$^{4b}$, together with the nitrogen to which they are attached, are joined to form piperazinyl, either unsubstituted or substituted with unsubstituted alkyl on the nitrogen at the 4-position. In an exemplary embodiment, R$^{4a}$ and R$^{4b}$, together with the nitrogen to which they are attached, are joined to form N-methyl piperazinyl. In an exemplary embodiment, R$^{4a}$ and R$^{4b}$, together with the nitrogen to which they are attached, are joined to form piperidinyl, either unsubstituted or substituted with unsubstituted alkyl. In an exemplary embodiment, $R^{4a}$ and $R^{4b}$, together with the nitrogen to which they are attached, are joined to form 4-methyl piperidinyl. In an exemplary embodiment, $R^{4a}$ and $R^{4b}$, together with the nitrogen to which they are attached, are joined to form unsubstituted morpholinyl.

In an exemplary embodiment, X is N or CH, $R^b$ is $NH_2$. In an exemplary embodiment, X is N or CH, $R^b$ is $NR^4R^5$ wherein $R^4$ is a member selected from H and unsubstituted alkyl, and $R^5$ is a member selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, X is N or CH, $R^b$ is $NR^4R^5$, $R^4$ is as described herein, $R^5$ is unsubstituted alkyl. In an exemplary embodiment, X is N or CH, $R^b$ is $NR^4R^5$, wherein $R^4$ is H, $R^5$ is as described herein. In an exemplary embodiment, X is N or CH, $R^b$ is $NR^4R^5$, wherein $R^4$ is unsubstituted alkyl, $R^5$ is as described herein. In an exemplary embodiment, X is N or CH, $R^b$ is $NR^4R^5$, wherein $R^5$ is as described herein, $R^4$ is unsubstituted $C_1$ or $C_2$ or $C_3$ or $C_4$ or $C_5$ or $C_6$ alkyl. In an exemplary embodiment, X is N or CH, $R^b$ is $NR^4R^5$, wherein $R^4$ is unsubstituted $C_1$ or $C_2$ or $C_3$ alkyl and $R^5$ is as described herein. In an exemplary embodiment, X is N or CH, $R^b$ is $NR^4R^5$, wherein $R^4$ is methyl and $R^5$ is as described herein. In an exemplary embodiment, X is N or CH, $R^b$ is $NR^4R^5$, wherein $R^4$ is as described herein $R^5$ is unsubstituted $C_1$ or $C_2$ or $C_3$ or $C_4$ or $C_5$ or $C_6$ alkyl. In an exemplary embodiment, X is N or CH, $R^b$ is $NR^4R^5$, wherein $R^5$ is a member selected from methyl and tert-butyl, and $R^4$ is as described herein.

In an exemplary embodiment, X is N or CH, $R^b$ is $NR^4R^5$, wherein $R^4$ is as described herein, $R^5$ is alkyl, substituted with a member selected from OH, unsubstituted arylalkoxy, unsubstituted alkoxy, and unsubstituted aryl. In an exemplary embodiment, X is N or CH, $R^b$ is $NR^4R^5$, wherein $R^5$ is —$(CH_2)_{m8}$Ph.

In an exemplary embodiment, X is N or CH, $R^b$ is $NR^4R^5$, wherein $R^5$ is —$(CH_2)_{m8}OR^{26}$, wherein m8 is a number selected from 1 or 2 or 3 or 4 or 5 or 6 and $R^{26}$ is a member selected from H, unsubstituted or aryl substituted $C_1$ or $C_2$ or $C_3$ or $C_4$ or $C_5$ or $C_6$ alkyl. In an exemplary embodiment, m8 is 1 or 2 or 3. In an exemplary embodiment, m8 is 2. In an exemplary embodiment, $R^{26}$ is unsubstituted $C_1$ or $C_2$ or $C_3$ or $C_4$ or $C_5$ or $C_6$ alkyl. In an exemplary embodiment, $R^{26}$ is methyl. In an exemplary embodiment, $R^{26}$ is benzyl. In an exemplary embodiment, X is N or CH, $R^b$ is $NR^4R^5$, wherein $R^4$ is as described herein, $R^5$ is —$(CH_2)_{m8}$O$(CH_2)_{m9}$Ph, wherein m8 and m9 are each independently selected from 1 or 2 or 3 or 4 or 5 or 6. In an exemplary embodiment, X is N or CH, $R^b$ is $NR^4R^5$, wherein $R^4$ is as described herein $R^5$ is —$(CH_2)_{m8}$O$(CH_2)_{m9}$Ph, wherein m8 and m9 are each independently selected from 1 or 2 or 3. In an exemplary embodiment, X is N or CH, $R^b$ is $NR^4R^5$, wherein $R^4$ is as described herein, $R^5$ is —$(CH_2)_{m8}$O$(CH_2)$Ph. In an exemplary embodiment, X is N or CH, $R^b$ is $NR^4R^5$, wherein $R^4$ is as described herein $R^5$ is —$(CH_2)_2$O$(CH_2)_{m9}$Ph. In an exemplary embodiment, X is N or CH, $R^b$ is $NR^4R^5$, wherein $R^4$ is as described herein $R^5$ is —$(CH_2)_2$O$(CH_2)$Ph.

In an exemplary embodiment, X is N or CH, $R^b$ is a member selected from —$NH(CH_2)_2OH$, —$NH(CH_2)_2OCH_3$, —$NHCH_3$, —$NHC(CH_3)_3$, —$NH(CH_2)Ph$, —$NH(CH_2)_2O(CH_2)Ph$.

In an exemplary embodiment, X is N or CH, $R^b$ is a member selected from —$N(CH_3)_2$, —$N(CH_3)(CH_2)_2OH$, —$N(CH_3)(CH_2)_2OCH_3$, —$NHCH_3$, —$NHC(CH_3)_3$, —$NH(CH_2)Ph$, —$NH(CH_2)_2O(CH_2)Ph$.

In an exemplary embodiment, X is N or CH, $R^b$ is —$NR^4R^5$, wherein $R^4$ and $R^5$, together with the nitrogen to which they are attached, are joined to form a substituted or unsubstituted 4 to 8 membered ring. In an exemplary embodiment, the only non-carbon atom which forms the ring is the nitrogen to which $R^4$ and $R^5$ are attached. In an exemplary embodiment, X is N or CH, $R^b$ is —$NR^4R^5$, wherein $R^4$ and $R^5$, together with the nitrogen to which they are attached, are joined to form a member selected from substituted or unsubstituted pyrrolidinyl and substituted or unsubstituted piperidinyl. In an exemplary embodiment, X is N or CH, $R^b$ is —$NR^4R^5$, wherein $R^4$ and $R^5$, together with the nitrogen to which they are attached, are joined to form a member selected from unsubstituted pyrrolidinyl and unsubstituted piperidinyl. In an exemplary embodiment, the only non-carbon atom which forms the ring is nitrogen. In an exemplary embodiment, the ring contains one nitrogen atom and one oxygen atom. In an exemplary embodiment, the ring contains one nitrogen atom and one oxygen atom. In an exemplary embodiment, X is N or CH, $R^b$ is —$NR^4R^5$, wherein $R^4$ and $R^5$, together with the nitrogen to which they are attached, are joined to form substituted or unsubstituted morpholinyl. In an exemplary embodiment, X is N or CH, $R^b$ is —$NR^4R^5$, wherein $R^4$ and $R^5$, together with the nitrogen to which they are attached, are joined to form unsubstituted morpholinyl.

In an exemplary embodiment, the compound has a structure according to the following formula:

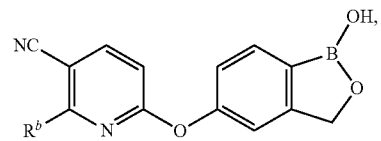

and salts thereof, wherein $R^b$ is as described herein.

In an exemplary embodiment, the compound has a structure according to the following formula:

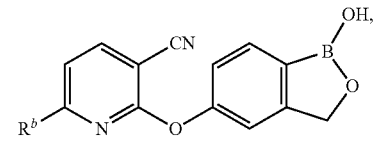

and salts thereof, wherein $R^b$ is as described herein.

In an exemplary embodiment, the compound has a structure according to the following formula:

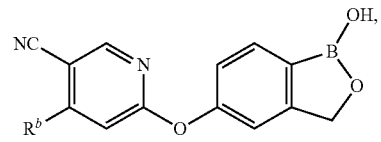

and salts thereof, wherein $R^b$ is as described herein.

In an exemplary embodiment, the compound has a structure according to the following formula:

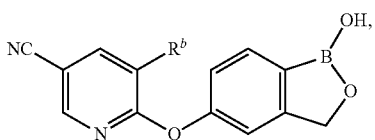

and salts thereof, wherein $R^b$ is as described herein.

In an exemplary embodiment, the compound has a structure according to the following formula:

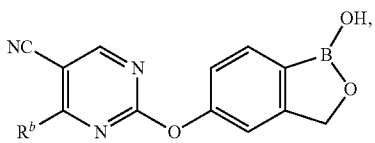

and salts thereof, wherein $R^b$ is as described herein.

In an exemplary embodiment, the compound has a structure according to the following formula:

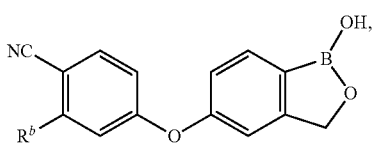

and salts thereof, wherein $R^b$ is as described herein.

In an exemplary embodiment, the compound has a structure according to the following formula:

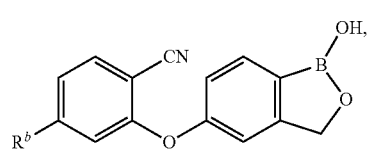

and salts thereof, wherein $R^b$ is as described herein.

In an exemplary embodiment, the compound has a structure according to the following formula:

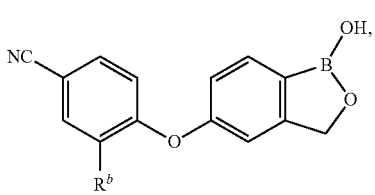

and salts thereof, wherein $R^b$ is as described herein.

In an exemplary embodiment, the compound, or a salt thereof, has a structure which is selected from the group consisting of

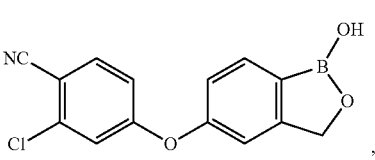

-continued

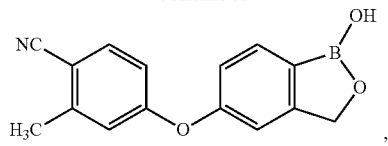

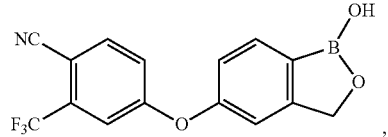

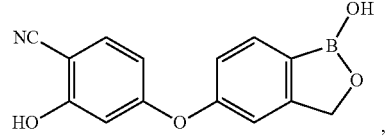

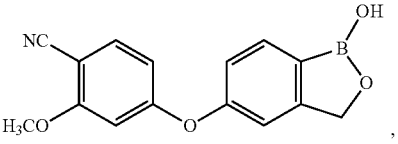

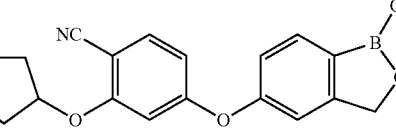

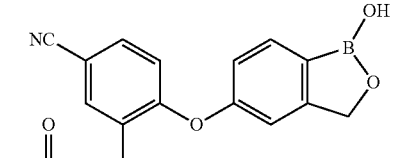

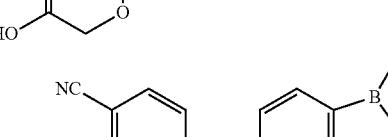

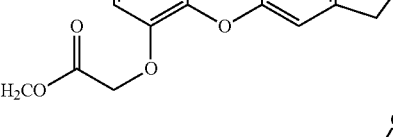

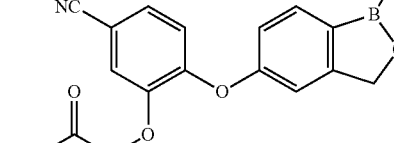

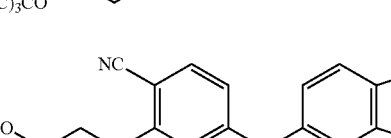

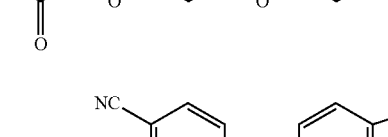

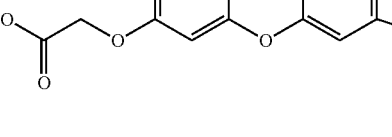

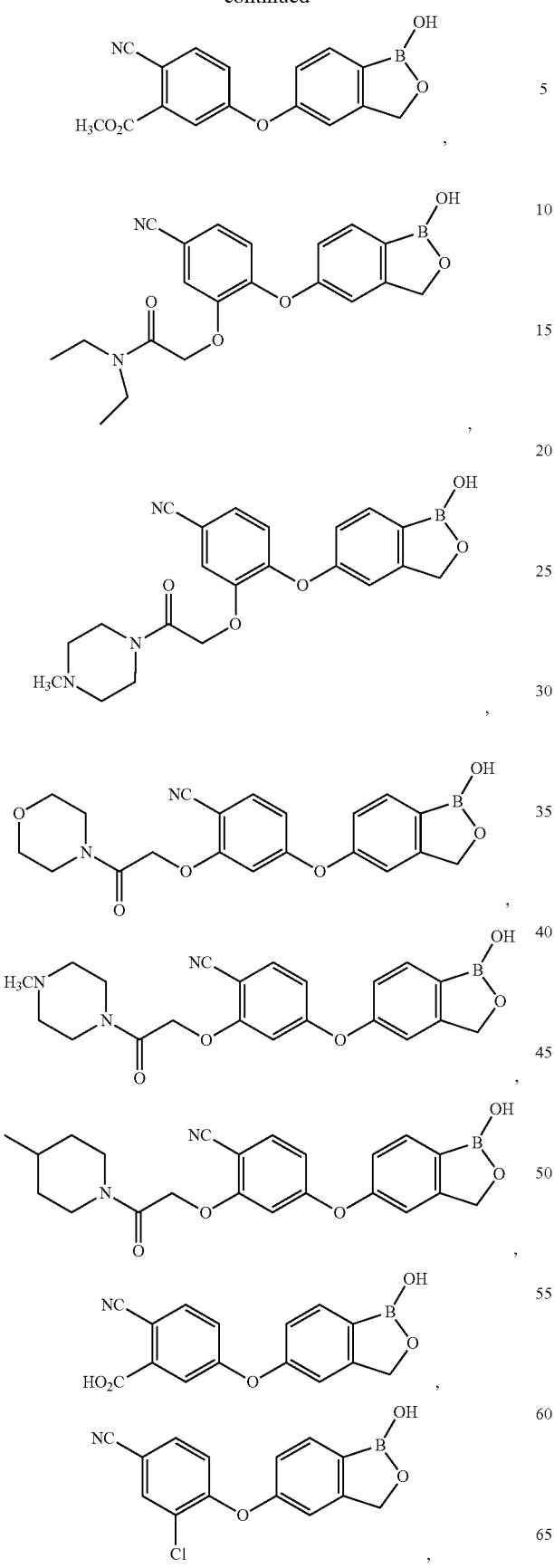
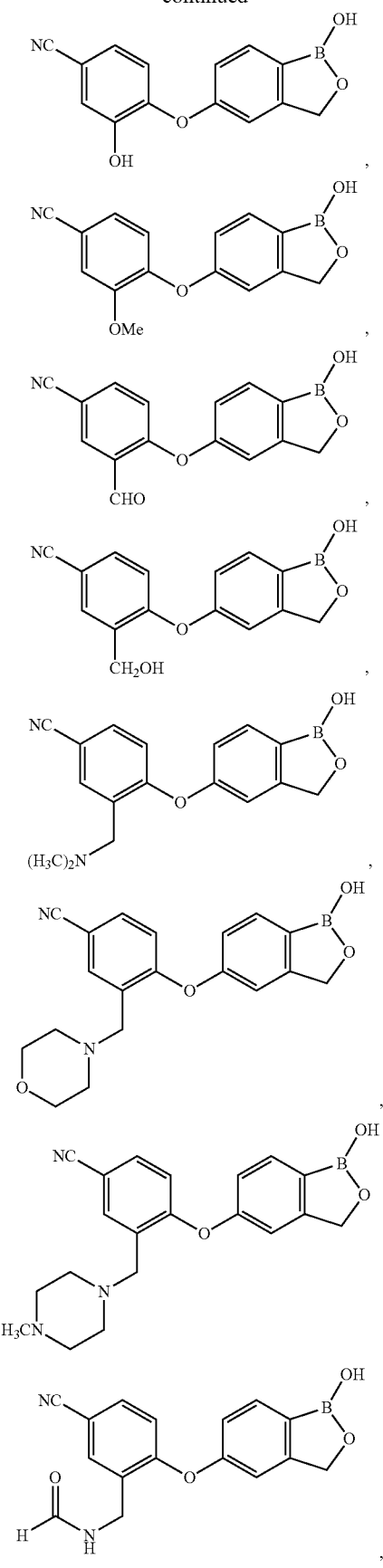

83
-continued

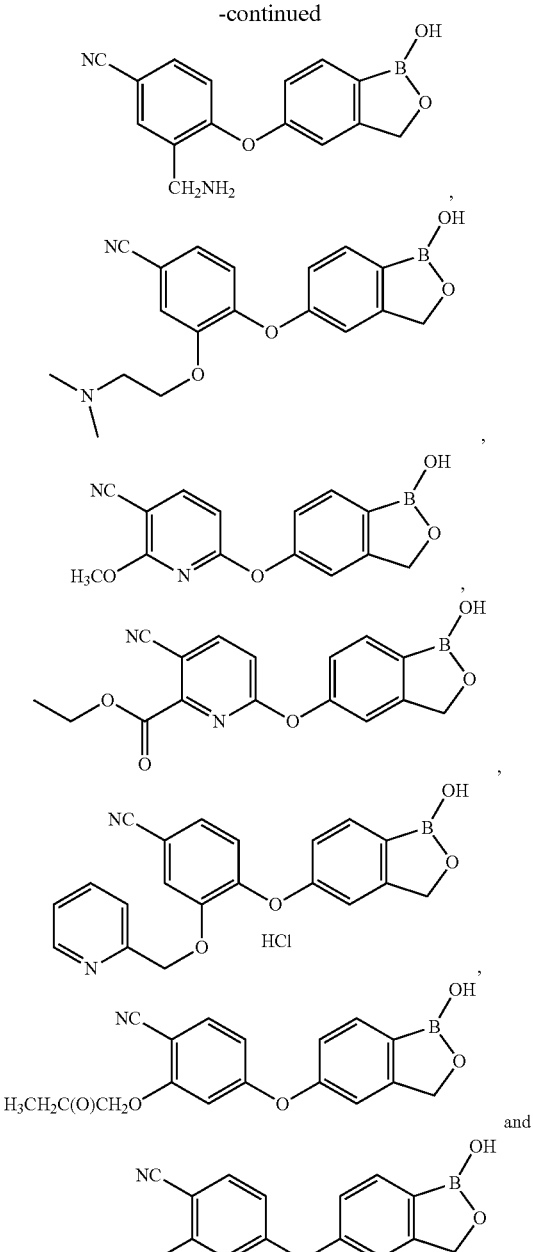

In another exemplary embodiment, the invention provides poly- or multi-valent species of the compounds of the invention. In an exemplary embodiment, the invention provides a dimer of the compounds described herein. In an exemplary embodiment, the invention provides a dimer of the compounds described herein. In an exemplary embodiment, the invention provides a dimer of a compound which is D230 or D231.

In an exemplary embodiment, the invention provides an anhydride of the compounds described herein. In an exemplary embodiment, the invention provides an anhydride of the compounds described herein. In an exemplary embodiment, the invention provides an anhydride of a compound which is D230 or D231.

In an exemplary embodiment, the invention provides a trimer of the compounds described herein. In an exemplary embodiment, the invention provides a trimer of the com-

84 pounds described herein. In an exemplary embodiment, the invention provides a trimer of a compound which is D230 or D231.

In an exemplary embodiment, the compound has a structure which is selected from the group consisting of

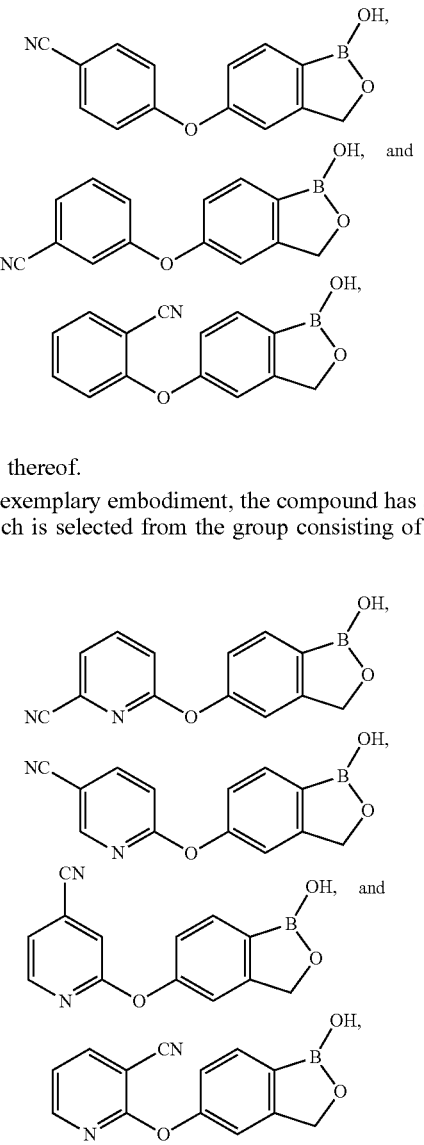

or a salt thereof.

In an exemplary embodiment, the compound has a structure which is selected from the group consisting of or a salt thereof.

In an exemplary embodiment, the compound has a structure which is

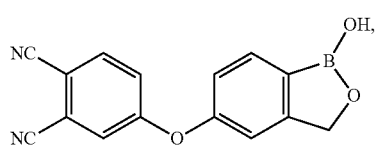 [SMILES: N#Cc1ccc(Oc2ccc3c(c2)COB3O)cc1C#N]

or a salt thereof.

In an exemplary embodiment, the compound has a structure which is

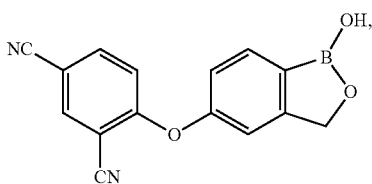

or a salt thereof.

In an exemplary embodiment, the compound has a structure which is

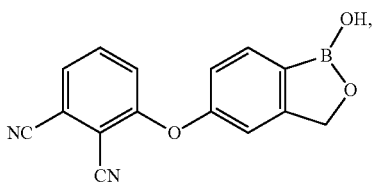 [SMILES: N#Cc1cccc(Oc2ccc3c(c2)COB3O)c1C#N]

or a salt thereof.

In an exemplary embodiment, the compound has a structure which is

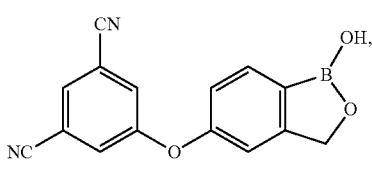 [SMILES: N#Cc1cc(C#N)cc(Oc2ccc3c(c2)COB3O)c1]

or a salt thereof.

In an exemplary embodiment, the compound has a structure which is

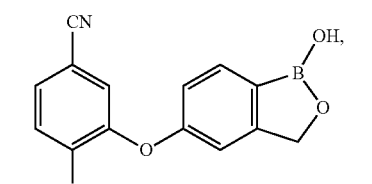

or a salt thereof.

In an exemplary embodiment, the compound has a structure which is

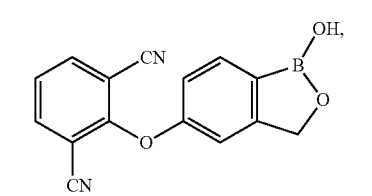 [SMILES: N#Cc1cccc(C#N)c1Oc1ccc2c(c1)COB2O]

or a salt thereof.

In an exemplary embodiment, the compound has a structure which is

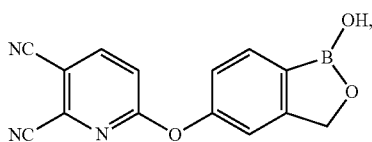 [SMILES: N#Cc1ccc(Oc2ccc3c(c2)COB3O)nc1C#N]

or a salt thereof.

In an exemplary embodiment, the compound has a structure which is

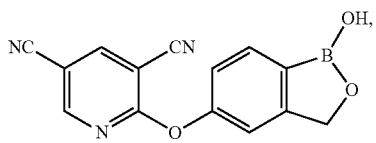 [SMILES: N#Cc1cnc(Oc2ccc3c(c2)COB3O)c(C#N)c1]

or a salt thereof.

In an exemplary embodiment, the compound has a structure which is

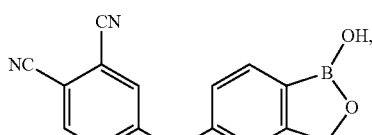

or a salt thereof.

In an exemplary embodiment, the compound has a structure which is

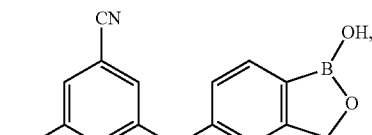

or a salt thereof.

In an exemplary embodiment, the compound has a structure which is

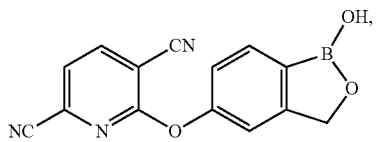 [SMILES: N#Cc1ccc(C#N)c(Oc2ccc3c(c2)COB3O)n1]

or a salt thereof.

In an exemplary embodiment, the compound has a structure which is

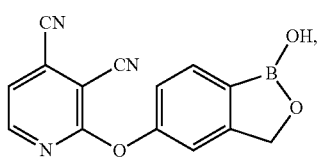 [SMILES: N#Cc1ccnc(Oc2ccc3c(c2)COB3O)c1C#N]

or a salt thereof.

In an exemplary embodiment, the invention provides a compound described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the salt is a pharmaceutically acceptable salt. In an exemplary embodiment, the invention provides a compound described herein, or a hydrate thereof. In an exemplary embodiment, the invention provides a compound described herein, or a solvate thereof. In an exemplary embodiment, the invention provides a compound described herein, or a prodrug thereof. In an exemplary embodiment, the invention provides a salt of a compound described herein. In an exemplary embodiment, the invention provides a pharmaceutically acceptable salt of a compound described herein. In an exemplary embodiment, the invention provides a hydrate of a compound described herein. In an exemplary embodiment, the invention provides a solvate of a compound described herein. In an exemplary embodiment, the invention provides a prodrug of a compound described herein.

In an exemplary embodiment, alkyl is linear alkyl. In an exemplary embodiment, alkyl is branched alkyl. In another exemplary embodiment, heteroalkyl is linear heteroalkyl. In another exemplary embodiment, heteroalkyl is branched heteroalkyl.

Additional compounds which are useful in the methods of the invention are disclosed in U.S. Prov. Pat. App. 60/654,060; Filed Feb. 16, 2005; U.S. patent application Ser. No. 11/357,687, Filed Feb. 16, 2006; U.S. patent application Ser. No. 11/505,591, Filed Aug. 16, 2006, U.S. Prov. Pat. App. 60/823,888 filed on Aug. 29, 2006 and 60/774,532 filed on Feb. 16, 2006; U.S. patent application Ser. No. 11/676,120, Filed Feb. 16, 2007, which are herein incorporated by reference in their entirety for all purposes. Methods of producing the compounds of the invention are also described in these patent applications.

IIIc. Methods of Making the Compounds

The following exemplary schemes illustrate methods of preparing boron-containing molecules of the present invention. These methods are not limited to producing the compounds shown, but can be used to prepare a variety of molecules such as the compounds and complexes described herein. The compounds of the present invention can also be synthesized by methods not explicitly illustrated in the schemes but are well within the skill of one in the art. The compounds can be prepared using readily available materials of known intermediates.

The compounds of the invention can be produced according to the strategies described herein. Strategy A is described below for the production of compound [Ia]:

Strategy A:

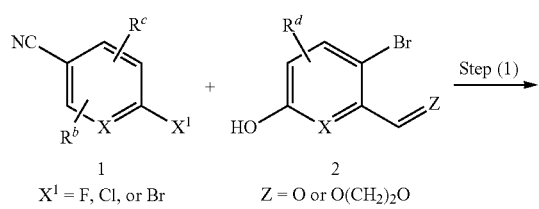

X¹ = F, Cl, or Br    Z = O or O(CH₂)₂O

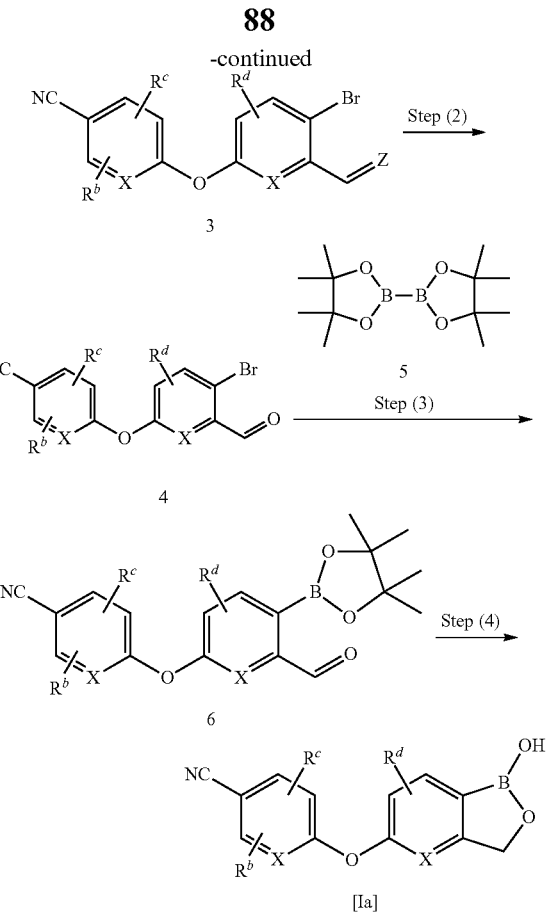

Step 1: Compounds 1 and 2 are coupled in the presence of a base to give 3. As for the base, carbonates, such as potassium carbonate, cesium carbonate, and sodium carbonate, sodium hydride, potassium tert-butoxide, and the like are used. The amount is between from about 1 to about 5 equivalent. Copper reagent (from about 0.1 to 2 equivalent) may be added to the reaction, such as copper powder, copper(I) chloride, copper(I) bromide, or copper(I) iodide. Useful solvents include N,N-dimethylformamide, N,N-dimethylacetamide, dimethylsulfoxide, acetonitrile, and the like. The reaction is carried out at from about 70 to about 150° C. and completed in from about 1 to about 24 hours.

Step 2: When Z=O(CH₂)₂O, compound 3 is treated with acid in an aqueous solvent to hydrolyze the acetal. Useful acids include hydrochloric acid, hydrobromic acid, para-toluenesulfonic acid, methansulfonic acid, acetic acid, and the like in amounts of from about 1 to about 50 equivalents. Useful solvents include methanol, ethanol, tetrahydrofuran, 1,4-dioxane, 1,2-dimethoxyethane, acetone, and the like. The reaction is carried out at room temperature to reflux. The reaction is complete in from about 1 to about 24 hours. When Z=O, this step is skipped.

Step 3: Compound 4 is subjected to Miyaura coupling to introduce a boron atom. A mixture of compounds 4, 5, [1,1'-bis(diphenylphosphino)ferrocene]dichloropalladium (II) complex with dichloromethane, and potassium carbonate in a solvent is stirred at about 50° C. to reflux. The solvent is chosen from 1,4-dioxane, 1,2-dimethoxyethane, tetrahydrofuran, dimethylsulfoxide, dimethylformamide, toluene, and the like. The palladium catalyst is used at from about 1 to about 10 mol %, and the base is used from about 2 to about 5 equivalent. The reaction is completed in from about 1 to about 24 hours.

Step 4: Compound 6 is treated with a reducing agent, such as sodium borohydride and lithium aluminum hydride, in an inert solvent. Reducing agent is used from about 0.5 to about 2 equivalent. Inert solvent is methanol, ethanol, tetrahydrofuran, ether, and the like. The reaction is carried out at about 0° C. to room temperature, and complete in from about 1 to about 12 hours. Pinacol is removed by washing with aqueous boric acid during the extraction, treating crude product with water, or by freeze drying after purification.

Some 2-alkoxy-6-chloronicotinonitriles (1a) are prepared as follows:

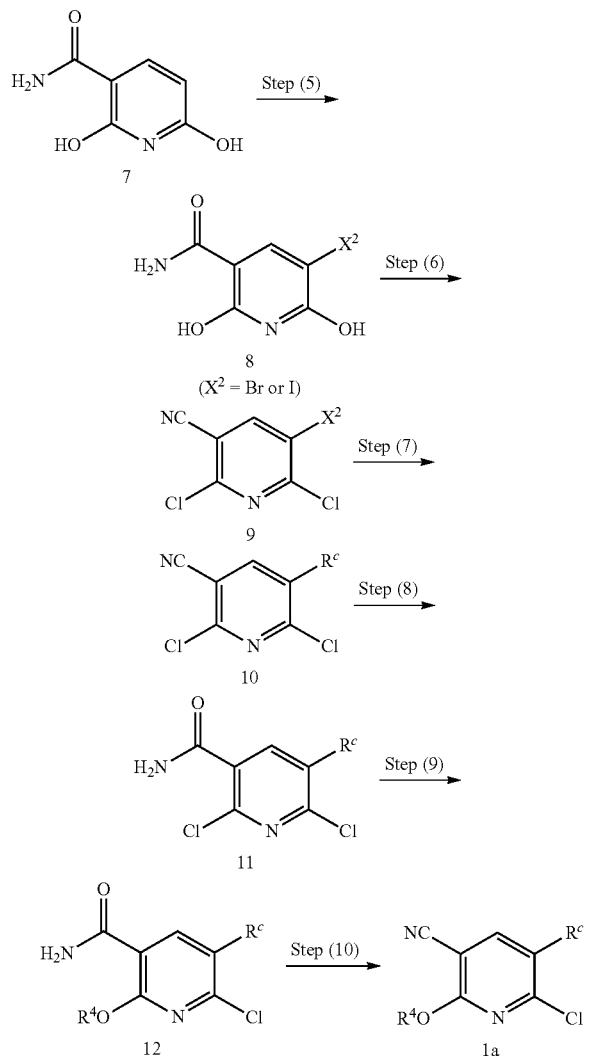

Step 5: Compound 8 is obtained by treating 7 with 0.5 to 2 equivalent, preferably 0.9 to 1.1 equivalent of bromine, N-bromosuccinimide, iodine, or N-iodosuccinimide. As for the solvent, tetrahydrofuran, 1,4-dioxane, N,N-dimethylformamide, 1,2-dimethoxyethane, toluene, and the like are used. The reaction is carried out at about 0° C. to room temperature for from about 0.1 to about 24 hours.

Step 6: Compound 9 is obtained by treating 8 with 1 to 10 equivalent of phosphorous oxychloride and/or phosphorous pentachloride at about 100 to 140° C. for from about 12 to 48 hours.

Step 7: Compound 10 is obtained by treating 9 with various different conditions known as Suzuki coupling, Sonogashira coupling, Heck reaction, Ullmann coupling, and the like, optionally in combination with modifications such as hydrogenation, hydrolysis, and the like. Using these conditions, groups such as the following can be introduced as $R^c$; methyl, ethyl, isopropyl, cyclopropyl, cyclobutyl, trifluoromethyl, alkoxy, alkoxyalkyl, and the like.

Step 8: Compound 11 is obtained by treating 10 with sulfuric acid at about 50 to 120° C. for from about 0.5 to 24 hours.

Step 9: Compound 12 is obtained by treating 11 with corresponding alkoxide. As for the alkoxide, commercially available sodium methoxide or sodium ethoxide can be used. Otherwise, it is prepared in situ from alcohol ($R^4OH$) and a base, such as sodium, sodium hydride, potassium hydride, sodium hydroxide, potassium hydroxide, butyllithium, and the like. As for the solvent, tetrahydrofuran, 1,4-dioxane, N,N-dimethylformamide, 1,2-dimethoxyethane, toluene, and the like are used. The reaction is carried out at about 0° C. to room temperature for from about 1 to about 24 hours.

Step 10: Compound 12 is treated with phosphorous oxychloride and pyridine to give 1a. Phosphorous oxychloride and pyridine are used in about 3 to about 6 equivalent. The solvent is chosen from acetonitrile, tetrahydrofuran, toluene, and the like The reaction is carried out at room temperature to reflux and complete in from about 1 to about 24 hours.

Some 2,6-dichloronicotinonitriles (10) are prepared as follows:

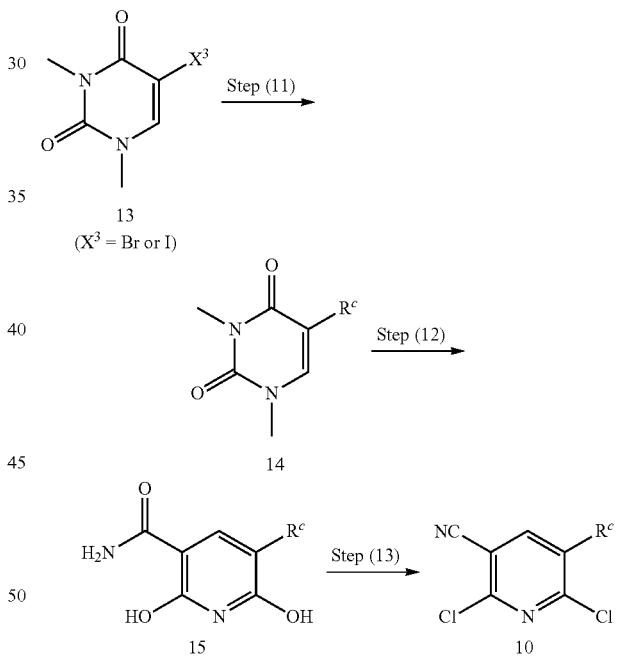

Step 11: Compound 14 is obtained by treating 13 with various different conditions known as Suzuki coupling, Sonogashira coupling, Heck reaction, Ullmann coupling, and the like optionally in combination with following modification, such as hydrogenation, hydrolysis, and the like. Using these conditions, following groups can be introduced as $R^c$; methyl, ethyl, isopropyl, cyclopropyl, cyclobutyl, trifluoromethyl, alkoxy, alkoxyalkyl, and the like.

Step 12: Compounds 14 and malonamide are reacted in the presence of a base to give 15. Malonamide is used from about 1 to about 5 equivalent. As for the base, carbonates, such as potassium carbonate, cesium carbonate, and sodium carbonate, sodium methoxide, sodium ethoxide, sodium hydride, potassium tert-butoxide, and the like are used. The amount is from about 1 to about 5 equivalent. Useful solvents include methanol, ethanol, tetrahydrofuran, 1,4-dioxane, N,N-dimethylformamide, N,N-dimethylacetamide, dimethylsulfoxide, and the like. The reaction is carried out at from about 50 to about 150° C. and completed in from about 0.2 to about 24 hours.

Step 13: Compound 10 is obtained by treating 15 with 1 to 10 equivalent of phosphorous oxychloride and/or phosphorous pentachloride at about 100 to 140° C. for from about 12 to 48 hours.

Some 2-alkoxy-6-chloronicotinonitriles (1a) are alternatively prepared as follows:

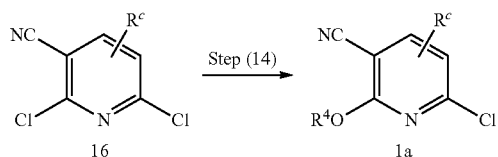

Compounds 1a is obtained in the same condition as described above for step 9 from 2,6-dichloronicotinonitrile (16).

Some 2-amino-6-chloronicotinonitrile derivatives (1b) are alternatively prepared as follows:

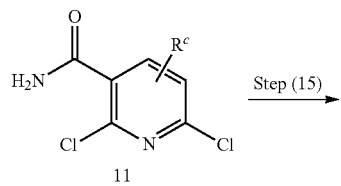

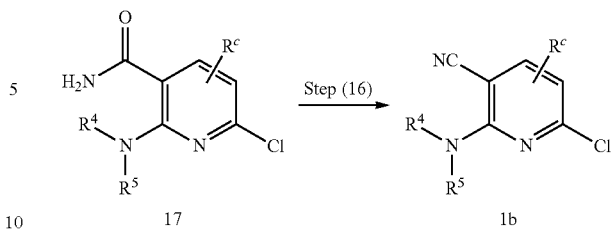

Step 15: Compound 17 is obtained by treating 11 with about 1 to 2 equivalent of corresponding amine ($R^4R^5NH$) in the presence of a base. As for the base, about 1 to 2 equivalent of sodium carbonate, potassium carbonate, cesium carbonate, sodium hydride, potassium hydride, sodium hydroxide, potassium hydroxide, and the like are used. As for the solvent, tetrahydrofuran, 1,4-dioxane, N,N-dimethylformamide, 1,2-dimethoxyethane, toluene, and the like are used. The reaction is carried out at from about 0° C. to 100° C. for from about 1 to about 24 hours.

Step 16: Compound 17 is treated with phosphorous oxychloride and pyridine to give 1b. Phosphorous oxychloride and pyridine are used in about 3 to about 6 equivalents. The solvent is chosen from acetonitrile, tetrahydrofuran, toluene, and the like. The reaction is carried out at room temperature to reflux and complete in from about 1 to about 24 hours.

Strategy B is described below for the production of compound [Ib]:

Strategy B:

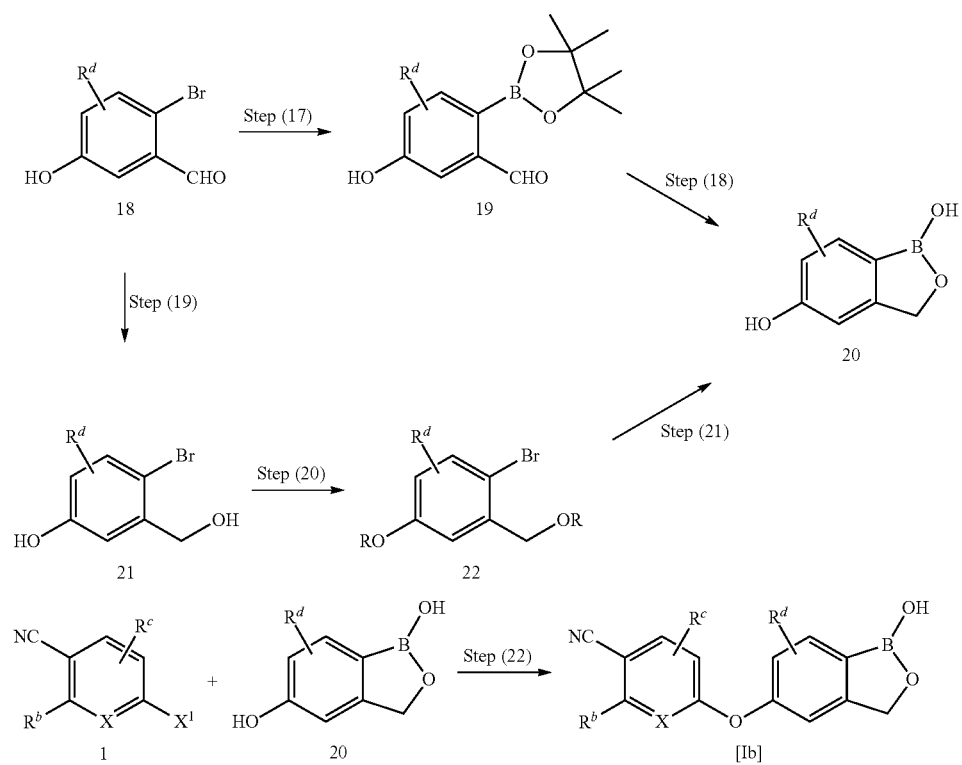

Step 17: Compound 19 is obtained from compound 18 in the similar manner to Step 3.

Step 18: Compound 20 is obtained from compound 19 in the similar manner to Step 4.

Step 19: Compound 20 is also obtained in an alternative way. Compound 21 is obtained from compound 18 in a similar manner to Step 4.

Step 20: Two hydroxyl groups of compound 21 are protected with a protecting group, such as 2-tetrahydropyranyl, methoxymethyl, ethoxymethyl, trimethylsilyl, or tert-butyldimethylsilyl group, using typical conditions described in literature (Theodora W. Greene, Protective Groups in Organic Synthesis, John Wiley & Sons) to give compound 22.

Step 21: Compound 22 was treated with from about 1 to 2 equivalent of n-butyllithium, sec-butyllithium, or tert-butyllithium followed by the addition of from about 1 to 3 equivalent of borate, such as trimethyl borate, triethyl borate, or triisopropyl borate. As for the solvent, diethyl ether, tetrahydrofuran, toluene, hexane are used as a single or mixed solvent. The reaction is carried out at from −100° C. to room temperature and complete in from about 0.5 to about 24 hours.

Step 22: Compound [Ib] is prepared by coupling compounds 1 and 20 in the presence of a base in an inert solvent. As for the base, potassium carbonate, sodium carbonate, cesium carbonate, sodium hydride, and the like, is used from about 1 to about 5 equivalent. As for the solvent, tetrahydrofuran, 1,4-dioxane, N,N-dimethylformamide, 1,2-dimethoxyethane, toluene, dimethylsulfoxide, and the like are used. The reaction is carried out at 0° C. to the boiling point of the solvent, preferably between room temperature and 100° C., for from about 1 to about 24 hours.

Strategy C is described below for the production of compound [Ic] and [Id]:

Strategy C:

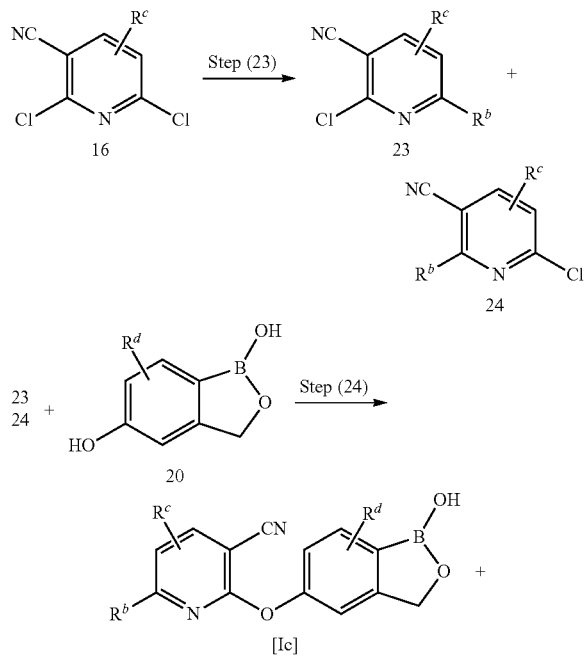

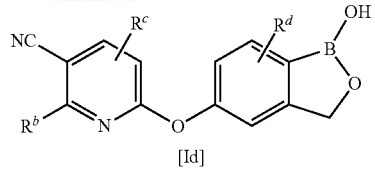

Step 23: A mixture of compounds 23 and 24 is obtained in the same condition as described above for step 9 or step 15 from 2,6-dichloronicotinonitrile (16).

Step 24: Compounds [Ic] and [Id] are obtained in the same condition as described above for step 22 from compounds 23/24 and 20. The reaction gives a mixture of compounds [Ic] and [Id], which can be separated by silica gel column chromatography or preparative HPLC.

The compounds of the invention can be converted into hydrates and solvates by methods similar to those described herein.

III.d) Combinations Comprising Additional Therapeutic Agents

The compounds of the invention may also be used in combination with additional therapeutic agents. The invention thus provides, in a further aspect, a combination comprising a compound described herein or a pharmaceutically acceptable salt thereof together with at least one additional therapeutic agent. In an exemplary embodiment, the additional therapeutic agent is a compound of the invention. In an exemplary embodiment, the additional therapeutic agent includes a boron atom. In an exemplary embodiment, the additional therapeutic agent does not contain a boron atom. In an exemplary embodiment, the additional therapeutic agent is a compound described in sections III a)-d).

When a compound of the invention is used in combination with a second therapeutic agent active against the same disease state, the dose of each compound may differ from that when the compound is used alone. Appropriate doses will be readily appreciated by those skilled in the art. It will be appreciated that the amount of a compound of the invention required for use in treatment will vary with the nature of the condition being treated and the age and condition of the patient and will be ultimately at the discretion of the attendant physician or veterinarian. In an exemplary embodiment, the additional therapeutic agent is an antiinflammatory. In an exemplary embodiment, the additional therapeutic agent is a steroid or cyclosporine or psoralen or UVA or retinoid or methotrexate or vitamin $D_3$ analog. In an exemplary embodiment, the steroid is a systemic steroid or a topical steroid. In an exemplary embodiment, the additional therapeutic agent is topical steroid or antihistamine or calcineurin inhibitor. In an exemplary embodiment, the additional therapeutic agent is a corticosteroid or an NSAID. In an exemplary embodiment, the additional therapeutic agent is a PDE4 inhibitor. In an exemplary embodiment, the additional therapeutic agent is rolipram or roflumilast or apremilast.

In an exemplary embodiment, the additional therapeutic agent is cyclosporine. In an exemplary embodiment, the additional therapeutic agent is an anti-TNF antibody. In an exemplary embodiment, the additional therapeutic agent is selected from the group consisting of infliximab (Remicade), adalimumab (Humira), certolizumab pegol (Cimzia), and golimumab (Simponi). In an exemplary embodiment, the additional therapeutic agent is a circulating receptor fusion protein. In an exemplary embodiment, the additional therapeutic agent is etanercept (Enbrel). In an exemplary embodiment, the additional therapeutic agent is an antibody which specifically targets IL-23. In an exemplary embodiment, the additional therapeutic agent is ustekinumab. In an exemplary embodiment, the additional therapeutic agent is an antibody which specifically targets the LFA-1 binder. In an exemplary embodiment, the additional therapeutic agent is Efalizumab.

In an exemplary embodiment, the additional therapeutic agent is an antiworm agent. In an exemplary embodiment, the additional therapeutic agent is an antihelmintic agent. In an exemplary embodiment, the additional therapeutic agent is selected from the group consisting of abamectin, diethylcarbamazine, mebendazole, niclosamide, suramin, thiabendazole, pyrantel pamoate, levamisole, piperazine, piperazine analogs, praziquantel, thiacetarsamide, triclabendazole, flubendazole, fenbendazole, Ooctadepsipeptides, such as emodepside, amino acetonitrile derivatives (such as monepantel). In an exemplary embodiment, the additional therapeutic agent is albendazole. In an exemplary embodiment, the additional therapeutic agent is ivermectin. In an exemplary embodiment, the additional therapeutic agent is melarsomine. In an exemplary embodiment, the additional therapeutic agent is praziquantel. In an exemplary embodiment, the additional therapeutic agent is oxamniquine. In an exemplary embodiment, the additional therapeutic agent is selected from the group consisting of selamectin, milbemycin, and moxidectin. In an exemplary embodiment, the additional therapeutic agent is selected from the group consisting of tobacco, *Moringa oleifera* (Moringaceae), black walnut (*Juglans nigra*), wormwood (*Artemisia absynthium*), clove (*Syzygium aromaticum*), tansy tea (*Tanacetum vulgare*), hagenia (*Hagenia abyssinica*), garlic (*Allium sativum*), pineapple (*Ananas comosus*), kalonji (*Nigella sativa*) seeds, male fern (*Dryopteris filix-mas*), plumeria (*P. acutifolia* or *P. rubra*), and *Peganum harmala*.

The individual components of such combinations may be administered either simultaneously or sequentially in a unit dosage form. The unit dosage form may be a single or multiple unit dosage forms. In an exemplary embodiment, the invention provides a combination in a single unit dosage form. An example of a single unit dosage form is a capsule wherein both the compound of the invention and the additional therapeutic agent are contained within the same capsule. In an exemplary embodiment, the invention provides a combination in a two unit dosage form. An example of a two unit dosage form is a first capsule which contains the compound of the invention and a second capsule which contains the additional therapeutic agent. Thus the term 'single unit' or 'two unit' or 'multiple unit' refers to the object which the patient ingests, not to the interior components of the object. Appropriate doses of known therapeutic agents will be readily appreciated by those skilled in the art.

The combinations referred to herein may conveniently be presented for use in the form of a pharmaceutical formulation. Thus, an exemplary embodiment of the invention is a pharmaceutical formulation comprising a) a compound of the invention; b) an additional therapeutic agent and c) a pharmaceutically acceptable excipient. In an exemplary embodiment, the pharmaceutical formulation is a unit dosage form. In an exemplary embodiment, the pharmaceutical formulation is a single unit dosage form. In an exemplary embodiment, the pharmaceutical formulation is a two unit dosage form. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an additional therapeutic agent and d) a second pharmaceutically acceptable excipient.

IV. The Methods

In another aspect of the invention, the compounds of the invention can be utilized in the methods described herein. In an exemplary embodiment, in any of the methods described herein, the organism being administered the compound of the invention is not otherwise in need of being administered said compound of the invention. In an exemplary embodiment, in any of the methods described herein, the animal being administered the compound of the invention is not otherwise in need of treatment with said compound of the invention.

a) Decreasing the Production of a Cytokine and/or Chemokine

In another aspect, the invention provides a method for decreasing the production of a cytokine and/or a chemokine, the method comprising: contacting a cell with a compound of the invention, wherein production of the cytokine and/or chemokine by the cell is decreased. In another aspect, the invention provides a method for decreasing the production of a cytokine and/or a chemokine, the method comprising: contacting a cell with a compound described herein or a pharmaceutically acceptable salt thereof, wherein production of the cytokine and/or chemokine by the cell is decreased. In an exemplary embodiment, the compound of the invention is a compound described herein, or a pharmaceutically acceptable salt thereof. In an exemplary embodiment, the compound of the invention is a compound described herein. In an exemplary embodiment, the cell is contacted with a therapeutically effective amount of the compound. In an exemplary embodiment, the compound is according to a formula described herein. In an exemplary embodiment, the compound is D230 or a salt thereof. In an exemplary embodiment, the compound is D231 or a salt thereof.

In an exemplary embodiment, the method is for decreasing the production of a cytokine, which is a TH1 cytokine. In an exemplary embodiment, the TH1 cytokine is IFN-γ or IL-2.

In an exemplary embodiment, the method is for decreasing the production of a cytokine, which is a TH2 cytokine. In an exemplary embodiment, the TH2 cytokine is selected from the group consisting of IL-4, IL-5, and IL-10.

In an exemplary embodiment, the method is for decreasing the production of a cytokine, which is selected from the group consisting of IL-1α, IL-1β, IL-2, IL-3, IL-6, IL-7, IL-9, IL-12, IL-17, IL-18, IL-23, TNF-α, LT, LIF, Oncostatin, IFNα, IFNβ and IFN-γ. In another exemplary embodiment, the cytokine is selected from the group consisting of IL-2, IL-3, IL-6, IL-7, IL-9, IL-12, IL-23, TNF-α, LT, LIF, Oncostatin, and IFN-γ. In another exemplary embodiment, the cytokine is selected from the group consisting of IL-2, IL-23, TNF-α and IFN-γ. In another exemplary embodiment, the cytokine is TNF-α.

In an exemplary embodiment, the method is for decreasing the production of a cytokine, which is selected from the group consisting of IL-2, IL-4, IL-5, IL-6, IL-8, IL-10, IL-12, IL-23, TNF-α and IFN-γ. In an exemplary embodiment, the method is for decreasing the production of IL-4. In an exemplary embodiment, the method is for decreasing the production of IL-23.

In an exemplary embodiment, the method is for decreasing the production of a cytokine, which is selected from the group consisting of IL-4, IL-10, IL-11, W-13 and TGF-β.

In an exemplary embodiment, the method is for decreasing the production of a chemokine, which is selected from the group consisting of IL-8, Gro-α, MIP-1, MCP-1, PGE2, ENA-78, and RANTES. In an exemplary embodiment, the chemokine is MCP-1 or PGE2.

In an exemplary embodiment, for any of the methods described herein, the compound of the invention is present in an amount which will inhibit the production of a cytokine and/or a chemokine by at least about 5 to about 100%, or at least about 30 to about 100%, 40 to about 100%, or at least about 50 to about 100%, or at least about 60 to about 100%, or at least about 70 to about 100%, or at least about 80 to about 100%, or at least about 90 to about 100%, or at least about 30 to about 70%, or at least about 40 to about 90%, or at least about 45 to about 80%, or at least about 55 to about 75%, or at least about 75 to about 98%, or at least about 55 to about 99%, or at least about 5% to about 20% or at least about 10% to about 25%. In an exemplary embodiment, the compound of the invention is a compound described herein.

b) Increasing the Production of a Cytokine and/or a Chemokine

In another aspect, the invention provides a method for increasing the production of a cytokine and/or a chemokine, the method comprising: contacting a cell with a compound of the invention, wherein production of the cytokine and/or chemokine by the cell is increased. In an exemplary embodiment, the compound is described herein or a pharmaceutically acceptable salt thereof. In an exemplary embodiment, the compound of the invention is a compound described herein. In an exemplary embodiment, the cell is contacted with a therapeutically effective amount of the compound. In an exemplary embodiment, the compound is according to a formula described herein. In an exemplary embodiment, the compound is D230 or a salt thereof. In an exemplary embodiment, the compound is D231 or a salt thereof.

In an exemplary embodiment, the method is for increasing the production of a cytokine, which is a TH1 cytokine. In an exemplary embodiment, the TH1 cytokine is IFN-γ or IL-2.

In an exemplary embodiment, the method is for increasing the production of a cytokine, which is a TH2 cytokine. In an exemplary embodiment, the TH2 cytokine is selected from the group consisting of IL-4, IL-5 and IL-10.

In an exemplary embodiment, the method is for increasing the production of a cytokine, which is selected from the group consisting of IL-4, IL-10, IL-11, W-13 and TGF-β.

In an exemplary embodiment, the method is for increasing the production of a chemokine, which is selected from the group consisting of IL-8, Gro-α, MIP-1, MCP-1, PGE2, ENA-78, and RANTES. In an exemplary embodiment, the chemokine is MCP-1 or PGE2.

In an exemplary embodiment, for any of the methods described herein, the compound of the invention is present in an amount which will increase the production of a cytokine and/or a chemokine by at least about 5 to about 100%, or at least about 30 to about 100%, 40 to about 100%, or at least about 50 to about 100%, or at least about 60 to about 100%, or at least about 70 to about 100%, or at least about 80 to about 100%, or at least about 90 to about 100%, or at least about 30 to about 70%, or at least about 40 to about 90%, or at least about 45 to about 80%, or at least about 55 to about 75%, or at least about 75 to about 98%, or at least about 55 to about 99%, or at least about 5% to about 20% or at least about 10% to about 25%. In an exemplary embodiment, the compound of the invention is a compound described herein.

c) Decreasing the Release of a Cytokine and/or Chemokine

In another aspect, the invention provides a method for decreasing the release of a cytokine and/or a chemokine, the method comprising: contacting a cell with a compound of the invention, wherein the release of the cytokine and/or chemokine by the cell is decreased. In an exemplary embodiment, the compound of the invention is a compound described herein or a pharmaceutically acceptable salt thereof. The compound of the invention is a compound described herein. In an exemplary embodiment, the cell is contacted with a therapeutically effective amount of the compound. In an exemplary embodiment, the compound is according to a formula described herein. In an exemplary embodiment, the compound is D230 or a salt thereof. In an exemplary embodiment, the compound is D231 or a salt thereof.

In an exemplary embodiment, the method is for decreasing the release of a cytokine, which is a TH1 cytokine. In an exemplary embodiment, the TH1 cytokine is a IFN-γ or IL-2.

In an exemplary embodiment, the method is for decreasing the release of a cytokine, which is a TH2 cytokine. In an exemplary embodiment, the TH2 cytokine is selected from the group consisting of IL-4, IL-5 and IL-10.

In an exemplary embodiment, the method is for decreasing the release of a cytokine, which is selected from the group consisting of IL-1α, IL-1β, IL-2, IL-3, IL-6, IL-7, IL-9, IL-12, IL-17, IL-18, IL-23, TNF-α, LT, LIF, Oncostatin, IFNα, IFNβ and IFN-γ. In another exemplary embodiment, the cytokine is selected from the group consisting of IL-2, IL-3, IL-6, IL-7, IL-9, IL-12, IL-23, TNF-α, LT, LIF, Oncostatin, and IFN-γ. In another exemplary embodiment, the cytokine is selected from the group consisting of IL-2, IL-23, TNF-α and IFN-γ. In another exemplary embodiment, the cytokine is TNF-α. In another exemplary embodiment, the cytokine is IFN-γ.

In an exemplary embodiment, the method is for decreasing the release of a cytokine, which is selected from the group consisting of IL-1β, IL-2, IL-4, IL-5, IL-6, IL-8, IL-10, IL-12, IL-23, TNF-α and IFN-γ.

In an exemplary embodiment, the compound of the invention decreases the release of IL-1β, IL-2, IL-4, IL-5, IL-6, IL-8, IL-10, IL-12, IL-23, TNF-α and IFN-γ.

In an exemplary embodiment, the method is for decreasing the release of a cytokine, which is selected from the group consisting of IL-4, IL-10, IL-11, W-13 and TGF-β. In an exemplary embodiment, the method is for decreasing the release of IL-4. In an exemplary embodiment, the method is for decreasing the release of IL-23.

In an exemplary embodiment, the method is for decreasing the release of a chemokine, which is selected from the group consisting of IL-8, Gro-α, MIP-1, MCP-1, PGE2, ENA-78, and RANTES. In an exemplary embodiment, the chemokine is MCP-1 or PGE2.

In an exemplary embodiment, the compound of the invention decreases the release of a member selected from the group consisting of TNF-α, IL-2, IFNγ, IL-5, and IL-10. In an exemplary embodiment, the compound of the invention does not substantially decrease the release of IL-1β, IL-6 and IL-8. In an exemplary embodiment, the compound of the invention does not substantially decrease the release of IL-1β. In an exemplary embodiment, the compound of the invention does not substantially decrease the release of IL-4. In an exemplary embodiment, the compound decreases the release of IL-12 and IL-23.

In an exemplary embodiment, for any of the methods described herein, the compound of the invention is present in an amount which will decrease the release of a cytokine and/or a chemokine by at least about 5 to about 100%, or at least about 30 to about 100%, 40 to about 100%, or at least about 50 to about 100%, or at least about 60 to about 100%, or at least about 70 to about 100%, or at least about 80 to about 100%, or at least about 90 to about 100%, or at least about 30 to about 70%, or at least about 40 to about 90%, or at least about 45 to about 80%, or at least about 55 to about 75%, or at least about 75 to about 98%, or at least about 55 to about 99%, or at least about 5% to about 20% or at least about 10% to about 25%. In another exemplary embodiment, the compound of the invention is a compound described herein or a pharmaceutically acceptable salt thereof.

d) Increasing the Release of a Cytokine and/or a Chemokine

In another aspect, the invention provides a method for increasing the production of a cytokine and/or a chemokine, the method comprising: contacting a cell with a compound of the invention, wherein release of the cytokine and/or chemokine by the cell is increased. In an exemplary embodiment, the compound of the invention is a compound described herein or a pharmaceutically acceptable salt thereof. In an exemplary embodiment, the compound is described herein. In an exemplary embodiment, the cell is contacted with a therapeutically effective amount of the compound. In an exemplary embodiment, the compound is according to a formula described herein. In an exemplary embodiment, the compound is D230 or a salt thereof. In an exemplary embodiment, the compound is D231 or a salt thereof.

In an exemplary embodiment, the method is for increasing the release of a cytokine, which is a TH1 cytokine. In an exemplary embodiment, the TH1 cytokine is IFN-γ or IL-2.

In an exemplary embodiment, the method is for increasing the release of a cytokine, which is a TH2 cytokine. In an exemplary embodiment, the TH2 cytokine is selected from the group consisting of IL-4, IL-5 and IL-10.

In an exemplary embodiment, the method is for increasing the release of a cytokine, which is selected from the group consisting of IL-4, IL-10, IL-11, W-13 and TGF-β.

In an exemplary embodiment, the method is for increasing the release of a chemokine, which is selected from the group consisting of IL-8, Gro-α, MIP-1, MCP-1, PGE2, ENA-78, and RANTES. In an exemplary embodiment, the chemokine is MCP-1 or PGE2.

In an exemplary embodiment, for any of the methods described herein, the compound of the invention is present in an amount which will increase release of a cytokine and/or a chemokine by at least about 5 to about 100%, or at least about 30 to about 100%, 40 to about 100%, or at least about 50 to about 100%, or at least about 60 to about 100%, or at least about 70 to about 100%, or at least about 80 to about 100%, or at least about 90 to about 100%, or at least about 30 to about 70%, or at least about 40 to about 90%, or at least about 45 to about 80%, or at least about 55 to about 75%, or at least about 75 to about 98%, or at least about 55 to about 99%, or at least about 5% to about 20% or at least about 10% to about 25%. In an exemplary embodiment, the compound of the invention is a compound described herein or a pharmaceutically acceptable salt thereof.

e) Inhibiting a Phosphodiesterase

In another aspect, the invention provides a method for inhibiting a phosphodiesterase (PDE), the method comprising: contacting the phosphodiesterase with a compound of the invention, wherein the phosphodiesterase is inhibited. In an exemplary embodiment, the compound of the invention is a compound described herein or a pharmaceutically acceptable salt thereof. In an exemplary embodiment, the compound of the invention is a compound described herein. In an exemplary embodiment, the amount of the compound is a therapeutically effective amount. In an exemplary embodiment, the compound is according to a formula described herein. In an exemplary embodiment, the compound is D230 or a salt thereof. In an exemplary embodiment, the compound is D231 or a salt thereof.

In an exemplary embodiment, the phosphodiesterase is selected from the group consisting of PDE1, PDE2, PDE3, PDE4, PDE5, PDE6, PDE7, PDE8, PDE9, PDE10 and PDE11. In an exemplary embodiment, the phosphodiesterase is PDE4. In an exemplary embodiment, the PDE4 is selected from the group consisting of PDE4A, PDE4B, PDE4C and PDE4D. In an exemplary embodiment, the PDE4 is PDE4B. In an exemplary embodiment, the phosphodiesterase is PDE7.

In an exemplary embodiment, the invention provides a method for inhibiting a phosphodiesterase4 (PDE4), but not significantly inhibiting at least one PDE which is selected from the group consisting of PDE1, PDE2, PDE3, PDE5 and PDE6, involving contacting a cell with a compound of the invention, thereby providing said inhibition.

In an exemplary embodiment, for any of the methods described herein, the invention, or a compound described by a formula presented herein, is present in an amount which will inhibit a phosphodiesterase described herein by at least about 5 to about 100%, or at least about 30 to about 100%, 40 to about 100%, or at least about 50 to about 100%, or at least about 60 to about 100%, or at least about 70 to about 100%, or at least about 80 to about 100%, or at least about 90 to about 100%, or at least about 30 to about 70%, or at least about 40 to about 90%, or at least about 45 to about 80%, or at least about 55 to about 75%, or at least about 75 to about 98%, or at least about 55 to about 99%, or at least about 5% to about 20% or at least about 10% to about 25%. In an exemplary embodiment, the compound of the invention is a compound described herein or a pharmaceutically acceptable salt thereof.

f) Conditions and Effects

In another aspect, the invention provides a method of treating and/or preventing a condition, and/or enhancing an effect, in an animal, the method comprising administering to the animal an effective amount of a compound of the invention, thereby treating and/or preventing the condition. In an exemplary embodiment, the compound of the invention is a compound described herein. In an exemplary embodiment, the compound of the invention is a pharmaceutically acceptable salt of a compound described herein. In an exemplary embodiment, the effective amount is an amount effective to treat the condition. In an exemplary embodiment, the effective amount is an amount effective to prevent the condition. In an exemplary embodiment, the animal is not otherwise is need of treatment with the compound of the invention. In an exemplary embodiment, the compound is according to a formula described herein. In another aspect, the invention provides a method of treating a condition in an animal in need of the treatment, the method comprising administering to the animal an amount of a compound of the invention, thereby treating the condition. In another aspect, the invention provides a method of treating a condition in an animal in need of the treatment, the method comprising administering to the animal a therapeutically effective amount of a compound of the invention, thereby treating the condition. In another aspect, the invention provides a method of preventing a condition, in an animal, the method comprising administering to the animal an amount of a compound of the invention, thereby preventing the condition. In another aspect, the invention provides a method of enhancing an effect, in an animal, the method comprising administering to the animal an effective amount of a compound of the invention, thereby enhancing the effect. In an exemplary embodiment, the compound is according to a formula described in the section entitled "Inhibiting a phosphodiesterase". In an exemplary embodiment, the compound is D230 or a salt thereof. In an exemplary embodiment, the compound is D231 or a salt thereof.

In an exemplary embodiment, the condition is a disease. In an exemplary embodiment, the condition is an inflammatory-related condition. In an exemplary embodiment, the condition involves the increase of production of a cytokine and/or a chemokine. In an exemplary embodiment, the condition involves the decrease of production of a cytokine and/or a chemokine. In an exemplary embodiment, the condition involves the increase of release of a cytokine and/or a chemokine. In an exemplary embodiment, the condition involves the decrease of release of a cytokine and/or a chemokine. In an exemplary embodiment, the condition involves the inhibition of a phosphodiesterase. In an exemplary embodiment, the compound is in an amount sufficient to treat the inflammatory-related disease by inhibiting pro-inflammatory cytokine expression or by stimulating anti-inflammatory cytokine expression, but the amount is less than sufficient to substantially inhibit cyclin dependent kinases. In an exemplary embodiment, the condition is mediated by a cytokine. In an exemplary embodiment, the condition is mediated by a chemokine. In an exemplary embodiment, the condition is mediated by a neutrophil. In an exemplary embodiment, the condition is mediated by a phosphodiesterase. In an exemplary embodiment, the condition is mediated by a phosphodiesterase-4. In an exemplary embodiment, the condition is mediated by a phosphodiesterase-7.

In an exemplary embodiment, the condition is a member selected from periodontitis, keratoconjunctivitis sicca, rheumatoid arthritis, osteoarthritis, Crohn's disease, ulcerative colitis, psoriatic arthritis, traumatic arthritis, rubella arthritis, inflammatory bowel disease, multiple sclerosis, psoriasis, graft versus host disease, systemic lupus erythematosus, cutaneous lupus erythematosus, toxic shock syndrome, irritable bowel syndrome, muscle degeneration, allograft rejections, pancreatitis, insulitis, glomerulonephritis, diabetic nephropathy, renal fibrosis, chronic renal failure, gout, leprosy, acute synovitis, Reiter's syndrome, gouty arthritis, Behcet's disease, spondylitis, endometriosis, non-articular inflammatory conditions, such as intervertebral disk syndrome conditions, bursitis, tendonitis, tenosynovitis or fibromyalgic syndrome; and acute or chronic pain, including but not limited to neurological pain, neuropathies, polyneuropathies, diabetes-related polyneuropathies, trauma, migraine, tension and cluster headache, Horton's disease, varicose ulcers, neuralgias, musculo-skeletal pain, osteo-traumatic pain, fractures, algodystrophy, spondyloarthritis, fibromyalgia, phantom limb pain, back pain, vertebral pain, post-surgery pain, herniated intervertebral disc-induced sciatica, cancer-related pain, vascular pain, visceral pain, childbirth, or HIV-related pain. Other cytokine mediated diseases are allergy, a metabolic disease, a chemotherapy/radiation related complication; diabetes type I; diabetes type II; a liver disease; a gastrointestinal disorder; an ophthalmological disease; allergic conjunctivitis; diabetic retinopathy; Sjogren's syndrome; uveitis; a pulmonary disorder, a renal disease; dermatitis; HIV-related cachexia; cerebral malaria; ankylosing spondylitis; leprosy; anemia; fibromyalgia, kidney failure, stroke, chronic heart failure, endotoxemia, reperfusion injury, ischemia reperfusion, myocardial ischemia, restenosis, thrombosis, angiogenesis, Coronary Heart Disease, Coronary Artery Disease, acute coronary syndrome, Takayasu arteritis, cardiac failure such as heart failure, aortic valve stenosis, cardiomyopathy, myocarditis, vasculitis, vascular restenosis, valvular disease or coronary artery bypass; hypercholesterolemia, diseases or conditions related to blood coagulation or fibrinolysis, such as for example, acute venous thrombosis, pulmonary embolism, thrombosis during pregnancy, hemorrhagic skin necrosis, acute or chronic disseminated intravascular coagulation (DIC), clot formation from surgery, long bed rest or long periods of immobilization, venous thrombosis, fulminant meningococcemia, acute thrombotic strokes, acute coronary occlusion, acute peripheral arterial occlusion, massive pulmonary embolism, axillary vein thrombosis, massive iliofemoral vein thrombosis, occluded arterial or venous cannulae, cardiomyopathy, venoocclusive disease of the liver, hypotension, decreased cardiac output, decreased vascular resistance, pulmonary hypertension, diminished lung compliance, leukopenia or thrombocytopenia; or atherosclerosis.

In an exemplary embodiment, the condition is selected from the group consisting of allergic conjunctivitis, uveitis, glaucoma, optic neuritis, retinal ischemia, diabetic retinopathy, laser induced optic damage, or surgery or trauma-induced proliferative vitreoretinopathy.

In an exemplary embodiment, the condition is selected from the group consisting of allergic rhinitis, asthma, adult respiratory distress syndrome, chronic pulmonary inflammation, chronic obstructive pulmonary disease, emphysema, bronchitis, mucus hypersecretion, silicosis, SARS infection and respiratory tract inflammation.

In an exemplary embodiment, the condition is selected from the group consisting of psoriasis, eczema, atopic dermatitis, contact dermatitis, inflammatory alopecia and acne.

In an exemplary embodiment, the condition is a member selected from Guillain-Barre syndrome, Parkinson's disease, Huntington's disease, Alzheimer's disease, amyotrophic lateral sclerosis, multiple sclerosis and other demyelinating diseases, viral and bacterial meningitis, CNS trauma, spinal cord injury, seizures, convulsions, olivopontocerebellar atrophy, AIDS dementia complex, MERRF and MELAS syndromes, Leber's disease, Wernicke's encephalopathy, Rett syndrome, homocystinuria, hyperprolinemia, hyperhomocysteinemia, nonketotic hyperglycinemia, hydroxybutyric aminoaciduria, sulfite oxidase deficiency, combined systems disease, lead encephalopathy, Tourette's syndrome, hepatic encephalopathy, drug addiction, drug tolerance, drug dependency, depression, bipolar depression, attention deficit disorder (ADD), anxiety and schizophrenia, aneurism, or epilepsy.

In an exemplary embodiment, the condition is selected from the group consisting of bone resorption diseases, osteopetrosis, osteoporosis, and osteoarthritis.

In an exemplary embodiment, the condition is selected from the group consisting of diabetes, systemic cachexia, cachexia secondary to infection or malignancy, cachexia secondary to acquired immune deficiency syndrome (AIDS), obesity, anorexia and bulimia nervosa. In an exemplary embodiment, the condition is selected from the group consisting of sepsis, HIV, HCV, malaria, infectious arthritis, leishmaniasis, Lyme disease, cancer, including but not limited to breast cancer, colon cancer, lung cancer, prostate cancer, multiple myeloma, acute myelogenous leukemia, myelodysplastic syndrome, non-Hodgkins lymphoma, follicular lymphoma, Castleman's disease, and drug resistance.

In an exemplary embodiment, the condition is selected from the group consisting of is bronchial asthma, rhinitis, influenza, stroke, myocardial infarction, thermal injury, adult respiratory distress syndrome (ARDS), multiple organ injury secondary to trauma, acute glomerulonephritis, dermatoses with acute inflammatory components, acute purulent meningitis, hemodialysis, leukapheresis, granulocyte transfusion associated syndromes, and necrotizing enterocolitis.

In an exemplary embodiment, the condition is selected from the group consisting of inflammatory bowel disease (IBD), psoriasis, rheumatoid arthritis (RA), multiple sclerosis (MS), neurodegenerative disorder, cardiovascular disease (CVD) and atherosclerosis, and metabolic disease (the metabolic syndrome and diabetes) as well as infection-related inflammation. In an exemplary embodiment, the condition is a neurodegenerative disorder which is selected from the group consisting of Alzheimer's disease and Parkinson disease. In an exemplary embodiment, the condition is inflammatory bowel disease which is Crohn's disease or ulcerative colitis. In an exemplary embodiment, the condition is a gastrointestinal complication. In an exemplary embodiment, the condition is diarrhea. In an exemplary embodiment, the condition is celiac disease or non-specific colitis. In an exemplary embodiment, the condition is a liver disease. In an exemplary embodiment, the condition is selected from the group consisting of an autoimmune hepatitis, hepatitis C, primary biliary cirrhosis, primary sclerosing cholangitis, and fulminant liver failure. In an exemplary embodiment, the condition is a bone disease. In an exemplary embodiment, the condition is osteoporosis. In an exemplary embodiment, the condition is a pulmonary disorder. In an exemplary embodiment, the condition is selected from the group consisting of: allergic rhinitis, asthma, chronic obstructive pulmonary disease, chronic granulomatous inflammation, cystic fibrosis, and sarcoidosis. In an exemplary embodiment, condition is cardiovascular disease. In an exemplary embodiment, the cardiovascular disease is selected from the group consisting of atherosclerotic cardiac disease, congestive heart failure and restenosis. In an exemplary embodiment, the condition is a renal disease. In an exemplary embodiment, the condition is glomerulonephritis or vasculitis. In an exemplary embodiment, the condition is a member selected from post-radiotherapy related disease or atherosclerosis. In yet another embodiment the condition is atopic dermatitis. In yet another embodiment the condition is actinic keratosis.

In an exemplary embodiment, the condition is selected from the group consisting of psoriasis, inflammatory arthritis, rheumatoid arthritis, asthma, chronic bronchitis, inflammatory bowel disease (IBD), chronic obstructive pulmonary disease (COPD), atopic dermatitis, urticaria, allergic rhinitis, allergic conjunctivitis, vernal conjunctivitis, colitis, esoniophilic granuloma, septic shock, reperfusion injury of the myocardium, reperfusion injury of the brain, chronic glomerulonephritis, endotoxic shock, adult respiratory distress syndrome, cystic fibrosis, arterial restenosis, atherosclerosis, keratosis, rheumatoid spondylitis, osteoarthritis, pyresis, diabetes mellitus, pneumoconiosis, chronic obstructive airways disease, toxic contact eczema, allergic contact eczema, atopic eczema, seborrheic eczema, lichen simplex, sunburn, pruritus in the anogenital area, alopecia areata, hypertrophic scars, discoid lupus erythematosus, systemic lupus erythematosus, follicular pyodermas, wide-area pyodermas, endogenous acne, exogenous acne, acne rosacea, Behcet's disease, anaphylactoid purpura nephritis, leukemia, multiple sclerosis, gastrointestinal disease and autoimmune disease. In an exemplary embodiment, the colitis is selected from the group consisting of ulcerative colitis, Crohn's colitis, diversion colitis, ischemic colitis, infectious colitis, fulminant colitis, chemical colitis, microscopic colitis, lymphocytic colitis, and atypical colitis. In an exemplary embodiment, the colitis is ulcerative colitis or Crohn's colitis. In an exemplary embodiment, the condition is sunburn. In an exemplary embodiment, the condition is inflammation caused by sunburn.

In an exemplary embodiment, the condition is psoriasis. In an exemplary embodiment, the condition is plaque psoriasis or flexural psoriasis (inverse psoriasis) or guttate psoriasis or pustular psoriasis or nail psoriasis or psoriatic arthritis or erythrodermic psoriasis. In an exemplary embodiment, the condition is plaque psoriasis. In an exemplary embodiment, the condition is nail psoriasis.

In an exemplary embodiment, the disorder is selected from the group consisting of cognition impairment or decline or memory impairment. In an exemplary embodiment, the memory impairment is due to dementia. In an exemplary embodiment, the patient is suffering from memory impairment due to Alzheimer's disease, schizophrenia, Parkinson's disease, Huntington's disease, Pick's disease, Creutzfeld-Jakob disease, depression, aging, head trauma, stroke, CNS hypoxia, cerebral senility, multiinfarct dementia, an acute neuronal disease, age-related cognitive decline, HIV or a cardiovascular disease.

In an exemplary embodiment, the disorder is spondyloarthropathy. In an exemplary embodiment, the disorder is selected from the group consisting of psoriatic arthritis, reactive arthritis, uveitis, arthritis associated with ulcerative colitis, arthritis associated with Crohn's disease, juvenile SpA (spondylarthropathy), and ankylosing spondylitis.

Compounds such as those described in this invention may also be used to treat various neurological diseases including: to regulate sleep—insomnia; to aid the recovery CNS tissue from ischemia—recovery from stroke, spinal cord injury and aneurysm; to treat depression; to treat psychosis; to treat memory and learning impairment; to treat inflammatory brain diseases—multiple sclerosis or myasthenia gravis; to suppress brain tumor growth.

In an exemplary embodiment, the PDE4 inhibition is enhancing an effect, wherein the enhanced effect is cognition or memory.

In an exemplary embodiment, the invention provides a method for stimulating ovarian follicular growth in a female, comprising administering to a female a medicament comprising a compound of the invention, whereby ovarian follicular growth is stimulated in the female. In an exemplary embodiment, the compound of the invention is a compound described herein or a pharmaceutically acceptable salt thereof. In an exemplary embodiment, the female is undergoing ovulation induction. In an exemplary embodiment, the female is undergoing controlled ovarian hyperstimulation. In an exemplary embodiment, the medicament is administered simultaneously, separately or sequentially with follicle stimulating hormone (FSH), or an agent having FSH activity, or an agent that stimulates endogenous FSH release.

The invention also provides a method of treating an inflammatory-related disease associated with cytokine expression levels, which comprises administering to an animal in need of such treatment the compound of the invention. In an exemplary embodiment, the compound is according to a formula described herein. In an exemplary embodiment, the compound of the invention is a compound described herein or a pharmaceutically acceptable salt thereof.

In an exemplary embodiment, the invention provides a method of treating or preventing an inflammatory-related disease in an animal, the method comprising administering to the animal a therapeutically effective amount of a compound of the invention, wherein the compound is in an amount sufficient to treat the inflammatory-related disease by inhibiting pro-inflammatory cytokine expression or by stimulating anti-inflammatory cytokine expression, but the amount is less than sufficient to substantially inhibit cyclin dependent kinases. In an exemplary embodiment, the compound of the invention is a compound described herein or a pharmaceutically acceptable salt thereof.

In an exemplary embodiment, the invention provides a method for inhibiting the production of an inflammatory cytokine by cells capable of producing the inflammatory cytokine, the method comprises contacting a cell with a therapeutic amount of compound of the invention, wherein production of the inflammatory cytokine by the cells is inhibited. In an exemplary embodiment, the therapeutic amount is sufficient to inhibit the production of the inflammatory cytokine protein between about 50% and about 99%.

In an exemplary embodiment, the invention provides a method for inhibiting an inflammatory response in an animal, the method comprising: contacting the animal with a therapeutic amount of a compound of the invention, wherein the inflammatory response is inhibited.

In an exemplary embodiment, for any of the methods described herein, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, for any of the methods described herein, the animal is selected from the group consisting of a human, cattle, goat, pig, sheep, horse, cow, bull, dog, guinea pig, gerbil, rabbit, cat, chicken and turkey. In another exemplary embodiment, for any of the methods described herein, the animal is a human.

In an exemplary embodiment, for any of the methods described herein, a compound of the invention and/or a pharmaceutical formulation described herein can be used.

In another exemplary embodiment, in any of the methods described herein, the animal being administered the compound of the invention is not otherwise in need of treatment with the compound of the invention. In another exemplary embodiment, in any of the methods of treating/preventing a condition or enhancing an effect described herein, the animal being administered the compound of the invention is not otherwise in need of treatment with the compound of the invention.

In another exemplary embodiment, the method involves preventing psoriasis by administering a compound of the invention to an animal, thereby preventing said psoriasis. In another exemplary embodiment, the method involves treating psoriasis by administering a compound of the invention to an animal not otherwise in need of treatment with said compound of the invention, thereby treating said psoriasis. In another exemplary embodiment, the method involves treating psoriasis by administering a therapeutically effective amount of a compound of the invention to an animal not otherwise in need of treatment with said compound of the invention, thereby treating said psoriasis.

In another exemplary embodiment, the method involves preventing plaque psoriasis by administering a compound of the invention to an animal, thereby preventing said plaque psoriasis. In another exemplary embodiment, the method involves treating plaque psoriasis by administering a compound of the invention to an animal not otherwise in need of treatment with said compound of the invention, thereby treating said plaque psoriasis. In another exemplary embodiment, the method involves treating plaque psoriasis by administering a therapeutically effective amount of a compound of the invention to an animal not otherwise in need of treatment with said compound of the invention, thereby treating said plaque psoriasis.

In another exemplary embodiment, the method involves preventing nail psoriasis by administering a compound of the invention to an animal, thereby preventing said nail psoriasis. In another exemplary embodiment, the method involves treating nail psoriasis by administering a compound of the invention to an animal not otherwise in need of treatment with said compound of the invention. In another exemplary embodiment, the method involves treating nail psoriasis by administering a therapeutically effective amount of a compound of the invention to an animal not otherwise in need of treatment with said compound of the invention, thereby treating said nail psoriasis.

In another exemplary embodiment, the method involves treating atopic dermatitis by administering a compound of the invention to an animal, thereby preventing said atopic dermatitis. In another exemplary embodiment, the method involves preventing atopic dermatitis by administering a compound of the invention to an animal not otherwise in need of treatment with said compound of the invention. In another exemplary embodiment, the method involves treating atopic dermatitis by administering a therapeutically effective amount of a compound of the invention to an animal not otherwise in need of treatment with said compound of the invention, thereby treating said atopic dermatitis.

g) Methods of Inhibiting Worm Growth or Killing Worms

The compounds of the present invention exhibit potency against worms, and therefore have the potential to kill and/or inhibit the growth of such worms. The invention therefore provides a method of killing a worm, comprising: contacting the worm with an effective amount of the compound of the invention, thereby killing the worm. The invention provides a method of inhibiting the growth of a worm, comprising: contacting the worm with an effective amount of the compound of the invention, thereby inhibiting the growth of the worm. The invention provides a method of inducing hypermotility in a worm, comprising: contacting the worm with an effective amount of the compound of the invention, thereby inducing hypermotility in the worm. The invention provides a method of inducing spasms in a worm, comprising: contacting the worm with an effective amount of the compound of the invention, thereby inducing spasms in the worm. In an exemplary embodiment, the worm is female. In an exemplary embodiment, the worm is male. In an exemplary embodiment, the worm is a hermaphrodite. In an exemplary embodiment, the worm is an egg. In an exemplary embodiment, the worm is an unfertilized egg. In an exemplary embodiment, the worm is fertilized egg. In an exemplary embodiment, the worm is a larvae. In an exemplary embodiment, the worm is mature. In an exemplary embodiment, the worm is fully mature. In an exemplary embodiment, the worm is contacted with the compound of the invention inside an animal. In an exemplary embodiment, the worm is contacted with the compound of the invention outside of an animal.

In an exemplary embodiment, the worm is a parasitic worm. In an exemplary embodiment, the worm is a helminthes. In an exemplary embodiment, the worm is a nematode. In an exemplary embodiment, the nematode is selected from the group consisting of ascarids, filarids, hookworms, pinworms, and whipworms. In an exemplary embodiment, the nematode is a member of Filarioidea. In an exemplary embodiment, the nematode is a filarid. In an exemplary embodiment, the nematode is a filarial worm. In an exemplary embodiment, the nematode is a member of the genus *Wuchereria*. In an exemplary embodiment, the nematode is *Wuchereria bancrofti*. In an exemplary embodiment, the nematode is a member of the genus *Brugia*. In an exemplary embodiment, the nematode is *Brugia malayi*. In an exemplary embodiment, the nematode is *Brugia timori*. In an exemplary embodiment, the *Brugia* is a microfilariae. In an exemplary embodiment, the *Brugia* is a larvae. In an exemplary embodiment, the *Brugia* is mature. In an exemplary embodiment, the *Brugia* is contacted by the compound of the invention in the skin of the animal. In an exemplary embodiment, the *Brugia* is contacted by the compound of the invention in the lymphatic system of the animal. In an exemplary embodiment, the *Brugia* is contacted by the compound of the invention in the blood of the animal. In an exemplary embodiment, the *Brugia* is contacted by the compound of the invention in the muscle of the animal. In an exemplary embodiment, the *Brugia* is contacted by the compound of the invention in the salivary gland of the animal.

In an exemplary embodiment, the nematode is a member of the genus *Loa*. In an exemplary embodiment, the nematode is *Loa loa*. In an exemplary embodiment, the nematode is a member of the genus *Mansonella*. In an exemplary embodiment, the nematode is selected from the group consisting of *Mansonella streptocerca, Mansonella perstans*, and *Monsonella ozzardi*. In an exemplary embodiment, the nematode is a member of the genus *Onchocerca*. In an exemplary embodiment, the nematode is *Onchocerca volvulus*. In an exemplary embodiment, the nematode is *Onchocerca ochengi*.

In an exemplary embodiment, the nematode is a pinworm. In an exemplary embodiment, the nematode is *Enterobius vermicularis*. In an exemplary embodiment, the nematode is a member of the genus *Ascaris*. In an exemplary embodiment, the nematode is *Ascaris lumbricoides*. In an exemplary embodiment, the nematode is a member of the genus *Dracunculus*. In an exemplary embodiment, the nematode is *Dracunculus medinensis*. In an exemplary embodiment, the nematode is a member of the genus *Ancylostoma*. In an exemplary embodiment, the nematode is *Ancylostoma duodenale*. In an exemplary embodiment, the nematode is selected from the group consisting of *Ancylostoma braziliense, Ancylostoma tubaeforme*, and *Ancylostoma caninum*. In an exemplary embodiment, the nematode is a member of the genus *Necator*. In an exemplary embodiment, the nematode is *Necator americanus*.

In an exemplary embodiment, the nematode is a member of the genus *Trichuris*. In an exemplary embodiment, the nematode is selected from the group consisting of *Trichuris trichiura, Trichuris vulpis, Trichuris campanula, Trichuris suis*, and *Trichuris muris*. In an exemplary embodiment, the nematode is a member of the genus *Strongyloides*. In an exemplary embodiment, the nematode is selected from the group consisting of *Strongyloides stercoralis, Strongyloides canis, Strongyloides fuelleborni, Strongyloides cebus*, and *Strongyloides kellyi*. In an exemplary embodiment, the nematode is a member of the genus *Nematodirus*. In an exemplary embodiment, the nematode is a member of the genus *Moniezia*.

In an exemplary embodiment, the nematode is a member of the genus *Oesophagostomum*. In an exemplary embodiment, the nematode is *Oesophagostomum bifurcum*. In an exemplary embodiment, the nematode is *Oesophagostomum aculeatum*. In an exemplary embodiment, the nematode is *Oesophagostomum brumpti*. In an exemplary embodiment, the nematode is *Oesophagostomum stephanostomum*. In an exemplary embodiment, the nematode is *Oesophagostomum stephanostomum* var *thomasi*. In an exemplary embodiment, the nematode is a member of the genus *Cooperia*. In an exemplary embodiment, the nematode is *Cooperia ostertagi* or *Cooperia oncophora*. In an exemplary embodiment, the nematode is a member of the genus *Haemonchus*. In an exemplary embodiment, the nematode is a member of the genus *Ostertagia*. In an exemplary embodiment, the nematode is *Ostertagia ostertagi*. In an exemplary embodiment, the nematode is a member of the genus *Trichostrongylus*. In an exemplary embodiment, the nematode is *Trichostrongylus axei*.

In an exemplary embodiment, the nematode is a heartworm. In an exemplary embodiment, the nematode is a member of the genus *Dirofilaria*. In an exemplary embodiment, the nematode is *Dirofilaria immitis*. In an exemplary embodiment, the nematode is *Dirofilaria tenuis* or *Dirofilaria repens*.

In an exemplary embodiment, the worm is a trematode. In an exemplary embodiment, the trematode is a blood fluke or bilharzia. In an exemplary embodiment, the trematode is a member of the genus *Schistosoma*. In an exemplary embodiment, the trematode is selected from the group consisting of *Schistosoma incognitum, Schistosoma ovuncatum*, and *Schistosoma sinensium*. In an exemplary embodiment, the trematode is a member of the group *Schistosoma indicum*. In an exemplary embodiment, the trematode is selected from the group consisting of *Schistosoma indicum, Schistosoma nasale*, and *Schistosoma spindale*. In an exemplary embodiment, the trematode is a member of the group *Schistosoma japonicam*. In an exemplary embodiment, the trematode is selected from the group consisting of *Schistosoma japonicum, Schistosoma malayensis*, and *Schistosoma mekongi*. In an exemplary embodiment, the trematode is a member of the group *Schistosoma haematobium*. In an exemplary embodiment, the trematode is selected from the group consisting of *Schistosoma bovis, Schistosoma curassoni, Schistosoma guineensis, Schistosoma haematobium, Schistosoma intercalatum, Schistosoma leiperi, Schistosoma margrebowiei*, and *Schistosoma mattheei*. In an exemplary embodiment, the trematode is a member of the group *Schistosoma mansoni*. In an exemplary embodiment, the trematode is selected from the group consisting of *Schistosoma edwardiense, Schistosoma hippotami, Schistosoma mansoni*, and *Schistosoma rodhaini*. In an exemplary embodiment, the trematode is *Schistosoma mansoni*. In an exemplary embodiment, the trematode is *Schistosoma intercalatum*. In an exemplary embodiment, the trematode is *Schistosoma haematobium*. In an exemplary embodiment, the trematode is *Schistosoma japonicum*. In an exemplary embodiment, the trematode is *Schistosoma mekongi*. In an exemplary embodiment, the trematode is *Schistosoma bovis*. In an exemplary embodiment, the trematode is *Schistosoma mattheei*. In an exemplary embodiment, the trematode is *Schistosoma margrebowiei*. In an exemplary embodiment, the trematode is *Schistosoma curassoni*. In an exemplary embodiment, the trematode is *Schistosoma rodhaini*. In an exemplary embodiment, the *Schistosoma* is an egg. In an exemplary embodiment, the *Schistosoma* is a miracidia. In an exemplary embodiment, the *Schistosoma* is a sporocyst. In an exemplary embodiment, the *Schistosoma* is a primary sporocyst. In an exemplary embodiment, the *Schistosoma* is a secondary sporocyst. In an exemplary embodiment, the *Schistosoma* is a cercaria. In an exemplary embodiment, the *Schistosoma* is a schistosomulum. In an exemplary embodiment, the schistosomulum is contacted by the compound of the invention in the skin of the animal. In an exemplary embodiment, the schistosomulum is contacted by the compound of the invention in the lung of the animal. In an exemplary embodiment, the schistosomulum is contacted by the compound of the invention in the liver of the animal. In an exemplary embodiment, the schistosomulum is contacted by the compound of the invention in the digestive tract of the animal. In an exemplary embodiment, the schistosomulum is contacted by the compound of the invention in the urinary tract of the animal.

In an exemplary embodiment, the worm is a plant nematode. In an exemplary embodiment, the worm is a nematode which consumes corn and/or a corn plant. In an exemplary embodiment, the worm is a nematode which consumes corn plant roots. In an exemplary embodiment, the worm is a sting nematode. In an exemplary embodiment, the worm is from the *Belonolaimus* genus. In an exemplary embodiment, the worm is selected from the group consisting of *Belonolaimus anama, Belonolaimus euthychilus, Belonolaimus gracilis, Belonolaimus jara, Belonolaimus lineatus, Belonolaimus lolii, Belonolaimus longicaudatus, Belonolaimus maritimus*, and *Belonolaimus nortoni*. In an exemplary embodiment, the worm is *Belonolaimus gracilis*.

In an exemplary embodiment, the worm is a needle nematode. In an exemplary embodiment, the worm is *Longidorus elongatus*. In an exemplary embodiment, the worm is *Longidorus breviannulatus*. In an exemplary embodiment, the worm is *Longidorus attenuatus*.

In an exemplary embodiment, the worm is a ring nematode. In an exemplary embodiment, the worm is from the *Criconemoides* genus. In an exemplary embodiment, the worm is *Criconemoides inusitatus*.

In an exemplary embodiment, the worm is a root-knot nematode. In an exemplary embodiment, the worm is from the *Meloidogyne* genus. In an exemplary embodiment, the worm is selected from the group consisting of *Meloidogyne chitwoodi, Meloidogyne graminis, Meloidogyne hapla, Meloidogyne mayaguensis*, and *Meloidogyne partityla*. In an exemplary embodiment, the worm is selected from the group consisting of *Meloidogyne arenaria, Meloidogyne incognita, Meloidogyne javanica, Meloidogyne hapla*, and *Meloidogyne chitwoodi*. In an exemplary embodiment, the worm is selected from the group consisting of *Meloidogyne acronea, Meloidogyne arabicida, Meloidogyne artiellia, Meloidogyne citri, Meloidogyne coffeicola, Meloidogyne donghaiensis, Meloidogyne exigua, Meloidogyne fallax, Meloidogyne fujianensis, Meloidogyne indica, Meloidogyne jianyangensis, Meloidogyne kongi, Meloidogyne mali, Meloidogyne mingnanica, Meloidogyne paranaensis, Meloidogyne mayaguensis*. In an exemplary embodiment, the worm is *Meloidogyne hapla*.

In an exemplary embodiment, the worm is a spiral nematode. In an exemplary embodiment, the worm is from the *Helicotylenchus* genus. In an exemplary embodiment, the worm is selected from the group consisting of *H. digonicus, H. labiodiscinus, H. leiocephalus, H. platyurus*, and *H. pseudorobustus*.

In an exemplary embodiment, the worm is a lesion nematode. In an exemplary embodiment, the worm is from the *Pratylenchus* genus. In an exemplary embodiment, the worm is selected from the group consisting of *Pratylenchus agilis, Pratylenchus alleni, Pratylenchus coffeae, Pratylenchus convallariae, Pratylenchus crenatus, Pratylenchus flakkensis, Pratylenchus hexincisus, Pratylenchus loosi, Pratylenchus penetrans, Pratylenchus pseudopratensis, Pratylenchus scribneri*, and *Pratylenchus thornei*. In an exemplary embodiment, the worm is *Pratylenchus fallax*.

In an exemplary embodiment, the worm is a corn cyst nematode. In an exemplary embodiment, the worm is from the *Heterodera* genus. In an exemplary embodiment, the worm is *Heterodera schachtii*. In an exemplary embodiment, the worm is *Heterodera zeae*. In an exemplary embodiment, the worm is *Heterodera cajani*. In an exemplary embodiment, the worm is *Heterodera ciceri*. In an exemplary embodiment, the worm is *Heterodera delvii*. In an exemplary embodiment, the worm is *Heterodera elachista*. In an exemplary embodiment, the worm is *Heterodera latipons*. In an exemplary embodiment, the worm is *Heterodera oryzae*. In an exemplary embodiment, the worm is *Heterodera oryzicola*. In an exemplary embodiment, the worm is *Heterodera sacchari*. In an exemplary embodiment, the worm is *Heterodera schachtii*. In an exemplary embodiment, the worm is *Heterodera carotae*. In an exemplary embodiment, the worm is *Heterodera goettingiana*. In an exemplary embodiment, the worm is *Heterodera glycines* (soybean cyst nematode).

In an exemplary embodiment, the worm is a stubby-root nematode. In an exemplary embodiment, the worm is from the *Paratrichodorus* genus.

In an exemplary embodiment, the worm is from the *Trichodorus* genus. In an exemplary embodiment, the worm is *Trichodorus obtusus*. In an exemplary embodiment, the worm is *Trichodorus proximus*.

In an exemplary embodiment, the worm is a lance nematode. In an exemplary embodiment, the worm is from the *Hoplolaimus* genus. In an exemplary embodiment, the worm is selected from the group consisting of *Hoplolaimus tylenchiformis, Hoplolaimus galeatus*, and *Hoplolaimus columbus*. In an exemplary embodiment, the worm is *Hoplolaimus indicus*.

In an exemplary embodiment, the worm is a stunt nematode. In an exemplary embodiment, the worm is from the *Tylenchorhynchus* genus. In an exemplary embodiment, the worm is selected from the group consisting of *Tylenchorhynchus cylindricus, Tylenchorhynchus hordei, Tylenchorhynchus nudus, Tylenchorhynchus robustus, Tylenchorhynchus acutoides, Tylenchorhynchus acutus, Tylenchorhynchus canalis, Tylenchorhynchus maximus*, and *Tylenchorhynchus pachys*.

In an exemplary embodiment, the worm is a nematode which consumes potatoes and/or a potato plant. In an exemplary embodiment, the worm is a nematode which consumes potato plant roots. In an exemplary embodiment, the worm is a nematode which consumes soybeans and/or a soybean plant. In an exemplary embodiment, the worm is a nematode which consumes soybean plant roots.

In an exemplary embodiment, the worm is a nematode which consumes sugar beets and/or a sugar beet plant. In an exemplary embodiment, the worm is a nematode which consumes sugar beet roots.

In an exemplary embodiment, the worm is from the *Nacobbus* genus. In an exemplary embodiment, the worm is *Nacobbus dorsalis*. In an exemplary embodiment, the worm is *Nacobbus aberrans*.

In an exemplary embodiment, the worm is a nematode which consumes grass and/or turf. In an exemplary embodiment, the worm is a nematode which consumes grass or turf roots. In an exemplary embodiment, the worm is a nematode which consumes a tree. In an exemplary embodiment, the worm is a nematode which consumes the roots of a tree. In an exemplary embodiment, the worm is a nematode which consumes a spruce tree. In an exemplary embodiment, the worm is a nematode which consumes the roots of a spruce tree. In an exemplary embodiment, the worm is a nematode which consumes a pine tree. In an exemplary embodiment, the worm is a nematode which consumes the roots of a pine tree.

In an exemplary embodiment, the worm is from the *Bursaphelenchus* genus. In an exemplary embodiment, the worm is *Bursaphelenchus xylophilus*. In an exemplary embodiment, the worm is *Bursaphelenchus cocophilus*. In an exemplary embodiment, the worm is *Bursaphelenchus mucronatus*. In an exemplary embodiment, the worm is a citrus nematode. In an exemplary embodiment, the worm is a nematode which consumes a citrus fruit or a citrus tree. In an exemplary embodiment, the worm is a nematode which consumes the roots of a citrus tree.

In an exemplary embodiment, the worm is *Tylenchulus* genus. In an exemplary embodiment, the worm is *Tylenchulus semipenetrans*.

In an exemplary embodiment, the worm is from the *Radopholus* genus. In an exemplary embodiment, the worm is *Radopholus similis*. In an exemplary embodiment, the worm is *Radopholus citri*. In an exemplary embodiment, the worm is a citrus nematode. In an exemplary embodiment, the worm is a nematode which consumes a banana or a banana plant. In an exemplary embodiment, the worm is a nematode which consumes the roots of a banana plant.

In an exemplary embodiment, the worm is a nematode which consumes an ornamental or an ornamental plant. In an exemplary embodiment, the worm is a nematode which consumes the roots of an ornamental plant.

In an exemplary embodiment, the worm is a nematode which consumes a vegetable or a vegetable plant. In an exemplary embodiment, the worm is a nematode which consumes the roots of a vegetable plant.

In an exemplary embodiment, the worm is from the *Aphelenchoides* genus. In an exemplary embodiment, the worm is selected from the group consisting of *Aphelenchoides besseyi*, *Aphelenchoides*, *bicaudatus*, *Aphelenchoides centralis*, *Aphelenchoides clarus*, *Aphelenchoides confusus*, *Aphelenchoides dactylocercus*, *Aphelenchoides obtusus*, *Aphelenchoides parietinus*, *Aphelenchoides pusillus*, *Aphelenchoides sacchari*, and *Aphelenchoides vigor*. In an exemplary embodiment, the worm is *Aphelenchoides arachidis*. In an exemplary embodiment, the worm is *Aphelenchoides besseyi*. In an exemplary embodiment, the worm is *Aphelenchoides fragariae*.

In an exemplary embodiment, the worm is from the *Ditylenchus* genus. In an exemplary embodiment, the worm is *Ditylenchus dipsaci*. In an exemplary embodiment, the worm is *Ditylenchus africanus*. In an exemplary embodiment, the worm is *Ditylenchus angustus*. In an exemplary embodiment, the worm is *Ditylenchus destructor*. In an exemplary embodiment, the worm is from the *Belonolaimus* genus. In an exemplary embodiment, the worm is *Belonolaimus longicaudatus*.

In an exemplary embodiment, the worm is a nematode which consumes a vine. In an exemplary embodiment, the worm is a nematode which consumes the roots of a vine. In an exemplary embodiment, the worm is a nematode which consumes grapes or a grape vine. In an exemplary embodiment, the worm is a nematode which consumes the roots of a grape vine. In an exemplary embodiment, the worm is a dagger nematode. In an exemplary embodiment, the worm is from the *Xiphinema* genus. In an exemplary embodiment, the worm is *Xiphinema ifacolum*. In an exemplary embodiment, the worm is *Xiphinema americanum*. In an exemplary embodiment, the worm is *Xiphinema pachtaicum*. In an exemplary embodiment, the worm is *Xiphenema index*.

In an exemplary embodiment, the worm is a nematode which consumes a peach or a peach tree. In an exemplary embodiment, the worm is a nematode which consumes the roots of a peach tree. In an exemplary embodiment, the worm is from the *Macroposthonia* genus. In an exemplary embodiment, the worm is *Macroposthonia xenoplax*.

In an exemplary embodiment, the worm is a stunt nematode. In an exemplary embodiment, the worm is from the *Tylenchorynchus* genus. In an exemplary embodiment, the worm is selected from the group consisting of *Tylenchorynchus cylindricus*, *Tylenchorynchus hordei*, *Tylenchorynchus nudus*, and *Tylenchorynchus robustus*.

In an exemplary embodiment, the worm is a reniform nematode. In an exemplary embodiment, the worm is from the *Rotylenchulus* genus. In an exemplary embodiment, the worm is *Rotylenchulus reniformis*. In an exemplary embodiment, the worm is *Rotylenchulus macrodoratus*.

In an exemplary embodiment, the worm is from the *Globodera* genus. In an exemplary embodiment, the worm is selected from the group consisting of *Globodera achilleae*, *Globodera artemisiae*, *Globodera chaubattia*, *Globodera hypolysi*, *Globodera leptonepia*, *Globodera millefolii*, *Globodera mirabilis*, *Globodera pallida*, *Globodera pseudorostochiensis*, *Globodera rostochiensis*, *Globodera tabacum solanacearum*, *Globodera tabacum tabacum*, *Globodera tabacum virginiae*, and *Globodera zelandica*. In an exemplary embodiment, the worm is *Globodera pallida*. In an exemplary embodiment, the worm is *Globodera pallida*. In an exemplary embodiment, the worm is *Globodera rostochiensis*.

In an exemplary embodiment, the worm is from the *Achlysiella* genus. *Achlysiella williamsi*. In an exemplary embodiment, the worm is from the *Anguina* genus. In an exemplary embodiment, the worm is *Anguina funesta*. In an exemplary embodiment, the worm is *Anguina tritici*. In an exemplary embodiment, the worm is from the *Punctodera* genus. In an exemplary embodiment, the worm is *Punctodera chalcoensis*. In an exemplary embodiment, the worm is from the *Rotylenchulus* genus. In an exemplary embodiment, the worm is *Rotylenchulus macrodoratus*. In an exemplary embodiment, the worm is from the *Subanguina* genus. In an exemplary embodiment, the worm is *Subanguina wevelli*. In an exemplary embodiment, the worm is from the *Thecavermiculatus* genus. In an exemplary embodiment, the worm is *Thecavermiculatus andinus*. In an exemplary embodiment, the worm is from the *Zygotylenchus* genus. In an exemplary embodiment, the worm is *Zygotylenchus guevarai*.

In an exemplary embodiment, the compounds of the invention exhibit potency against bacteria which are associated with worms. In an exemplary embodiment, the compounds of the invention exhibit potency against bacteria which live inside of worms. In an exemplary embodiment, the invention provides a method of killing and/or inhibiting the growth of a bacteria which is associated with a worm, comprising: contacting the bacteria with an effective amount of the compound of the invention, thereby killing and/or inhibiting the growth of the bacteria. In an exemplary embodiment, the bacteria is of the *Wolbachia* genus. In an exemplary embodiment, the bacteria is *Wolbachia pipientis*.

h) Methods of Treating and/or Preventing Disease

In another aspect, the invention provides a method of treating and/or preventing a disease. The method includes administering to the animal a therapeutically effective amount of the compound of the invention, sufficient to treat and/or prevent the disease. In an exemplary embodiment, the compound of the invention can be used in human medical therapy, particularly in the treatment of worm-associated disease. In an exemplary embodiment, the compound of the invention can be used in human medical therapy, particularly in the prophylaxis of worm-associated disease. In an exemplary embodiment, the compound of the invention can be used in veterinary medical therapy, particularly in the treatment of worm-associated disease. In an exemplary embodiment, the compound of the invention can be used in veterinary medical therapy, particularly in the prophylaxis of worm-associated disease. In an exemplary embodiment, the compound of the invention can be used in human medical therapy, particularly in the treatment of helminth-associated disease. In an exemplary embodiment, the compound of the invention can be used in human medical therapy, particularly in the prophylaxis of helminth-associated disease. In an exemplary embodiment, the compound of the invention can be used in veterinary medical therapy, particularly in the treatment of helminth-associated disease. In an exemplary embodiment, the compound of the invention can be used in veterinary medical therapy, particularly in the prophylaxis of helminth-associated disease. In an exemplary embodiment, the animal being administered the compound is not otherwise in need of treatment with a compound of the invention.

In an exemplary embodiment, the disease is associated with a worm. In an exemplary embodiment, the disease is caused by a worm. In an exemplary embodiment, the disease is associated with a worm described herein. In an exemplary embodiment, the disease is associated with a helminth described herein. In an exemplary embodiment, the disease is associated with a nematode. In an exemplary embodiment, the disease is associated with a nematode described herein. In an exemplary embodiment, the nematode is *Wuchereria bancrofti*. In an exemplary embodiment, the nematode is *Brugia malayi*. In an exemplary embodiment, the nematode is *Brugia timori*. In an exemplary embodiment, the nematode is *Dirofilaria immitis*. In an exemplary embodiment, the disease is associated with a trematode. In an exemplary embodiment, the disease is associated with a trematode described herein. In an exemplary embodiment, the disease is associated with *Schistosoma*. In an exemplary embodiment, the disease is associated with *Schistosoma mansoni*. In an exemplary embodiment, the disease is a member selected from enterobiasis, oxyuriasis, ascariasis, dracunculiasis, filariasis, onchocerciasis, schistosomiasis, and trichuriasis. In an exemplary embodiment, the disease is schistosomiasis. In an exemplary embodiment, the disease is urinary schistosomiasis. In an exemplary embodiment, the disease is intestinal schistosomiasis. In an exemplary embodiment, the disease is Asian intestinal schistosomiasis. In an exemplary embodiment, the disease is visceral schistosomiasis. In an exemplary embodiment, the disease is acute schistosomiasis. In an exemplary embodiment, the disease is lymphatic filariasis. In an exemplary embodiment, the disease is bancroftian filariasis. In an exemplary embodiment, the disease is lymphadenitis. In an exemplary embodiment, the disease is lymphangitis. In an exemplary embodiment, the disease is lymphedema. In an exemplary embodiment, the disease is subcutaneous filariasis. In an exemplary embodiment, the disease is serious cavity filariasis. In an exemplary embodiment, the disease is elephantiasis. In an exemplary embodiment, the disease is elephantiasis *tropica*. In an exemplary embodiment, the disease is onchocerciasis.

In an exemplary embodiment, the compound is described herein, or a salt, prodrug, hydrate or solvate thereof, or a combination thereof. In an exemplary embodiment, the invention provides a compound described herein, or a salt, hydrate or solvate thereof. In an exemplary embodiment, the invention provides a compound described herein, or a prodrug thereof. In an exemplary embodiment, the invention provides a compound described herein, or a salt thereof. In another exemplary embodiment, the compound of the invention is a compound described herein, or a pharmaceutically acceptable salt thereof. In another exemplary embodiment, the compound is described by a formula listed herein, or a pharmaceutically acceptable salt thereof. In an exemplary embodiment, the compound is part of a pharmaceutical formulation described herein. In another exemplary embodiment, the contacting occurs under conditions which permit entry of the compound into the worm. Such conditions are known to one skilled in the art and specific conditions are set forth in the Examples appended hereto.

In another exemplary embodiment, the animal is a member selected from human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human. In another exemplary embodiment, the animal is a mouse. In another exemplary embodiment, the animal is a member selected from goat, pig, sheep, horse, cow, bull, dog, guinea pig, gerbil, rabbit, cat, chicken and turkey. In another exemplary embodiment, the animal is an ungulate. In another exemplary embodiment, the ungulate is selected from the group consisting of horse, zebra, donkey, cattle/bison, rhinoceros, camel, hippopotamus, goat, pig, sheep, giraffe, okapi, moose, elk, deer, tapir, antelope, and gazelle. In another exemplary embodiment, the ungulate is cattle. In another exemplary embodiment, the ungulate is selected from the group consisting of goat, pig, and sheep. In another exemplary embodiment, the animal is a ruminant. In another exemplary embodiment, the ruminant is selected from the group consisting of cattle, goats, sheep, giraffes, bison, yaks, water buffalo, deer, camels, alpacas, llamas, wildebeast, antelope, pronghorn, and nilgai. In another exemplary embodiment, the cattle is a cow. In another exemplary embodiment, the cattle is a bull. In another exemplary embodiment, the cattle is a calf. In another exemplary embodiment, the animal is a snail. In another exemplary embodiment, the animal is an insect. In another exemplary embodiment, the animal is a mosquito. In another exemplary embodiment, the animal is a fly.

In an exemplary embodiment, the disease is treated through oral administration of the compound of the invention. In an exemplary embodiment, the disease is treated through intravenous administration of the compound of the invention. In an exemplary embodiment, the disease is treated through topical administration of the compound of the invention. In an exemplary embodiment, the disease is treated through intraperitoneal administration of the compound of the invention. In an exemplary embodiment, the compound is administered in a topically effective amount. In an exemplary embodiment, the compound is administered in a cosmetically effective amount. In an exemplary embodiment, the pharmaceutical formulation is administered in an orally effective amount.

V. Pharmaceutical Formulations

In another aspect, the invention provides a pharmaceutical formulation comprising: (a) a pharmaceutically acceptable excipient; and (b) a compound of the invention. In an exemplary embodiment, the compound of the invention is a compound described herein or a pharmaceutically acceptable salt thereof. In an exemplary embodiment, the compound of the invention is a compound described herein or a pharmaceutically acceptable salt thereof. In an exemplary embodiment, the compound is according to a formula described herein. In an exemplary embodiment, the compound is D230 or a salt thereof. In an exemplary embodiment, the compound is D231 or a salt thereof. In another aspect, the pharmaceutical formulation includes: (a) a pharmaceutically acceptable excipient; and (b) a compound according to a formula described herein. In another aspect, the pharmaceutical formulation includes: (a) a pharmaceutically acceptable excipient; and (b) a compound described herein, or a salt, prodrug, hydrate or solvate thereof, or a combination thereof. In another aspect, the pharmaceutical formulation includes: (a) a pharmaceutically acceptable excipient; and (b) a compound described herein, or a salt, hydrate or solvate thereof, or a combination thereof. In another aspect, the pharmaceutical formulation includes: (a) a pharmaceutically acceptable excipient; and (b) a compound described herein, or a salt, hydrate or solvate thereof. In another aspect, the pharmaceutical formulation includes: (a) a pharmaceutically acceptable excipient; and (b) a salt of a compound described herein. In an exemplary embodiment, the salt is a pharmaceutically acceptable salt. In another aspect, the pharmaceutical formulation includes: (a) a pharmaceutically acceptable excipient; and (b) a prodrug of a compound described herein. In another aspect, the pharmaceutical formulation includes: (a) a pharmaceutically acceptable excipient; and (b) a compound described herein. In an exemplary embodiment, the pharmaceutical formulation is a unit dosage form. In an exemplary embodiment, the pharmaceutical formulation is a single unit dosage form. In an exemplary embodiment, the formulation is an oral unit dosage form. In an exemplary embodiment, the formulation is for oral use. In an exemplary embodiment, the formulation is a topical unit dosage form. In an exemplary embodiment, the topical unit dosage form is selected from the group consisting of a lotion, an ointment and a cream. In an exemplary embodiment, the formulation is for topical use.

In an exemplary embodiment, the compound of the invention is present in the pharmaceutical formulation in an amount of between about 0.0001% to about 60% (w/w). In an exemplary embodiment, the amount is between about 0.05% to about 0.2% (w/w). In an exemplary embodiment, the amount is between about 0.075% to about 0.15% (w/w). In an exemplary embodiment, the amount is between about 0.01% to about 10% (w/w). In an exemplary embodiment, the amount is between about 0.1% to about 10% (w/w). In an exemplary embodiment, the amount is between about 0.25% to about 6% (w/w). In an exemplary embodiment, the amount is between about 0.5% to about 5% (w/w). In an exemplary embodiment, the amount is between about 0.1% and about 1.0% (w/w). In an exemplary embodiment, the amount is between about 0.25% and about 0.75% (w/w). In an exemplary embodiment, the amount is between about 0.4% and about 0.6% (w/w). In an exemplary embodiment, the amount is between about 1.0% and about 2.0% (w/w). In an exemplary embodiment, the amount is between about 1.3% and about 1.7% (w/w). In an exemplary embodiment, the amount is between about 2.0% and about 3.0% (w/w). In an exemplary embodiment, the amount is between about 3.0% and about 4.0% (w/w). In an exemplary embodiment, the amount is between about 4.0% and about 5.0% (w/w). In an exemplary embodiment, the amount is between about 4.5% and about 5.5% (w/w). In an exemplary embodiment, the amount is between about 10% to about 20% (w/w). In an exemplary embodiment, the amount is between about 13% to about 17% (w/w). In an exemplary embodiment, the amount is between about 14% to about 16% (w/w). In an exemplary embodiment, the amount is selected from the group consisting of about 0.1%, 0.3, 0.5%, 1.0%, 1.5%, 2.0%, 5.0%, 10% and 15% (w/w).

The pharmaceutical formulations of the invention can take a variety of forms adapted to the chosen route of administration. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the invention, such as water, ethanol, propylene glycol, mineral oil, vegetable oil and dimethylsulfoxide (DMSO).

The pharmaceutical formulations of the invention may be administered orally, topically, ocularly, intraperitoneally, parenterally, by inhalation or spray or rectally in unit dosage forms containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In an exemplary embodiment, the pharmaceutical formulation is administered orally. In an exemplary embodiment, the pharmaceutical formulation is administered intravenously. In an exemplary embodiment, the pharmaceutical formulation is administered in a topically effective dose. In an exemplary embodiment, the pharmaceutical formulation is administered in a cosmetically effective dose. In an exemplary embodiment, the pharmaceutical formulation is administered in an orally effective dose. In an exemplary embodiment, the formulation is a transdermal delivery formulation.

The pharmaceutical formulations containing compounds of the invention are preferably in a form suitable for oral use, for example, as tablets, troches, lozenges, aqueous or oily suspensions, dispersible powders or granules, emulsion, hard or soft capsules, or syrups or elixirs.

Pharmaceutical formulations intended for oral use may be prepared according to any method known in the art for the manufacture of pharmaceutical formulations, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or *acacia*; lubricating agents, for example magnesium stearate, stearic acid or talc; and extenders and bulking agents, such as microcrystalline cellulose. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum *acacia*; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Other dispersing agents include hydrophilic polymers, electrolytes, Tween™ 60 or 80, PEG, polyvinylpyrrolidone (PVP; commercially known as Plasdone™), and the carbohydrate-based dispersing agents such as, for example, hydroxypropylcellulose and hydroxypropylcellulose ethers (e.g., HPC, HPC-SL, and HPC-L), hydroxypropylmethylcellulose and hydroxypropylmethylcellulose ethers (e.g. HPMC K100, HPMC K4M, HPMC K15M, and HPMC K100M), carboxymethylcellulose sodium, methylcellulose, hydroxyethylcellulose, hydroxypropylmethylcellulose phthalate, hydroxypropylmethylcellulose acetate stearate, noncrystalline cellulose, magnesium aluminum silicate, triethanolamine, polyvinyl alcohol (PVA), polyvinylpyrrolidone/vinyl acetate copolymer (Plasdone™ e.g., S-630), 4-(1,1,3,3-tetramethylbutyl)-phenol polymer with ethylene oxide and formaldehyde (also known as tyloxapol), poloxamers (e.g., Pluronics F68™ F88™ and F108™, which are block copolymers of ethylene oxide and propylene oxide); and poloxamines (e.g., Tetronic 9080, also known as Poloxamine 9080, which is a tetrafunctional block copolymer derived from sequential addition of propylene oxide and ethylene oxide to ethylenediamine (BASF Corporation, Parsippany, N.J.)). Additional excipients, for example sweetening, flavoring and coloring agents, may also be present.

Pharmaceutical formulations of the invention may also be in the form of oil-in-water emulsions and water-in-oil emulsions. The oily phase may be a vegetable oil, for example olive oil or *arachis* oil, or a mineral oil, for example liquid paraffin or mixtures of these. Suitable emulsifying agents may be naturally-occurring gums, for example gum *acacia* or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The pharmaceutical formulations may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Alternatively, the pharmaceutical formulations can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

In some embodiments, the pharmaceutical formulations may be administered ocularly. In some embodiments, the ophthalmic formulation contains a liquid vehicle. The compound, depending on the vehicle and concentration used, can either be suspended or dissolved in the vehicle. Such ophthalmic formulations can then be administered to the eye in the form of a droplet. Suitable vehicles, and optional tear substitute components, are known in the art.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also added as a food or drink supplement for humans.

Dosage levels of the order of from about 5 mg to about 250 mg per kilogram of body weight per day and more preferably from about 25 mg to about 150 mg per kilogram of body weight per day, are useful in the treatment of the above-indicated conditions. The amount of active ingredient that may be combined with the carrier materials to produce a unit dosage form will vary depending upon the condition being treated and the particular mode of administration. Unit dosage forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

In an exemplary embodiment, the unit dosage form contains from about 1 mg to about 800 mg of a compound of the invention. In an exemplary embodiment, the unit dosage form contains from about 1 mg to about 500 mg of an active ingredient. In an exemplary embodiment, the unit dosage form contains from about 100 mg to about 800 mg of a compound of the invention. In an exemplary embodiment, the unit dosage form contains from about 200 mg to about 500 mg of a compound of the invention. In an exemplary embodiment, the unit dosage form contains from about 500 mg to about 800 mg of a compound of the invention. In an exemplary embodiment, the unit dosage form contains from about 1 mg to about 100 mg of a compound of the invention. In an exemplary embodiment, the unit dosage form contains from about 10 mg to about 100 mg of a compound of the invention. In an exemplary embodiment, the unit dosage form contains from about 50 mg to about 100 mg of a compound of the invention. In an exemplary embodiment, the unit dosage form contains from about 25 mg to about 75 mg of a compound of the invention. In an exemplary embodiment, the unit dosage form contains from about 40 mg to about 60 mg of a compound of the invention. In an exemplary embodiment, the unit dosage form contains from about 75 mg to about 200 mg of a compound of the invention. In an exemplary embodiment, the unit dosage form contains from about 10 mg to about 25 mg of a compound of the invention. In an exemplary embodiment, the unit dosage form contains from about 50 mg to about 350 mg of a compound of the invention. In an exemplary embodiment, the unit dosage form contains from about 200 mg to about 400 mg of a compound of the invention. In an exemplary embodiment, the unit dosage form contains from about 5 mg to about 20 mg of a compound of the invention. In an exemplary embodiment, the unit dosage form contains from about 10 mg to about 20 mg of a compound of the invention. In an exemplary embodiment, the unit dosage form contains from about 7 mg to about 12 mg of a compound of the invention. In an exemplary embodiment, the unit dosage form contains from about 0.1 mg to about 10 mg of a compound of the invention. In an exemplary embodiment, the unit dosage form contains from about 0.1 mg to about 6 mg of a compound of the invention. In an exemplary embodiment, the unit dosage form contains from about 0.1 mg to about 5 mg of a compound of the invention. In an exemplary embodiment, the unit dosage form contains from about 1 mg to about 5 mg of a compound of the invention. In an exemplary embodiment, the unit dosage form contains from about 0.1 mg to about 2 mg of a compound of the invention. In an exemplary embodiment, the unit dosage form contains from about 0.1 mg to about 1 mg of a compound of the invention. In an exemplary embodiment, the unit dosage form contains from about 0.1 mg to about 0.5 mg of a compound of the invention. In an exemplary embodiment, the unit dosage form contains from about 0.5 mg to about 3 mg of a compound of the invention. In an exemplary embodiment, the unit dosage form contains from about 0.75 mg to about 2 mg of a compound of the invention. In an exemplary embodiment, the unit dosage form contains from about 0.5 mg to about 4 mg of a compound of the invention.

In an exemplary embodiment, the daily dosage contains from about 1 mg to about 800 mg of a compound of the invention. In an exemplary embodiment, the daily dosage contains from about 1 mg to about 500 mg of an active ingredient. In an exemplary embodiment, the daily dosage contains from about 100 mg to about 800 mg of a compound of the invention. In an exemplary embodiment, the daily dosage contains from about 200 mg to about 500 mg of a compound of the invention. In an exemplary embodiment, the daily dosage contains from about 500 mg to about 800 mg of a compound of the invention. In an exemplary embodiment, the daily dosage contains from about 1 mg to about 100 mg of a compound of the invention. In an exemplary embodiment, the daily dosage contains from about 10 mg to about 100 mg of a compound of the invention. In an exemplary embodiment, the daily dosage contains from about 50 mg to about 100 mg of a compound of the invention. In an exemplary embodiment, the daily dosage contains from about 75 mg to about 200 mg of a compound of the invention. In an exemplary embodiment, the daily dosage contains from about 1 mg to about 5 mg of a compound of the invention. In an exemplary embodiment, the daily dosage contains from about 10 mg to about 25 mg of a compound of the invention. In an exemplary embodiment, the daily dosage contains from about 50 mg to about 350 mg of a compound of the invention. In an exemplary embodiment, the daily dosage contains from about 200 mg to about 400 mg of a compound of the invention. In an exemplary embodiment, the daily dosage contains from about 0.1 mg to about 10 mg of a compound of the invention. In an exemplary embodiment, the daily dosage contains from about 0.1 mg to about 6 mg of a compound of the invention. In an exemplary embodiment, the daily dosage contains from about 0.1 mg to about 5 mg of a compound of the invention. In an exemplary embodiment, the daily dosage contains from about 1 mg to about 5 mg of a compound of the invention. In an exemplary embodiment, the daily dosage contains from about 0.1 mg to about 2 mg of a compound of the invention. In an exemplary embodiment, the daily dosage contains from about 0.1 mg to about 1 mg of a compound of the invention. In an exemplary embodiment, the daily dosage contains from about 0.1 mg to about 0.5 mg of a compound of the invention. In an exemplary embodiment, the daily dosage contains from about 0.5 mg to about 3 mg of a compound of the invention. In an exemplary embodiment, the daily dosage contains from about 0.75 mg to about 2 mg of a compound of the invention. In an exemplary embodiment, the daily dosage contains from about 0.5 mg to about 4 mg of a compound of the invention.

Preferred compounds of the invention will have desirable pharmacological properties that include, but are not limited to, oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocytes may be used to predict compound toxicity. Penetration of the blood brain barrier of a compound in humans may be predicted from the brain levels of laboratory animals that receive the compound intravenously.

Serum protein binding may be predicted from albumin binding assays. Such assays are described in a review by Oravcova, et al. (Journal of Chromatography B (1996) volume 677, pages 1-27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120-1127).

The amount of the composition required for use in treatment will vary not only with the particular compound selected but also with the route of administration, the nature of the condition being treated and the age and condition of the patient and will ultimately be at the discretion of the attendant physician or clinician.

In an exemplary embodiment, the pharmaceutical composition described herein includes an additional active ingredient. In another exemplary embodiment, the additional active ingredient is an immunosuppressive agent. In still another exemplary embodiment, the additional active ingredient is selected from the group consisting of corticosteroids, aminosalicylates, azathioprine (6-mercaptopurine), methotrexate and cyclosporine, etanercept, infliximab, adalimumab, alefacept, efalizumab and anakinra.

In an exemplary embodiment, the additional active ingredient is selected from the group consisting of cilostazol, rolipram, apremilast, roflumilast, piclamilast, CDP-840 and cilomilast.

In still another exemplary embodiment, the additional active ingredient is selected from the group consisting of betamethasone, tacrolimus and pimecrolimus. In still another exemplary embodiment, the additional active ingredient is selected from the group consisting of an activated vitamin D analog and an arotinoid (an aromatic retinoic acid analog). In still another exemplary embodiment, the additional active ingredient is a carcipotriol, such as Tazorac (tazarotene).

V. a) Topical Formulations

In a preferred embodiment, the methods of the invention can be employed through the topical application of the compounds described herein. Topical administration includes for example, transmucosal, transdermal, ungual and transungual routes of administration.

The compositions of the present invention comprises fluid or semi-solid vehicles that may include but are not limited to polymers, thickeners, buffers, neutralizers, chelating agents, preservatives, surfactants or emulsifiers, antioxidants, waxes or oils, emollients, sunscreens, and a solvent or mixed solvent system. The solvent or mixed solvent system is important to the formation because it is primarily responsible for dissolving the drug. The best solvent or mixed solvent systems are also capable of maintaining clinically relevant levels of the drug in solution despite the addition of a poor solvent to the formulation. The topical compositions useful in the subject invention can be made into a wide variety of product types. These include, but are not limited to, lotions, creams, gels, sticks, sprays, ointments, pastes, foams, mousses, masks, eye ointments, eye or ear drops, impregnated dressings, wipes, cleansers including soaps, body washes and shampoos, and make-up products, such as bases, blushes, lipsticks, and eye shadows, among others. These product types can comprise several types of carrier systems including, but not limited to particles, nanoparticles, and liposomes. If desired, disintegrating agents can be added, such as the cross-linked polyvinyl pyrrolidone, agar or alginic acid or a salt thereof such as sodium alginate. Techniques for formulation and administration can be found in *Remington: The Science and Practice of Pharmacy*, supra. The formulation can be selected to maximize delivery to a desired target site in the body. The formulations can also include various conventional colorants, fragrances, thickeners, preservatives, humectants, emollients, demulcents, solubilizing excipients, dispersants, penetration enhancers, plasticizing agents, preservatives, stabilizers, demulsifiers, wetting agents, sunscreens, emulsifiers, moisturizers, astringents, deodorants, and the like, which can be added to provide additional benefits such as, for example, improving the feel and/or appearance of the topical preparation.

Lotions, which are preparations that are to be applied to the skin, nail, hair, claw or hoof surface without friction, are typically liquid or semi-liquid preparations in which finely divided solid, waxy, or liquid are dispersed. Lotions will typically contain suspending agents to produce better dispersions as well as compounds useful for localizing and holding the active agent in contact with the skin, nail, hair, claw or hoof, e.g., methylcellulose, sodium carboxymethylcellulose, or the like.

Creams containing the active agent for delivery according to the present invention are viscous liquid or semisolid emulsions, either oil-in-water or water-in-oil. Cream bases are water-washable, and contain an oil phase, an emulsifier and an aqueous phase. The oil phase is generally comprised of petrolatum or a fatty alcohol, such as cetyl- or stearyl alcohol; the aqueous phase usually, although not necessarily, exceeds the oil phase in volume, and generally contains a humectant. The emulsifier in a cream formulation, as explained in *Remington: The Science and Practice of Pharmacy*, supra, is generally a nonionic, anionic, cationic or amphoteric surfactant.

A lotion or cream may include a relatively large aqueous phase and a relatively small oil phase. Furthermore, the lotions and creams of the invention may include the active compound "all-in-solution" in the oil phase so that substantially none of the active compound crystallizes out at room temperature. In one embodiment, the lotion or cream may comprise a biphasic system, that is, a system wherein a portion (from about 30 to about 75% by weight) of the active compound is in solution in the oil phase and the remainder is in suspension in the aqueous phase.

Gel formulations can also be used in connection with the present invention. As will be appreciated by those working in the field of topical drug formulation, gels are semisolid. Single-phase gels contain organic macromolecules distributed substantially uniformly throughout the carrier liquid, which is typically aqueous, but also may be a solvent or solvent blend. In various embodiments, conventional gelling agents can be used. In an exemplary embodiment, cellulose or its derivatives are used. In an exemplary embodiment, hydroxypropyl methyl cellulose, such as Methocel E4M, is used. Other gelling agents include methyl cellulose, hydroxypropyl cellulose, hydroxypropyl methyl cellulose, cellulose acetate, ethyl cellulose, methyl hydroxy ethyl cellulose, hydroxy ethyl cellulose, and cellulose gum. Cellulose based gelling agents, particularly hydroxymethylcellulose and hydroxypropyl methyl cellulose, are also useful in some embodiments. In some embodiments, cross-linked acrylic polymers including Carbopol may be used.

In one embodiment, the formulation of the invention is viscous enough to form a firm gel. In one embodiment, the viscosity is in the range of 25,000-300,000 cps (centipoise) or 75,000-200,000 cps, based on Brookfield (LV) analysis.

For ease of preparation, it may be convenient to prepare a first gel composition, named speed-gel herein, which can be used to add to other components in the formulation of a final composition for topical administration. There are several possible formulations of the speed-gel. For example, a speed-gel may be prepared by mixing lecithin organogel (L.O.), as a 1:1 (m/m) mixture of lecithin and isopropyl myristate, with LID oil (a 1:1 [m/m] mixture of L.O. and docusate sodium), dissolving additional docusate sodium powder into this mixture, and then adding aqueous urea.

Ointments, which are semisolid preparations, are typically based on petrolatum or other petroleum derivatives. As will be appreciated by the ordinarily skilled artisan, the specific ointment base to be used is one that provides for optimum delivery for the active agent chosen for a given formulation, and, preferably, provides for other desired characteristics as well, e.g., emolliency or the like. As with other carriers or vehicles, an ointment base should be inert, stable, nonirritating and non-sensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Examples of oleaginous ointment bases include White Ointment USP, Yellow Ointment NF, Oleic Acid USP, Olive Oil USP, Paraffin USP, Petrolatum NF, White Petrolatum USP, Spermaceti Wax USP, Synthetic Spermaceti NF, Starch Glycerite NF, White Wax USP, and Yellow Wax USP. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, reference may be had to Remington: The Science and Practice of Pharmacy, supra, for further information.

Useful formulations of the invention also encompass sprays and aerosols. Sprays generally provide the active agent in an aqueous and/or alcoholic solution which can be misted onto the skin, nail, hair, claw or hoof for delivery. Such sprays include those formulated to provide for concentration of the active agent solution at the site of administration following delivery, e.g., the spray solution can be primarily composed of alcohol or other like volatile liquid in which the drug or active agent can be dissolved. Upon delivery to the skin, nail, hair, claw or hoof, the carrier evaporates, leaving concentrated active agent at the site of administration. Examples of aerosol technology are disclosed in U.S. Pat. Nos. 6,682,716; 6,716,415; 6,716,417; 6,783,753; 7,029,658; and 7,033,575.

The topical pharmaceutical compositions may also comprise suitable solid or gel phase carriers. Examples of such carriers include but are not limited to calcium carbonate, calcium phosphate, various sugars, starches, cellulose derivatives, gelatin, and polymers such as polyethylene glycols.

The topical pharmaceutical compositions may also comprise a suitable emulsifier which refers to an agent that enhances or facilitates mixing and suspending oil-in-water or water-in-oil. The emulsifying agent used herein may consist of a single emulsifying agent or may be a nonionic, anionic, cationic or amphoteric surfactant or blend of two or more such surfactants; preferred for use herein are nonionic or anionic emulsifiers. Such surface-active agents are described in "McCutcheon's Detergent and Emulsifiers," North American Edition, 1980 Annual published by the McCutcheon Division, MC Publishing Company, 175 Rock Road, Glen Rock, N.J. 07452, USA.

Examples of useful ionic surfactants include sodium caproate, sodium caprylate, sodium caprate, sodium laurate, sodium myristate, sodium myristolate, sodium palmitate, sodium palmitoleate, sodium oleate, sodium ricinoleate, sodium linoleate, sodium linolenate, sodium stearate, sodium lauryl sulfate (dodecyl), sodium tetradecyl sulfate, sodium lauryl sarcosinate, sodium dioctyl sulfosuccinate, sodium cholate, sodium taurocholate, sodium glycocholate, sodium deoxycholate, sodium taurodeoxycholate, sodium glycodeoxycholate, sodium ursodeoxycholate, sodium chenodeoxycholate, sodium taurochenodeoxycholate, sodium glyco cheno deoxycholate, sodium cholylsarcosinate, sodium N-methyl taurocholate, egg yolk phosphatides, hydrogenated soy lecithin, dimyristoyl lecithin, lecithin, hydroxylated lecithin, lysophosphatidylcholine, cardiolipin, sphingomyelin, phosphatidylcholine, phosphatidyl ethanolamine, phosphatidic acid, phosphatidyl glycerol, phosphatidyl serine, diethanolamine, phospholipids, polyoxyethylene-10 oleyl ether phosphate, esterification products of fatty alcohols or fatty alcohol ethoxylates, with phosphoric acid or anhydride, ether carboxylates (by oxidation of terminal OH group of, fatty alcohol ethoxylates), succinylated monoglycerides, sodium stearyl fumarate, stearoyl propylene glycol hydrogen succinate, mono/diacetylated tartaric acid esters of mono- and diglycerides, citric acid esters of mono-, diglycerides, glyceryl-lacto esters of fatty acids, acyl lactylates, lactylic esters of fatty acids, sodium stearoyl-2-lactylate, sodium stearoyl lactylate, alginate salts, propylene glycol alginate, ethoxylated alkyl sulfates, alkyl benzene sulfones, α-olefin sulfonates, acyl isethionates, acyl taurates, alkyl glyceryl ether sulfonates, sodium octyl sulfosuccinate, sodium undecylenamideo-MEA-sulfosuccinate, hexadecyl triammonium bromide, decyl trimethyl ammonium bromide, cetyl trimethyl ammonium bromide, dodecyl ammonium chloride, alkyl benzyldimethylammonium salts, diisobutyl phenoxyethoxydimethyl benzylammonium salts, alkylpyridinium salts, betaines (trialkylglycine), lauryl betaine (N-lauryl,N,N-dimethylglycine), and ethoxylated amines (polyoxyethylene-15 coconut amine) For simplicity, typical counterions are provided above. It will be appreciated by one skilled in the art, however, that any bioacceptable counterion may be used. For example, although the fatty acids are shown as sodium salts, other cation counterions can also be used, such as, for example, alkali metal cations or ammonium. Formulations of the invention may include one or more of the ionic surfactants above.

Preferred for use herein are high molecular weight alcohols such as cetearyl alcohol, cetyl alcohol, stearyl alcohol, emulsifying wax, glyceryl monostearate, and oleyl alcohol. Other examples are ethylene glycol distearate, sorbitan tristearate, propylene glycol monostearate, sorbitan monooleate, sorbitan monostearate (SPAN 60), diethylene glycol monolaurate, sorbitan monopalmitate, sucrose dioleate, sucrose stearate (CRODESTA F-160), polyoxyethylene lauryl ether (BRIJ 30), polyoxyethylene (2) stearyl ether (BRIJ 72), polyoxyethylene (21) stearyl ether (BRIJ 721), polyoxyethylene monostearate (Myrj 45), polyoxyethylene (20) sorbitan monolaurate (TWEEN 20, polysorbate 20), polyoxyethylene (20) sorbitan monopalmitate (TWEEN 40, polysorbate 40), polyoxyethylene (20) sorbitan monostearate (TWEEN 60, polysorbate 60), polyoxyethylene (20) sorbitan monooleate (TWEEN 80, polysorbate 80), other non-ionic polyoxyalkylene derivatives of hexitol anhydride partial long chain fatty acid esters, and sodium oleate. In an exemplary embodiment, the emulsifier is octyldodecanol. In an exemplary embodiment, xanthan gum or a xanthan gum blend is used. Cholesterol and cholesterol derivatives may also be employed in externally used emulsions and promote w/o emulsions.

Especially suitable nonionic emulsifying agents are those with hydrophile-lipophile balances (HLB) of about 3 to 6 for w/o system and 8 to 18 for o/w system as determined by the method described by Paul L. Lindner in "Emulsions and Emulsion", edited by Kenneth Lissant, published by Dekker, New York, N.Y., 1974, pages 188-190. More preferred for use herein are one or more nonionic surfactants that produce a system having HLB of about 8 to about 18.

Examples of such nonionic emulsifiers include but are not limited to "BRIJ 72", the trade name for a polyoxyethylene (2) stearyl ether having an HLB of 4.9; "BRIJ 721", the trade name for a polyoxyethylene (21) stearyl ether having an HLB of 15.5, "Brij 30", the trade name for polyoxyethylene lauryl ether having an HLB of 9.7; "Polawax", the trade name for emulsifying wax having an HLB of 8.0; "Span 60", the trade name for sorbitan monostearate having an HLB of 4.7; "Crodesta F-160", the trade name for sucrose stearate" having an HLB of 14.5. All of these materials are available from Ruger Chemicals Inc.; Croda; ICI Americas, Inc.; Spectrum Chemicals; and BASF. When the topical formulations of the present invention contain at least one emulsifying agent, each emulsifying agent is present in amount from about 0.5 to about 2.5 wt %, preferably 0.5 to 2.0%, more preferably 1.0% or 1.8%. Preferably the emulsifying agent comprises a mixture of steareth 21 (at about 1.8%) and steareth 2 (at about 1.0%).

The topical pharmaceutical compositions may also comprise suitable emollients. Emollients are materials used for the prevention or relief of dryness, as well as for the protection of the skin, nail, hair, claw or hoof. Useful emollients include, but are not limited to, hydrocarbon oils, waxes, silicone, cetyl alcohol, isopropyl myristate, stearyl alcohol, oleyl alcohol, octyl hydroxystearate, glycerin, other fatty alcohols including short or medium chain fatty alcohols having a carbon length of up to 18, medium or short chain fatty acid triglycerides, esters such as fatty acid esters, lecithins and related polar compounds such as phosphatidylcholine, phosphatidylethanolamine, phosphatidylserine, phosphatidylinositol, phosphatidic acid, lyso-phosphatidylcholine, lyso-phosphatidylethanolamine, and sphingomyelin and the like. Other suitable emollients include triglyceride oils like vegetable oils such as wheat germ, maize, sunflower, karite, castor, sweet almond, macadamia, apricot, soybean, cottonseed, alfalfa, poppy, pumpkinseed, sesame, cucumber, rapeseed, avocado, hazelnut, grape seed, blackcurrant seed, evening primrose, millet, barley, *quinoa*, olive, rye, safflower, candlenut, soya, palm, passion flower, or musk rose oil; triglycerides of caprylic/capric acid, such as those sold under the tradenames MIGLYOL™ (Condea Chemie, Germany) and CRODAMOL (Croda, Inc., Edison, N.J.); fatty alcohols such as caprylic alcohol, lauryl alcohol, myristyl alcohol, cetyl alcohol, and stearyl alcohol; and fatty esters such as oleyl acetate, isotridecyl benzoate, diisooctyl sebacate, isopropyl myristate, cetyl octanoate, isopropyl palmitate, butyl stearate, hexyl laurate, myristyl myristate, decyl oleate, hexyldecyl dimethyloctanoate, cetyl lactate, myristyl lactate, lanoline acetate, isocetyl stearate, isocetyl isostearate, cholesteryl 12-hydroxystearate, dipentaerythritol fatty acid ester, and isostearyl malate. A wide variety of suitable emollients are known and can be used herein. See e.g., Sagarin, Cosmetics, Science and Technology, 2nd Edition, Vol. 1, pp. 32-43 (1972), and U.S. Pat. No. 4,919,934, to Deckner et al., issued Apr. 24, 1990, both of which are incorporated herein by reference in their entirety. These materials are available from Ruger Chemical Co, (Irvington, N.J.).

When the topical formulations of the present invention contain at least one emollient, each emollient is present in an amount from about 0.1 to 15%, preferably 0.1 to about 3.0, more preferably 0.5, 1.0, or 2.5 wt %. Preferably the emollient is a mixture of cetyl alcohol, isopropyl myristate and stearyl alcohol in a 1/5/2 ratio. The emollient may also be a mixture of cetyl alcohol and stearyl alcohol in a 1/2 ratio.

The topical pharmaceutical compositions may also comprise suitable antioxidants, substances known to inhibit oxidation. Antioxidants suitable for use in accordance with the present invention include, but are not limited to, butylated hydroxytoluene, ascorbic acid, sodium ascorbate, calcium ascorbate, ascorbic palmitate, butylated hydroxyanisole, 2,4,5-trihydroxybutyrophenone, 4-hydroxymethyl-2,6-di-tert-butylphenol, erythorbic acid, gum guaiac, propyl gallate, thiodipropionic acid, dilauryl thiodipropionate, tert-butylhydroquinone and tocopherols such as vitamin E, and the like, including pharmaceutically acceptable salts and esters of these compounds. Preferably, the antioxidant is butylated hydroxytoluene, butylated hydroxyanisole, propyl gallate, ascorbic acid, pharmaceutically acceptable salts or esters thereof, or mixtures thereof. Most preferably, the antioxidant is butylated hydroxytoluene. These materials are available from Ruger Chemical Co, (Irvington, N.J.). Antioxidants that may be incorporated into the formulations of the invention include natural antioxidants prepared from plant extracts, such as extracts from aloe vera; avocado; chamomile; *echinacea*; ginko *biloba; ginseng*; green tea; heather; jojoba; lavender; lemon grass; licorice; mallow; oats; peppermint; St. John's wort; willow; wintergreen; wheat wild yam extract; marine extracts; and mixtures thereof.

When the topical formulations of the present invention contain at least one antioxidant, the total amount of antioxidant present is from about 0.001 to 0.5 wt %, preferably 0.05 to about 0.5 wt %, more preferably 0.1%.

The topical pharmaceutical compositions may also comprise suitable preservatives. Preservatives are compounds added to a pharmaceutical formulation to act as an antimicrobial agent. Among preservatives known in the art as being effective and acceptable in parenteral formulations are benzalkonium chloride, benzethonium, chlorohexidine, phenol, m-cresol, benzyl alcohol, methylparaben, propylparaben and other parabens, chlorobutanol, o-cresol, p-cresol, chlorocresol, phenylmercuric nitrate, thimerosal, benzoic acid, and various mixtures thereof. See, e.g., Wallhausser, K.-H., Develop. Biol. Standard, 24:9-28 (1974) (S. Krager, Basel). Preferably, the preservative is selected from methylparaben, propylparaben and mixtures thereof. These materials are available from Inolex Chemical Co(Philadelphia, Pa.) or Spectrum Chemicals.

When the topical formulations of the present invention contain at least one preservative, the total amount of preservative present is from about 0.01 to about 0.5 wt %, preferably from about 0.1 to 0.5%, more preferably from about 0.03 to about 0.15. Preferably the preservative is a mixture of methylparaben and proplybarben in a 5/1 ratio. When alcohol is used as a preservative, the amount is usually 15 to 20%.

The topical pharmaceutical compositions may also comprise suitable chelating agents to form complexes with metal cations that do not cross a lipid bilayer. Examples of suitable chelating agents include ethylene diamine tetraacetic acid (EDTA), ethylene glycol-bis(beta-aminoethyl ether)-N,N,N',N'-tetraacetic acid (EGTA) and 8-Amino-2-[(2-amino-5-methylphenoxy)methyl]-6-methoxyquinoline-N,N,N',N'-tetraacetic acid, tetrapotassium salt (QUIN-2). Preferably the chelating agents are EDTA and citric acid. A chelating agent may comprise salts of the above, such as edetate disodium, for example. These materials are available from Spectrum Chemicals.

When the topical formulations of the present invention contain at least one chelating agent, the total amount of chelating agent present is from about 0.005% to 2.0% by weight, preferably from about 0.05% to about 0.5 wt %, more preferably about 0.1% by weight.

The topical pharmaceutical compositions may also comprise suitable neutralizing agents used to adjust the pH of the formulation to within a pharmaceutically acceptable range. Examples of neutralizing agents include but are not limited to trolamine, tromethamine, sodium hydroxide, hydrochloric acid, sodium carbonate, citric acid, acetic acid and corresponding acids or bases thereof. Such materials are available from are available from Spectrum Chemicals (Gardena, Calif.).

When the topical formulations of the present invention contain at least one neutralizing agent, the total amount of neutralizing agent present is from about 0.1 wt to about 10 wt %, preferably 0.1 wt % to about 5.0 wt %, and more preferably about 1.0 wt %. The neutralizing agent is generally added in whatever amount is required to bring the formulation to the desired pH. In one embodiment, the pH is about 6.0 to about 8.0. In one embodiment, the pH is about 3.0 to about 4.0.

The topical pharmaceutical compositions may also comprise suitable thickening or viscosity increasing agents. These components are diffusible compounds capable of increasing the viscosity of a polymer-containing solution through the interaction of the agent with the polymer. For example, CARBOPOL ULTREZ 10, polymethyl methacrylate (PMMA), and fumed silica may be used as a viscosity-increasing agent. These materials are available from Noveon Chemicals, Cleveland, Ohio Other examples of thickeners include monoglycerides and fatty alcohols, fatty acid esters of alcohols having from about 3 to about 16 carbon atoms. Examples of suitable monoglycerides are glyceryl monostearate and glyceryl monopalmitate. Examples of fatty alcohols are cetyl alcohol and stearyl alcohol. Examples of suitable esters are myristyl stearate and cetyl stearate. The monoglyceride also functions as an auxiliary emulsifier. Other emollients or oleaginous material which may be employed include petrolatum, glyceryl monooleate, myristyl alcohol, and isopropyl palmitate. In one embodiment, the thickener is used in combination with an emulsifying agent.

When the topical formulations of the present invention contain at least one viscosity increasing agent, the total amount of viscosity increasing agent present is from about 0.25% to about 5.0% by weight, preferably from about 0.25% to about 1.0 wt %, and more preferably from about 0.4% to about 0.6% by weight.

The topical pharmaceutical compositions may also comprise a disintegrating agent including starch, e.g., a natural starch such as corn starch or potato starch, a pregelatinized starch such as National 1551 or Amijele™, or sodium starch glycolate such as Promogel™ or Explotab™; a cellulose such as a wood product, microcrystalline cellulose, e.g., Avicel™, Avicel™ PH101, Avicel™ PH102, Avicel™ PH105, Elcema™ P100, Emcocel™, Vivacel™, Ming Tia™, and Solka-Floc™, methylcellulose, croscarmellose, or a cross-linked cellulose, such as cross-linked sodium carboxymethylcellulose (Ac-Di-Sol™), cross-linked carboxymethylcellulose, or cross-linked croscarmellose; a cross-linked starch such as sodium starch glycolate; a cross-linked polymer such as crosspovidone; a cross-linked polyvinylpyrrolidone; alginate such as alginic acid or a salt of alginic acid such as sodium alginate; a clay such as Veegum™ HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

The topical pharmaceutical compositions may also comprise suitable nail penetration enhancers. Examples of nail penetration enhancers include mercaptan compounds, sulfites and bisulfites, keratolytic agents and surfactants. Nail penetration enhancers suitable for use in the invention are described in greater detail in Malhotra et al., *J. Pharm. Sci.*, 91:2, 312-323 (2002), which is incorporated herein by reference in its entirety.

The topical pharmaceutical compositions may also comprise an anti-foaming anti-whitening agent that increases the elegancy of the cream or lotion and inhibits the formation of a white soapy look upon rubbing the cream or lotion on the skin. An example of such material includes silicone fluid. Other anti-foaming agents include simethicone, polyglycol, and sorbitan sesquioleate.

The topical pharmaceutical compositions may also comprise a post-foaming agent. "Post-foaming" refers to a gel that remains a gel as it is expelled from a container but foams up after it is spread over the skin. Post-foaming agents include saturated aliphatic hydrocarbons having from 4-6 carbon atoms, such as butane, pentane and hexane (in particular is opentane and isobutene). Other suitable post-foaming agents include partially, or wholly halogenated hydrocarbons, such as trichlorofluroethane. Also, mixtures of aliphatic and halogenated hydrocarbon propellants, or post-foaming agents can be used. Generally suitable post-foaming agents are those substances that have a low solubility in water, for example less than about 20 cc of gas in 100 grams of water at one atmosphere and 20° C.

The topical pharmaceutical compositions may also comprise one or more suitable solvents. The ability of any solid substance (solute) to dissolve in any liquid substance (solvent) is dependent upon the physical properties of the solute and the solvent. When solutes and solvents have similar physical properties the solubility of the solute in the solvent will be the greatest. This gives rise to the traditional understanding that "like dissolves like." Solvents can be characterized in one extreme as non-polar, lipophilic oils, while in the other extreme as polar hydrophilic solvents. Oily solvents dissolve other non-polar substances by Van der Wals interactions while water and other hydrophilic solvents dissolve polar substances by ionic, dipole, or hydrogen bonding interactions. All solvents can be listed along a continuum from the least polar, i.e. hydrocarbons such as decane, to the most polar solvent being water. A solute will have its greatest solubility in solvents having equivalent polarity. Thus, for drugs having minimal solubility in water, less polar solvents will provide improved solubility with the solvent having polarity nearly equivalent to the solute providing maximum solubility. Most drugs have intermediate polarity, and thus experience maximum solubility in solvents such as propylene glycol or ethanol, which are significantly less polar than water. If the drug has greater solubility in propylene glycol (for example 8% (w/w)) than in water (for example 0.1% (w/w)), then addition of water to propylene glycol should decrease the maximum amount of drug solubility for the solvent mixture compared with pure propylene glycol. Addition of a poor solvent to an excellent solvent will decrease the maximum solubility for the blend compared with the maximum solubility in the excellent solvent.

When compounds are incorporated into topical formulations the concentration of active ingredient in the formulation may be limited by the solubility of the active ingredient in the chosen solvent and/or carrier. Non-lipophilic drugs typically display very low solubility in pharmaceutically acceptable solvents and/or carriers. For example, the solubility of some compounds in the invention in water is less than 0.00025% wt/wt. The solubility of the same compounds in the invention can be less than about 2% wt/wt in either propylene glycol or isopropyl myristate.

Examples of solubilizing excipients include polyethoxylated fatty acids, PEG-fatty acid diesters, PEG-fatty acid mono-ester and di-ester mixtures, polyethylene glycol glycerol fatty acid esters, alcohol-oil transesterification products, polyglycerized fatty acids, propylene glycol fatty acid esters, mixtures of propylene glycol esters-glycerol esters, mono- and diglycerides, sterol and sterol derivatives, polyethylene glycol sorbitan fatty acid esters, polyethylene glycol alkyl ethers, sugar esters, polyethylene glycol alkyl phenols, polyoxyethylene-polyoxypropylene block copolymers, sorbitan fatty acid esters, lower alcohol fatty acid esters, ionic surfactants, tocopherol esters, and sterol esters. In one embodiment of the present invention, ethylhexyl hydroxystearate is the solvent used to dissolve the compounds described herein. In one embodiment of the present invention, diethylene glycol monoethyl ether (DGME) is the solvent used to dissolve the compounds described herein. In one embodiment of the present invention, diethylene glycol monoethyl ether (DGME) is the solvent used to dissolve a compound of the invention. The compounds in the invention useful in the present formulation are believed to have a solubility of from about 10% wt/wt to about 25% wt/wt in DGME. In another embodiment a DGME water cosolvent system is used to dissolve the compounds described herein. In another embodiment a DGME water cosolvent system is used to dissolve a compound of the invention. The solvent capacity of DGME drops when water is added; however, the DGME/water cosolvent system can be designed to maintain the desired concentration of from about 0.1% to about 5% wt/wt active ingredient. Preferably the active ingredient is present from about 0.5% to about 3% wt/wt, and more preferably at about 1% wt/wt, in the as-applied topical formulations. Because DGME is less volatile than water, as the topical formulation evaporates upon application, the active agent becomes more soluble in the cream formulation. This increased solubility reduces the likelihood of reduced bioavailability caused by the drug precipitating on the surface of the skin, nail, hair, claw or hoof.

In one embodiment, the vehicle is lipophilic. Lipophilic materials include oleaginous material such as petrolatum, mineral oil thickened or gelled with polyethylene, high molecular weight paraffin waxes, mono and diglycerides of fatty acids gelled with high molecular weight fatty acids or polyamide complex of hydroxystearate, propylene glycol isostearate or isostearyl alcohol gelled with high molecular weight fatty acids, and mixtures thereof.

Liquid forms, such as lotions suitable for topical administration or suitable for cosmetic application, may include a suitable aqueous or nonaqueous vehicle with buffers, suspending and dispensing agents, thickeners, penetration enhancers, and the like. Solid forms such as creams or pastes or the like may include, for example, any of the following ingredients, water, oil, alcohol or grease as a substrate with surfactant, polymers such as polyethylene glycol, thickeners, solids and the like. Liquid or solid formulations may include enhanced delivery technologies such as liposomes, microsomes, microsponges and the like. Liposomal formulations, which help allow compounds to enter the skin, are described in U.S. Pat. Nos. 5,169,637; 5,000,958; 5,049,388; 4,975,282; 5,194,266; 5,023,087; 5,688,525; 5,874,104; 5,409,704; 5,552,155; 5,356,633; 5,032,582; 4,994,213; and PCT Publication No. WO 96/40061.

Additionally, the compounds can be delivered using a sustained-release system, such as semipermeable matrices of solid hydrophobic polymers containing the therapeutic agent. Various sustained-release materials have been established and are well known by those skilled in the art. Thus, at least two different dosage forms, each of which contains a compound of the invention, may be formulated for topical administration by including such dosage forms in an oil-in-water emulsion, or a water-in-oil emulsion. In such a formulation, the delayed release dosage forms are in the continuous phase, and the delayed sustained release dosage form is in a discontinuous phase. The formulation may also be produced in a manner for delivery of three dosage forms as hereinabove described. For example, there may be provided an oil-in-water-in-oil emulsion, with oil being a continuous phase that contains the third delayed sustained release component, water dispersed in the oil containing a first delayed release dosage form, and oil dispersed in the water containing a second delayed release dosage form.

Topical treatment regimens according to the practice of this invention comprise applying the composition directly to the skin, nail, hair, claw or hoof at the application site, from one to several times daily.

Formulations of the present invention can be used to treat, ameliorate or prevent conditions or symptoms associated with bacterial infections, acne, inflammation and the like.

In an exemplary embodiment, the pharmaceutical formulation includes a simple solution. In an exemplary embodiment, the simple solution includes a polyether. In an exemplary embodiment, the polyether is polyethylene glycol or polypropylene glycol. In an exemplary embodiment, the simple solution includes an alcohol. In an exemplary embodiment, the alcohol is methanol, ethanol, propanol, isopropanol or butanol. In an exemplary embodiment, the simple solution includes a polyether and an alcohol. In another exemplary embodiment, the simple solution includes a polypropylene glycol and ethanol. In another exemplary embodiment, the simple solution is selected from the group consisting of about 10% polypropylene glycol and about 90% ethanol; about 20% polypropylene glycol and about 80% ethanol; about 30% polypropylene glycol and about 70% ethanol; about 40% polypropylene glycol and about 60% ethanol; about 50% polypropylene glycol and about 50% ethanol; about 60% polypropylene glycol and about 40% ethanol; about 70% polypropylene glycol and about 30% ethanol; about 80% polypropylene glycol and about 20% ethanol; about 90% polypropylene glycol and about 10% ethanol.

In an exemplary embodiment, the simple solution includes acetone. In an exemplary embodiment, the simple solution includes acetone and an alcohol. In an exemplary embodiment, the simple solution includes acetone and is selected from the group consisting of methanol, ethanol, propanol, isopropanol or butanol. In an exemplary embodiment, the simple solution includes acetone, an alcohol and a polyether. In another exemplary embodiment, the simple solution includes acetone, an alcohol and polyethylene glycol or polypropylene glycol. In an exemplary embodiment, the simple solution includes acetone and ethanol. In another exemplary embodiment, the simple solution is selected from the group consisting of about 10% acetone and about 90% ethanol; about 20% acetone and about 80% ethanol; about 30% acetone and about 70% ethanol; about 40% acetone and about 60% ethanol; about 50% acetone and about 50% ethanol; about 60% acetone and about 40% ethanol; about 70% acetone and about 30% ethanol; about 80% acetone and about 20% ethanol; about 90% acetone and about 10% ethanol.

In an exemplary embodiment, the pharmaceutical formulation is a lacquer.

V. b) Additional Active Agents

The following are examples of the cosmetic and pharmaceutical agents that can be added to the topical pharmaceutical formulations of the present invention. The following agents are known compounds and are readily available commercially.

Anti-inflammatory agents include, but are not limited to, bisabolol, mentholatum, dapsone, aloe, hydrocortisone, and the like.

Vitamins include, but are not limited to, Vitamin B, Vitamin E, Vitamin A, Vitamin D, and the like and vitamin derivatives such as tazarotene, calcipotriene, tretinoin, adapalene and the like.

Anti-aging agents include, but are not limited to, niacinamide, retinol and retinoid derivatives, AHA, Ascorbic acid, lipoic acid, coenzyme Q 10, beta hydroxy acids, salicylic acid, copper binding peptides, dimethylaminoethyl (DAEA), and the like.

Sunscreens and or sunburn relief agents include, but are not limited to, PABA, jojoba, aloe, padimate-O, methoxycinnamates, proxamine HCl, lidocaine and the like. Sunless tanning agents include, but are not limited to, dihydroxyacetone (DHA). Ultraviolet (UV) light blockers include, for example, amino benzoic acids, benzophenones, camphors, cinnamates, dibenzoyl methanes, salicylates, metal oxides, and mixtures thereof.

Psoriasis-treating agents and/or acne-treating agents include, but are not limited to, salicylic acid, benzoyl peroxide, coal tar, selenium sulfide, zinc oxide, pyrithione (zinc and/or sodium), tazarotene, calcipotriene, tretinoin, adapalene and the like.

Agents that are effective to control or modify keratinization, including without limitation: tretinoin, tazarotene, and adapalene.

The compositions comprising an compound/active agent described herein, and optionally at least one of these additional agents, are to be administered topically. In a primary application, this leads to the compounds of the invention and any other active agent working upon and treating the skin, nail, hair, claw or hoof. Alternatively, any one of the topically applied active agents may also be delivered systemically by transdermal routes.

In such compositions an additional cosmetically or pharmaceutically effective agent, such as an anti-inflammatory agent, vitamin, anti-aging agent, sunscreen, and/or acne-treating agent, for example, is usually a minor component (from about 0.001% to about 20% by weight or preferably from about 0.01% to about 10% by weight) with the remainder being various vehicles or carriers and processing aids helpful for forming the desired dosing form.

V. c) Testing

Preferred compounds for use in the pharmaceutical formulations described herein will have certain pharmacological properties. Such properties include, but are not limited to, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcova et al. (1996, *J. Chromat*. B677: 1-27). Compound half-life is inversely proportional to the frequency of dosage of a compound. In vitro half-lives of compounds may be predicted from assays of microsomal half-life as described by Kuhnz and Gleschen (Drug Metabolism and Disposition, (1998) volume 26, pages 1120-1127).

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the unit dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch. 1, p. 1).

V. d) Administration

For any compound used in the method of the invention, the therapeutically effective dose can be estimated initially from in vitro assays, as disclosed herein. For example, a dose can be formulated in animal models to achieve a circulating concentration range that includes the $IC_{50}$ (Inhibitory dose causing a 50% decrease) as determined in cell culture, i.e., the concentration of the test compound which achieves a half-maximal inhibition of helminth growth or survival or inhibition of an enzyme involved in inflammation. Such information can be used to more accurately determine useful doses in humans.

In general, the compounds prepared by the methods, and from the intermediates, described herein will be administered in a therapeutically or cosmetically effective amount by any of the accepted modes of administration for agents that serve similar utilities. It will be understood, however, that the specific dose level for any particular patient will depend upon a variety of factors including the activity of the specific compound employed, the age, body weight, general health, sex, diet, time of administration, route of administration, rate of absorption, rate of excretion, drug combination, and the severity of the particular disease undergoing therapy and the judgment of the prescribing physician. The drug can be administered from once or twice a day, or up to 3 or 4 times a day or, if required, by continuous infusion over a number of days.

Dosage amount and interval can be adjusted individually to provide plasma levels of the active moiety that are sufficient to maintain helminth survival inhibition effects. In an exemplary embodiment, usual patient dosages for systemic administration range from 0.1 to 1000 mg/day, preferably, 1-500 mg/day, more preferably 10-200 mg/day, even more preferably 100-200 mg/day. Stated in terms of patient body surface areas, usual dosages can range from 50-91 mg/m²/day.

The amount of the compound in a formulation can vary within the full range employed by those skilled in the art. Typically, the formulation will contain, on a weight percent (wt %) basis, from about 0.01-100 wt % of the drug based on the total formulation, with the balance, if required, being one or more suitable pharmaceutical excipients. Preferably, the compound is present at a level of about 0.1-3.0 wt %, more preferably, about 1.0 wt %.

In an exemplary embodiment, the pharmaceutical formulation is an ointment, and comprises a compound of the invention.

In another exemplary embodiment, the pharmaceutical formulation comprises a compound of the invention and at least one emollient described herein.

In another exemplary embodiment, the pharmaceutical formulation includes a compound of the invention, and petrolatum.

Exemplary embodiments are summarized herein below.

In an exemplary embodiment, the invention provides a compound having a structure according to a formula which is:

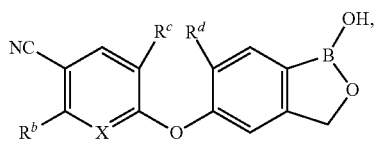

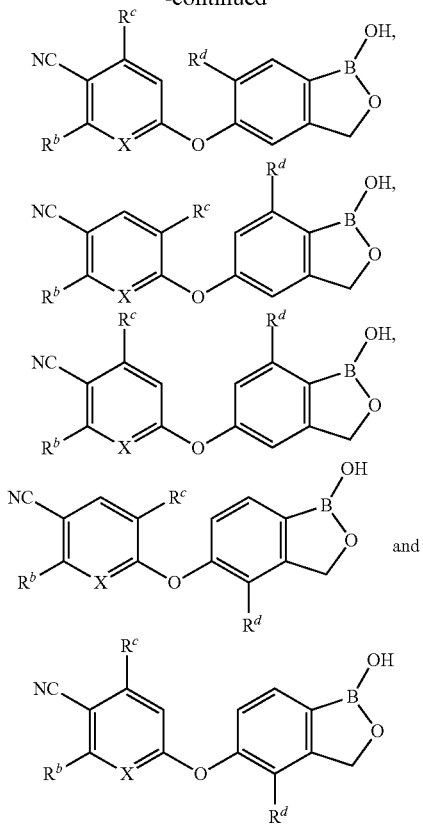

wherein $R^d$ is selected from the group consisting of H, halogen, and unsubstituted alkyl; $R^c$ is selected from the group consisting of cyano, halogen, substituted or unsubstituted alkyl, substituted or unsubstituted cycloalkyl, and substituted or unsubstituted alkoxy; X is N or CH; $R^b$ is selected from the group consisting of $OR^4$ and $NR^4R^5$, wherein $R^4$ and $R^5$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, with the proviso that $R^4$ and $R^5$, together with the atoms to which they are attached, are optionally combined to form a 4- to 8-membered substituted or unsubstituted heterocycloalkyl ring, or a salt thereof.

In an exemplary embodiment, according to the above paragraph, $R^c$ is fluorine or chlorine.

In an exemplary embodiment, according to any of the above paragraphs, $R^c$ is cyclopropyl or cyano.

In an exemplary embodiment, according to any of the above paragraphs, $R^b$ is $R^4$ or $NR^4R^5$.

In an exemplary embodiment, according to any of the above paragraphs, $R^b$ is $OR^4$, and $R^4$ is selected from the group consisting of substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, according to any of the above paragraphs, $R^b$ is $OR^4$, and $R^4$ is selected from the group consisting of substituted or unsubstituted alkyl, substituted or unsubstituted heteroalkyl and substituted or unsubstituted cycloalkyl.

In an exemplary embodiment, according to any of the above paragraphs, $R^b$ is $OR^4$, and $R^4$ is unsubstituted $C_1$-$C_6$ alkyl.

In an exemplary embodiment, according to any of the above paragraphs, $R^b$ is $OR^4$, and $R^4$ is unsubstituted cycloalkyl.

In an exemplary embodiment, according to any of the above paragraphs, $R^b$ is $OR^4$, and $R^4$ is alkyl, substituted with a substituted or unsubstituted $C_1$-$C_6$ alkoxy.

In an exemplary embodiment, according to any of the above paragraphs, $R^b$ is $OR^4$, and $R^4$ is alkyl, substituted with at least one halogen.

In an exemplary embodiment, according to any of the above paragraphs, $R^b$ is $OR^4$, and $R^4$ is alkyl, substituted with at least one oxo moiety.

In an exemplary embodiment, according to any of the above paragraphs, $R^b$ is $OR^4$, and $R^4$ is selected from the group consisting of —$CH_3$, —$CH_2CH_3$, —$(CH_2)_2CH_3$, —$CH(CH_3)_2$, —$CH_2CF_3$, —$CH_2CHF_2$, —$CH_2CH_2OH$, —$CH_2CH_2OCH_3$, —$CH_2CH_2OCH(CH_3)_2$, —$C(O)CH_3$, —$CH_2CH_2OC(O)CH_3$, —$CH_2C(O)OCH_2CH_3$, —$CH_2C(O)OC(CH_3)_3$, —$(CH_2)_3C(O)CH_3$, —$CH_2C(O)OC(CH_3)_3$, cyclopentyl, cyclohexyl, $CH_2CH(OCH_3)CH_2OCH_3$, $(CH_2)_3CH(OH)CH_3$, $(CH_2)_3C(OH)(CH_3)_2$,

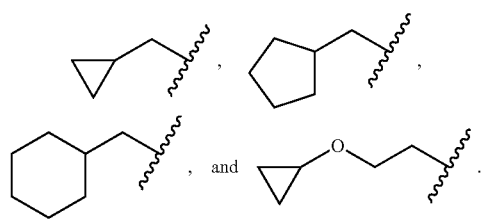

In an exemplary embodiment, according to any of the above paragraphs, the compound has a formula which is selected from the group consisting of

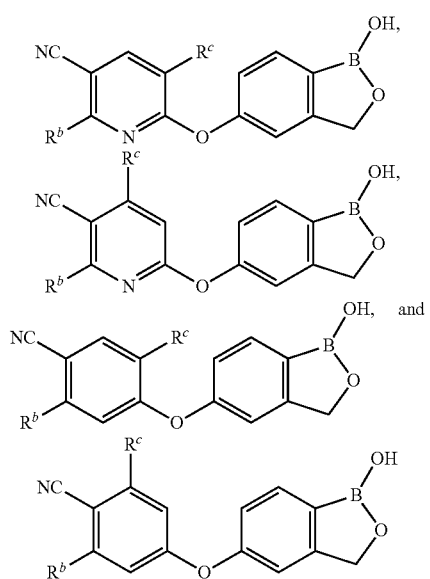

wherein $R^c$ is fluorine or chlorine.

In an exemplary embodiment, according to any of the above paragraphs, the compound has a formula which is selected from the group consisting of

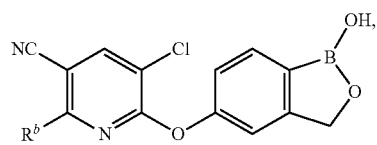

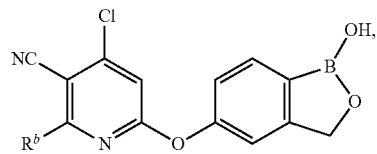

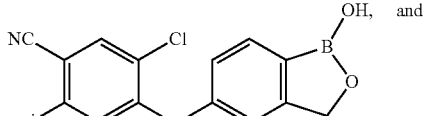

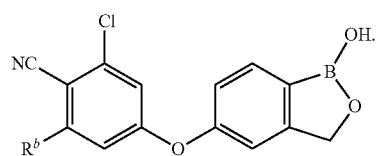

In an exemplary embodiment, according to any of the above paragraphs, the compound has a formula which is selected from the group consisting of

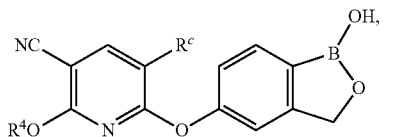

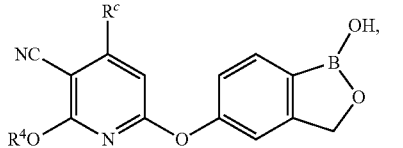

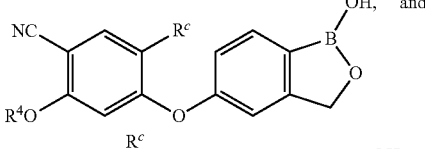

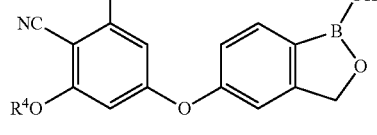

wherein $R^4$ is selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, according to any of the above paragraphs, the compound has a formula which is

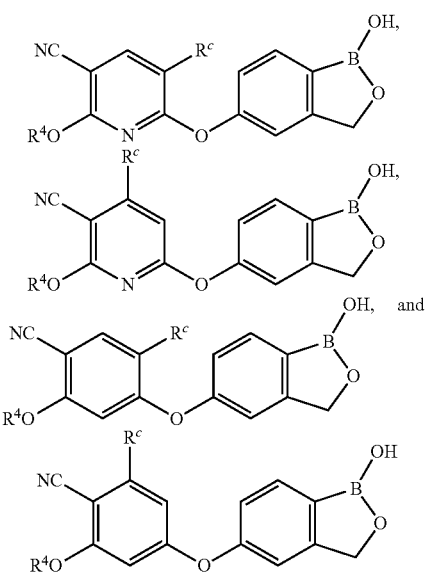

wherein R⁴ is selected from the group consisting of H, substituted or unsubstituted alkyl, and substituted or unsubstituted heteroalkyl.

In an exemplary embodiment, according to any of the above paragraphs, the compound has a formula which is

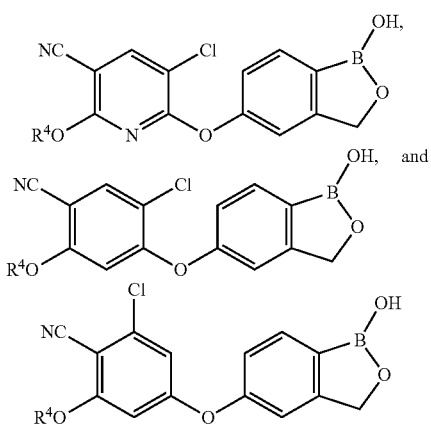

wherein R⁴ is selected from the group consisting of H, substituted or unsubstituted alkyl, substituted or unsubstituted heteroalkyl.

In an exemplary embodiment, according to any of the above paragraphs, the compound has a formula which is

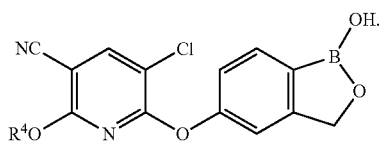

In an exemplary embodiment, according to any of the above paragraphs, wherein R⁴ is selected from the group consisting of H, substituted or unsubstituted alkyl and substituted or unsubstituted heteroalkyl.

In an exemplary embodiment, according to any of the above paragraphs, having a structure which is

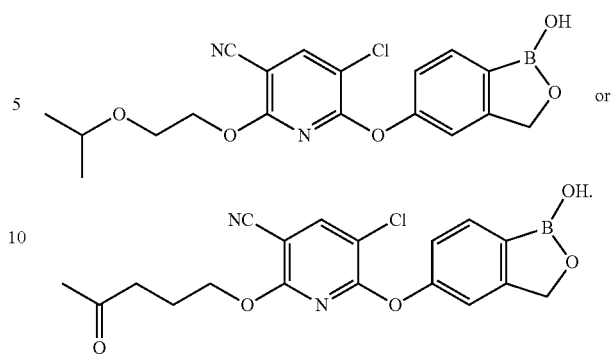

In an exemplary embodiment, the invention provides a pharmaceutical formulation comprising: (a) a compound according to any of the above paragraphs; and (b) a pharmaceutically acceptable excipient.

In an exemplary embodiment, according to any of the above paragraphs, the formulation is in a unit dosage form.

In an exemplary embodiment, according to any of the above paragraphs, the formulation is for oral or topical use.

In an exemplary embodiment, the invention provides a method of decreasing the release of a cytokine or a chemokine, the method comprising: contacting a cell with a compound according to any of the above paragraphs or a pharmaceutically acceptable salt thereof, wherein the release of the cytokine or chemokine by the cell is decreased.

In an exemplary embodiment, according to any of the above paragraphs, the cytokine is selected from the group consisting of IL-1α, IL-1β, IL-2, IL-3, IL-6, IL-7, IL-9, IL-12, IL-17, IL-18, IL-23, TNF-α, LT, LIF, Oncostatin, IFNα, IFNβ and IFN-γ.

In an exemplary embodiment, according to any of the above paragraphs, the cytokine is selected from the group consisting of IL-2, IL-4, IL-5, IL-6, IL-8, IL-10, IL-12, IL-23, TNF-α and IFN-γ.

In an exemplary embodiment, according to any of the above paragraphs, the cytokine is selected from the group consisting of IL-2, IL-5, IL-10, IL-12, IL-23, TNF-α and IFN-γ.

In an exemplary embodiment, according to any of the above paragraphs, the chemokine is selected from the group consisting of IL-8, Gro-α, MIP-1, MCP-1, PGE2, ENA-78, and RANTES.

In an exemplary embodiment, the invention provides a method of treating a condition, in an animal, the method comprising administering to the animal a therapeutically effective amount of a compound according to any of the above paragraphs, or a pharmaceutically acceptable salt thereof, thereby treating the condition.

In an exemplary embodiment, according to any of the above paragraphs, the condition is selected from the group consisting of arthritis, rheumatoid arthritis, an inflammatory bowel disease, psoriasis, a pulmonary disease, multiple sclerosis, a neurodegenerative disorder, congestive heart failure, stroke, aortic valve stenosis, kidney failure, lupus, pancreatitis, allergy, fibrosis, anemia, atherosclerosis, a metabolic disease, a bone disease, a cardiovascular disease, a chemotherapy/radiation related complication, diabetes type I, diabetes type II, a liver disease, a gastrointestinal disorder, an ophthalmological disease, allergic conjunctivitis, diabetic retinopathy, Sjogren's syndrome, uveitis, a pulmonary disorder, a renal disease, dermatitis, HIV-related cachexia, cerebral malaria, ankylosing spondylitis, leprosy, anemia and fibromyalgia.

In an exemplary embodiment, according to any of the above paragraphs, the condition is selected from the group consisting of psoriasis, atopic dermatitis, rheumatoid arthritis, an inflammatory bowel disease, asthma and chronic obstructive pulmonary disease.

In an exemplary embodiment, according to any of the above paragraphs, the condition is plaque psoriasis or flexural psoriasis or Guttate psoriasis or pustular psoriasis or nail psoriasis or erythrodermic psoriasis.

In an exemplary embodiment, according to any of the above paragraphs, the psoriasis is plaque psoriasis or nail psoriasis.

In an exemplary embodiment, the invention provides a method of treating or preventing a disease, in an animal, the method comprising administering to the animal a therapeutically effective amount of a compound according to any of the above paragraphs, or a pharmaceutically acceptable salt thereof, thereby treating the disease.

In an exemplary embodiment, according to any of the above paragraphs, the disease is a helminth-associated disease.

In an exemplary embodiment, according to any of the above paragraphs, the disease is schistosomiasis.

In an exemplary embodiment, according to any of the above paragraphs, the animal is a human.

In an exemplary embodiment, according to any of the above paragraphs, the animal is in need of treatment.

In an exemplary embodiment, according to any of the above paragraphs, the animal is not already in need of treatment by the compound.

In an exemplary embodiment, the invention provides a method of inhibiting a phosphodiesterase (PDE), the method comprising: contacting the phosphodiesterase with a compound according to any of the above paragraphs, or a pharmaceutically acceptable salt thereof, thereby inhibiting the phosphodiesterase.

In an exemplary embodiment, according to any of the above paragraphs, the phosphodiesterase is phosphodiesterase4 (PDE4).

The invention is further illustrated by the Examples that follow. The Examples are not intended to define or limit the scope of the invention.

EXAMPLES

Proton NMR are recorded on Varian AS 300 (300 MHz) or AS400 (400 MHz) spectrometer and chemical shifts are reported as δ (ppm) down field from tetramethylsilane. Mass spectra are determined on Agilent 1200 series plus 6120 Quadrupole LC/MS, Micromass Quattro II, SHIMADZU LCMS-2010 EV, or Waters MS consisting of an Alliance 2795 (LC) and Waters Micromass ZQ detector. The mass spectrometer was equipped with an electrospray ion source (ES) operated in a positive or negative mode.

The following abbreviations have been used: aqueous is aq.; acetonitrile is MeCN; N,N-dimethylformamide is DMF; dimethylsulfoxide is DMSO; acetic acid is HOAc; ethyl acetate is EtOAc; dichloromethane is DCM; 1,2-dimethoxyethane is DME; tetrahydrofuran is THF; methanol is MeOH; ethanol is EtOH; trifluoroacetic acid is TFA; Diisopropylethylamine is DIPEA; 1-propanol is PrOH; 2-propanol is iPrOH; triisopropyl borate is (i-PrO)$_3$B; azobisisobutylonitrile is AIBN; phosphorous oxychloride is POCl$_3$; cesium carbonate is Cs$_2$CO$_3$; sodium sulfate is Na$_2$SO$_4$; potassium tert-butoxide is tert-BuOK; room temperature is r.t.; and melting point is mp.

All solvents used were commercially available and were used without further purification. Reactions were typically run using anhydrous solvents under an inert atmosphere of nitrogen.

Compounds are named either manually or by using ChemDraw, or using their catalogue name if commercially available.

Thin layer chromatography (TLC) was performed on Silica gel 60 F$_{254}$ and UV was typically used to visualize the spots. Additional visualization methods were also employed in some cases. In these cases the TLC plate was developed with iodine (generated by adding approximately 1 g of I$_2$ to 10 g silica gel and thoroughly mixing), vanillin (generated by dissolving about 1 g vanillin in 100 mL 10% H$_2$SO$_4$), ninhydrin (available commercially from Aldrich), or Magic Stain (generated by thoroughly mixing 25 g (NH$_4$)$_6$Mo$_7$O$_{24}$.4H$_2$O, 5 g (NH$_4$)$_2$Ce(IV)(NO$_3$)$_6$ in 450 mL water and 50 mL concentrated H$_2$SO$_4$) to visualize the compound. Flash chromatography was preformed using typically 40-63 µm (230-400 mesh) silica gel following analogous techniques to those disclosed in Still, W. C.; Kahn, M.; and Mitra, M. *Journal of Organic Chemistry*, 1978, 43, 2923-2925. Typical solvents used for flash chromatography or thin layer chromatography were mixtures of chloroform/methanol, dichloromethane/methanol, ethyl acetate/methanol petroleum ether/ethyl acetate and hexanes/ethyl acetate.

Intermediate 1:
Benzo[c][1,2]oxaborole-1,5(3H)-diol

Into a 250-mL 3-necked round-bottom flask purged and maintained with an inert atmosphere of nitrogen were placed a solution of 2-bromo-5-hydroxybenzaldehyde (5 g, 25.00 mmol, 1.00 equiv) in 1,4-dioxane (100 mL), 4,4,5,5-tetramethyl-2-(4,4,5,5-tetramethyl-1,3,2-dioxaborolan-2-yl)-1,3, 2-dioxaborolane (12.7 g, 50.0 mmol, 2.00 equiv), Pd(dppf)$_2$Cl$_2$ (1.83 g, 2.50 mmol, 0.10 equiv) and KOAc (7.35 g, 75.0 mmol, 3.00 equiv). The resulting mixture was stirred for 2 h at 100° C. The reaction mixture was cooled and filtered. The filtrate was concentrated under vacuum. The residue was applied onto a silica gel column and eluted with ethyl acetate/petroleum ether (1/10). This resulted in 3.12 g (45%) of 5-hydroxy-2-(4,4,5,5-tetramethyl-1,3,2-dioxaborolan-2-yl)benzaldehyde as a white solid.

Into a 100-mL 3-necked round-bottom flask purged and maintained with an inert atmosphere of nitrogen was placed a solution of 5-hydroxy-2-(4,4,5,5-tetramethyl-1,3,2-dioxaborolan-2-yl)benzaldehyde (5.5 g, 22 mmol, 1.0 equiv) in methanol (25 mL). This was followed by the addition of NaBH$_4$ (1.24 g, 32.6 mmol, 1.5 equiv) in several batches at 0° C. The resulting solution was stirred for 10 min at 0° C., then it was concentrated under vacuum to get rid of half methanol at low temperature. To the residual solution was added water (6 mL) and HCl (6M, 14.5 mL) dropwise at 0° C. The resulting solution was stirred overnight at room temperature. Then it was concentrated under vacuum at low temperature to remove MeOH. The solid was collected by filtration. This resulted in 2.0 g of benzo[c][1,2]oxaborole-1,5(3H)-diol as a white solid.

Intermediate 2:
6-Fluorobenzo[c][1,2]oxaborole-1,5(3H)-diol

A solution of 4-fluoro-3-methoxybenzaldehyde (4.3 g, 28 mmol), potassium bromide (16.6 g, 140 mmol), bromine (3.6 mL, 70 mmol), and water (45 mL) were stirred at room temperature for 24 hours. More bromine (1.4 mL, 28 mmol) was added and the reaction was stirred at room temperature overnight. The product precipitated out of solution and was collected via filtration and dried under reduced pressure to give 2-bromo-4-fluoro-5-methoxybenzaldehyde (6.01 g, 92%).

A solution of 2-bromo-4-fluoro-5-methoxybenzaldehyde (1.19 g, 8.20 mmol), 48% HBr (57 mL) and glacier acetic acid (57 mL) were refluxed at 130° C. for 5 h. The glacier acetic acid was removed under reduced pressure. The solution was neutralized using sodium carbonate. Water was added and the mixture was extracted using ethyl acetate. The organic layer was washed with brine, dried over anhydrous sodium sulfate, and filtered. The solvent was removed under reduced pressure. The residue was purified by silica gel column using Combiflash to give 2-bromo-4-fluoro-5-hydroxybenzaldehyde (1.15 g, 64%).

A solution of 2-bromo-4-fluoro-5-hydroxybenzaldehyde (2.0 g, 9.1 mmol) in MeOH (15 mL) was cooled in an ice bath before treatment of $NaBH_4$ (390 mg, 10.3 mmol). After the complete addition of $NaBH_4$, the reaction mixture was allowed to stir for 1 h at room temperature before it was quenched with equal volume of water. EtOAc (20 mL) was added to the reaction solution and the layers were separated. The aqueous layer was further extracted with equal volume of EtOAc before the organic layers were combined and dried over anhydrous $Na_2SO_4$ and filtered. The solvent was removed under reduced pressure. The residue was purified by silica gel column using Combiflash to give 4-bromo-2-fluoro-5-(hydroxymethyl)phenol (2.0 g, 83%).

Protection of the alcohol was carried out by making a solution of 4-bromo-2-fluoro-5-(hydroxymethyl)phenol (1.37 g, 6.19 mmol), 3,4 dihydro-2H-pyran (1.4 mL, 15 mmol) in 20 mL of $CH_2Cl_2$. The reaction mixture was then treated with camphor sulfonic acid (58 mg, 0.25 mmol) before stirring at room temperature for 21 hr. The reaction mixture was then quenched with equal volumes of 0.2 M NaOH and EtOAc (1:1, 20 mL) before the layers were separated. The water phase was further extracted with equal volume of EtOAc before the organic layers were combined and dried over anhydrous $Na_2SO_4$ and filtered. The solvent was removed under reduced pressure. The residue was purified by silica gel column using Combiflash to give 2-(4-bromo-2-fluoro-5-((tetrahydro-2H-pyran-2-yloxy)methyl)phenoxy)tetrahydro-2H-pyran (2.0 g, 83%).

A solution of 2-(4-bromo-2-fluoro-5-((tetrahydro-2H-pyran-2-yloxy)methyl)phenoxy)tetrahydro-2H-pyran (6.31 g, 16.2 mmol) in anhydrous THF (13.5 mL) was made before cooling the reaction mixture in a −78° C. bath. Reaction mixture was then treated, drop-wise, with n-BuLi (12.15 mL, 19.45 mmol) and allowed to stir for 1.0 hr before (i-PrO)$_3$B (5.59 mL, 24.3 mmol) was added via syringe. After the addition of (i-PrO)$_3$B, the reaction mixture was warmed to room temperature and allowed to stir for 2 hr before quenching the reaction with equal volume of concentrated $NH_4Cl_{(aq)}$ and EtOAc (1:1, 30 mL). The layers were separated and the water phase was further extracted with equal volume of EtOAc before the organic layers were combined and dried over anhydrous $Na_2SO_4$ and filtered. The solvent was removed under reduced pressure. The residue was purified by silica gel column using Combiflash to give 6-fluorobenzo[c][1,2]oxaborole-1,5(3H)-diol (2.01 g, 73.93%). $^1$H-NMR (400 MHz, DMSO-d$_6$) δ (ppm) 4.85 (s, 2H), 6.95 (d, J=5.4 Hz, 1H), 7.36 (d, J=8.1 Hz, 1H), 8.98 (s, 1H), 10.22 (s, 1H).

Intermediate 3:
4-Fluorobenzo[c][1,2]oxaborole-1,5(3H)-diol

To a solution of diisopropylamine (11 mL) in anhydrous THF (50 mL) was cooled to 0° C. and was added 1.6 M n-butyl lithium/hexanes (47 mL) dropwise under nitrogen atmosphere. The mixture was stirred for 10 min at 0° C. and was then cooled to −78° C. with an acetone dry ice bath. A solution of 4-bromo-2-fluoro-1-methoxybenzene (7.9 mL, 61 mmol) in anhydrous THF (50 mL) was added dropwise. The mixture was then allowed to stir for 30 min at −78° C. DMF (7.5 mL) was added dropwise at −78° C. The reaction was stirred for 1 h at room temperature. Half of the solvent from the solution was removed under reduced pressure and the solution was extracted using ethyl acetate, water (300 mL), and 1 M HCl (65 mL). The organic layer was washed with brine, dried over anhydrous sodium sulfate, and filtered. The solvent was removed under reduced pressure. The residue was crystallized by washing with hexanes. The solid was collected by filtration and dried under reduced pressure to give 6-bromo-2-fluoro-3-methoxybenzaldehyde (8.21 g, 58%).

A solution of 6-bromo-2-fluoro-3-methoxybenzaldehyde (2.0 g, 8.6 mmol) in dichloromethane (43 mL) under a nitrogen balloon was cooled to −78° C. in an acetone dry ice bath. Boron tribromide (1 M in dichloromethane, 9.5 mL) was added dropwise under nitrogen atmosphere. The reaction was stirred at room temperature overnight. The flask was then put on an ice water bath and the excess boron tribromide was quenched with ice chips. Water was added and the solution was extracted with dichloromethane. The aqueous layer was extracted twice with dichloromethane. The organic layers were combined, washed with brine, dried over anhydrous sodium sulfate, and filtered. The solvent was removed under reduced pressure to give 6-bromo-2-fluoro-3-hydroxybenzaldehyde (1.61 g, 86%).

4-Fluorobenzo[c][1,2]oxaborole-1,5(3H)-diol was prepared from 6-bromo-2-fluoro-3-hydroxybenzaldehyde in a similar manner to that of Intermediate 2.

Intermediate 4:
7-Fluorobenzo[c][1,2]oxaborole-1,5(3H)-diol

To a solution of 3-fluoro-5-methylphenol (19.7 g, 156 mmol) and tert-butyldimethylsilyl chloride (25.9 g, 172 mmol) in dichloromethane (250 mL) was added imidazole (12.7 g, 187 mmol) at 0° C., and the mixture was stirred at room temperature for 2 h. The mixture was washed with water and brine and dried on anhydrous sodium sulfate. The solvent was removed in vacuo, and the residue was purified by silica gel chromatography (98:2 hexane/ethyl acetate) to give tert-butyl(3-fluoro-5-methylphenoxy)dimethylsilane (38.6 g, 100%).

To a solution of tert-butyl(3-fluoro-5-methylphenoxy)dimethylsilane (17.0 g, 70.8 mmol) in THF (300 mL) as added N-bromosuccinimide (18.9 g, 106 mmol) at room temperature, and the mixture was stirred for 1 h. The mixture was poured into ethyl acetate and water. The organic layer was washed with brine and dried on anhydrous sodium sulfate. The solvent was removed in vacuo, and the residue was purified by silica gel chromatography (98:2 hexane/ethyl acetate) to give a mixture (ca. 4:1) of (4-bromo-3-fluoro-5-methylphenoxy)(tert-butyl)dimethylsilane and (2-bromo-5-fluoro-3-methylphenoxy)(tert-butyl)dimethylsilane (20.9 g).

To a solution of the mixture obtained above (20.9 g) in carbon tetrachloride (350 mL) were added N-bromosuccinimide (14.0 g, 78.6 mmol) and azobisisobutylonitrile (537 mg, 5 mol %), and the mixture was hated at reflux for 2 h. The mixture was washed with water and brine and dried on anhydrous sodium sulfate. The solvent was removed in vacuo. To a solution of the crude product in methanol (150 mL) was added 1 M NaOH (50 mL) at room temperature, and the mixture was stirred at room temperature for 3 h. The pH was adjusted to 4 with 6 M HCl, and the mixture was extracted with ethyl acetate. The organic layer was washed with brine and dried on anhydrous sodium sulfate. The solvent was removed in vacuo, and the residue was purified by silica gel chromatography (85:15 to 55:45 hexane/ethyl acetate) to give 4-bromo-3-fluoro-5-(hydroxymethyl)phenol (5.64 g, 3 steps 39%).

A mixture of 4-bromo-3-fluoro-5-(hydroxymethyl)phenol (5.64 g, 25.5 mmol), 3,4-dihydro-2H-pyran (5.8 mL, 64 mmol), and dl-camphorsulfonic acid (118 mg, 2 mol %) in dichloromethane (150 mL) was stirred at room temperature for overnight. The mixture was washed with saturated aqueous sodium bicarbonate and brine, and dried on anhydrous sodium sulfate. The solvent was removed in vacuo, and the residue was purified by silica gel chromatography (9:1 hexane/ethyl acetate) to give 2-(4-bromo-3-fluoro-5-((tetrahydro-2H-pyran-2-yloxy)methyl)phenoxy)tetrahydro-2H-pyran (9.14 g, 92%).

To a solution of 2-(4-bromo-3-fluoro-5-((tetrahydro-2H-pyran-2-yloxy)methyl)phenoxy)tetrahydro-2H-pyran (9.13 g, 23.5 mmol) was added n-butyllithium (1.6 M in hexanes, 16 mL, 26 mmol) dropwise at −78° C. After stirring 5 min, triisopropyl borate (8.7 mL, 38 mmol) was added, and the mixture was allowed to warm to room temperature and stirred for 2 h. 6 M HCl (10 mL) was added, and the mixture was stirred for 2 h. Water was added, and the mixture was extracted with ethyl acetate. The organic layer was washed with brine and dried on anhydrous sodium sulfate. The solvent was removed in vacuo, and the residue was purified by silica gel chromatography (1:1 hexane/ethyl acetate) to give 7-fluorobenzo[c][1,2]oxaborole-1,5(3H)-diol (3.54 g, 90%). $^1$H-NMR (400 MHz, DMSO-$d_6$) δ (ppm) 4.86 (s, 2H), 6.40 (dd, J=9.9, 1.5 Hz, 1H), 6.59 (s, 1H), 8.92 (br s, 1H), 10.2 (s, 1H).

Intermediate 5:
7-Methylbenzo[c][1,2]oxaborole-1,5(3H)-diol

A mixture of 4-bromo-3,5-dimethylphenol (4.6 g, 22.88 mmol), 3,4 dihydro-2H-pyran (2.69 mL, 29.7 mmol) in 8.0 mL of $CH_2Cl_2$, and camphorsulfonic acid (106 mg, 4.56 mmol) was stirred at room temperature for 21 h. The reaction mixture was then quenched with equal volumes of 0.2 M NaOH and EtOAc (1:1, 20 mL) before the layers were separated. The water phase was further extracted with equal volume of EtOAc before the organic layers were combined and dried over anhydrous $Na_2SO_4$ and filtered. The solvent was removed under reduced pressure. The residue was purified by silica gel column using Combiflash to give 2-(4-bromo-3,5-dimethylphenoxy)tetrahydro-2H-pyran (23.68 g, 92%).

To a mixture of 2-(4-bromo-3,5-dimethylphenoxy)tetrahydro-2H-pyran (12.58 g, 48.72 mmol) and n-bromosuccinimide (6.94 g, 39.0 mmol) in $CCl_4$ (240 mL) under $N_2$ was added AIBN (400 mg, 2.44 mmol), and the mixture was allowed to stir till no visible solid was in the reaction mixture. The reaction solution was then refluxed for 5.5 h before cooling to room temperature and filtering off solid. The solvent was removed under reduced pressure. The residue was purified by silica gel column using Combiflash to give mixture of 2-(4-bromo-3-(bromomethyl)-5-methylphenoxy)tetrahydro-2H-pyran and 2-(4-bromo-3,5-bis(bromomethyl)phenoxy)tetrahydro-2H-pyran. Both intermediates were not separable and carried on to the next step.

Intermediates 2-(4-bromo-3-(bromomethyl)-5-methylphenoxy)tetrahydro-2H-pyran and 2-(4-bromo-3,5-bis(bromomethyl)phenoxy)tetrahydro-2H-pyran from above reaction was made into a solution with 33 mL of DMF. The reaction mixture was then treated with KOAc (6.95 g, 70.83 mmol) before heating to 60° C. for 2 hr. The reaction was worked-up with equal volumes of water and $CH_2Cl_2$ (1:1, 50 mL). The layers were separated and the water phase was further extracted with equal volume of EtOAc before the organic layers were combined and dried over anhydrous $Na_2SO_4$ and filtered. The solvent was removed under reduced pressure. The residue was purified by silica gel column using Combiflash to give 2-bromo-3-methyl-5-(tetrahydro-2H-pyran-2-yloxy)benzyl acetate (2.24 g, two steps 52%).

A solution of 2-bromo-3-methyl-5-(tetrahydro-2H-pyran-2-yloxy)benzyl acetate (2.2 g, 7.34 mmol), NaOH (440 mg, 11.01 mmol) in MeOH (13 mL) was made allowed and allowed to stir for 4.5 hr before quenching with an equal volume of water. The water phase was further extracted with equal volume of EtOAc before the organic layers were combined and dried over anhydrous $Na_2SO_4$ and filtered. The solvent was removed under reduced pressure. The residue was purified by silica gel column using Combiflash to give (2-bromo-3-methyl-5-(tetrahydro-2H-pyran-2-yloxy)phenyl)methanol phenol (1.78 g, 88%).

To a solution of (2-bromo-3-methyl-5-(tetrahydro-2H-pyran-2-yloxy)phenyl)methanol (2.54 g, 8.43 mmol) and 3,4 dihydro-2H-pyran (0.92 mL, 10.12 mmol) in $CH_2Cl_2$ (8 mL) was added camphorsulfonic acid (40 mg, 0.17 mmol), and the mixture was stirred at room temperature for 21 h. The reaction mixture was then quenched with equal volumes of 0.2 M NaOH and EtOAc (1:1, 20 mL) before the layers were separated. The water phase was further extracted with equal volume of EtOAc before the organic layers were combined and dried over anhydrous $Na_2SO_4$ and filtered. The solvent was removed under reduced pressure. The residue was purified by silica gel column using Combiflash to give 2-(4-bromo-3-methyl-5-((tetrahydro-2H-pyran-2-yloxy)methyl)phenoxy)tetrahydro-2H-pyran (2.93 g, 90%).

A solution of 2-(4-bromo-3-methyl-5-((tetrahydro-2H-pyran-2-yloxy)methyl)phenoxy)tetrahydro-2H-pyran (2.93 g, 7.61 mmol) in anhydrous THF (25 mL) was made before cooling the reaction mixture on a −78° C. bath. Reaction mixture was then treated, dropwise, with n-BuLi (13.08 mL, 20.92 mmol) and allowed to stir for 1.0 h before (i-PrO)$_3$B (77 mL, 25 mmol) was added via syringe. After the addition of (i-PrO)$_3$B, the reaction mixture was warmed to room temperature and allowed to stir for 3 h before addition of 12 mL of 1N HCl. The reaction mixture was allowed to stir 20 hr before addition of EtOAc and water (1:1, 50 mL). The layers were separated and the water phase was further extracted with equal volume of EtOAc before the organic layers were combined and dried over anhydrous $Na_2SO_4$ and filtered. The solvent was removed under reduced pressure. The residue was purified by silica gel column using Combiflash to give 7-methylbenzo[c][1,2]oxaborole-1,5(3H)-diol (415 mg, 33%). $^1$H-NMR (400 MHz, DMSO-$d_6$) δ (ppm) 2.33 (s, 3H), 4.82 (s, 2H), 6.51 (ds, 1H), 6.53 (s, 1H), 8.57 (s, 1H), 9.59 (s, 1H).

Intermediate 6:
3,3-Dideuteriobenzo[c][1,2]oxaborole-1,5(3H)-diol

A mixture of methyl-2-bromo-5-hydroxybenzoate (1.0 g, 4.33 mmol), benzyl bromide (0.62 mL, 5.19 mmol), and $K_2CO_3$ (780 mg, 5.63 mmol) in anhydrous DMF (8 mL) was stirred at room temperature for 21 h under nitrogen atmosphere. The mixture was poured into equal volumes of water and EtOAc (1:1, 20 mL), then the layers were separated. The aqueous layer was further extracted with equal volume of EtOAc before the organic layers were combined and dried over anhydrous $Na_2SO_4$ and filtered. The solvent was removed under reduced pressure. The residue was purified by silica gel column using Combiflash to give methyl 5-(benzyloxy)-2-bromobenzoate (1.39 g, 100%).

A solution of methyl 5-(benzyloxy)-2-bromobenzoate (1.08 g, 3.36 mmol) in anhydrous THF (7 mL) was made before cooling the reaction mixture in a −78° C. bath. Reaction mixture was then treated, dropwise, with $LiAlD_4$ (1 M solution in THF; 3.7 mL, 3.7 mmol) and allowed to stir for 21 h. before the reaction mixture was warmed to room temperature and quenched with 1N HCl to adjust pH 7 before addition of 10 mL of EtOAc. The organic layer was separated and the aqueous layer was further extracted with equal volume of EtOAc before the organic layers were combined and dried over anhydrous $Na_2SO_4$ and filtered. The solvent was removed under reduced pressure. The residue was purified by silica gel column using Combiflash to give (5-(benzyloxy)-2-bromo-3-methylphenyl)methanol-$d_2$ (2.00 g, 86%).

To a solution of (5-(benzyloxy)-2-bromophenyl)methanol-$d_2$ (1.1 g, 3.72 mmol) and 3,4 dihydro-2H-pyran (0.44 mL, 4.84 mmol) in $CH_2Cl_2$ (10 mL) was added camphorsulfonic acid (17 mg, 0.074 mmol), and the mixture was stirred at room temperature for 21 h. The reaction mixture was then quenched with equal volumes of 0.2 M NaOH and EtOAc (1:1, 20 mL) before the layers were separated. The aqueous layer was further extracted with equal volume of EtOAc before the organic layers were combined and dried over anhydrous $Na_2SO_4$ and filtered. The solvent was removed under reduced pressure. The residue was purified by silica gel column using Combiflash to give 2-(5-(benzyloxy)-2-bromo-3-methylbenzyloxy)tetrahydro-2H-pyran-$d_2$ (1.02 g, 79%).

A solution of 2-(5-(benzyloxy)-2-bromo-3-methylbenzyloxy)tetrahydro-2H-pyran-$d_2$ (852 mg, 2.25 mmol) in anhydrous THF (8 mL) was made before cooling the reaction mixture in a −78° C. bath. Reaction mixture was then treated, drop-wise, with n-BuLi (2.02 mL, 3.23 mmol) and allowed to stir for 1.0 hr before (i-PrO)$_3$B (0.77 mL, 3.37 mmol) was added via syringe. After the addition of (i-PrO)$_3$B, the reaction mixture was warmed to room temperature and allowed to stir for 3.0 hr. Cyclization of the bicyclic ring was done in situ by via the addition of 1.9 mL of 6N HCl. The reaction solution was stirred in HCl for 2.0 hr before quenching the reaction with equal volume of concentrated $NH_4Cl_{(aq)}$ and EtOAc (1:1, 15 mL). The organic layer was separated and the aqueous layer was further extracted with equal volume of EtOAc before the organic layers were combined and dried over anhydrous $Na_2SO_4$ and filtered. The solvent was removed under reduced pressure. The residue was purified by silica gel column using Combiflash to give 5-benzyloxy-3,3-dideuterio-1-hydroxy-1,3-dihydrobenzo[c][1,2]oxaborole (1.76 g, 65.3%).

To a solution of 5-benzyloxy-3,3-dideuterio-1-hydroxy-1,3-dihydrobenzo[c][1,2]oxaborole (400 mg, 1.65 mmol) in EtOAc and MeOH (4:1) was added 10% Pd over carbon (40 mg) before the $N_{2(g)}$ was replaced with $H_2(g)$. The reaction mixture was stirred at room temperature for 2 days before it was filtered through a Celite pad and washed with EtOAc. The eluent was collected and the solvent was removed under reduced pressure. The residue was purified by silica gel column using Combiflash to give 1,3-dihydroisobenzofuran-1,5-diol-$d_2$ (132 mg, 53%). $^1$H-NMR (400 MHz, DMSO-$d_6$) δ (ppm) 6.73 (d, J=2.7 Hz, 1H), 7.51 (d, J=6.3 Hz, 1H), 8.84 (s, 1H), 9.73 (s, 1H).

Intermediate 7:
3-Methylbenzo[c][1,2]oxaborole-1,5(3H)-diol

To a solution of 2-bromo-5-hydroxybenzaldehyde (10 g, 49.75 mmol) and 3,4 dihydro-2H-pyran (4.96 mL, 54.7 mmol) in $CH_2Cl_2$ (35 mL) was added camphorsulfonic acid (230 mg, 0.99 mmol), and the mixture was stirred at room temperature for 21 h. The reaction mixture was then quenched with equal volumes of 0.2 M NaOH and EtOAc (1:1, 70 mL) before the layers were separated. The water phase was further extracted with equal volume of EtOAc before the organic layers were combined and dried over anhydrous $Na_2SO_4$ and filtered. The solvent was removed under reduced pressure. The residue was purified by silica gel column using Combiflash to give 2-bromo-5-(tetrahydro-2H-pyran-2-yloxy)benzaldehyde (2.22 g, 20%).

A solution of 2-bromo-5-(tetrahydro-2H-pyran-2-yloxy)benzaldehyde (2.99 g, 7.76 mmol) in anhydrous THF (20 mL) was made before cooling the reaction mixture on a −78° C. bath. Reaction mixture was then treated, dropwise, with methylmagnesium bromide (11.7 mL, 11.7 mmol) and allowed to stir for 1 hr. before the reaction mixture was warmed to room temperature and quenched with equal volume of concentrated $NH_4Cl_{(aq)}$ and EtOAc (1:1, 50 mL). The layers were separated and the aqueous layer was further extracted with equal volume of EtOAc before the organic layers were combined and dried over anhydrous $Na_2SO_4$ and filtered. The solvent was removed under reduced pressure. The residue was purified by silica gel column using Combiflash to give 1-(2-bromo-5-(tetrahydro-2H-pyran-2-yloxy)phenyl)ethanol diol (2.00 g, 85%).

To a solution of 1-(2-bromo-5-(tetrahydro-2H-pyran-2-yloxy)phenyl)ethanol diol (3.55 g, 11.8 mmol) and 3,4 dihydro-2H-pyran (1.28 mL, 14.167 mmol) in 20 mL of $CH_2Cl_2$ (20 mL) was added camphorsulfonic acid (54 mg, 0.24 mmol), and the mixture was stirred at room temperature for 21 h. The reaction mixture was then quenched with equal volumes of 0.2 M NaOH and EtOAc (1:1, 40 mL) before the layers were separated. The aqueous layer was further extracted with equal volume of EtOAc before the organic layers were combined and dried over anhydrous $Na_2SO_4$ and filtered. The solvent was removed under reduced pressure. The residue was purified by silica gel column using Combiflash to give 2-(4-bromo-3-(1-(tetrahydro-2H-pyran-2-yloxy)ethyl)phenoxy)tetrahydro-2H-pyran (4.38 g, 96%).

A solution of 2-(4-bromo-3-(1-(tetrahydro-2H-pyran-2-yloxy)ethyl)phenoxy)tetrahydro-2H-pyran (4.38 g, 11.3 mmol) in anhydrous THF (11 mL) was made before cooling the reaction mixture on a −78° C. bath. Reaction mixture was then treated, drop-wise, with n-BuLi (8.48 mL, 13.6 mmol) and allowed to stir for 1 hr before (i-PrO)$_3$B (3.9 mL, 17 mmol) was added via syringe. After the addition of (i-PrO)$_3$B, the reaction mixture was warmed to room temperature and allowed to stir for 21 hr. Cyclization of the bicyclic ring was done in situ by the addition of 7 mL of 6 M HCl. The mixture was stirred for 3 h before quenching the reaction with equal volume of concentrated $NH_4Cl_{(aq)}$ and EtOAc (1:1, 20 mL). The layers were separated and the aqueous layer was further extracted with equal volume of EtOAc before the organic layers were combined and dried over anhydrous $Na_2SO_4$ and filtered. The solvent was removed under reduced pressure. The residue was purified by silica gel column using Combiflash give 3-methylbenzo[c][1,2]oxaborole-1,5(3H)-diol (1.51 g, 81%). $^1$H-NMR (400 MHz, DMSO-d$_6$) δ (ppm) 1.32 (d, J=5.1 Hz, 3H), 5.03-5.08 (m, 2H), 6.68 (s, 1H), 6.71 (dd, J=6.0, 1.5 Hz, 1H), 7.45 (d, J=6.0 Hz, 1H), 8.57 (s, 1H), 9.71 (s, 1H).

Intermediate 8: 2,5,6-Trichloronicotinamide

Into a 5000-mL 4-necked round-bottom flask, purged and maintained with an inert atmosphere of nitrogen, were placed 1,3-dimethylpyrimidine-2,4(1H,3H)-dione (200 g, 1.43 mol, 1.00 equiv), LiCl (72 g, 1.71 mol, 1.20 equiv), CAN (1566 g, 2.86 mol, 2.00 equiv), acetonitrile (1500 mL) and acetic acid (1500 mL). The resulting solution was stirred for 5.5 h at 80° C. The resulting mixture was cooled and concentrated under vacuum. The residue was diluted with 1500 mL of H$_2$O, then extracted with 3×500 mL of dichloromethane. The organic layers were combined, washed with 200 mL of water, dried and concentrated under vacuum. This resulted in 180 g (65%) of 5-chloro-1,3-dimethylpyrimidine-2,4(1H,3H)-dione as a white solid.

Into a 3000-mL 3-necked round-bottom flask were placed a solution of sodium ethoxide (155 g, 2.28 mol, 4.00 equiv) in ethanol (2000 mL), malonamide (233 g, 2.28 mol, 4.00 equiv) and 5-chloro-1,3-dimethylpyrimidine-2,4(1H,3H)-dione (100 g, 571.43 mmol, 1.00 equiv). The resulting solution was heated to reflux for 20 min. Then it was cooled and concentrated under vacuum. The residue was diluted with 500 mL of H$_2$O, and then adjusted to pH 2 with HCl. The solid was collected by filtration and dried in an oven under reduced pressure. This resulted in 50 g (crude) of 5-chloro-2,6-dihydroxynicotinamide as a white solid.

A mixture of 5-chloro-2,6-dihydroxynicotinamide (50 g, 264.55 mmol, 1.00 equiv) and PCl$_5$ (181.58 g, 873.02 mmol, 3.30 equiv) was stirred for 2.5 h at 140° C. The reaction mixture was then cooled and quenched by the addition of water/ice. The solid was collected by filtration. The crude product was dried and purified with a silica gel column eluting with ethyl acetate/petroleum ether (1:25). This resulted in 30 g of 2,5,6-trichloronicotinonitrile as a white solid.

A solution of 2,5,6-trichloronicotinonitrile (30 g, 144.92 mmol, 1.00 equiv) in sulfuric acid (98%, 162 mL, 1.00 equiv) was stirred for 1 h at 60° C. in an oil bath. The reaction mixture was cooled and then quenched by the addition of water/ice. The solid was collected by filtration and dried in an oven under reduced pressure. This resulted in 26 g of 2,5,6-trichloronicotinamide as a white solid. LC-MS (ES, m/z): 225 [M+H]$^+$. $^1$H-NMR (300 MHz, DMSO-d$_6$) δ (ppm) 9.38 (1H, s), 8.12 (1H, s), 7.95 (1H, s).

Intermediate 9:
5-Cyclopropyl-2,6-dichloronicotinamide

A mixture of compound 1,3-dimethylpyrimidine-2,4(1H,3H)-dione (14 g, 0.1 mol), malonamide (45 g, 0.44 mol) and sodium ethoxide (34 g, 0.4 mol) in EtOH (500 mL) was refluxed for 20 mins. The mixture was cooled to r.t, quenched by water and acidified with 1 M HCl to pH=1-2. The solid was filtered and the filter cake was concentrated in vacuo to afford compound 2,6-dihydroxynicotinamide. (10 g, yield: 65%). $^1$H-NMR (400 MHz, DMSO-d$_6$) δ (ppm) 7.90-7.88 (d, 1H), 5.66-5.64 (d, 1H).

A mixture of compound 2,6-dihydroxynicotinamide (20 g, 0.13 mol) and NIS (29.2 g, 0.13 mol) in DCM (1000 mL) was stirred at r.t for 20 min. The mixture was concentrated in vacuo to afford crude compound 2,6-dihydroxy-5-iodonicotinamide. (50 g) which was used for the next step directly. $^1$H-NMR (400 MHz, DMSO-d$_6$) δ (ppm) 11.04 (bs, 1H), 8.46 (s, 1H), 2.55 (s, 4H).

A mixture of crude compound 2,6-dihydroxy-5-iodonicotinamide (50 g) and PCl$_5$ (135 g, 0.65 mol) in POCl$_3$ (300 mL) was heated to reflux overnight. The mixture was quenched by ice water and extracted by EtOAc, the organic layer was concentrated in vacuo and the residue was purified by column chromatography (Petroleum ether:EtOAc=1: 0~10:1) to afford compound 2,6-dichloro-5-iodonicotinonitrile. (7 g). $^1$H-NMR (400 MHz, DMSO-d$_6$) δ (ppm) 9.04 (s, 1H)

A mixture of compound 2,6-dichloro-5-iodonicotinonitrile (10 g, 33.4 mmol), cyclopropylboronic acid (3.5 g, 40.1 mmol), K$_3$PO$_4$ (28 g, 133.6 mmol), Cy$_3$P (1 g, 3.3 mmol) and Pd(OAc)$_2$ (0.5 g, 2.2 mmol) in Toluene/H$_2$O (300 mL/15 mL) was stirred under refluxing overnight. The mixture was poured into water and extracted with EtOAc. The separated organics was dried, concentrated and purified by column chromatography (Petroleum ether:EtOAc=10:1) to give compound 2,6-dichloro-5-cyclopropylnicotinonitrile (5 g, 70%). $^1$H-NMR (400 MHz, CDCl$_3$) δ (ppm) 7.43 (s, 1H), 2.08 (m, 1H), 1.18 (m, 2H), 0.69 (m, 2H)

To a stirred mixture of compound 2,6-dichloro-5-cyclopropylnicotinonitrile (1.10 g, 5.16 mmol) and K$_2$CO$_3$ (351 mg, 2.58 mmol) in DMSO (10 mL) was added 30% H$_2$O$_2$ (1.90 mL, 15.5 mmol). The mixture was stirred for 2 hrs at rt. Then the mixture was poured into water and extracted with EtOAc. The separated organics was dried, concentrated and purified by column chromatography (Petroleum ether: EtOAc=10:1~1:1) to give compound 2,6-dichloro-5-cyclopropylnicotinamide (5 g, 70%). $^1$H-NMR (400 MHz, CDCl$_3$) δ (ppm) 7.69 (s, 1H), 6.70 (s, 1H), 6.20 (s, 1H), 2.08 (m, 1H), 1.18 (m, 2H), 0.69 (m, 2H).

Intermediate 10:
2,6-dichloro-5-trifluoromethylnicotinamide

KF (1.95 g, 33.5 mmol) and CuI (6.40 g, 33.5 mmol) were weighed in a flask, and the mixture was heated with a gas burner while gently shaking under high vacuum until the content becomes a pale-yellow green. After cooling to room temperature, anhydrous DMF (50 ml), anhydrous THF (20 ml) and trimethyl (trifluoromethyl) silane (4.80 g, 33.5 mmol) were added. The mixture was heated to 50° C., and stirred for 21 hrs. A mixed solution of Compound 2,6-dichloro-5-iodonicotinonitrile (5.00 g, 16.7 mmol) in anhydrous DMF (10 ml) anhydrous THF (20 ml) was added dropwise to the above mentioned reaction mixture at 50° C. and stirred for 30 hrs. The reaction mixture was cooled to room temperature, poured into 12% aqueous ammonia, and the mixture was extracted EtOAc. The combined organic layer was concentrated in vacuo and the residue was purified by flash chromatography on silica to afford Compound 2,6-dichloro-5-(trifluoromethyl)nicotinonitrile. (1.5 g, yield: 37.5%). $^1$H-NMR (400 MHz, DMSO-d$_6$) δ (ppm) 9.12 (s, 1H).

A mixture of 2,6-dichloro-5-(trifluoromethyl)nicotinonitrile (1 g, 4.15 mmol) in concentrated H$_2$SO$_4$ (10 mL) was stirred at 100° C. for 30 mins, quenched by ice water, the solid precipitate was filtered and dried in vacuo to afford Compound 2. (0.5 g, yield: 47%). $^1$H-NMR (400 MHz, DMSO-d$_6$) δ (ppm) 8.45 (s, 1H), 8.12 (bs, 1H), 7.98 (bs, 1H).

Example 1

1a. 5-chloro-6-(1-hydroxy-1,3-dihydrobenzo[c][1,2]oxaborol-5-yloxy)-2-(2-isopropoxyethoxy)nicotinonitrile D230

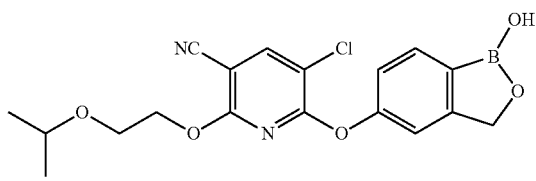 [SMILES: CC(C)OCCOc1nc(Oc2ccc3c(c2)COB3O)c(Cl)cc1C#N]

Into a 50-mL 3-necked round-bottom flask purged and maintained with an inert atmosphere of nitrogen was placed a solution of 2,5,6-trichloronicotinamide (4.00 g, 17.9 mmol, 1.00 equiv) in DMF (5 mL) and 2-isopropoxyethanol (1.857 g, 17.86 mmol, 1.00 equiv). This was followed by the addition of sodium hydride (714 mg, 29.8 mmol, 1.00 equiv) in portions at 0° C. The resulting solution was stirred for 3 h at room temperature, then quenched by the addition of 40 mL of H₂O. The solid was collected by filtration and dried in an oven under reduced pressure. This resulted in 3.4 g (59%) of 5,6-dichloro-2-(2-isopropoxyethoxyl)nicotinamide as a yellow solid.

Into a 100-mL 3-necked round-bottom flask was placed a solution of 5,6-dichloro-2-(2-isopropoxyethoxyl)nicotinamide (3.40 g, 10.5 mmol, 1.00 equiv) in acetonitrile (80 mL) and pyridine (5.52 g, 69.87 mmol, 6.00 equiv), then added POCl₃ (3.2 mL, 3.00 equiv). The resulting solution was stirred for 2 h at 50° C., then it was cooled and quenched by the addition of sodium hydroxide solution (0.2M, 50 mL). The resulting solution was extracted with 3×50 mL of ethyl acetate. The organic layers were combined, dried over anhydrous sodium sulfate and concentrated under vacuum. This resulted in 2.5 g (77%) of 5,6-dichloro-2-(2-isopropoxyethoxy) nicotinonitrile as a light yellow green oil.

Into a 250-mL 3-necked round-bottom flask purged and maintained with an inert atmosphere of nitrogen were placed a solution of 5,6-dichloro-2-(2-isopropoxyethoxy)nicotinonitrile (1.13 g, 4.12 mmol, 1.00 equiv) in DMSO (80 mL), benzo[c][1,2]oxaborole-1,5(3H)-diol (650 mg, 4.33 mmol, 1.00 equiv) and Cs₂CO₃ (1.6 g, 4.91 mmol, 1.20 equiv). The resulting mixture was stirred for 2 h at 40° C., then quenched by the addition of 50 mL of water. The resulting solution was extracted with 3×30 mL of ethyl acetate. The organic layers were combined, washed with 2×50 mL of water, then dried over anhydrous sodium sulfate and concentrated under vacuum. This resulted in 5-chloro-6-(1-hydroxy-1,3-dihydrobenzo[c][1,2]oxaborol-5-yloxy)-2-(2-isopropoxyethoxy) nicotinonitrile (1.3 g, 80%) as a white solid. LC-MS (ES, m/z): 389 [M+H]⁺. ¹H-NMR (300 MHz, DMSO-d₆) δ (ppm) 9.260 (1H, s), 8.596 (1H, s), 7.817-7.791 (1H, d, J=7.8 Hz), 7.337 (1H, s), 7.268-7.235 (1H, m), 5.007 (2H, s), 4.105-4.072 (2H, t), 3.495-3.435 (2H, m), 3.415-3.395 (1H, t), 1.016-0.995 (6H, d, J=6.3 Hz).

1b. 5-Chloro-6-(1-hydroxy-1,3-dihydrobenzo[c][1,2]oxaborol-5-yloxy)-2-(4-oxopentyloxy)nicotinonitrile D231

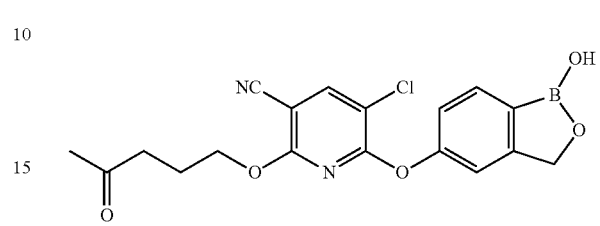

Into a 100-mL 3-necked round-bottom flask purged and maintained with an inert atmosphere of nitrogen were placed a solution of 2,5,6-trichloronicotinamide (4.00 g, 17.9 mmol, 1.00 equiv) in DMF (30 mL) and 5-hydroxypentan-2-one (2.00 g, 19.6 mmol, 1.10 equiv). This was followed by the addition of sodium hydride (470 mg, 19.58 mmol, 1.10 equiv) in portions at 0° C. The resulting solution was stirred overnight at room temperature. The reaction was then quenched by the addition of 40 mL of water. The solid was collected by filtration and dried in an oven under reduced pressure. This resulted in 2.31 g (40%) of 5,6-dichloro-2-(4-oxopentyloxy)nicotinamide as a yellow solid.

Into a 250-mL round-bottom flask was placed a solution of 5,6-dichloro-2-(4-oxopentyloxy)nicotinamide (2 g, 6.90 mmol, 1.00 equiv) in CH₃CN (48 mL), then added POCl₃ (3.144 g, 20.69 mmol, 3.00 equiv) and pyridine (3.27 g, 41.4 mmol, 6.00 equiv). After stirred for 2 h at room temperature, the resulting mixture was diluted with 50 mL of sodium hydroxide solution (0.2 M), then extracted with 2×25 mL of ethyl acetate. The organic layers were combined, washed with 2×20 mL of water, dried and concentrated under vacuum. This resulted in 1.2 g (61%) of 5,6-dichloro-2-(4-oxopentyloxy)nicotinonitrile as a white solid.

Into a 250-mL 3-necked round-bottom flask purged and maintained with an inert atmosphere of nitrogen were placed a solution of 5,6-dichloro-2-(4-oxopentyloxy)nicotinonitrile (1.12 g, 4.12 mmol, 1.00 equiv) in DMSO (50 mL), benzo[c][1,2]oxaborole-1,5(3H)-diol (650 mg, 4.33 mmol, 1.05 equiv) and Cs₂CO₃ (1.60 g, 4.92 mmol, 1.20 equiv). The resulting solution was stirred for 2 h at 40° C., then quenched by the addition of 100 mL of ice water. The resulting solution was extracted with 3×50 mL of ethyl acetate. The organic layers were combined, washed with 2×50 mL of water and 1×50 mL of brine, then dried over Na₂SO₄ and concentrated under vacuum. This resulted in 1.3 g (80%) of 5-chloro-6-(1-hydroxy-1,3-dihydrobenzo[c][1,2]oxaborol-5-yloxy)-2-(4-oxopentyloxy)nicotinonitrile as a white solid. LC-MS (ES, m/z): 387 [M+H]⁺. ¹H-NMR (300 MHz, DMSO-d₆) δ (ppm) 9.28 (1H, s), 8.60 (1H, s), 7.81 (1H, d, J=7.8 Hz), 7.33 (1H, s), 7.25 (1H, d, J=7.8 Hz), 5.02 (2H, s), 4.00 (2H, t), 2.35 (2H, t), 2.05 (3H, s), 1.8-1.6 (2H, m).

1c. 5-Chloro-2-(2,3-dimethoxypropoxy)-6-(1-hydroxy-1,3-dihydrobenzo[c][1,2]oxaborol-5-yloxy)nicotinonitrile D232

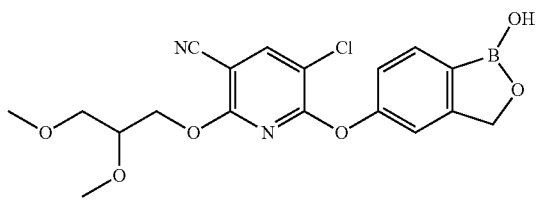 [SMILES: COCC(COc1nc(Oc2ccc3c(c2)COB3O)c(Cl)cc1C#N)OC]

Into a 250-mL round-bottom flask was placed a solution of (2,2-dimethyl-1,3-dioxolan-4-yl)methanol (20.0 g, 151 mmol, 1.00 equiv) in DMF (150 mL), then added sodium hydride (5.45 g, 227 mmol, 1.50 equiv). This was followed by the addition of 1-(bromomethyl)benzene (51.82 g, 303.0 mmol, 2.00 equiv) dropwise with stirring at 0° C. over 15 min. The resulting solution was stirred for 4.5 h at room temperature, then quenched by the addition of 20 ml of ice water. The resulting solution was extracted with 3×50 mL of ethyl acetate. The organic layers were combined, washed with 3×50 mL of H₂O, dried over anhydrous sodium sulfate and concentrated under vacuum. The residue was applied onto a silica gel column and eluted with ethyl acetate/petroleum ether (1:10). This resulted in 18 g (53%) of 4-(benzyloxymethyl)-2,2-dimethyl-1,3-dioxolane as a yellow oil.

Into a 250-mL round-bottom flask was placed a solution of 4-(benzyloxymethyl)-2,2-dimethyl-1,3-dioxolane (18.0 g, 81.0 mmol, 1.00 equiv, 99.9%) in methanol (130 mL). This was followed by the addition of HCl (37%, 10 mL) dropwise with stirring over 3 min. The resulting solution was stirred for 1.5 h at room temperature. Then it was adjusted to pH 7 with sodium carbonate. The methanol was removed under vacuum. The residual solution was extracted with 3×50 mL of dichloromethane. The organic layers were combined, dried over anhydrous sodium sulfate and concentrated under vacuum. This resulted in 10.41 g (68%) of 3-(benzyloxy)propane-1,2-diol as a yellow oil.

Into a 500-mL round-bottom flask was placed a solution of 3-(benzyloxy)propane-1,2-diol (10.41 g, 55.48 mmol, 1.00 equiv, 97%) in DMF (200 mL). This was followed by the addition of sodium hydride (5.49 g, 137 mmol, 2.40 equiv, 60%) in several batches at 0° C. To this was added iodomethane (29.1 g, 206 mmol, 3.60 equiv) dropwise with stirring at 0° C. over 15 min. After stirred for 4.5 h at room temperature, the reaction mixture was quenched by the addition of water/ice. The resulting solution was extracted with 3×50 mL of ethyl acetate. The organic layers were combined, washed with 3×30 mL of H₂O, dried over anhydrous sodium sulfate and concentrated under vacuum. The residue was applied onto a silica gel column and eluted with ethyl acetate/petroleum ether (1:5). This resulted in 11.5 g (85%) of 1-((2,3-dimethoxypropoxy)methyl)benzene as a yellow oil.

A mixture of 1-((2,3-dimethoxypropoxy)methyl)benzene (12.95 g, 52.42 mmol, 1.00 equiv) and Palladium carbon (10%, 6 g) in methanol (100 mL) was stirred for 2 days at 30° C. under a hydrogen atmosphere. The solid was filtered out. The filtrate was concentrated under vacuum. The residue was applied onto a silica gel column and eluted with ethyl acetate/petroleum ether (1:1). This resulted in 5.18 g (78%) of 2,3-dimethoxypropan-1-ol as a light red oil.

Into a 250-mL round-bottom flask purged and maintained with an inert atmosphere of nitrogen were placed a solution of 2,5,6-trichloronicotinamide (8.01 g, 31.8 mmol, 0.90 equiv) in DMF (200 mL) and 2,3-dimethoxypropan-1-ol (4.75 g, 37.2 mmol, 1.00 equiv, 94%). This was followed by the addition of sodium hydride (950 mg, 39.6 mmol, 1.00 equiv) in portions at 0° C. The resulting solution was stirred for 4 h at room temperature. The reaction was then quenched by the addition of water/ice. The reaction mixture was cooled with a water/ice bath. The solid was collected by filtration. This resulted in 4.95 g (41%) of 5,6-dichloro-2-(2,3-dimethoxypropoxy)nicotinamide as a light yellow solid.

Into a 250-mL 3-necked round-bottom flask was placed a solution of 5,6-dichloro-2-(2,3-dimethoxypropoxy)nicotinamide (4.75 g, 14.7 mmol, 1.00 equiv, 95%) in MeCN (105 mL) and pyridine (7.31 g, 92.5 mmol, 6.00 equiv), then added POCl₃ (7.07 g, 46.2 mmol, 3.00 equiv). The resulting solution was stirred for 4 h at room temperature, then quenched by the addition of NaOH solution (0.2M, 250 mL). The resulting solution was extracted with 3×100 mL of ethyl acetate. The organic layers were combined, washed with 3×50 mL of H₂O, dried over anhydrous sodium sulfate and concentrated under vacuum. The residue was applied onto a silica gel column and eluted with ethyl acetate/petroleum ether (1:10). This resulted in 3.8 g (85%) of 5,6-dichloro-2-(2,3-dimethoxypropoxy)nicotinonitrile as a white solid.

Into a 50-mL 3-neck-bottle purged and maintained with an inert atmosphere of nitrogen were placed a solution of 5,6-dichloro-2-(2,3-dimethoxypropoxy) nicotinonitrile (1.40 g, 4.59 mmol, 1.00 equiv, 95%) in DMSO (20 mL), benzo[c][1,2]oxaborole-1,5(3H)-diol (800 mg, 5.07 mmol, 1.10 equiv, 95%) and Cs₂CO₃ (1.88 g, 5.78 mmol, 1.20 equiv). The resulting solution was stirred for 2 h at 50° C. in an oil bath. The reaction mixture was then cooled and quenched by the addition of 20 mL of water. The resulting solution was extracted with 3×20 mL of ethyl acetate. The organic layers were combined, dried and concentrated under vacuum. The residue was applied onto a silica gel column and eluted with EtOAc/petroleum ether (1:5). This resulted in 1.09 g (57%) of 5-chloro-2-(2,3-dimethoxypropoxy)-6-(1-hydroxy-1,3-dihydrobenzo[c][1,2]oxaborol-5-yloxy) nicotinonitrile as a white solid. LC-MS (ES, m/z): 405 [M+H]⁺. ¹H-NMR (300 MHz, DMSO-d₆) δ (ppm) 9.27 (1H, m); 8.61 (1H, m); 7.82 (1H, d, J=8.1 Hz); 7.34 (1H, m); 7.26 (1H, m); 5.00 (2H, s); 4.12-4.17 (1H, m); 3.97-4.03 (1H, m); 3.25-3.30 (1H, m); 3.17 (6H, s).

1d. 5-Chloro-6-(1-hydroxy-1,3-dihydrobenzo[c][1,2]oxaborol-5-yloxy)-2-(3-(1-hydroxycyclopropyl)propoxy)nicotinonitrile D233; and 1e. 5-chloro-6-(1-hydroxy-1,3-dihydrobenzo[c][1,2]oxaborol-5-yloxy)-2-(4-oxohexyloxy)nicotinonitrile D234

D233

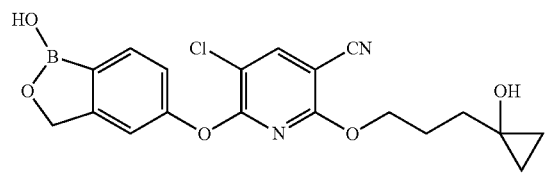

-continued

D234

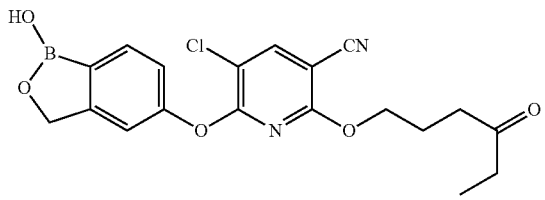

To a mixture of dihydrofuran-2(3H)-one (15.0 g, 174 mmol) and titanium tetraisopropoxide (52 ml, 174 mmol) in anhydrous THF (500 mL) was added dropwise a solution of ethylmagnesium bromide (180 mL, 480 mmol) in ether at 15° C. and the mixture was stirred at the same temperature for 1 h. The reaction was quenched with 100 mL of water and the product was extracted with EtOAc three times. The combined organic layers were washed with brine, dried over $Na_2SO_4$, concentrated and purified by silica gel chromatography (Petroleum ether: EtOAc=1:0 to 5:1) to give colorless oil 1-(3-hydroxypropyl)cyclopropanol (13.7 g, 68%). $^1$H-NMR (400 MHz, CDCl$_3$) δ (ppm) 3.68 (t, 2H, J=6.0 Hz), 2.80 (s, 2H), 1.72 (m, 2H), 1.60 (m, 2H), 0.78 (m, 2H), 0.69 (m, 2H).

A mixture of compound 2,5,6-trichloronicotinamide (0.6 g, 2.7 mmol), 1-(3-hydroxypropyl)cyclopropanol (370 mg, 3.2 mmol) and tert-BuOK (363 mg, 3.2 mmol) in DMF was stirred at room temperature overnight and the reaction mixture was then poured into cold water, the mixture was extracted twice with ethyl acetate, the combined organic layers were washed with brine twice, dried over $Na_2SO_4$ and concentrated, the residue was purified by column chromatography (silica gel, Petroleum ether: EtOAc=1:0 to 5:1) to give the 5,6-dichloro-2-(3-(1-hydroxycyclopropyl)propoxy) nicotinamide (0.72 g, 73%). $^1$H-NMR (400 MHz, DMSO-d$_6$) δ (ppm) 8.65 (s, 1H), 8.29 (s, 1H), 8.03 (s, 1H), 5.48 (s, 1H), 4.82 (t, 2H, J=6.4 Hz), 2.36 (m, 2H), 1.97 (m, 2H), 0.94 (t, 2H), 0.73 (t, 2H).

To a mixture of compound 5,6-dichloro-2-(3-(1-hydroxycyclopropyl) propoxy)nicotinamide (0.72 g, 2.4 mmol) and Et$_3$N (1.5 g, 14.4 mmol) in DCM was added trifluoroacetic anhydride on an ice-water bath and the resulting mixture was stirred at room temperature overnight. The mixture was then poured into cold water, the organic phase was separated and the aqueous phase was further extracted twice with dichloromethane. The combined organic layers were washed with brine twice, dried over $Na_2SO_4$ and concentrated to give crude 1-(3-(3-carbamoyl-5,6-dichloropyridin-2-yloxy) propyl)cyclopropyl 2,2,2-trifluoroacetate.

To the crude 1-(3-(3-carbamoyl-5,6-dichloropyridin-2-yloxy)propyl) cyclopropyl 2,2,2-trifluoroacetate in MeCN (20 mL) was added POCl$_3$ (700 mg, 4.6 mmol) and pyridine (720 mg, 9 mmol) at room temperature. After being stirred for 2 h at room temperature, the mixture was diluted with 30 mL of sodium hydroxide solution, then extracted with ethyl acetate (2×50 mL), the combined organic layers were washed with brine twice, dried over $Na_2SO_4$, concentrated and purified by column chromatography (silica gel, Petroleum ether: EtOAc=1:0 to 10:1) to give the product 1-(3-(5,6-dichloro-3-cyanopyridin-2-yloxy)propyl)cyclopropyl 2,2,2-trifluoroacetate (0.87 g, 97%). $^1$H-NMR (400 MHz, DMSO-d$_6$) δ (ppm) 8.68 (s, 1H), 4.39 (t, 2H, J=6.4 Hz), 1.90 (m, 4H), 1.05 (t, 2H, J=6.8 Hz), 0.84 (t, 2H, J=6.8 Hz).

To a mixture of compound 1-(3-(5,6-dichloro-3-cyanopyridin-2-yloxy)propyl)cyclopropyl 2,2,2-trifluoroacetate (0.87 g, 2.3 mmol) and benzo[c][1,2]oxaborole-1,5(3H)-diol (0.36 g, 2.4 mmol) in DMSO was added Cs$_2$CO$_3$ (0.89 g, 2.7 mmol) at room temperature and the resulting mixture was stirred at 40° C. overnight. The mixture was then poured into cold water, diluted with EtOAc, the organic phase was separated and the aqueous phase was further extracted twice with EtOAc. The combined organic layers were washed with brine twice, dried over $Na_2SO_4$ and concentrated, the residue was purified by Prep-HPLC (column: Luna 300×50.0 mm, 10µ; liquid phase: [A-H$_2$O; B—CH$_3$CN] B %: 35%-62%, 23 min) to give the product D233 (105 mg) and D234 (112 mg), total yield 24%.

D233: $^1$H-NMR (400 MHz, DMSO-d$_6$) δ (ppm) 9.24 (s, 1H), 8.58 (s, 1H), 7.77 (d, 1H, J=8.0 Hz), 7.32 (s, 1H), 7.24 (d, 1H, J=8.0 Hz), 5.02 (s, 2H), 4.95 (s, 1H), 4.07 (t, 2H, J=7.2 Hz), 1.70 (m, 2H), 1.40 (t, 2H, J=7.2 Hz), 0.46 (t, 2H, J=4.8 Hz), 0.17 (t, 2H, J=4.8 Hz).

D234: $^1$H-NMR (400 MHz, DMSO-d$_6$) δ (ppm) 9.26 (s, 1H), 8.57 (s, 1H), 7.78 (d, 1H, J=8.0 Hz), 7.31 (s, 1H), 7.23 (d, 1H, J=8.0 Hz), 4.99 (s, 2H), 3.97 (t, 2H, J=6.4 Hz), 2.32 (m, 4H), 1.69 (q, 2H, J=7.2 Hz), 0.88 (t, 2H, J=7.2 Hz).

1f. 5-Chloro-6-(1-hydroxy-1,3-dihydrobenzo[c][1,2] oxaborol-5-yloxy)-2-(3-(1-hydroxycyclopropyl) propoxy)nicotinonitrile D235

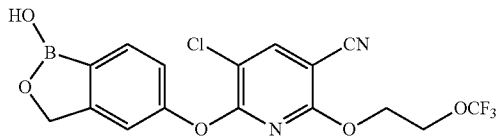 [SMILES: N#Cc1cc(Cl)c(Oc2ccc3c(c2)COB3O)nc1OCCOC(F)(F)F]

To a mixture of compound 2-(trifluoromethoxy)ethanol (9.5 mmol) in DMF/DME (20/50 mL) was added 2,5,6-trichloronicotinamide (2.1 g, 9.5 mmol) and tert-BuOK (1.30 g, 11.4 mmol) and the reaction mixture was stirred at room temperature overnight. The mixture was poured into 100 mL of cold water, diluted with 100 mL of EtOAc, the organic layer was separated and the aqueous phase was further extracted twice with EtOAc, the combined organic layers were washed with brine twice, dried over Na2SO4 and concentrated, the residue was purified by silica gel chromatography (Petroleum ether: EtOAc=1:0 to 5:1) to give 5,6-dichloro-2-(2-(trifluoromethoxy)ethoxy)nicotinamide (0.24 g, 8%). $^1$H-NMR (400 MHz, DMSO-d$_6$) δ (ppm) 8.31 (s, 1H), 7.97 (s, 1H), 7.59 (s, 1H), 4.62 (t, 2H, J=4.0 Hz), 4.51 (t, 2H, J=4.0 Hz).

To a mixture of 5,6-dichloro-2-(2-(trifluoromethoxy) ethoxy)nicotinamide (240 mg, 0.75 mmol) in MeCN (10 mL) were added POCl$_3$ (350 mg, 2.3 mmol) and pyridine (360 mg, 4.5 mmol) at room temperature. After being stirred for 2 hours at room temperature, the mixture was diluted with 10 mL of sodium hydroxide solution, then extracted with ethyl acetate (2×50 mL), the combined organic layers were washed with brine twice, dried over $Na_2SO_4$ and concentrated to give 5,6-dichloro-2-(2-(trifluoromethoxy) ethoxy)nicotinonitrile (0.20 g, 88%).

To a mixture of 5,6-dichloro-2-(2-(trifluoromethoxy) ethoxy)nicotinonitrile (0.20 g, 0.66 mmol) and benzo[c][1, 2]oxaborole-1,5(3H)-diol (0.11 g, 0.70 mmol) in DMSO was added Cs$_2$CO$_3$ (0.26 g, 0.80 mmol) at room temperature and the resulting mixture was stirred at 40° C. overnight. The mixture was then poured into cold water, diluted with EtOAc, the organic phase was separated and the aqueous phase was further extracted twice with EtOAc. The combined organic layers were washed with brine twice, dried over $Na_2SO_4$ and concentrated, the residue was purified by Prep-HPLC (column: Luna 300×50.0 mm, 10µ; liquid phase: [A-$H_2O$+0.025% TFA; B—$CH_3CN$] B %: 40%-70%, 25 min). The product was acidified with 1 N aq. HCl (3 drops) and freeze-dried to give 5-chloro-6-(1-hydroxy-1,3-dihydrobenzo[c][1,2]oxaborol-5-yloxy)-2-(3-(1-hydroxycyclopropyl)propoxy) nicotinonitrile (90 mg, yield: 66%). $^1$H-NMR (400 MHz, DMSO-$d_6$) δ (ppm) 8.61 (s, 1H), 7.77 (d, 1H, J=8.0 Hz), 7.31 (s, 1H), 7.23 (d, 1H, J=8.0 Hz), 4.99 (s, 2H), 4.22 (m, 4H).

1g. -Cyclopropyl-6-(1-hydroxy-1,3-dihydrobenzo[c][1,2]oxaborol-5-yloxy)-2-(4-oxopentyloxy)nicotinonitrile D236

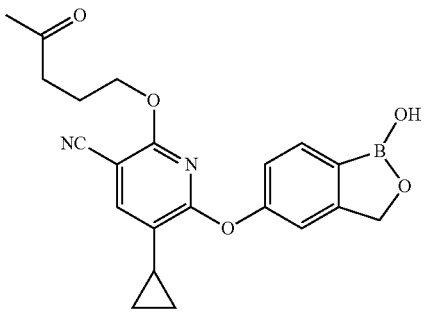 [SMILES: CC(=O)CCCOc1nc(Oc2ccc3c(c2)COB3O)c(C2CC2)cc1C#N]

To a mixture of 2,6-dichloro-5-cyclopropylnicotinamide (2.00 g, 8.66 mmol) and 5-hydroxypentan-2-one (883 mg, 8.66 mmol) in DMF (30 mL) was added and NaH (416 mg, 10.4 mmol) in portions at 0° C. The mixture was stirred at r.t. overnight, quenched by water, extracted by EtOAc. The separated organics was dried, concentrated and purified by column chromatography (Petroleum ether:EtOAc=10:1~1:1) to give 6-chloro-5-cyclopropyl-2-(4-oxopentyloxy)nicotinamide (500 mg, 19.4%).

To a solution of 6-chloro-5-cyclopropyl-2-(4-oxopentyloxy)nicotinamide (298 mg, 1 mmol) in acetonitrile (20 mL) was added $POCl_3$ (460 mg, 3 mmol) and pyridine (474 mg, 6 mmol). After stirred at r.t for 2 hrs, the mixture was poured into aq. $NaHCO_3$, extracted with EtOAc. The separated organics was dried and concentrated in vacuo to afford 6-chloro-5-cyclopropyl-2-(4-oxopentyloxy) nicotinonitrile. (300 mg).

A mixture of 6-chloro-5-cyclopropyl-2-(4-oxopentyloxy) nicotinonitrile (360 mg, 1.29 mmol), compound benzo[c][1,2]oxaborole-1,5(3H)-diol (232 mg, 1.55 mmol) and $Cs_2CO_3$ (505 mg, 1.55 mmol) in DMSO (20 mL) was stirred at 40° C. overnight. The mixture was diluted by water, extracted by EtOAc, the separated organic layer was concentrated in vacuo and the residue was purified by column chromatography (Petroleum ether:EtOAc=10:1~3:1) to afford 5-cyclopropyl-6-(1-hydroxy-1,3-dihydrobenzo[c][1,2]oxaborol-5-yloxy)-2-(4-oxopentyloxy) nicotinonitrile. (200 mg, 40%). $^1$H-NMR (400 MHz, DMSO-$d_6$) δ (ppm) 9.20 (s, 1H), 7.86 (s, 1H), 7.75 (d, J=8.0, 1H), 7.24 (d, J=2.0, 1H), 7.16 (dd, J=8.0, 2.0, 1H), 4.97 (s, 2H), 3.94 (t, J=7.8, 2H), 3.29 (t, J=7.8, 2H), 2.02 (m, 4H), 1.65 (t, J=7.8, 2H), 0.92 (m, 2H), 0.77 (m, 2H).

1h. 5-Cyclopropyl-6-(1-hydroxy-1,3-dihydrobenzo[c][1,2]oxaborol-5-yloxy)-2-(4-oxopentyloxy)nicotinonitrile D237

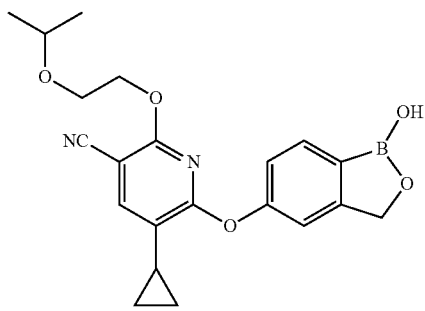 [SMILES: CC(C)OCCOc1nc(Oc2ccc3c(c2)COB3O)c(C2CC2)cc1C#N]

To a mixture of 2,6-dichloro-5-cyclopropylnicotinamide (450 mg, 1.95 mmol) and 2-isopropoxyethanol (223 mg, 2.14 mmol) in DMF (30 mL) was added and NaH (86 mg, 2.14 mmol) in portions at 0° C. The mixture was stirred at r.t overnight, quenched by water, extracted by EtOAc. The separated organics was dried, concentrated and purified by column chromatography (Petroleum ether:EtOAc=10:1~1:1) to give 6-chloro-5-cyclopropyl-2-(2-isopropoxyethoxyl) nicotinamide (180 mg, 31%). $^1$H-NMR (400 MHz, $CDCl_3$) δ (ppm) 8.08 (s, 1H), 7.93 (s, 1H), 5.85 (s, 1H), 4.60 (m, 2H), 3.78 (m, 2H), 3.66 (m, 1H), 2.05 (m, 1H), 1.18 (d, J=6.0, 6H), 1.02 (m, 2H), 0.71 (m, 2H).

To a solution of 6-chloro-5-cyclopropyl-2-(2-isopropoxyethoxyl) nicotinamide (180 mg, 0.6 mmol) in acetonitrile (20 mL) was added $POCl_3$ (276 mg, 1.8 mmol) and pyridine (285 mg, 3.6 mmol). After stirred at r.t for 2 hrs, the mixture was poured into aq. $NaHCO_3$, extracted with EtOAc. The separated organics was dried and concentrated in vacuo to afford crude 6-chloro-5-cyclopropyl-2-(2-isopropoxyethoxy)nicotinonitrile (150 mg).

A mixture of 6-chloro-5-cyclopropyl-2-(2-isopropoxyethoxy) nicotinonitrile (150 mg, 0.53 mmol), benzo[c][1,2]oxaborole-1,5(3H)-diol (84 mg, 0.56 mmol) and $Cs_2CO_3$ (209 mg, 0.64 mmol) in DMSO (20 mL) was stirred at 40° C. overnight. The mixture was diluted by water, extracted by EtOAc, the separated organic layer was concentrated in vacuo and the residue was purified by column chromatography (Petroleum ether:EtOAc=10:1~1:1) to afford 5-cyclopropyl-6-(1-hydroxy-1,3-dihydrobenzo[c][1,2]oxaborol-5-yloxy)-2-(2-isopropoxyethoxy) nicotinonitrile. (120 mg, 57%). $^1$H-NMR (400 MHz, DMSO-$d_6$) δ (ppm) 9.18 (s, 1H), 7.86 (s, 1H), 7.76 (d, J=8.0, 1H), 7.24 (d, J=2.0, 1H), 7.16 (dd, J=8.0, 2.0, 1H), 4.96 (s, 2H), 4.04 (m, 2H), 3.42 (m, 2H), 2.05 (m, 2H), 0.97 (d, J=6.0, 6H), 0.92 (m, 2H), 0.77 (m, 2H).

1h. 6-(1-Hydroxy-1,3-dihydrobenzo[c][1,2]oxaborol-5-yloxy)-2-(2-isopropoxyethoxy)-5-(trifluoromethyl)nicotinonitrile D238

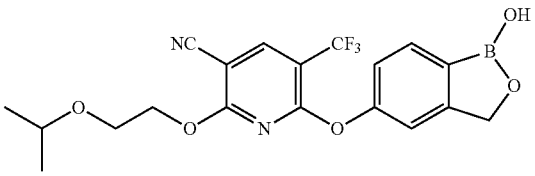 [SMILES: CC(C)OCCOc1nc(Oc2ccc3c(c2)COB3O)c(C(F)(F)F)cc1C#N]

A mixture of 2,6-dichloro-5-(trifluoromethyl)nicotinamide (0.35 g, 1.35 mmol) and 2-isopropoxyethanol (0.14 g, 1.35 mol) in DMF (20 mL) was added sodium hydride (59 mg, 1.48 mmol) in portions at 0° C. The mixture was stirred at r.t for 2 hrs, quenched by water, extracted by EtOAc and the organic layer was concentrated in vacuo to afford 6-chloro-2-(2-isopropoxyethoxy)-5-(trifluoromethyl) nicotinamide (0.2 g, 45.4%). $^1$H-NMR (400 MHz, DMSO-$d_6$) δ (ppm) 8.45 (s, 1H), 8.05 (bs, 1H), 7.63 (bs, 1H), 4.54-4.52 (m, 2H), 3.75-3.72 (m, 2H), 3.64-3.58 (m, 1H), 1.07-1.06 (d, 6H).

A mixture of 6-chloro-2-(2-isopropoxyethoxy)-5-(trifluoromethyl) nicotinamide (0.2 g, 0.61 mmol) in acetonitrile (20 mL) was added POCl$_3$ (0.28 g, 1.84 mmol) and pyridine (0.29 g, 3.68 mmol). After stirred at r.t for 1 hr, the mixture was diluted by 0.2 M NaOH solution, extracted by EtOAc and the organic layer was concentrated in vacuo to afford 6-chloro-2-(2-isopropoxyethoxy)-5-(trifluoromethyl)nicotinonitrile. (180 mg, 95.7%). $^1$H-NMR (400 MHz, CDCl$_3$) δ (ppm) 8.14 (s, 1H), 4.64-4.61 (t, 2H), 3.83-3.81 (t, 2H), 3.72-3.66 (m, 1H), 1.19-1.17 (d, 6H).

A mixture of 6-chloro-2-(2-isopropoxyethoxy)-5-(trifluoromethyl) nicotinonitrile (180 mg, 0.58 mmol), benzo[c][1,2]oxaborole-1,5(3H)-diol (87 mg, 0.58 mmol) and Cs$_2$CO$_3$ (228 mg, 0.7 mmol) in DMSO (20 mL) was stirred at 40° C. for 1 hr, the mixture was diluted by water, extracted by EtOAc, the organic layer was concentrated in vacuo and the residue was purified by prep. HPLC (column: Gemini 100× 21.2 mm, 5μ; liquid phase: [A-H$_2$O; B—CH$_3$CN+0.4% NH$_4$OH] B %: 45%-65%, 15 min) to afford 6-(1-hydroxy-1,3-dihydrobenzo[c][1,2]oxaborol-5-yloxy)-2-(2-isopropoxyethoxy)-5-(trifluoromethyl)nicotinonitrile (170 mg, 69%). 1H-NMR (400 MHz, DMSO-$d_6$) δ (ppm) 9.24 (s, 1H), 8.73 (s, 1H), 7.79-7.77 (d, 1H), 7.31-7.31 (d, 1H), 7.23-7.21 (q, 1H), 4.97 (s, 2H), 4.14-4.11 (t, 2H), 3.47-3.45 (t, 2H), 3.43-3.37 (m, 1H), 0.98-0.96 (d, 6H).

1i. 5-Chloro-2-(2-cyclopropoxyethoxy)-6-(1-hydroxy-1,3-dihydrobenzo[c][1,2]oxaborol-5-yloxy)nicotinonitrile D239

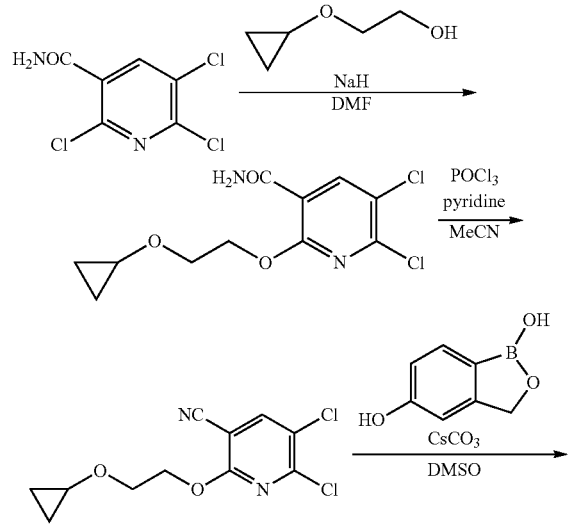

This compound was prepared from 2,5,6-trichloronicotinamide, 2-cyclopropoxyethanol, and benzo[c][1,2]oxaborole-1,5(3H)-diol in a similar manner to that of D230. $^1$H-NMR (400 MHz, DMSO-$d_6$) δ (ppm) 0.35-0.4 (m, 4H), 3.2-3.32 (m, 1H), 3.55-3.62 (m, 3H), 4.1-4.12 (m, 2H), 5.0 (s, 2H), 7.24 (dd, J=6.0, 1.4 Hz, 1H), 7.33 (s, 1H), 7.8 (d, J=6.7 Hz, 1H), 8.6 (s, 1H), 9.26 (s, 1H).

1j. 5-Chloro-6-(1-hydroxy-1,3-dihydrobenzo[c][1,2]oxaborol-5-yloxy)-2-(tetrahydro-2H-pyran-4-yloxy)nicotinonitrile D240

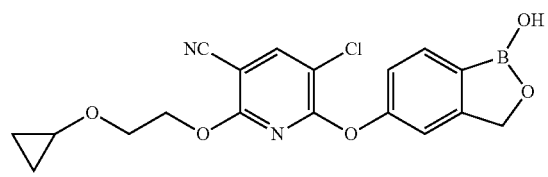

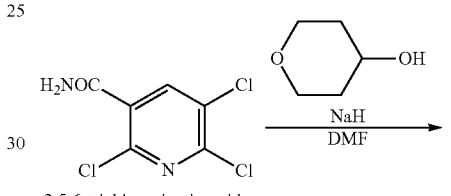

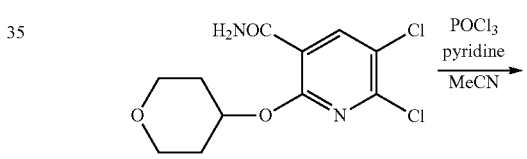

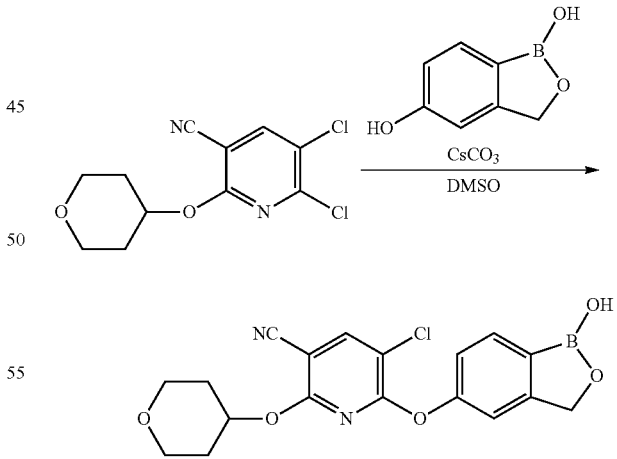

This compound was prepared from 2,5,6-trichloronicotinamide, tetrahydro-2H-pyran-4-ol, and benzo[c][1,2]oxaborole-1,5(3H)-diol in a similar manner to that of D230. $^1$H-NMR (400 MHz, DMSO-$d_6$) δ (ppm) 2.49-2.5 (m, 2H), 3.06-3.12 (m, 2H), 3.06-3.2 (m, 2H), 3.68-3.73 (m, 2H), 4.51-4.54 (m, 1H), 5.0 (s, 2H), 7.23 (dd, J=6.0, 1.7 Hz, 1H), 7.32 (s, 1H), 7.8 (d, J=6.0 Hz, 1H), 8.57 (s, 1H), 9.25 (s, 1H).

1k 6-(1-hydroxy-1,3-dihydrobenzo[c][1,2]oxaborol-5-yloxy)-2-(2-isopropoxyethoxy)-4-(trifluoromethyl)nicotinonitrile D241

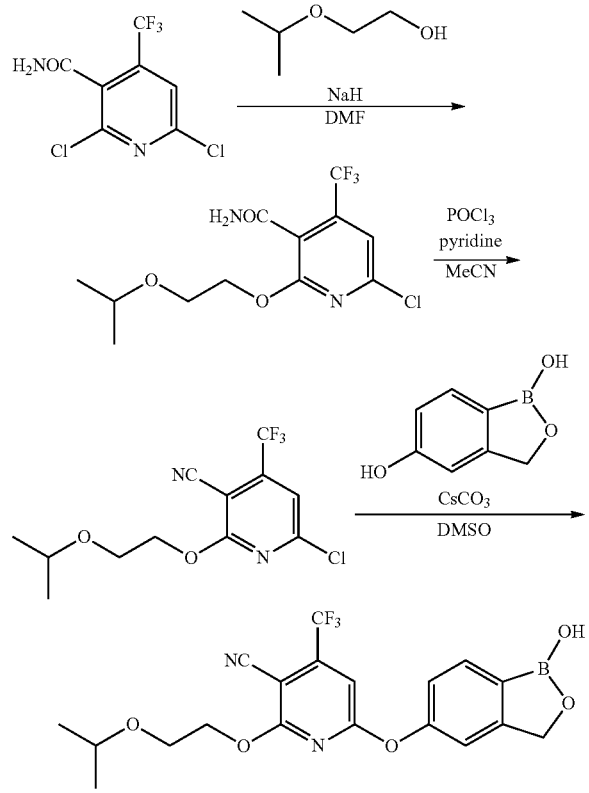

This compound was prepared from 2,6-dichloro-4-(trifluoromethyl) nicotinamide (obtained from Peakdale), 2-isopropoxyethanol, and benzo[c][1,2]oxaborole-1,5(3H)-diol in a similar manner to that of D230. $^1$H-NMR (400 MHz, DMSO-d$_6$) δ (ppm) 1.72-1.75 (m, 2H), 2.05 (s, 3H), 2.38 (t, J=5.4 Hz, 2H), 4.03 (t, J=5.4 Hz, 2H), 5.03 (s, 2H), 7.13 (d, J=7.8 Hz, 1H), 7.2 (s, 1H), 8.61 (s, 1H), 9.36 (s, 1H).

1L. 6-(1-Hydroxy-1,3-dihydrobenzo[c][1,2]oxaborol-5-yloxy)-2-(4-oxopentyloxy)-4-(trifluoromethyl)nicotinonitrile D242

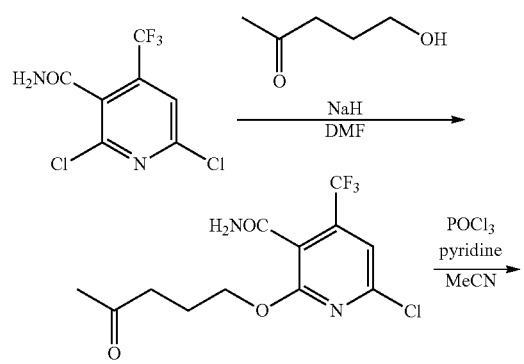

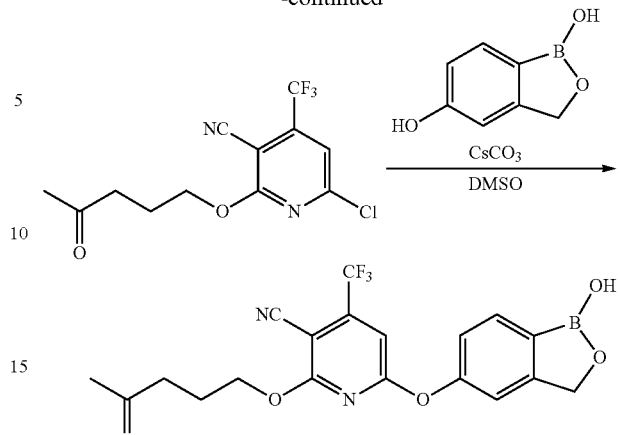

This compound was prepared from 2,6-dichloro-4-(trifluoromethyl) nicotinamide, 5-hydroxypentan-2-one, and benzo[c][1,2]oxaborole-1,5(3H)-diol in a similar manner to that of D230. $^1$H-NMR (400 MHz, DMSO-d$_6$) δ (ppm) 1.85-1.88 (m, 2H), 1.93 (s, 3H), 2.95-2.99 (t, J=4.9 Hz, 2H), 3.91-3.94 (t, J=5.4 Hz, 2H), 5.01 (s, 2H), 7.21 (dd, J=6.0, 1.5 Hz, 1H), 7.3 (s, 1H), 7.64 (s, 1H), 7.81 (d, J=6.0 Hz, 1H), 9.26 (s, 1H).

1m. 2-(1-Hydroxy-1,3-dihydrobenzo[c][1,2]oxaborol-5-yloxy)-6-(2-isopropoxyethoxyl)pyridine-3,5-dicarbonitrile D243

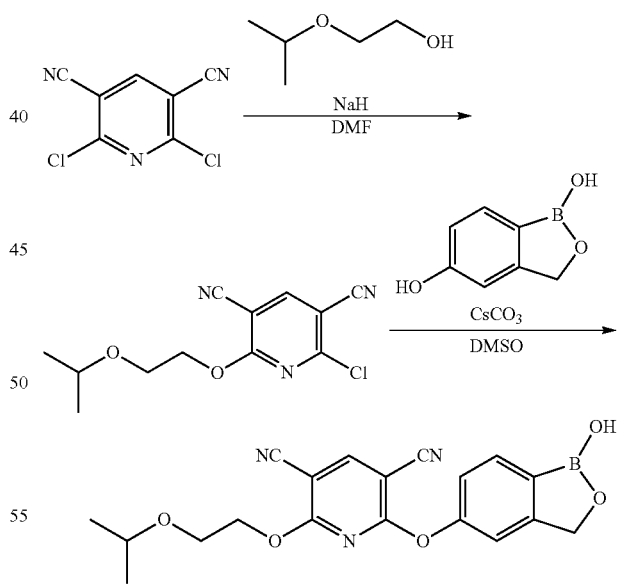

This compound was prepared from 2,6-dichloropyridine-3,5-dicarbonitrile (obtained from Aces Pharma), 2-isopropoxyethanol, and benzo[c][1,2]oxaborole-1,5(3H)-diol in a similar manner to that of D230. $^1$H-NMR (400 MHz, DMSO-d$_6$) δ (ppm) 1.0 (d, J=4.5 Hz, 6H), 3.42-3.45 (m, 1H), 3.49-3.51 (m, 2H), 4.14-4.16 (m, 2H), 5.01 (s, 2H), 7.3 (d, J=6.3 Hz, 1H), 7.39 (s, 1H), 7.81 (d, J=6.6 Hz, 1H), 8.94 (s, 1H), 9.28 (s, 1H).

1n. 2-(1-Hydroxy-1,3-dihydrobenzo[c][1,2]oxaborol-5-yloxy)-6-(4-oxopentyloxy)pyridine-3,5-dicarbonitrile D244

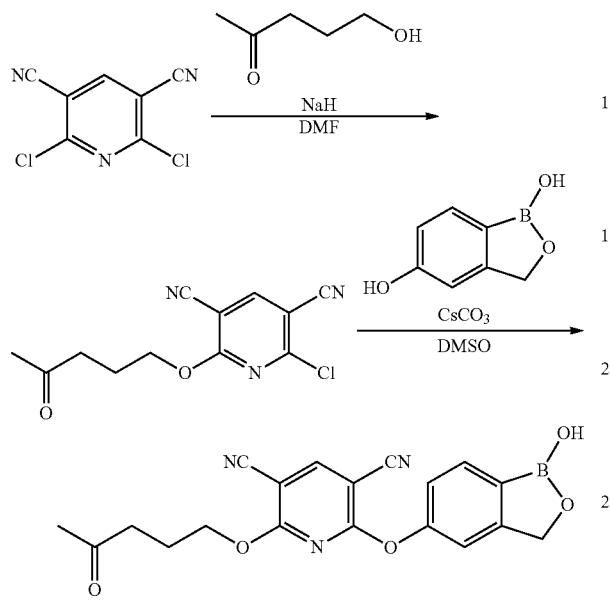

This compound was prepared from 2,6-dichloropyridine-3,5-dicarbonitrile, 5-hydroxypentan-2-one, and benzo[c][1,2]oxaborole-1,5(3H)-diol in a similar manner to that of D230. $^1$H-NMR (400 MHz, DMSO-$d_6$) δ (ppm) 1.7-1.73 (m, 2H), 2.04 (s, 3H), 2.35 (t, J=5.4 Hz, 2H), 4.06 (t, J=5.1 Hz, 2H), 5.02 (s, 2H), 7.29 (dd, J=6.3, 1.5 Hz, 1H), 7.39 (d, J=1.2 Hz, 1H), 7.81 (d, J=6.0 Hz, 1H), 8.94 (s, 1H), 9.3 (s, 1H).

1o. 5-Chloro-6-(1-hydroxy-7-methyl-1,3-dihydrobenzo[c][1,2]oxaborol-5-yloxy)-2-(2-isopropoxyethoxy)nicotinonitrile D245

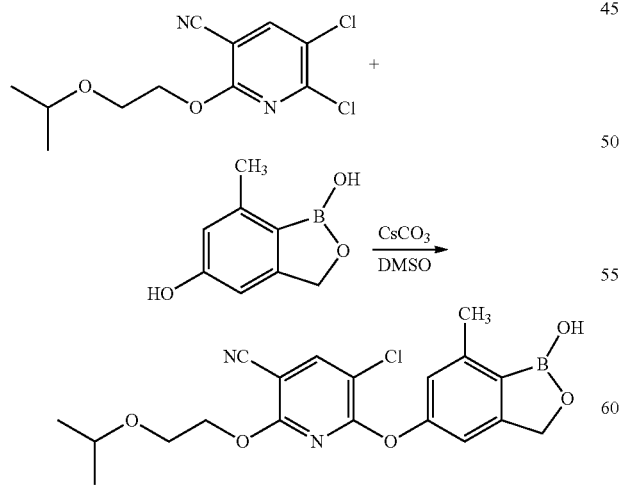

This compound was prepared from 5,6-dichloro-2-(2-isopropoxyethoxy)nicotinonitrile and 7-methylbenzo[c][1,2]oxaborole-1,5(3H)-diol in a similar manner to that of D230. $^1$H-NMR (400 MHz, DMSO-$d_6$) δ (ppm) 1.02 (d, J=4.8 Hz, 6H), 2.44 (s, 3H), 3.45-3.56 (m, 3H), 4.21-4.23 (m, 2H), 5.02 (s, 2H), 7.03 (s, 1H), 7.11 (s, 1H), 8.58 (s, 1H), 10.0 (s, 1H).

1p. 5-Chloro-6-(1-hydroxy-7-methyl-1,3-dihydrobenzo[c][1,2]oxaborol-5-yloxy)-2-(4-oxopentyloxy)nicotinonitrile D246

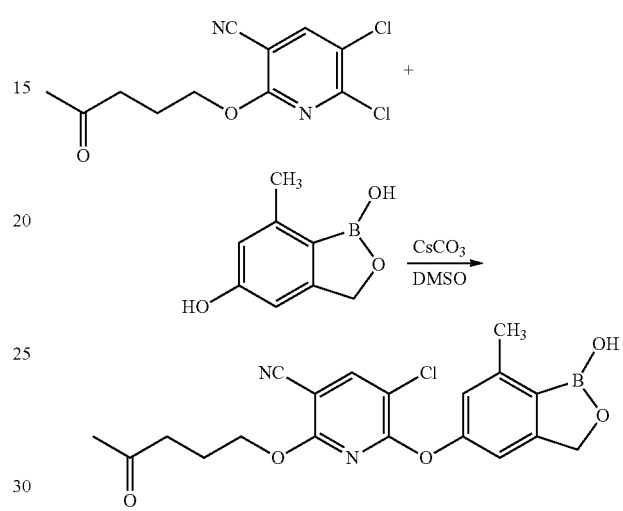

This compound was prepared from 5,6-dichloro-2-(4-oxopentyloxy)nicotinonitrile and 7-methylbenzo[c][1,2]oxaborole-1,5(3H)-diol in a similar manner to that of D230. $^1$H-NMR (400 MHz, DMSO-$d_6$) δ (ppm) 1.67-1.71 (m, 2H), 2.02 (s, 3H), 2.33 (t, J=5.4 Hz, 2H), 2.44 (s, 3H), 4.01 (t, J=5.3 Hz, 2H), 4.95 (s, 2H), 7.0 (s, 1H), 7.07 (s, 1H), 8.56 (s, 1H), 9.0 (s, 1H).

1q. 5-Chloro-6-(7-fluoro-1-hydroxy-1,3-dihydrobenzo[c][1,2]oxaborol-5-yloxy)-2-(2-isopropoxyethoxy)nicotinonitrile D247

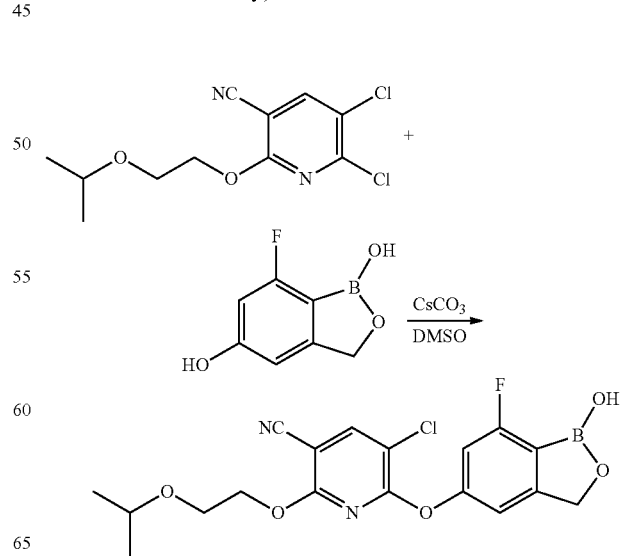

This compound was prepared from 5,6-dichloro-2-(2-isopropoxyethoxy)nicotinonitrile and 7-fluorobenzo[c][1,2]oxaborole-1,5(3H)-diol in a similar manner to that of D230. $^1$H-NMR (400 MHz, DMSO-d$_6$) δ (ppm) 1.01 (d, J=4.5 Hz, 6H), 3.45-3.48 (m, 1H), 3.51-3.53 (m, 2H), 4.11-4.14 (m, 2H), 5.03 (s, 2H), 7.14 (d, J=8.6 Hz, 1H), 7.22 (s, 1H), 8.62 (s, 1H), 9.35 (s, 1H).

1r. 5-Chloro-6-(7-fluoro-1-hydroxy-1,3-dihydrobenzo[c][1,2]oxaborol-5-yloxy)-2-(4-oxopentyloxy)nicotinonitrile D248

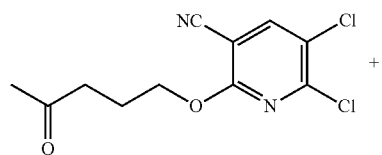
+
→
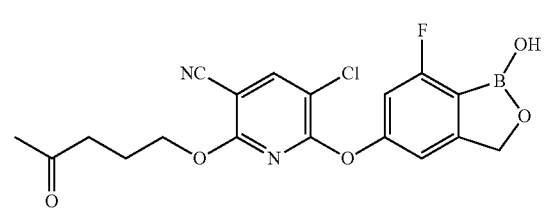

This compound was prepared from 5,6-dichloro-2-(4-oxopentyloxy)nicotinonitrile and 7-fluorobenzo[c][1,2]oxaborole-1,5(3H)-diol in a similar manner to that of D230. $^1$H-NMR (400 MHz, DMSO-d$_6$) δ (ppm) 1.72-1.75 (m, 2H), 2.05 (s, 3H), 2.38 (t, J=5.4 Hz, 2H), 4.03 (t, J=5.4 Hz, 2H), 5.03 (s, 2H), 7.13 (d, J=7.8 Hz, 1H), 7.2 (s, 1H), 8.61 (s, 1H), 9.36 (s, 1H).

1s. 5-Chloro-6-(6-fluoro-1-hydroxy-1,3-dihydrobenzo[c][1,2]oxaborol-5-yloxy)-2-(2-isopropoxyethoxy)nicotinonitrile D249

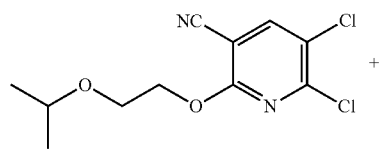
+
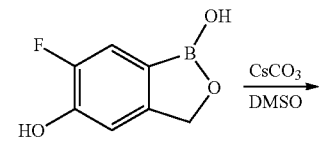
→

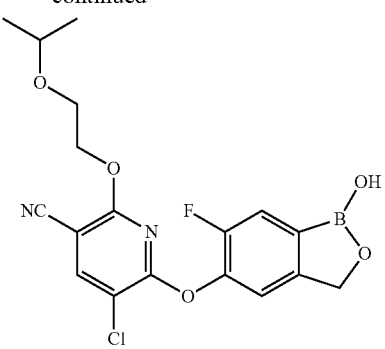

This compound was prepared from 5,6-dichloro-2-(2-isopropoxyethoxy)nicotinonitrile and 6-fluorobenzo[c][1,2]oxaborole-1,5(3H)-diol in a similar manner to that of D230. $^1$H-NMR (400 MHz, DMSO-d$_6$) δ (ppm) 1.0 (d, J=4.5 Hz, 6H), 3.32-3.45 (m, 3H), 4.04-4.05 (m, 2H), 5.0 (s, 2H), 7.53 (d, J=4.8 Hz, 1H), 7.65 (d, J=7.2 Hz, 1H), 8.63 (s, 1H), 9.4 (s, 1H).

1t. 5-Chloro-6-(6-fluoro-1-hydroxy-1,3-dihydrobenzo[c][1,2]oxaborol-5-yloxy)-2-(4-oxopentyloxy)nicotinonitrile D250

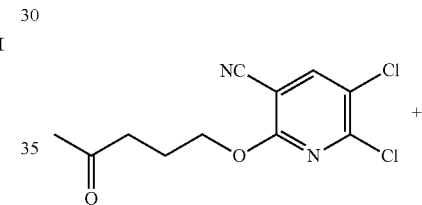
+
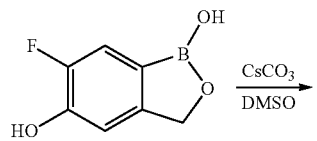
→
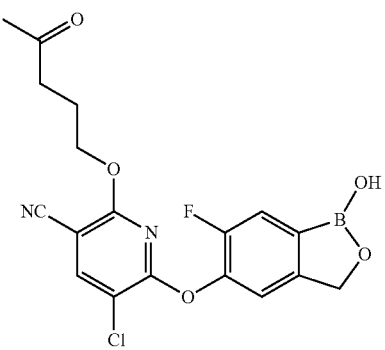

This compound was prepared from 5,6-dichloro-2-(4-oxopentyloxy)nicotinonitrile and 6-fluorobenzo[c][1,2]oxaborole-1,5(3H)-diol in a similar manner to that of D230. $^1$H-NMR (400 MHz, DMSO-d$_6$) δ (ppm) 1.63-1.67 (m, 2H), 2.02 (s, 3H), 2.3 (t, J=5.25 Hz, 2H), 3.94 (t, J=4.95 Hz, 2H), 5.0 (s, 2H), 7.51 (d, J=4.8 Hz, 1H), 7.63 (d, J=9.0 Hz, 1H), 8.62 (s, 1H), 9.4 (s, 1H).

1u. 5-Chloro-6-(3,3-dideuterio-1-hydroxy-1,3-dihydrobenzo[c][1,2]oxaborol-5-yloxy)-2-(2-isopropoxyethoxy)nicotinonitrile D251

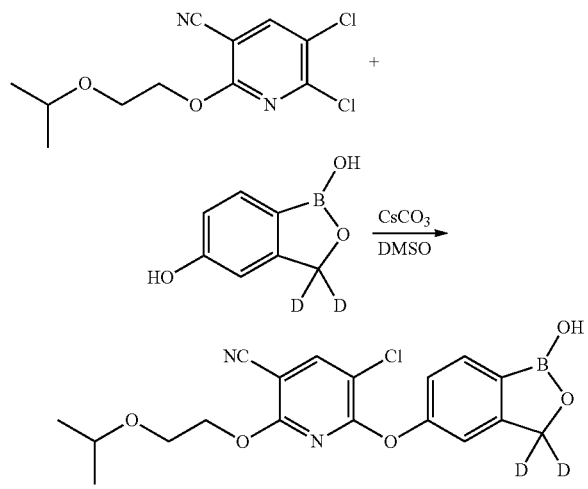

This compound was prepared from 5,6-dichloro-2-(2-isopropoxyethoxy)nicotinonitrile and 3,3-Dideuteriobenzo[c][1,2]oxaborole-1,5(3H)-diol in a similar manner to that of D230. $^1$H-NMR (400 MHz, DMSO-$d_6$) δ (ppm) 1.0 (d, J=4.5 Hz, 6H), 3.42-3.48 (m, 3H), 4.06-4.09 (m, 2H), 7.25 (dd, J=6.0, 1.5 Hz, 1H), 7.33 (d, J=1.5 Hz, 1H), 7.79 (d, J=6.0 Hz, 1H), 8.59 (s, 1H), 9.25 (s, 1H).

1v. 5-Chloro-6-(1-hydroxy-3-methyl-1,3-dihydrobenzo[c][1,2]oxaborol-5-yloxy)-2-(2-isopropoxyethoxy)nicotinonitrile D252

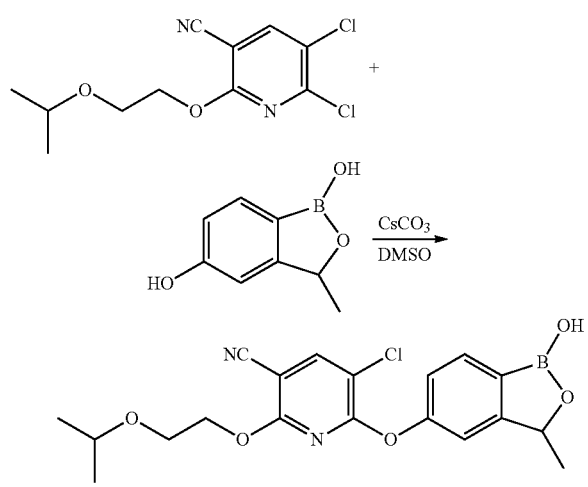

This compound was prepared from 5,6-dichloro-2-(2-isopropoxyethoxy)nicotinonitrile and 3-methylbenzo[c][1,2]oxaborole-1,5(3H)-diol in a similar manner to that of D230. $^1$H-NMR (400 MHz, DMSO-$d_6$) δ (ppm) 1.0 (d, J=4.5 Hz, 6H), 1.40 (d, J=4.8 Hz, 3H), 3.4-3.47 (m, 3H), 4.07-4.1 (m, 2H), 5.2-5.22 (m, 1H), 7.23 (dd, J=6.0, 1.5 Hz, 1H), 7.36 (s, 1H), 7.75 (d, J=6.0 Hz, 1H), 8.59 (s, 1H), 9.18 (s, 1H).

1w. 5-Chloro-2-(1-hydroxy-1,3-dihydrobenzo[c][1,2]oxaborol-5-yloxy)-6-(4-oxopentyloxy)nicotinonitrile D253

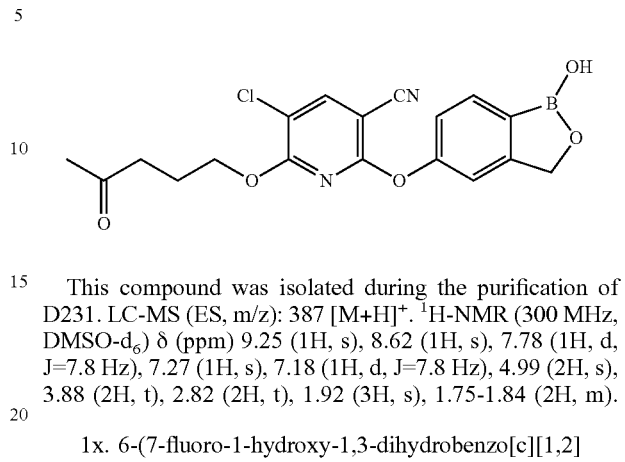

This compound was isolated during the purification of D231. LC-MS (ES, m/z): 387 [M+H]$^+$. $^1$H-NMR (300 MHz, DMSO-$d_6$) δ (ppm) 9.25 (1H, s), 8.62 (1H, s), 7.78 (1H, d, J=7.8 Hz), 7.27 (1H, s), 7.18 (1H, d, J=7.8 Hz), 4.99 (2H, s), 3.88 (2H, t), 2.82 (2H, t), 1.92 (3H, s), 1.75-1.84 (2H, m).

1x. 6-(7-fluoro-1-hydroxy-1,3-dihydrobenzo[c][1,2]oxaborol-5-yloxy)-2-(2-isopropoxyethoxy)-4-(trifluoromethyl)nicotinonitrile D254

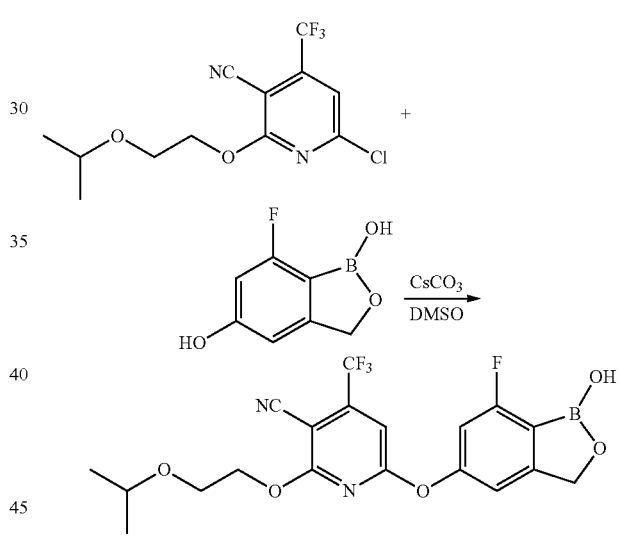

This compound was prepared from 6-chloro-2-(2-isopropoxyethoxy)-4-(trifluoromethyl)nicotinonitrile and 7-fluorobenzo[c][1,2]oxaborole-1,5(3H)-diol in a similar manner to that of D230. $^1$H-NMR (400 MHz, DMSO-$d_6$) δ (ppm) 1.06 (d, J=6 Hz, 6H), 3.52-3.55 (m, 1H), 3.59-3.61 (t, J=4.8 Hz, 2H), 4.26-4.28 (t, J=4.8 Hz, 2H), 5.07 (s, 2H), 7.18 (d, J=8.0 Hz, 1H), 7.27 (s, 1H), 7.38 (s, 1H), 9.39 (s, 1H).

Example 2

In Vivo TNF-α—

In vivo TNF-α release was measured in Swiss Webster mice, 10/group. Animals were dosed via oral gavage with drug 1% CMC suspension. Thirty minutes later LPS, 1.5 mg/kg was administered by intraperitoneal injection. Ninety minutes later animals were sacrificed, blood was collected by exsangination and serum prepared for analysis. TNF-α concentration was assessed by ELISA, non-drug treated animals had TNF-α levels 1000-3000 pg/mL. 6-(1-Hydroxy-1,3-dihydrobenzo[c][1,2]oxaborol-5-yloxy)-2-(2-isopropoxyethoxy)nicotinonitrile (D140) and 6-(1-hydroxy-1,3-dihydrobenzo[c][1,2]oxaborol-5-yloxy)-2-(4-oxopentyloxy) nicotinonitrile (D141) are disclosed in U.S. patent application Ser. No. 12/399,015, filed Mar. 5, 2009.

| Oral Dose (mg/kg) | % Inhibition of TNFa Blood Levels in LPS Treated Mice | | | | | | |
|---|---|---|---|---|---|---|---|
| | Prednisolone | Rolipram | D141 | D140 | D230 | D231 | Roflumilast |
| 0 | 0 | 0 | 0 | 0 | 0 | 0 | 0 |
| 0.01 | 16 | | | | | | |
| 0.03 | | | | | | 0 | |
| 0.1 | 54.3 | | | | 39 | 22 | |
| 0.3 | | | | 26.4 | 59 | 33.6 | 0 |
| 0.5 | | | | 30 | 55 | | |
| 1 | | | | 50.2 | 76 | 69.5 | 24.9 |
| 1.5 | | | | | | 58 | |
| 3 | 81.6 | | 36.1 | 59.35 | 80 | 75.6 | 52.5 |
| 5 | | | | 72 | 77 | 85.5 | |
| 10 | 84.5 | 8.6 | 52.4 | 74 | 77 | 85.6 | 71.5 |
| 15 | | | | | | 81.3 | |
| 30 | | 62.7 | 67.1 | 83.5 | | 97.3 | 73.5 |
| 100 | 85.9 | | | | | | |

The compounds of the invention provide increased potency over previously known compounds.

Example 3

Measurement of Phosphodiesterase 4 (PDE4) Inhibition

Inhibition of the human PDE4 enzyme, using semi-purified enzyme from human U937 cells. The PDE4 enzyme was partially purified from human U937 myeloid leukemia cells and activity was assayed using a method optimized from Cortijo et al (10, Cortijo 1993) and Nicholson et al. (11, Nicholson, 1991). Test article and/or vehicle was incubated with 0.2 mg of enzyme and 1 µM cAMP containing 0.01 µM [$^3$H]cAMP in Tris buffer (50 mM Tris-HCl pH 7.5, 5 mM $MgCl_2$) for 20 minutes at 25° C. The reaction was terminated by boiling for 2 minutes and the resulting AMP was converted to adenosine by addition of 10 mg/ml snake venom nucleotidase and further incubation at 37° C. for 10 min. Unhydrolyzed cAMP was bound to AG1-X2 resin, and the remaining [$^3$H] adenosine in the aqueous phase was quantitated by scintillation counting. Test articles were tested often tested at 9 concentrations using half-log dilutions series. All assays used a substrate concentration below the Km determined for each enzyme so that the Ki approximates the $IC_{50}$. The $IC_{50}$ value of 6-(1-Hydroxy-1,3-dihydrobenzo[c][1,2]oxaborol-5-yloxy)-2-(2-isopropoxyethoxy) nicotinonitrile (D140) under similar conditions is 9 nM. The $IC_{50}$ value of 6-(1-hydroxy-1,3-dihydrobenzo[c][1,2]oxaborol-5-yloxy)-2-(4-oxopentyloxy) nicotinonitrile (D141) under similar conditions is 3.1 nM.

$IC_{50}$ values and Hill coefficients (nH) were determined by non-linear regression analysis of the inhibition curves generated with mean replicate values using four parameter logistic equation: $Y=D+[(A-D)/(1+(C/IC_{50})^{nH})]$, where Y=activity, D=minimum activity, A=maximum activity, C=compound concentration, and nH=slope factor).
1. Cortijo, J., Bou. J. Beleta, J, Cardelus, I, Llenas, J, Morcillo E and Gristwood R S (1993) Investigation into the role of phosphodiesterase IV in bronchorelaxation, including studies with human bronchus. Br. J. Pharmacol. 108:562-568.
2. Nicholson, C D, Chaliss, R A and Shalid, M. 1991. Differential modulation of tissue function and therapeutic potential of selective inhibitors of cyclic nucleotide phosphodiesterase isoenzymes. Trend Pharmacol. Sci. 12:19-27.

Analysis of TNF-α Inhibition in Peripheral Blood Mononuclear Cells.

Peripheral blood mononuclear cells (PBMCs) pooled from 10-20 donors were obtained from a local blood bank, ficoll gradient purified, and stored frozen in liquid nitrogen. Cells were thawed and seeded into 96-well plates at $5 \times 10^5$ cells/well in RPMI 1640 with 10% heat-inactivated fetal calf serum (MediaTech, Inc, Herndon, Va., USA), Test articles were evaluated at the indicated concentrations in 150 µL media containing <2% DMSO, final, with stimulant and PBMCs. Cells were stimulated with lipopolysaccharide (LPS, phenol-extract from E. coli, Sigma-Aldrich, St. Louis, Mo.) at 1 µg/mL. Stimulation was with LPS for 24 h to measure TNF-α. Cytokines in supernatants were analyzed with a FACSArray flow cytometer (BD Biosciences, San Jose, Calif., USA) using the BD Cytometric Bead Array (CBA) Flex Set (BD Biosciences). $IC_{50}$ values were calculated using the four parameter logistic equation. The $IC_{50}$ value of 6-(1-Hydroxy-1,3-dihydrobenzo[c][1,2]oxaborol-5-yloxy)-2-(2-isopropoxyethoxy)nicotinonitrile (D140) under similar conditions is 3.6 nM. The $IC_{50}$ value of 6-(1-hydroxy-1,3-dihydrobenzo[c][1,2]oxaborol-5-yloxy)-2-(4-oxopentyloxy) nicotinonitrile (D141) under similar conditions is 1.2 nM.

Data for compounds of the invention are provided in the table below:

| | Proinflammatory TNF-α IC50 (nM) | PDE4 IC50 (nM) |
|---|---|---|
| D230 | 2.50 | 5.2 |
| D231 | 0.44 | 0.8 |
| D232 | 98 | 23 |
| D233 | 13 | |
| D234 | 2.10 | |
| D235 | 2.20 | |
| D236 | 0.34 | |
| D237 | 1.50 | |
| D238 | 1.10 | |
| D239 | 0.65 | 1.3 |
| D240 | 3.80 | |
| D241 | 2.90 | 1.1 |
| D242 | 0.21 | 2.2 |
| D243 | 1.10 | 6.5 |
| D244 | 0.21 | |
| D245 | 26 | 2.0 |
| D246 | 11 | 1.3 |
| D247 | 2.90 | 19 |
| D248 | 0.93 | 1.7 |
| D249 | 2.30 | |
| D250 | 0.41 | |
| D251 | 2.30 | |
| D252 | 160 | |
| D253 | 0.57 | 0.25 |
| D254 | 3.50 | |

The compounds of the invention provide increased potency over previously known compounds.

Example 4

Pharmacokinetics

The objective of this study was to evaluate the pharmacokinetics and oral bioavailability of PDE4 inhibitors following intravenous (IV) administration and oral (PO) doses in female CD-1 mice.

A total of 24 mice were divided into 2 dose groups (n=12/group) to receive experimental compounds by intravenous injection via the tail vein at 5 mg/kg or by oral gavage at 30 mg/kg. After dosing, blood samples were collected through 24 h, twice from each animal at specific times (3 mice/time point), into microcentrifuge tubes containing K$_2$EDTA (anticoagulant), stored on wet ice and processed for plasma. The plasma samples were analyzed for concentrations of parent compound by LC/MS/MS using an internal standard/peak area method. Pharmacokinetic analysis of the mean plasma concentration-time profiles following IV and PO administration was performed.

On the morning of dosing, all animals were weighed and assigned randomly into 2 dose groups (n=12/group) to receive compound by intravenous injection via the tail vein at 5 mg/kg, or by oral gavage at 30 mg/kg, respectively. Dosing solutions for intravenous administration were prepared in 55% PEG300/25% PG/20% water. Oral dosing used a suspension prepared in 1% CMC in water with 0.1% Tween 80.

After dosing, blood samples were collected through 24 h, twice from each animal via retro-orbital bleed (~0.1 mL, 1$^{st}$ time point) or cardiac puncture (~0.6 mL, 2$^{nd}$ time point) at specific times (3 mice/time point), into microcentrifuge tubes containing K$_2$EDTA (anticoagulant) and stored on wet ice prior to processing.

Plasma was prepared by centrifugation of blood samples for 6 min at approximately 2000×g or 6000 rpm at 4° C. All processed plasma samples (~50 μL and 300 μL) were transferred to analysis tubes, placed on dry ice immediately and later stored at −80° C. until analysis for concentrations of experimental compound by LC/MS/MS.

Mouse IV clearance, Mouse Oral AUC and Oral Bioavailability are provided below. 6-(1-Hydroxy-1,3-dihydrobenzo[c][1,2]oxaborol-5-yloxy)-2-(2-isopropoxyethoxy) nicotinonitrile (D140) and 6-(1-hydroxy-1,3-dihydrobenzo[c][1,2]oxaborol-5-yloxy)-2-(4-oxopentyloxy) nicotinonitrile (D141) are disclosed in U.S. patent application Ser. No. 12/399,015, filed Mar. 5, 2009.

| Compound | Mouse IV clearance (mL/hr/kg) | Mouse Oral AUC (h · ug/mL) Using 10 mg/kg Oral Suspension Dose | Oral Bioavailability (%) |
|---|---|---|---|
| D140 | 3400 | 0.81 | 24 |
| D141 | 2600 | 1.3 | 32 |
| D230 | 2200 | 3 | 60 |
| D231 | 1500 | 8.5 | 96 |
| D235 | 1213 | 5.84 | |
| D236 | 2050 | 5.62 | 100 |
| D237 | 1610 | 6.92 | 100 |
| D238 | 591 | 11.2 | 65 |
| D241 | 849 | 14.9 | 100 |
| D242 | 34000 | 0.59 | 15 |
| D243 | 3000 | 3.9 | 96 |
| D244 | 1400 | 13.6 | 100 |
| D247 | 1100 | 21 | 100 |
| D248 | 110 | 91 | 79 |
| D249 | 3549 | 3.3 | 100 |
| D250 | 470 | 17 | 71 |
| D251 | 2671 | 6.3 | |
| D254 | 63 | 110 | 58 |

Compounds of the invention possess decreased clearance over previously known compounds. Compounds of the invention possess increased oral bioavailability over previously known compounds.

Example 5

*Brugia malayi* In Vitro Assays

Materials and Methods

Worms

Adult female worms are shipped from TRS Labs Inc. (Nonglak Supakorndej, Lab Director, 295 Research Dr., Athens, Ga. 30605; 706-549-0764) via Fed Ex. Individual worms are shipped in 2 mls vials with RPMI on Mondays and arrive at the Sandler Center lab on Tuesday mornings.

Assays

Individual worms are poured into each well (24-well tissue culture plates) to avoid handling worms since they are very delicate and easily broken. Transport media is removed and replaced with 0.5 mls of RPMI-1640 (25 mM HEPES, 2 g/L NaHCO$_3$, Antibiotic/Antimycotic, 5% HI FBS). Worms are maintained in a 37° C. 5% CO$_2$ incubator.

Compounds are added directly to each duplicate well (5 ul of 5 mM for a final concentration of 50 uM). DMSO (5 ul) is used as a negative control and Ivermectin (Sigma) is used as a positive control at 100 uM/well and 20 uM/well.

Adult filarial nematodes can shed/give birth to microfilarial worms (mf) during the course of the assay. Wells were reviewed for the presence of mf, and the viability of mf, by visual observation of the well on the last day of observation (Day 7).

The Read Out

Plates are examined once a day for 4-7 days. Worms are highly active and easily observed without the use of a dissecting microscope. If changes are observed, worms are more closely examined under a dissecting microscope. The worms are monitored for changes in activity and scored based on the following:

4=highly active (controls)
3=active
2=slightly moving around
1=barely moving
0=not moving Results Results for *B. malayi* are as follows:

| Cmpd | | Day 1 | Day 2 | Day 3 | Day 7 | Day 7 |
|---|---|---|---|---|---|---|
| 6-(1-hydroxy-1,3-dihydrobenzo[c][1,2]oxaborol-5-yloxy)-2-(4-isopropoxyethoxy)nicotinonitrile | trial one | hyper-coiled | hyper-coiled | hyper-coiled | 0, coiled | mf alive |
| | trial two | hyper-coiled | hyper-coiled | 4 | 0, coiled | no mf obs |

-continued

| Cmpd | | Day 1 | Day 2 | Day 3 | Day 7 | Day 7 |
|---|---|---|---|---|---|---|
| 5-Chloro-6-(1-hydroxy-1,3-dihydrobenzo[c][1,2]oxaborol-5-yloxy)-2-(4-oxopentyloxy) nicotinonitrile | trial one | hyper-coiled | hyper-coiled | 2 to 3 | 0, coiled | no mf obs |
| | trial two | hyper-coiled | hyper-coiled | 2 to 3 | 0, coiled | no mf obs |

Example 6

Activity Against *Schistosoma mansoni*

Preparation of Schistosomula and Adult Worms

Puerto Rican isolates of *S. mansoni* using *Biomphalaria glabrata* snails and golden hamsters as intermediate and definitive hosts, respectively, were maintained and handled in the University of California-San Francisco Sandler Center for Tropical Medicine. Patent *B. glabrata* snails (6-8 weeks after exposure to 5-10 infectious miracidia) were induced to shed infective larvae (cercariae) under light stimulus into the surrounding water. Cercariae were washed in rounds of ice-cold water and concentrated through and over sieves of varying pore sizes. They were then mechanically sheared (separation of heads from tails) as described in Colley D G, et al. *Exp Parasitol* 1974, 35:44-51, in ice-cold Incomplete Medium 169 (as described in Basch P F. *J Parasitol* 1981, 67:179-185, minus FBS and antibiotics) by passing 15 times through a double headed 22-gauge syringe needle connected to two 10 mL syringes. The resulting cercarial heads (schistosomula) were separated from their tails by swirling in a petri dish. Concentrated schistosomula were added to a sterile 1.5 mL centrifuge tube and allowed to settle over ice. Schistosomula were transferred to a sterile environment and washed 4 times in Incomplete Medium 169 prior to plating.

Two sets of screening were performed. In the first set, compounds were screened against schistosomula and observations were made at 24 hours, 2 days, 3 days, 4 days, and 6 days. In the second set, compounds were screened against schistosomula with observations at 24 hours, 2 days, 3 days, and 4 days and adult worms at 7 hours, 24 hours, 4 days, and 6 days.

Plating and Compound Screening of Schistosomula

Plates contain 200 schistosomula/well in 200 pL complete Basch medium and were maintained at 37° C. in a 5% $CO_2$ atmosphere. All compounds were tested in duplicate with at least two experimental replicates. Compounds and control compounds were added to the plates using the Biomek FXp using 96-well disposable tips. Final concentration of DMSO in each well was 0.5%.

Plating and Compound Screening of Adults

Given the delicacy and size (0.5-1.5 cm in length) of this stage all operations were performed manually by the Sandler Center. 24-well plates were set up with compound (final DMSO concentration=0.5%) containing approximately 5 pairs of worms (*S. mansoni* has separate sexes) in 2 mL complete Basch medium per well. Plates were maintained at 37° C. in a 5% $CO_2$ atmosphere. All compounds were tested in duplicate with at least two experimental replicates.

Phenotype Scoring In Vitro

A semi-quantitative and controlled nomenclature for phenotypes that can arise as a result of compound insult to both schistosomula and adults was utilized (Abdulla M H, et al., *PLoS Negl Trop Dis* 2009, 3:e478). Phenotypes were recorded by visual inspection and on a flexible time basis but at least at 24 h and 4 day time-points in the case of large scale screening. Visual recording of phenotypes proved both necessary and reliable in the context of thorough accounting for the multiple and changing phenotypes that were typically evident at any given time and for which death, while desired, was just one of several outcomes. To help eliminate bias, two screen analysts scored phenotypes 'blind' both to knowledge of the contents of each screening plate and the phenotypes scored by his/her colleague. Upon completing their individual assessments, each analyst's 'hit sheet' was then compared to derive a 'consensus hit sheet'. Discrepancies in analysts' hit sheets were re-evaluated under the microscope to eventually make a consensus hit call. All phenotypes were compared to those generated by the positive control compounds, PZQ, niclosamide and rafoxanide, which caused dose-dependent, rapid and severe phenotypes in both schistosomula and adult worms.

Adult *Schistosoma mansoni* Phenotypic Key:

O=overactive; S=slow; Dark; R=round; Deg-M=worms in morphological disarray but still living; D=dead; Partial D=partial killing of worm population; Dying; Sex sep=worm pairs have separated; On Sides=male worms do not adhere to dish bottom; Partial D=Some of the worms in the well have died; Blank means no phenotype out of ordinary observed. Hyper-coiled and coiled represent a verbal description of the visual phenotype as compared to the DMSO control. The + and ++ and +++ means more of the phenotype which preceded it. The − means less of the phenotype which preceded it.

Results

First Set—Tested for Schistosomula

| | 24 h | day 2 | day 3 | day 4 | day 6 |
|---|---|---|---|---|---|
| 2-tert-butylamino-6-(1-hydroxy-1,3-dihydro-benzo[c][1,2]oxaborol-5-yloxy)-nicotinonitrile | O | | | | |
| 2-Ethoxy-6-(1-hydroxy-1,3-dihydro-benzo[c][1,2]oxaborol-5-yloxy)-nicotinonitrile | O++ | | O+ partial D | | O+ R Partial D |

-continued

|  | 24 h | day 2 | day 3 | day 4 | day 6 |
|---|---|---|---|---|---|
| 6-(1-Hydroxy-1,3-dihydro-benzo[c][1,2]oxaborol-5-yloxy)-2-pyrrolidin-1-yl-nicotinonitrile | O+ |  | O+ Deg-M |  | R O Partial D |
| 6-(1-Hydroxy-1,3-dihydro-benzo[c][1,2]oxaborol-5-yloxy)-2-isopropoxy-nicotinonitrile | O+ |  | O+ Deg-M |  | R O+ Partial D |
| 6-(1-Hydroxy-1,3-dihydro-benzo[c][1,2]oxaborol-5-yloxy)-2-propoxy-nicotinonitrile | O+ |  | O+ Deg-M |  | R O partial D |
| 2-(2-Benzyloxy-ethylamino)-6-(1-hydroxy-1,3-dihydro-benzo[c][1,2]oxaborol-5-yloxy)-nicotinonitrile | O+ some deg-M |  | O+ Deg-M |  | R O+ Partial D |
| 6-(1-hydroxy-1,3-dihydro-benzo[c][1,2]oxaborol-5-yloxy)-2-(2-hydroxy-ethylamino)-nicotinonitrile | O− |  |  |  | O+ R |
| 6-(1-Hydroxy-1,3-dihydro-benzo[c][1,2]oxaborol-5-yloxy)-4-[2-(tetrahydro-pyran-2-yloxy)-ethoxy]-nicotinonitrile | O++ with deg-M |  | O++ deg-M |  | Deg-M D |
| 6-(1-Hydroxy-1,3-dihydro-benzo[c][1,2]oxaborol-5-yloxy)-2-[(2-hydroxy-ethyl)-methyl-amino]-nicotinonitrile | O− |  | O− |  | R O |
| 4-(1-Hydroxy-1,3-dihydro-benzo[c][1,2]oxaborol-5-yloxy)-2-(2-methoxyethoxy)-nicotinonitrile | R O+ |  | O+ some partial D |  | O+ R Partial D |
| 2-(2,2-Difluoro-ethoxy)-6-(1-hydroxy-1,3-dihydro-benzo[c][1,2]oxaborol-5-yloxy)-nicotinonitrile | O+ |  | O+ Deg-M |  | R O+ Partial D |
| 6-(1-hydroxy-1,3-dihydro-benzo[c][1,2]oxaborol-5-yloxy)-2-[(2-methoxy-ethyl)-methyl-amino]-nicotinonitrile | O+ |  | O+ Deg-M |  | R O Partial D |
| 2-((5-Cyano-2-(1-hydroxy-1,3-dihydrobenzo[c][1,2]oxaborol-5-yloxy)phenoxy)methyl)pyridine hydrochloride | R O++ | O+, deg-M− |  | O+, Partial D | O+, Partial D, R |
| 6-(1-Hydroxy-1,3-dihydro-benzo[c][1,2]oxaborol-5-yloxy)-2-(2,2,2-trifluoro-ethoxy)-nicotinonitrile | O |  |  |  | O+ R Partial D |
| 6-(1-Hydroxy-1,3-dihydro-benzo[c][1,2]oxaborol-5-yloxy)-2-(2-methoxy-ethylamino)-nicotinonitrile | O− |  |  |  | R O some partial D |
| 5-(4-Cyano-3-trifluoromethylphenoxy)-1,3-dihydro-1-hydroxy-2,1-benzoxaborole |  | O−, some deg-m− |  | O, some deg-m | O, some deg-m |
| 6-(1-hydroxy-1,3-dihydrobenzo[c][1,2]oxaborol-5-yloxy)nicotinonitrile |  |  |  | O−, R− |  |
| 2-(1-Hydroxy-1,3-dihydro-benzo[c][1,2]oxaborol-5-yloxy)-6-(2-methoxy-ethylamino)-nicotinonitrile | O+ |  |  |  | O+ R Partial D |
| 6-(1-Hydroxy-1,3-dihydro-benzo[c][1,2]oxaborol-5-yloxy)-2-(acetyloxyethoxy)-nicotinonitrile | O++ |  | O+ partial D |  | R O+ Partial D |
| 2-Benzylamino-6-(1-hydroxy-1,3-dihydro-benzo[c][1,2]oxaborol-5-yloxy)-nicotinonitrile | O++ some deg-M |  |  |  | R O Partial D |
| 3-(Cyclopentyloxy)-4-(1-hydroxy-1,3-dihydrobenzo[c][1,2]oxaborol-5-yloxy)benzonitrile | O++ with deg-M |  | O+ Partial D |  | R deg-M D |
| 3-(Cyclopropylmethoxy)-4-(1-hydroxy-1,3-dihydrobenzo[c][1,2]oxaborol-5-yloxy)benzonitrile | O+ |  | O+ partial D |  | partial D |
| 3-(Cyclopentylmethoxy)-4-(1-hydroxy-1,3-dihydrobenzo[c][1,2]oxaborol-5-yloxy)benzonitrile |  |  |  | R O− Deg-M D |  |
| 6-(1-Hydroxy-1,3-dihydro-benzo[c][1,2]oxaborol-5-yloxy)-2-isobutoxy-nicotinonitrile | R− O− |  | R O− |  |  |

-continued

| | 24 h | day 2 | day 3 | day 4 | day 6 |
|---|---|---|---|---|---|
| 6-(6-Fluoro-1-hydroxy-1,3-dihydrobenzo[c][1,2]oxaborol-5-yloxy)-2-methoxynicotinonitrile | O+ | | | | R O some partial D |
| Ethyl 5-chloro-6-(1-hydroxy-1,3-dihydrobenzo[c][1,2]oxaborol-5-yloxy)nicotinate | O++ | | | | R O deg-M partial D |
| 5-(2-Fluoro-4-isopropyloxycarbonylphenoxy)-1-hydroxy-2,1-benzoxaborole | | | | O–, R | O–, R |
| 5-[4-Ethoxycarbonyl-2-(4-cyanopyridin-2-yloxy)phenoxy]-1,3-dihydro-1-hydroxy-2,1-benzoxaborole | O+ | O, with deg-m | | O, some deg-m | R, O, Partial D |
| Ethyl 2-ethoxy-6-(1-hydroxy-1,3-dihydrobenzo[c][1,2]oxaborol-5-yloxy)nicotinate | O+ | O, with deg-m (shrunk) | | O, with deg-m | R, Partial D |
| n-Butyl 6-(1-hydroxy-1,3-dihydrobenzo[c][1,2]oxaborol-5-yloxy)nicotinate | | | O, deg-m (strong) | O, R, deg-m, (shrunk) | O, R, D, deg-m |
| Isopropyl 6-(1-hydroxy-1,3-dihydrobenzo[c][1,2]oxaborol-5-yloxy)nicotinate | O+ | O, some deg-m | | O, R, some deg-m | O, R, Partial D |
| n-Propyl 6-(1-hydroxy-1,3-dihydrobenzo[c][1,2]oxaborol-5-yloxy)nicotinate | O+ | O+ (shrunk) | | O, partial D | O, R, Partial D |
| N-[4-(1-Hydroxy-1,3-dihydro-benzo[c][1,2]oxaborol-5-yloxy)-benzyl]-acetamide | | | | D | |

Second Set—Tested Against Schistosomula and Adults

| | Schistosomula (juvenile infective form) worm screen at 5 uM; | | | |
|---|---|---|---|---|
| Compound | 24 h | 2 d | 3 d | 4 d |
| 6-(1-Hydroxy-1,3-dihydrobenzo[c][1,2]oxaborol-5-yloxy)nicotinonitrile | R–, O– | R–, O–, some deg-M | O, some deg-M | O, some deg-M |
| 2-Cyclopentyloxy-6-(1-hydroxy-1,3-dihydro-benzo[c][1,2]oxaborol-5-yloxy)-nicotinonitrile | R, O+ | O++, R–, some deg-M | O++, R–, some deg-M | O++, R–, some deg-M |
| 6-(6-Fluoro-1-hydroxy-1,3-dihydrobenzo[c][1,2]oxaborol-5-yloxy)-2-methoxynicotinonitrile | R, O++, some deg-m | O+++, R–, some deg-M | O+++, some deg-M | O+++, some deg-M |
| 6-(1-Hydroxy-1,3-dihydro-benzo[c][1,2]oxaborol-5-yloxy)-2-(2-isopropoxy-ethoxy)-nicotinonitrile | R, O++, some deg-m | O+++, R–, some deg-M | O+++, R, some deg-M | O+++, R, some deg-M |
| 6-(1-Hydroxy-1,3-dihydro-benzo[c][1,2]oxaborol-5-yloxy)-2-(4-oxo-pentyloxy)-nicotinonitrile | R, O++, some deg-m | O+++, R–, some deg-M | O+++, R, some deg-M | O+++, R, some deg-M |
| 6-(1-Hydroxy-1,3-dihydro-benzo[c][1,2]oxaborol-5-yloxy)-2-(4-oxo-pentyloxy)-5-chloro-nicotinonitrile | R, O++, some deg-m | O++, R–, more deg-M | O++, R–, more deg-M | O++, R–, more deg-M |

| | Adult worm screen at 5 uM; | | | |
|---|---|---|---|---|
| Compound | 7 h | 24 h | 4 d | 6 d* (see note) |
| 6-(1-Hydroxy-1,3-dihydrobenzo[c][1,2]oxaborol-5-yloxy)nicotinonitrile | O– | | | |

-continued

| Compound | Adult worm screen at 5 uM; | | | |
|---|---|---|---|---|
| | 7 h | 24 h | 4 d | 6 d* (see note) |
| 2-Cyclopentyloxy-6-(1-hydroxy-1,3-dihydro-benzo[c][1,2]oxaborol-5-yloxy)-nicotinonitrile | O+ | O− | v, slow, sex sep, on sides | Dark, S, Partial D |
| 6-(6-Fluoro-1-hydroxy-1,3-dihydrobenzo[c][1,2]oxaborol-5-yloxy)-2-methoxynicotinonitrile | O++ | O++ sex sep | O+, sex sep on sides, males dark | Dark, Partial D |
| 6-(1-Hydroxy-1,3-dihydro-benzo[c][1,2]oxaborol-5-yloxy)-2-(2-isopropoxy-ethoxy)-nicotinonitrile | O++ | O++ sex sep | O, sex sep, on sides | |
| 6-(1-Hydroxy-1,3-dihydro-benzo[c][1,2]oxaborol-5-yloxy)-2-(4-oxo-pentyloxy)-nicotinonitrile | O++, Sex sep (violent motion) | O++, Sex sep (violent motion) | O++, sex sep on sides, males dark | Dark, S, Partial D |
| 6-(1-Hydroxy-1,3-dihydro-benzo[c][1,2]oxaborol-5-yloxy)-2-(4-oxo-pentyloxy)-5-chloro-nicotinonitrile | O+++, Sex sep (violent motion) | O+++, Sex sep (violent motion) | O++, sex sep on sides, males dark | Dark, S |

Example 7

Additional Activity Against Worms

Compounds of the invention can be tested for efficacy against worms of the genus *Schistosoma* by using the assay described in Abdulla, M. H. et al. Drug Discovery for Schistosomiasis: Hit and Lead Compound Identification in a Library of Known Drugs by Medium Through-put Phenotypic Screening. July 2009. PLoS Neglected Tropical Diseases.

Compounds of the invention can be tested for efficacy against *W. bancrofti, B. timori* and *B. malayi* by using the assay described in Srinwasan, L. et al. In vitro antifilarial activity of glutathione-S-transferase inhibitors. *Parasitology Res.* 105:1179-1182. October 2009.

Compounds of the invention can be tested for efficacy against worms of the genus *Onchocerca* by using the assay described in Townson, S. et al. *Onchocerca gutturosa* and *O. volvulus*: Studies on the viability and drug responses of cryopreserved adult worms in vitro. *Transactions Royal Soc. Trop. Med Hygiene.* 83:664-669.

Compounds of the invention can be tested for efficacy against worms of the genus *Dirofilaria* by using the assay described in Abraham, D. et al. In vitro culture of *Dirofilaria immitis* third and fourth stage larvae under defined conditions. *J. Parasitol.* 73:377-383. 1987.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of decreasing the release of a cytokine or a chemokine, the method comprising: contacting a cell with the compound having a structure according to a formula which is selected from the group consisting of:

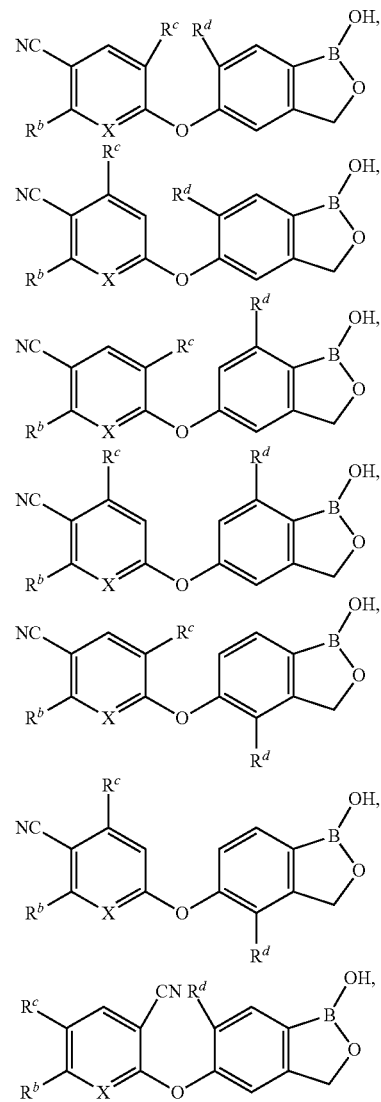

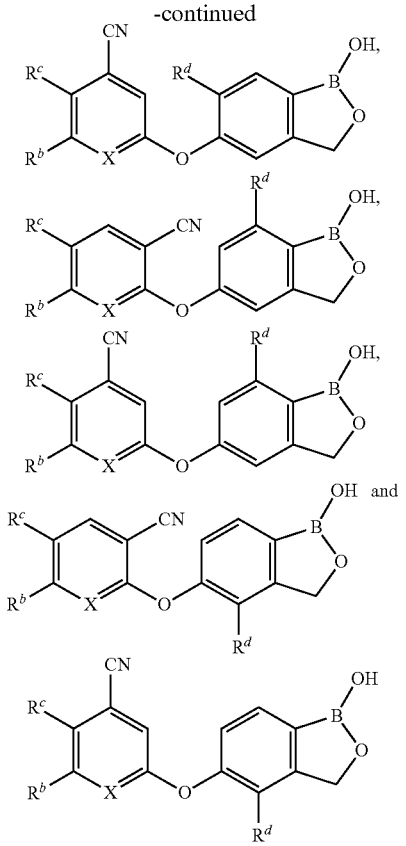

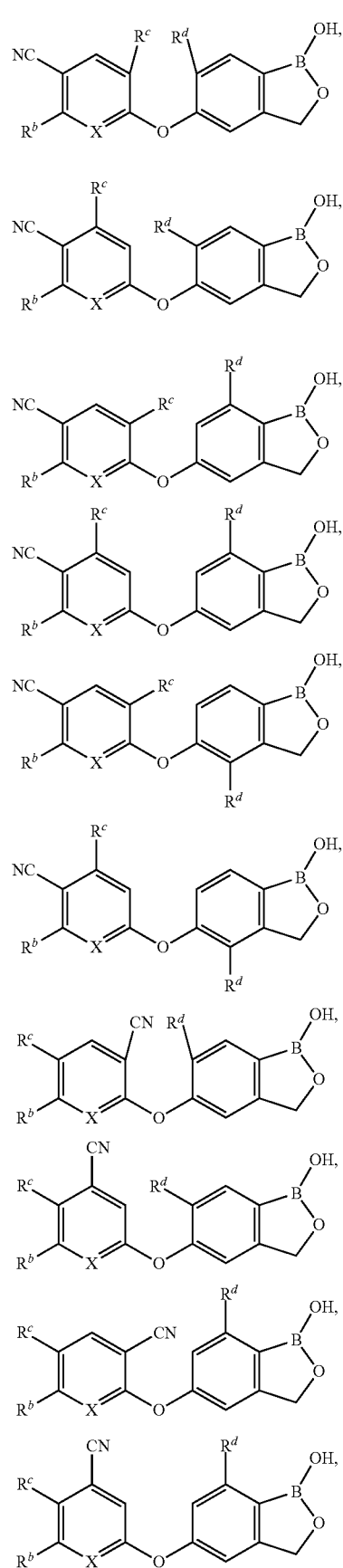

wherein
- $R^d$ is selected from the group consisting of H, halogen, and unsubstituted alkyl;
- $R^c$ is selected from the group consisting of cyano, substituted or unsubstituted alkyl, substituted or unsubstituted cycloalkyl, and substituted or unsubstituted alkoxy;
- X is N or CH,
- $R^b$ is selected from the group consisting of $OR^4$ and $NR^4R^5$
  - wherein $R^4$ and $R^5$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, with the proviso that $R^4$ and $R^5$, together with the atoms to which they are attached, are optionally combined to form a 4- to 8-membered substituted or unsubstituted heterocycloalkyl ring or a pharmaceutically acceptable salt thereof, wherein the release of the cytokine or chemokine by the cell is decreased.

2. A method of treating psoriasis, atopic dermatitis, rheumatoid arthritis, an inflammatory bowel disease, asthma and chronic obstructive pulmonary disease, in an animal, the method comprising administering to the animal a therapeutically effective amount of the compound having a structure according to a formula which is selected from the group consisting of:

-continued

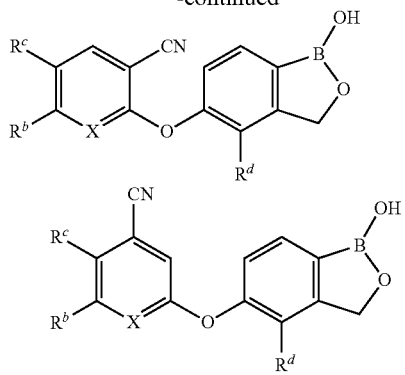

and

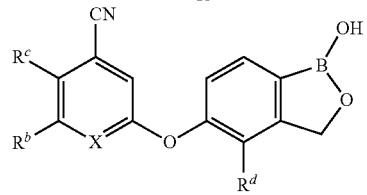

wherein
  R$^d$ is selected from the group consisting of H, halogen, and unsubstituted alkyl;
  R$^c$ is selected from the group consisting of cyano, substituted or unsubstituted alkyl, substituted or unsubstituted cycloalkyl, and substituted or unsubstituted alkoxy;
  X is N or CH,
  R$^b$ is selected from the group consisting of OR$^4$ and NR$^4$R$^5$
  wherein R$^4$ and R$^5$ are independently selected from the grow consisting of H, substituted or unsubstituted alkyl substituted or unsubstituted heteroalkyl, substituted or unsubstituted cycloalkyl, substituted or unsubstituted heterocycloalkyl, substituted or unsubstituted aryl, and substituted or unsubstituted heteroaryl,
with the proviso that R$^4$ and R$^5$, together with the atoms to which they are attached, are optionally combined to form a 4- to 8-membered substituted or unsubstituted heterocycloalkyl ring
or a pharmaceutically acceptable salt thereof,
thereby treating the psoriasis, atopic dermatitis, rheumatoid arthritis, an inflammatory bowel disease, asthma and chronic obstructive pulmonary disease.

3. A method of inhibiting a phosphodiesterase (PDE), the method comprising: contacting the phosphodiesterase with a compound having a structure according to a formula which is selected from the group consisting of:

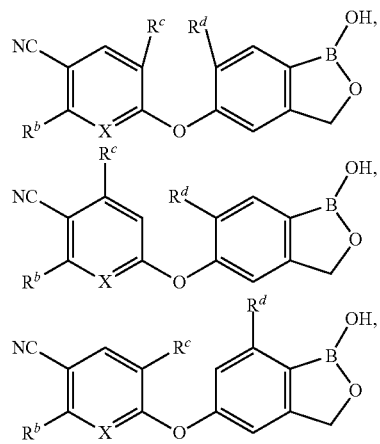

-continued

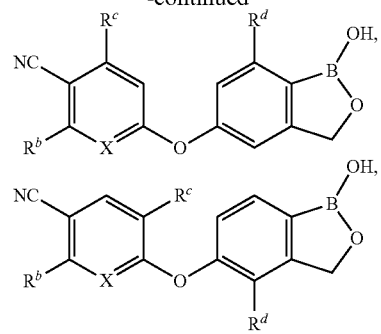

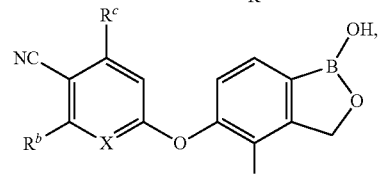

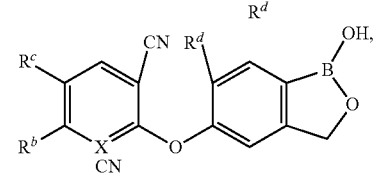

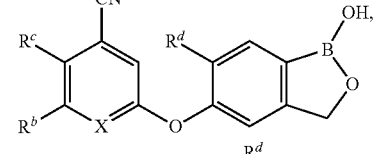

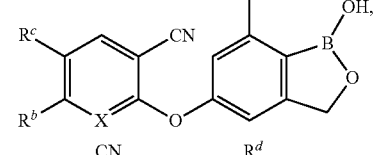

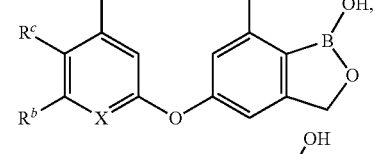

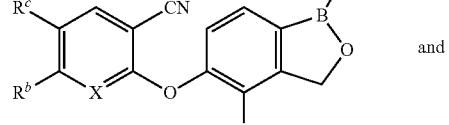

and

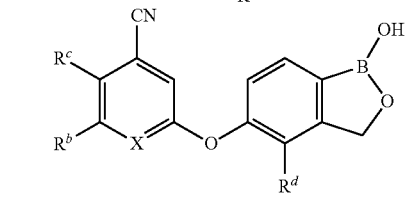

wherein
  R$^d$ is selected from the group consisting of H, halogen, and unsubstituted alkyl;
  R$^c$ is selected from the group consisting of cyano, substituted or unsubstituted alkyl, substituted or unsubstituted cycloalkyl, and substituted or unsubstituted alkoxy;
  X is N or CH, $R^b$ is selected from the group consisting of $OR^4$ and $NR^4R^5$ wherein $R^4$ and $R^5$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, with the proviso that $R^4$ and $R^5$, together with the atoms to which they are attached, are optionally combined to form a 4- to 8-membered substituted or unsubstituted heterocycloalkyl ring or a pharmaceutically acceptable salt thereof, thereby inhibiting the phosphodiesterase.

4. The method of claim 3, wherein said phosphodiesterase is phosphodiesterase4 (PDE4).

* * * * *